US010392619B2

(12) United States Patent
Smith

(10) Patent No.: US 10,392,619 B2
(45) Date of Patent: Aug. 27, 2019

(54) METHODS AND COMPOSITIONS FOR MODULATING GENE EXPRESSION USING OLIGONUCLEOTIDE BASED DRUGS ADMINISTERED IN VIVO OR IN VITRO

(71) Applicant: Larry J. Smith, Omaha, NE (US)

(72) Inventor: Larry J. Smith, Omaha, NE (US)

(*) Notice: Subject to any disclaimer, the term of this patent is extended or adjusted under 35 U.S.C. 154(b) by 0 days.

(21) Appl. No.: 15/010,837

(22) Filed: Jan. 29, 2016

(65) Prior Publication Data
US 2016/0186179 A1 Jun. 30, 2016

Related U.S. Application Data

(63) Continuation of application No. 14/148,191, filed on Jan. 6, 2014, now abandoned, which is a continuation of application No. 13/501,506, filed as application No. PCT/US2010/052399 on Oct. 12, 2010, now abandoned.

(60) Provisional application No. 61/250,714, filed on Oct. 12, 2009.

(51) Int. Cl.
*A61K 31/712* (2006.01)
*A61K 31/7125* (2006.01)
*C12N 15/113* (2010.01)
*A61K 31/713* (2006.01)

(52) U.S. Cl.
CPC ........ *C12N 15/1135* (2013.01); *A61K 31/712* (2013.01); *A61K 31/713* (2013.01); *A61K 31/7125* (2013.01); *C12N 15/113* (2013.01); *C12N 15/1136* (2013.01); *C12N 15/1137* (2013.01); *C12N 15/1138* (2013.01); *C12N 2310/11* (2013.01); *C12N 2310/14* (2013.01); *C12N 2310/31* (2013.01); *C12N 2310/315* (2013.01); *C12N 2310/321* (2013.01); *C12N 2310/322* (2013.01); *C12N 2310/3513* (2013.01); *C12N 2310/51* (2013.01); *C12N 2320/31* (2013.01); *C12N 2320/35* (2013.01); *C12N 2320/51* (2013.01)

(58) Field of Classification Search
CPC .............. C12N 15/113; C12N 2310/14; C12N 2330/51
USPC .......... 435/6.1, 6.11, 6.13, 7.21, 91.1, 91.31, 435/375, 455, 458; 514/19.3, 44; 536/23.1, 24.5
See application file for complete search history.

(56) References Cited

U.S. PATENT DOCUMENTS

| 5,670,633 | A | 9/1997 | Cook et al. |
|---|---|---|---|
| 5,898,031 | A | 4/1999 | Crooke et al. |
| 6,005,087 | A | 12/1999 | Cook et al. |
| 6,107,094 | A | 8/2000 | Crooke et al. |
| 6,268,490 | B1 | 7/2001 | Imanishi et al. |
| 6,506,559 | B1 | 1/2003 | Fire et al. |
| 6,531,584 | B1 | 3/2003 | Cook et al. |
| 6,573,099 | B2 | 6/2003 | Graham et al. |
| 7,056,704 | B2 | 6/2006 | Tuschl et al. |
| 7,078,196 | B2 | 7/2006 | Tuschl et al. |
| 7,138,517 | B2 | 11/2006 | Cook et al. |
| 7,365,058 | B2 | 4/2008 | Stoffel et al. |
| 7,432,249 | B2 | 10/2008 | Crooke et al. |
| 7,432,250 | B2 | 10/2008 | Crooke et al. |
| 7,585,969 | B2 | 9/2009 | Stoffel et al. |
| 7,629,321 | B2 | 12/2009 | Crooke et al. |
| 7,695,902 | B2 | 4/2010 | Crooke et al. |
| 7,772,389 | B2 | 8/2010 | Tuschl et al. |
| 7,786,290 | B2 | 8/2010 | Woppmann et al. |
| 7,790,691 | B2 | 9/2010 | Kraynack et al. |
| 7,838,662 | B2 | 11/2010 | Tuschl et al. |
| 7,838,663 | B2 | 11/2010 | Tuschl et al. |
| 7,838,664 | B2 | 11/2010 | Tuschl et al. |
| 2005/0004064 | A1 | 1/2005 | Kumiko et al. |
| 2005/0187178 | A1* | 8/2005 | Allerson ................ C07H 21/02 514/44 A |
| 2005/0227934 | A1 | 10/2005 | Stoffel et al. |
| 2005/0260755 | A1 | 11/2005 | Baker et al. |
| 2007/0117767 | A1 | 5/2007 | Hohjoh et al. |
| 2011/0197292 | A1* | 8/2011 | Sullenger .............. C12N 15/111 800/13 |
| 2013/0123342 | A1* | 5/2013 | Brown ................ C12N 15/1135 514/44 A |

(Continued)

FOREIGN PATENT DOCUMENTS

| EP | 1144623 | 8/2002 |
|---|---|---|
| EP | 1214945 | 6/2005 |

(Continued)

OTHER PUBLICATIONS

Elbashir et al., Duplexes of 21-nucleoside RNAs mediate RNA interference in cultured mammalian cells, Nature, 2001, 494-98, 411.

(Continued)

*Primary Examiner* — Jane J Zara

(74) *Attorney, Agent, or Firm* — Kathleen D. Rigaut; Howson & Howson LLP

(57) ABSTRACT

Compositions and method for down modulating target gene expression which RNA interference, as well as methods for administering said compositions are disclosed. The method comprises administering a first oligonucleotide strand to a cell, incubating the cells for a time period suitable for uptake of the first oligo nucleotide strand prior to administration of a second oligonucleotide strand, wherein the first strand and the second strand form an intracellular duplex which is effective to catalyze degradation of gene target mRNA or inhibit translation of said mRNA.

8 Claims, 54 Drawing Sheets

Specification includes a Sequence Listing.

(56) References Cited

U.S. PATENT DOCUMENTS

2015/0210733 A1* 7/2015 Manoharan .......... C07H 19/073
536/24.5

FOREIGN PATENT DOCUMENTS

| | | |
|---|---|---|
| EP | 1407044 | 9/2007 |
| EP | 1550719 | 12/2008 |
| EP | 1309726 | 12/2009 |
| WO | 2003029459 | 4/2003 |
| WO | 2003044188 | 5/2003 |
| WO | 2004007718 | 1/2004 |
| WO | 2004063375 | 7/2004 |
| WO | 2004083430 | 9/2004 |
| WO | 20050187178 | 8/2005 |
| WO | 2005079397 | 9/2005 |
| WO | 2006119266 | 11/2006 |
| WO | 20070066549 | 3/2007 |
| WO | 2007085485 | 8/2007 |
| WO | 2007107162 | 9/2007 |
| WO | 2008049078 | 4/2008 |
| WO | 2009029688 | 3/2009 |
| WO | 2009029690 | 3/2009 |
| WO | 2009078685 | 6/2009 |
| WO | 2005079533 | 9/2009 |
| WO | 2009152500 | 12/2009 |
| WO | 2010011895 | 1/2010 |
| WO | 2010065756 | 6/2010 |

OTHER PUBLICATIONS

Elbashir et al., RNA interference is mediated by 21- and 22-nucleotide RNAs, Genes & Dev, 2001, 188-200 15.

Weitzer et al., hClp1: a novel kinase revitalizes RNA metabolism, Cell Cycle, 2007, 2133-37, 6.

Yoda et al., ATP-dependent human RISC assembly pathways, Nat Struct Mol Biol, 2010, 17-23, 17.

Ui-Tei et al., Thermodynamic stability and Watson-Crick base pairing in the seed duplex are major determinants of the efficiency of the siRNA-based off-target effect, Nucleic Acids Res, 2008, 7100-9, 36.

Ui-Tei et al., Functional dissection of siRNA sequence by systematic DNA substitution: modified siRNA with a DNA seed arm is a powerful tool for mammalian gene silencing with significantly reduced off-target effect, Nucleic Acids Res, 2008, 2136-51, 36.

Fire et al., Potent and specific genetic interference by double-stranded RNA in Caenorhabditis elegans, Nature, 1998, 806-811, 391.

* cited by examiner

Figure 3: Compounds Directed to Human p53

5' C~A~G~A~C~C~U~A~U-G~G-A~A~A~C~U~A~C~U~U 3'

3' G~U~C~U~G~G~A~U~A-C--C~U~U~U~G~A~U~G~A~A 5'

Where in accordance with Prototype 7 Design 3a:

1) The nucleosides shown in bold have the 2'-O-methyl modification and those that are underlined are 2'-fluoro;
2) One or more contiguous dashes represent phosphodiester linkages and ~ represents phosphorothioate linkages

Figure 4: Compounds Directed to Human p53

5' C~C~G~U~C~C~C~A~A-G~C-A~A~U~G~G~A~C~G~A 3'

3' G~G~C~A~G~G~G-U~U-C--G~U~U--A~C~C~U~G~C~U 5'

Where:

1) In accordance with the design shown in Prototype 3, the U three nucleosides in from the 3'end of the sense strand is a C and the corresponding nucleoside in the antisense strand is a G. These changes result in the potential formation of hair pins in both of these strands. References human p53 gene sequence is provided in GenBank at NM_000546.4.
2) In accordance with Prototype 7 Design 3a
    a. The nucleosides shown in bold have the 2'-O-methyl modification and those that are underlined are 2'-fluoro.
    b. One or more contiguous dashes represent phosphodiester linkages and ~ represents phosphorothioate linkages
3) In a variant compound, the 5'end U of the antisense strand is changed to a C, the 3'end GA and the 5'end CCG are removed from the sense strand, the two phosphodiester linkages in the sense strand are changed to phosphorothioates. These changes are consistent with Design 4c in Prototype 8.
4) In a variant of this variant, the 2'-fluoros in the antisense strand are changed to 2'-O-methyls and the 2'-O-methyls, with the exception of the one at the 5'-end of the antisense strand, are changed to native ribose. These changes are consistent with those illustrated by Prototype 8 design 4c.

Figure 5: Compounds Directed to Human p53

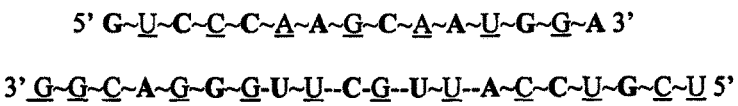

Where is in accordance with Design 4c illustrated in Prototype 8:

1) The nucleosides shown in bold have the 2'-0-methyl modification and those that are underlined are 2'-fluoro.
2) One or more contiguous dashes represent phosphodiester linkages and ~ represents phosphorothioate linkages

Figure 6: Compounds Directed to Human p53

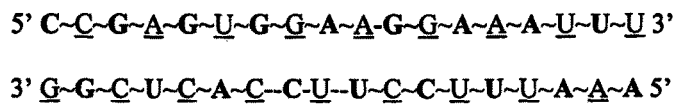

Where:

1) In accordance with Prototype 7 Design 3a
    a. The nucleosides shown in bold have the 2'-0-methyl modification and those that are underlined are 2'-fluoro.
    b. One or more contiguous dashes represent phosphodiester linkages and ~ represents phosphorothioate linkages
2) In a variant, the strands are reduced in size to 16-mers by removing the 3'-end UU from the sense strand and the 5'-end AA from the antisense strand. This requires the phosphodiester linkages to be shifted upstream two places on the sense strand and two places downstream on the antisense strand.

Figure 7: Compounds Directed to Human p53

5' G~G̲~A~G̲~A~A̲~U~A̲~U~U̲--U~C̲~A~C̲~C~C̲~U~U̲ 3'

3' C̲~C~U̲~C~U̲~U~A̲--U--A̲-A~A̲~G~U̲~G~G̲~G~A̲~A 5'

Where in accordance with Prototype 7 Design 3a

1) The nucleosides shown in bold have the 2'-0-methyl modification and those that are underlined are 2'-fluoro.
2) One or more contiguous dashes represent phosphodiester linkages and ~ represents phosphorothioate linkages

Figure 8: Compounds Directed to Human p53

5' G~G̲~A~G̲~G~G̲~A~G̲~A~A̲~U-A̲~U~U̲~U~C̲~A~C̲~C~C̲~U 3'

3' C̲~C~U̲~C~C̲~C~U̲~C~U̲--U~A̲-U--A̲--A~A̲-G~U̲~G~G̲~G~A̲~G̲ 5'

Where:

1) In accordance with the design shown in Prototypes 3 and 4 the 5'end A in the sense strand is change to a G, the corresponding nucleoside in the sense strand is deleted (also in keeping with the design principle illustrated in Prototype 1), the A four nucleosides from the 3' end of the antisense strand is changed to a C and the corresponding nucleoside in the sense strand is changed to a G. These changes result in the potential formation of a hair pin in the antisense strand.
2) In accordance with Prototype 7 Design 3a
   a. The nucleosides shown in bold have the 2'-0-methyl modification and those that are underlined are 2'-fluoro.
   b. One or more contiguous dashes represent phosphodiester linkages and ~ represents phosphorothioate linkages
3) In a variant compound the 2' fluoro modified nucleosides become 2'-0-methyl and the 2-0-methyl modified nucleosides become native ribose. These changes are consistent with those illustrated by Prototype 7 design 3a.
4) In a further modification of this variant the sense strand is shortened to a 16-mer by removing three nucleosides from the 5'end and two from the 3'end, changing the single phosphodiester linkage to phosphorothioate and making all the remaining nucleosides 2'-0-methyl. This is in keeping with the 4c design illustrated in Prototype 8.

Figure 9: Compounds Directed to Human p53

5' G~G~A~C~G~G~A~A~C~A-G~C~U~U~U~G~A~G~G~U 3'

3' C~C~U~G~C~C~U~U~G--U-C--G~A~A~A~C~U~C~C~A 5'

Where:

1) In accordance with Prototype 7 Design 3a:
    a. The nucleosides shown in bold have the 2'-O-methyl modification and those that are underlined are 2'-fluoro.
    b. One or more contiguous dashes represent phosphodiester linkages and ~ represents phosphorothioate linkages
2) In a variant 3 nucleosides are removed from the 5'-end of the sense strand, 2 from the 3'-end and the single phosphodiester linkage converted to phosphodiester. This is in keeping with Design 4c illustrated in Prototype 8.

Figure 10: Compounds Directed to Human p53

5' G~U~U~C~A~A~G~A~C~A~G~A~A~G~G~G 3'

3' G~U~A~C~A~A~G~U~U~C~U--G--U~C~U~U~C~C~C~G~G 5'

Where in accordance with the same 4c Design Prototype 8

1) The nucleosides shown in bold have the 2'-O-methyl modification and those that are underlined are 2'-fluoro.
2) One or more contiguous dashes represent phosphodiester linkages and ~ represents phosphorothioate linkages

Figure 11: Compounds Directed to Human Fas

5' G~<u>G</u>~A~<u>A</u>~G~<u>A</u>~C~<u>U</u>~G~<u>U</u>~U~<u>A</u>~C~<u>U</u>~A~<u>C</u>~A~<u>G</u>~T~<u>T</u> 3'

3' <u>C</u>~C~<u>U</u>~U~<u>C</u>~U~<u>G</u>~A~<u>C</u>~A--<u>A</u>-U~<u>G</u>~A~<u>U</u>~G~<u>U</u>~C~<u>A</u>~A 5'

Where:

1) In accordance with Prototype 7 Design 3a:
   a. The nucleosides shown in bold have the 2'-O-methyl modification and those that are underlined are 2'-fluoro.
   b. One or more contiguous dashes represent phosphodiester linkages and ~ represents phosphorothioate linkages

Figure 12: Compounds Directed to Human Fas

5' G~<u>G</u>~A~<u>A</u>~G~<u>A</u>~C~<u>U</u>~G-<u>U</u>~U-<u>A</u>~C~<u>U</u>-A~<u>C</u>~A~<u>G</u>~T~C~T 3'

3' <u>C</u>~C~<u>U</u>~U~<u>C</u>~U~<u>G</u>--A~<u>C</u>--A-<u>A</u>-U~<u>G</u>--A~<u>U</u>~G~<u>U</u>~C~<u>A</u>~G~A 5'

Where:

1) Addition of CT to the 3'-end of the sense strand and a corresponding GA to the 5'-end of the antisense strand form mismatches with the Fas gene target. The result is the potential formation of hair pins in both strands as provided for by the design show in Prototype 3.
2) Two phosphorothioate linkages in the antisense strand are changed to phosphodiester. These changes are consistent with the 3a Design illustrated in Prototype 7.
3) In a variant three nucleosides are removed from both ends of the sense strand and all the sense strand linkages are phosphorothioate. These changes are consistent with Design 4c illustrated in Prototype 8.

Figure 13: Compounds Directed to Human Fas

5' G~U~G~A~U~G~A~A~G~G~A~C~A~U~G~G~C~U~U~A 3'

3' C~A~C~U~A~C~U~U~C--C~U--G~U~A~C~C~G~A~A~U 5'

Where:

In accordance with Prototype 7 Design 3a:

1) The nucleosides shown in bold have the 2'-O-methyl modification and those that are underlined are 2'-fluoro 2) One or more contiguous dashes represent phosphodiester linkages and ~ represents phosphorothioate linkages

Figure 14: Compounds Directed to Human Fas

5' G~C~C~A~U~G~A~A~G~G~A~C~A~U~G~G~C~U~U~A 3'

3' C~G~G~U~A~C~U--U~C--C~U~G~U--A~C~C~G~A~A~U 5'

Where:

1) The two Gs near the 3' end of the antisense strand are mismatches with the Fas gene target while the terminal C is not a mismatch. These mismatches in the antisense strand with corresponding CC nucleosides in the sense strand give rise to the potential formation of hair pins in both strands as provided for by the design show in Prototype 3.
2) Two phosphorothioate linkages in the antisense strand are changed to phosphodiester. These changes are consistent with the 3a Design illustrated in Prototype 7.
3) In a variant two nucleosides are removed from the 5'-end and 3 from the 3'-end of the sense strand and all the sense strand linkages are phosphorothioate. These changes are consistent with Design 4c illustrated in Prototype 8.

Figure 15: Compounds Directed to Human Fas

5' G~A~A~G~C~G~U~A~U~G-A~C~A~C~A~U~U~G~A~T 3'

3' C~U~U~C~G~C~A~U~A--C-U--G~U~G~U~A~A~C~U~A 5'

Where:

1) In accordance with Prototype 7 Design 3a:
   a. The nucleosides shown in bold have the 2'-0-methyl modification and those that are underlined are 2'-fluoro.
   b. One or more contiguous dashes represent phosphodiester linkages and ~ represents phosphorothioate linkages
2) In a variant three nucleosides (GAA) are removed from the 5'-end and two nucleosides (AT) are removed from the 3'-end of the sense strand. These changes are consistent with Design 4c illustrated in Prototype 8.

Figure 16: Compounds Directed to Human Fas

5' G~G~A~C~A~U~U~A~C~U-A~G~U~G~A~C~U~C~A 3'

3' C~C~U~G~U~A~A~U--G-A--U~C~A~C~U~G~A~G~U 5'

Where:

In accordance with Prototype 7 Design 3a:
   a. The nucleosides shown in bold have the 2'-0-methyl modification and those that are underlined are 2'-fluoro.
   b. One or more contiguous dashes represent phosphodiester linkages and ~ represents phosphorothioate linkages

Figure 17: Compounds Directed to Human/Murine ApoB

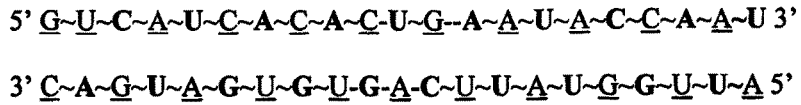

Where:

1) In accordance with Prototype 7 Design 3a:
    a. The nucleosides shown in bold have the 2'-0-methyl modification and those that are underlined are 2'-fluoro;
    b. One or more contiguous dashes represent phosphodiester linkages and ~ represents phosphorothioate linkages
2) In a variant, compound three nucleosides are deleted from the 5' end of the sense strand and three from the 3' end of the sense strand. This is in keeping with Design 4c shown in Prototype 8. In this variant all the sense strand linkages are phosphorothioate.

Figure 18: Compounds Directed to Human/Murine ApoB

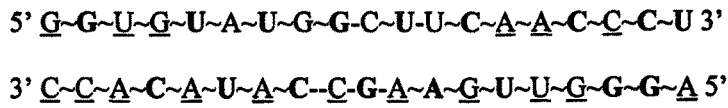

Where:

1) In accordance with Prototype 7 Design 3a
    a. The nucleosides shown in bold have the 2'-0-methyl modification and those that are underlined are 2'-fluoro. The distribution of these modifications at the terminal 4 nucleosides of both strands are consistent with the design consideration illustrated in Prototype 1.
    b. One or more contiguous dashes represent phosphodiester linkages and ~ represents phosphorothioate linkages
2) In a variant compound two nucleosides are deleted from the 5' end of the sense strand and two from the 3' end of the sense strand. In this case all of the linkages in the sense strand are phosphorothioate. These changes are in keeping with Design 4c shown in Prototype 8.

Figure 19: Compounds Directed to Human/Murine ApoB

5' A~G~G~G~U~G~U~A~U--G~G-C~U-U~C~A~A~C~C~C~U 3'

3' U~C~C~C~A~C~A~U--A~C--C-G-A~A--G~U~U~G~G~G~A 5'

Where:

1) Variant one is illustrated where:
   a. The nucleosides shown in bold have the 2'-0-methyl modification and those that are underlined are 2'-fluoro.
   b. One or more contiguous dashes represent phosphodiester linkages and ~ represents phosphorothioate linkages
2) In variant two: the 2'fluoro modified nucleosides in the antisense strand become 2'-0-methyl modified nucleosides and the 2'-0-methyl modified nucleosides become native ribose with the exception of the nucleosides in the second and third positions in from the 5'end which continue to have the 2'-0-methyl modification. This is consistent with Design 3a in Prototype 7.
3) In variant three: in addition to the changes in variant two, all the nucleosides in the sense strand have the 2'-0-methyl modification. This is consistent with Design 3a in Prototype 7.
4) In variant four: in addition to the changes in variant three, three 5' and three 3'-end nucleosides of the sense strand are deleted and the phosphodiester linkages in the sense strand are replaced by phosphorothioate linkages. These changes are consistent with Design 4c illustrated in Prototype 8.

Figure 20: Compounds Directed to Human/Murine ApoB

5' G~G~A~G~U~U~U~G~U~G~A~C~A-A~A~U~A~U~G~G~C~A 3'

3' C~C~U~C~A~A~A~C~A~C~U~G~U--U--U~A~U~A~C~C~C~G~U 5'

Where:

1) In accordance with Prototype 7 Design 3a:
   a. The nucleosides shown in bold have the 2'-0-methyl modification and those that are underlined are 2'-fluoro.
   b. One or more contiguous dashes represent phosphodiester linkages and ~ represents phosphorothioate linkages
2) In a variant compound three nucleosides are deleted from the 5' end of the sense strand, four from the 3' end of the sense strand and the 5'-end U from the antisense strand. In this case all of the linkages in the sense strand are phosphorothioate. These changes are in keeping with Design 4c shown in Prototype 8.
3) In another variant five nucleosides are removed from the 3'-end of the sense strand and five from the 5'-end of the antisense stand to produce am 18-mer blunt ended compound consistent with the design considerations illustrated in Prototype 1.

Figure 21: Compounds Directed to Human/Murine ApoB

5' G~A~U~U~G~A~U~U~G~A~C~C~U~G~U~C~C~A~U~U 3'

3' C~U~A~A~C~U~A~A~C--U-G-G~A~C~A~G~G~U~A~A 5'

Where:

1) In accordance with Prototype 7 Design 3a:
    a. The nucleosides shown in bold have the 2'-0-methyl modification and those that are underlined are 2'-fluoro. The distribution of these modifications at the terminal 4 nucleosides is consistent with the design considerations illustrated in Prototype 1.
    b. One or more contiguous dashes represent phosphodiester linkages and ~ represents phosphorothioate linkages
2) In a variant compound, three nucleosides are deleted from the 5' end of the sense strand and two from the 3' end of the sense strand. In this case all of the linkages in the sense strand are phosphorothioate. These changes are in keeping with Design 4c shown in Prototype 8.

Figure 22: Compounds Directed to Human/Murine ApoB

5' G~U~C~A~U~C~A~C~A~C-U~G~A~A~U~A~C~C~A~A~U 3'

3' C~A~G~U~A~G~U~G~U~G-A-C-U~U~A~U~G~G~U~U~A 5'

Where:

1) In accordance with Prototype 7 Design 3a:
    a. The nucleosides shown in bold have the 2'-0-methyl modification and those that are underlined are 2'-fluoro. The distribution of these modifications at the terminal 4 nucleosides is consistent with the design consideration illustrated in Prototype 1.
    b. One or more contiguous dashes represent phosphodiester linkages and ~ represents phosphorothioate linkages
2) In a variant compound, three nucleosides are deleted from the 5' end of the sense strand and three from the 3' end of the sense strand. In this case all of the linkages in the sense strand are phosphorothioate. These changes are in keeping with Design 4c shown in Prototype 8.

Figure 23: Compounds Directed to Human/Murine ApoB

5' G~U~A~U~U~C~A~C~A-C-U~G~A~A~U~A~C~C~A~A~U 3'

3' C~A~U~A~A~G~U~G-U~G-A-C-U~U--A~U~G~G~U~U~A 5'

Where:

1) The U and G in positions 18 and 19 from the 5'-end the antisense strand that are complementary to the Apo B target are changed to A and U. The corresponding nucleosides in the sense strand are U and A. These changes allow for the formation of potential hair pins in both strands that are in keeping with design illustrated in Prototype 3.
2) In keeping with Design 3a illustrated in Prototype 7.
    a. The nucleosides shown in bold have the 2'-0-methyl modification and those that are underlined are 2'-fluoro. The distribution of these modifications at the terminal 4 nucleosides is consistent with the design consideration illustrated in Structure 1.
    b. One or more contiguous dashes represent phosphodiester linkages and ~ represents phosphorothioate linkages

Figure 24: Compounds Directed to Human ApoB

5' G~G~U~G~C~G~A~A~G~C--A~G~A~C~U~G~A~G~G~C~T~A 3'

3' C~C~A~C~G~C~U~U~C~G~U-C~U--G~A~C~U~C~C~G~A~T 5'

Where:

1) In accordance with Prototype 7 Design 3a
    a. The nucleosides shown in bold have the 2'-O-methyl modification and those that are underlined are 2'-fluoro.
    b. One or more contiguous dashes represent phosphodiester linkages and ~ represents phosphorothioate linkages
2) In a variant compound the 3'-end TA of the sense strand and the corresponding AT from the antisense strand are removed along with three nucleosides from the 5' end of the sense strand and two from the 3' end of the sense strand. The phosphodiester linkages in the antisense strand are shifted upstream two places to maintain the design illustrated in Prototype 2. Further, all of the linkages in the sense strand are phosphorothioate. These changes are in keeping with Design 4c shown in Prototype 8.

Figure 25: Compounds Directed to Human ApoB

5' U~G~C~G~A~A~G~C~A~G~ A~C~U~G\*~A 3'

3'C~G~G~A~C~G~C~U-U~C--G--U--C~U~G-A~C\*~U~C~C~G 5'

Where:

1) The two Cs at the 3'end of the antisense stand that would base pair with the gene target were changed to Gs and a C was added. The effect of these changes is to create an antisense strand that forms a potential hair pin in accordance with the design presented in Prototype 3. The nuclease protective function of the hair pin allows for the placement of additional phosphodiester linkages.
2) In accordance with Prototype 7 Design 3a
    a. The nucleosides shown in bold have the 2'-0-methyl modification and those that are underlined are 2'-fluoro. The distribution of these modifications at the terminal 4 nucleosides is consistent with the design consideration illustrated in Prototype 1.
    b. One or more contiguous dashes represent phosphodiester linkages and ~ represents phosphorothioate linkages
3) In a variant compound the C in the antisense strand indicated by an asterisk is changed to a G to further increase the negative free energy of the hair pin and the corresponding G in the sense strand is changed to a C.
4) In another variants (with or without the changes indicated by the asterisks) the three nucleosides at the two ends of the antisense stand are all 2'-0-methyl and the residual 2-fluoro modifications in the antisense strand are changed to native ribose while the residual nucleosides with the 2'-0-methyl modification are retained. These changes are consistent with Design 4c shown in Prototype 8.
5) In variants of these variants all the nucleosides in the sense strand have the 2'-0-methyl modification. This is consistent with Design 4c in Prototype 8.

Figure 26: Compounds Directed to Human ApoB

A.

5' C̲~G~G̲~C~A̲~U~U̲~C~G̲~G~ C̲~U~A̲~U~G~U~G̲~U~U̲ 3'

3' G̲~C̲~C~G̲~U~A̲~A~G̲--C--C̲--G~A̲~U~A̲~C~A̲~C~A 5'

B. Variant illustrated as a 16-mers:

5' C̲~G~G̲~C~A̲~U~U̲~C~G̲~G~ C̲~U~A̲~U~G~U 3'

3' G̲~C̲~C~G̲~U--A̲--A--G̲~C~C̲~G~A̲~U~A̲~C~A̲ 5'

Where:

1) In accordance with Prototype 7 Design 3a
    a. The nucleosides shown in bold have the 2'-0-methyl modification and those that are underlined are 2'-fluoro. The distribution of these modifications at the terminal 4 nucleosides is consistent with the design consideration illustrated in Prototype 1.
    b. One or more contiguous dashes represent phosphodiester linkages and ~ represents phosphorothioate linkages
2) In a variant compound two nucleosides are deleted from each end of the sense strand in keeping with Design 4c illustrated in Prototype 8.
3) In other variant compounds (illustrated as 16-mer in B) at one or three nucleosides on the 3' end of the sense and the same number of nucleosides on the 5' end of the antisense strand are deleted to produce a blunt end duplex that is a 16 or an 18-mer in length. The linkages in the antisense strand are shifted down-stream one to three positions depending on the number of nucleoside deletions in keeping with the design consideration illustrated in Prototype 2.

Figure 27: Compounds Directed to Human ApoB

5' C~A~C~A~G~G~G~C~U~C~A~C~C~C~U 3'

3' U~G~U~G~U~G~U~C~C--C--G-A~G--U~G~G~G~A~C~U* 5'

Where:

1) The antisense and sense strands naturally forms a potential hair pin in accordance with the design presented in Prototype 3; In a variant compound the terminal 5' U in the antisense strand indicated by an asterisk is changed to an A to increase the negative free energy if the potential hair pin;
2) In accordance with Prototype 7 Design 3a
    a. The nucleosides shown in bold have the 2'-O-methyl modification, those that are underlined are 2'-fluoro and those that are neither bold nor underlined have native ribose;
    b. One or more contiguous dashes represent phosphodiester linkages and ~ represents phosphorothioate linkages
3) In variants A and B (with and with out the change in the nucleoside with the asterisk) the two native ribose nucleosides in the antisense strand have the 2'-fluoro modification.
4) The relative lengths of the sense and antisense stand and the location of the opposing nucleosides that constitute the duplex are in accordance with Design 4c shown in Prototype8.
5) In variants of A and B (variants C and D - with and without the change in the nucleoside indicated by an asterisk) the 2'-fluoro modified nucleosides in the antisense strand are changed to 2'-O-methyl and the 2'-O-methyl are changed to native ribose.
6) In variants E and F (of C and D) the 2'-fluoro modified nucleosides in the sense strand are changed to 2'-O-methyl.

Figure 28: Compounds Directed to Human/Murine/Rat/Nonhuman Primate PCSK9

5' G~C~C~U~G~G~A~G~U~U~U~A~U~U~C~G~G~A~A 3'

3' C~G~G~A~C~C~U~C~-A-A--A~U~A~A~G~C~C~U~U 5'

Where:

1) In accordance with Prototype 7 Design 3a
   a. The nucleosides shown in bold have the 2'-0-methyl modification, those that are underlined are 2'-fluoro;
   b. One or more contiguous dashes represent phosphodiester linkages and ~ represents phosphorothioate linkages
2) In a variant two nucleosides are removed from the 5'-end of the sense strand and two from the 3'-end. This is in keeping with the 4c Design illustrated in Prototype 8.
3) In a second variant a G is added to the 5'-end of the sense strand and a C to the 3'-end of the antisense strand. This addition to the antisense strand is in keeping with human PCSK9 gene sequence NM_174936.2 and so it does not represent a mismatch with the gene target. This change further increases the Tm differential between the two duplexed ends of the compound in accordance with the design consideration shown in Prototype 1.
4) In a variant of the second variant three nucleosides are removed from the 5'-end of the sense strand and two from the 3'-end. This is in keeping with the 4c Design illustrated in Prototype 8.

Figure 29: Compounds Directed to Human/Murine/Rat/Nonhuman Primate PCSK9

5' C~U~A~G~A~C~C~U~G~U~U~U~U~G~C~U~U~U 3'

3' G~A~U~C~U~G~G~A~C--A~A~A~A~C~G~A~A~A 5'

Where in accordance with Prototype 7 Design 3a:

1) The nucleosides shown in bold have the 2'-0-methyl modification, those that are underlined are 2'-fluoro;
2) One or more contiguous dashes represent phosphodiester linkages and ~ represents phosphorothioate linkages

Figure 30: Compounds Directed to Human/Murine/Rat/Nonhuman Primate PCSK9

5' G̲~A̲~G~G̲~U~G̲~U~A̲~U-C̲~U~C̲-C~U̲~A~G̲~A̲~C~A 3'

3' C̲~U~C̲~C~A̲~C~A̲~U--A̲-G-A̲~G~G̲~A~U̲~C~U̲~G~U̲ 5'

Where in accordance with Prototype 7 Design 3a:

1) The nucleosides shown in bold have the 2'-O-methyl modification, those that are underlined are 2'-fluoro;

2) One or more contiguous dashes represent phosphodiester linkages and ~ represents phosphorothioate linkages

Figure 31: Compounds Directed to Human/Murine/Rat/Nonhuman Primate PCSK9

5' G̲~A̲~G~G̲~U*~G̲~U~A̲~U-C̲~U~C̲-C~U̲~C~G̲~A̲~C~A 3'

3' C̲~U~C̲~C~A̲*~C~A̲~U--A̲-G-A̲~G~G̲~A~G̲~C~U̲~G~U̲ 5'

Where the following changes are made to the compounds in Figure 30:

The fifth nucleoside (a U) in from the 5'-end of the antisense strand is changed to a C and the corresponding A in the fifth position in from the 3'-end of the sense strand is changed to a G. These changes provide for potential hair pins to be formed by both strands. In a variant the negative free energy of the hair pins is increased by changing the U indicated by the asterisk in the sense strand to an A and the corresponding A indicated by an asterisk in the antisense strand to a U. These changes are in accordance with Design 3a illustrated in Prototype 7.

Figure 32: Compounds Directed to Human/Murine/Rat/Nonhuman Primate PCSK9

5' G̲~A̲~G~G~U*~G~U~A̲--U~C̲-U~C̲~C~U̲~C~G̲~A̲~C~A 3'

3' C̲~U~C̲~C~A̲*~C--A~U--A̲-G-A̲~G--G̲~A~G̲~C~U̲~G~U̲ 5'

Where the following changes are made to the compounds in Figure 31:

1) Two phosphorothioate linkages in the antisense strand are changed to phosphodiester (linkages 7 and 13 counting from the 5'-end) and the one phosphodiester linkage (in position 9 from the 5'-end) in the sense strand is removed and replaced by two phosphodiester linkages (in positions 8 and 10 from the 5'-end) as shown in the figure. These changes are in keeping with those of Design 3a illustrated in Prototype 7.

2) In two variants (with or with out the possible nucleoside changes at the asterisk) all the 2'-fluoro linkages in the antisense strand are changed to 2'-O-methyl and all the 2'-O-methyl linkages with the exceptions of the penultimate nucleosides from both the 5' and 3'-ends of the antisense strand are changed to native ribose. These changes are in keeping with those of Design 3a illustrated in Prototype 7.

3) In two variants of these all the 2'-fluoro linkages in the sense strand are changed to 2'-O-methyl and all the 2'-O-methyl linkages with the exceptions of the two at the 3'-end are changed to native ribose. These changes are in keeping with those of Design 3a illustrated in Prototype 7.

Figure 33: Compounds Directed to Human PCSK9

5' G~G~G~U~G~G~U~C~A~G-C~G-G~C~C~G~G~G~A~U 3'

3' C~C~C~A~C~C~A~G~U--C-G--C~C~G~G~C~C~C~U~A 5'

Variant A:

5' G~G~G~U~G~G~U~C~A~GXC~G-G~C~C~G~G~G~A~U 3'

3' C~C~C~A~C~C~A~G~U--C--G--C~C~G~G~C~C~C~U~A 5'

Variant B:

5' U~G~G~U~C~A~G~C~G~G~C~C~G~G~G 3'

3' C~C~C~A~C~C~A~G~U--C~G--C~C~G~G~C~C~C~U~A 5'

Variant C:

5' G~U~G~G~U~C~A~G~C~G~G~C~C~G~G 3'

3' C~C~C~A~C~C~A--G~U--C~G~C~C~G~G~C~C~C~A 5'

Where:

1) In accordance with Prototype 7 Design 3a
   a. The nucleosides shown in bold have the 2'-0-methyl modification and those that are underlined are 2'-fluoro;
   b. One or more contiguous dashes represent phosphodiester linkages and ~ represents phosphorothioate linkages
2) In variant A the X represents a missing linkage such that there are two contiguous sense strands. The 5'-end and 3'-end nucleosides in the second segment of the sense strand and the penultimate nucleoside from the 5'-end of the antisense strand are changed from 2'-0-methyl to 2'-fluoro. This is consistent with the fact that the design preference illustrated in Prototype 1 does not apply to compounds with the type of segmented sense strand described here. The single remaining phosphodiester linkage in the sense strand is changed to a phosphorothioate. This design is consistent with Prototype 7 Design 3b.
3) The two variants (B and C) produce compounds consistent with the 4c design shown in Prototype 8.

Figure 34: Compounds Directed to Human PCSK9

5' G~C~U~G~C~C~C~A~C~G~U~G~G~C~U~G~G~C~A~U* 3'

3' C~G~A~C~G~G~G~U~G~-C~A~C~C~G~A~C~C~G~U~A* 5'

Variant A:

5' G~C~U~G~C~C~C~A~C~G~U~G~G~C~U~G~G~C~A~U* 3'

3' C~G~A~C~G~G~G~U~G~-C~A~-C~C~G~A~C~C~G~U~A* 5'

Variant B:

5' G~C~U~G~C~C~C~A~C~GXU~G~G~C~U~G~G~C~A~U* 3'

3' C~G~A~C~G~G~G~U~G~-C~-A~-C~-G~A~C~C~G~U~A* 5'

Variant C:

5' G~C~C~C~A~C~G~U~G~G~C~U~G~G~C 3'

3' C~G~A~C~G~G~G~U~G~-C~A~C~C~G~A~C~C~G~U~A* 5'

Where:

1) Both of these strands naturally form potential hair pins in accordance with the design shown in Prototype 3. The negative free energy of the potential hair pins can be increased (more negative) by changing the 5'-end nucleoside in the antisense strand from an A to a C and by changing the corresponding 3'-end U in the sense strand to a G.

2) In accordance with Prototype 7 Design 3a
   a. The nucleosides shown in bold have the 2'-0-methyl modification and those that are underlined are 2'-fluoro;
   b. The relative distribution of 2'-0-methyl and 2'-fluoro modifications at the ends of the compound reflect the design consideration illustrated in Prototype 1.
   c. One or more contiguous dashes represent phosphodiester linkages and ~ represents phosphorothioate linkages 3) In Variants A (with and without the changes to the nucleosides indicated by an asterisk) the 2'fluoro modified nucleosides in the antisense strand are converted to 2'-0-methyl and the 2'-0-methyl with the exception of the 5'-end nucleoside of the antisense strand are converted to native ribose (neither bolded nor underlined). In a further variant all the nucleosides in the sense strand have the 2'-0-methyl modification. These changes are consistent with Design 3a shown in Prototype 7.

4) In Variants B (with and without the changes to the nucleosides indicated by an asterisk although in this case the segmented sense strand does not form a potential hair pin) the X represents a missing linkage such that there are two contiguous sense strands. The 5'-end nucleoside in the second segment of the sense strand and the 5'-end nucleoside in the antisense strand are changed from 2'-0-methyl to 2'-fluoro. This is consistent with the fact that the design preference illustrated in prototype 1 do not apply to compounds with the type of segmented sense strand described here. The single remaining phosphodiester linkage in the sense strand is changed to a phosphorothioate. This design is consistent with Prototype 7 Design 3b.

5) In Variants C (with and without the change to the nucleoside indicated by an asterisk) three nucleosides are removed from the 5'-end and two from the 3'-end of the sense strand. This is in keeping with the Design 4c illustrated in Prototype 8.

Figure 35: Compounds Directed to Human PCSK9

5' G̲~C~U̲~G~C~C̲~C~A̲~C~G̲~U~G~G̲~C~U̲ 3'

3' C̲~G~A̲~C~G̲~A~C̲~G~G~G--U--G~C--A~C̲~C~G̲~A*~C̲~C*5'

Where:

1) This antisense strand naturally forms a potential hair pin. The negative free energy of this hair pin can be increased (made more negative) in variants by changing one or both of the nucleosides indicated by an asterisk where the C is changed to a G and the A to a U. These changes are in keeping with the design illustrated in Prototype 3 and the 4c Design illustrated in Prototype 8.
2) In accordance with Prototype 8 Design 4c
   a. The nucleosides shown in bold have the 2'-0-methyl modification, those that are underlined are 2'-fluoro and the rest are native ribose (not underlined and not bolded);
   b. One or more contiguous dashes represent phosphodiester linkages and ~ represents phosphorothioate linkages
3) In variants (with or without one or both of the potential changes to the nucleosides indicated by an asterisk) the 2'-fluoro modifications are changed to 2'-0-methyl.

Figure 36: Compounds Directed to Human PCSK9

5' G~G~U~G~A~G~G~G~U~G~U~C~U~A*~C 3'

3' C~C~G~C~C~A~C~U--C~C--C--A--C~A--G~A~U*~G~C~G~G 5'

Where:

1) The third nucleoside (C) from the 3' end of the antisense strand that is complementary to the gene target is changed to a G. This results in a potential hair pin consistent with the design illustrated in Prototype 3 and the 4c design illustrated in Prototype 8. In a variant the U indicated by the asterisk in the antisense strand is change to a G to further increase (make more negative) the negative free energy of the hair pin. In this case the corresponding A indicated by an asterisk in the sense strand becomes a C.
2) In accordance with Prototype 8 Design 4c
    a. The nucleosides shown in bold have the 2'-0-methyl modification and those that are underlined are 2'-fluoro;
    b. One or more contiguous dashes represent phosphodiester linkages and ~ represents phosphorothioate linkages
3) In two other variants (with or without the changes in the nucleosides indicated by asterisks) the 2'fluoro modified nucleosides in the antisense strand are converted to 2'-0-methyl and the 2'-0-methyl modified sugars are converted to native ribose. This is consistent with Design 4c in Prototype 8.
4) In variants of these variants all the nucleosides in the sense strand have the 2'-0-methyl modification. This is consistent with Design 4c in Prototype 8.

Figure 37: Compounds Directed to Human PTEN

5' C~G~U~U~A~G~C~A~G~A~A~A~C~A~A~A~A~G~G~A 3'

3' G~C~A~A~U~C~G~U~C~U--U~U~G~U~U~U~C~C~U 5'

Where:

1) In accordance with Prototype 7 Design 3a
    a. The nucleosides shown in bold have the 2'-O-methyl modification and those that are underlined are 2'-fluoro;
    b. One or more contiguous dashes represent phosphodiester linkages and ~ represents phosphorothioate linkages

Figure 38: Compounds Directed to Human PTEN

5' <u>G</u>~U~<u>A</u>~A~<u>G</u>~G-<u>A</u>~C-<u>C</u>~A~<u>G</u>~A~<u>G</u>~A~<u>C</u> 3'

3' U~<u>U</u>~C~<u>A</u>~U~<u>U</u>~C~<u>C</u>-U--<u>G</u>-G~<u>U</u>~C~<u>U</u>~C~<u>U</u>~G~<u>U</u>~U 5'

Where in accordance with Prototype 8 Design 4c:

1) The nucleosides shown in bold have the 2'-O-methyl modification and those that are underlined are 2'-fluoro;
2) One or more contiguous dashes represent phosphodiester linkages and ~ represents phosphorothioate linkages

Figure 39: Compounds Directed to Human PTEN

5' G̲~G~G̲~U~A̲~A~A̲-U~A̲-C~A̲--U~U̲~C~U̲~U~C̲~A~U̲ 3'

3' C~C̲~C~A̲~U~U̲-U~A̲--U-G̲--U~A̲--A~G̲-A~A̲~G~U̲~A 5'

Where in accordance with Prototype 7 Design 3a:

> 1) The nucleosides shown in bold have the 2'-O-methyl modification and those that are underlined are 2'-fluoro;
> 2) One or more contiguous dashes represent phosphodiester linkages and ~ represents phosphorothioate linkages

Figure 40: Compounds Directed to Human PTEN

5' G̲~A~A̲~A~A̲-U~A̲--C~A̲--U~U̲~C~U̲~U~C̲ 3'

3' C~C̲~C~U̲~U~U̲-U~A̲--U-G̲--U~A̲--A~G̲--A~A̲~G~G̲~G 5'

Where:

1) The U and A at the 5'end of the antisense strand that base pair with the gene target were changed to Gs and an A in position 16 from the 5' end of the antisense stand that also base pairs with the gene target was change to a U. The effect of these changes are to create a antisense strand that forms a hair pin in accordance with the design presented in Prototype 3;
2) In accordance with Design 4c shown in Prototype 8
    a. The nucleosides shown in bold have the 2'-0-methyl modification and those that are underlined are 2'-fluoro;
    b. One or more contiguous dashes represent phosphodiester linkages and ~ represents phosphorothioate linkages

Figure 42

(human): hPTENa2-d

5' *G*~G~*G*~U~*A*~A-*A*-U-*A*-C-*A*-U-*U*-C~*U*~U~*C*~A~U 3' (207)

3' C~*C*~C~*A*~U~*U*-U-*A*-U-*G*-U-*A*-A-*G*~A~*A*~G~*U*~*A* 5' (208)

Where top strand is sense and bottom strand is antisense and where bold and italics is 2'-fluoro and underlined is 2'-O-methyl and all linkages indicated by dashes are phosphodiester and those indicated by a ~ are phosphorothioate.

(human): hPTENa3-d

5' *G*~G~*G*~U~*A*~A~*A*~U-*A*-C-*A*-U~*U*~C~*U*~U~*C*~A~U 3' (209)

3' C~*C*~C~*A*~U~*U*~U~*A*-U-*G*-U-*A*~A~*G*~A~*A*~G~*U*~*A* 5' (210)

Where top strand is sense and bottom strand is antisense and where bold and italics is 2'-fluoro and underlined is 2'-O-methyl and all linkages indicated by dashes are phosphodiester and those indicated by a ~ are phosphorothioate.

(human): hPTENa4-d

5' *G*~G~*G*~U-*A*-A-*A*~U-*A*-C-*A*-U~*U*-C-*U*-U~*C*~A~U 3' (211)

3' C~*C*~C~*A*-U-*U*-U~*A*-U-*G*-U-*A*~A-*G*-A-*A*~G~*U*~*A* 5' (212)

Where top strand is sense and bottom strand is antisense and where bold and italics is 2'-fluoro and underlined is 2'-O-methyl and all linkages indicated by dashes are phosphodiester and those indicated by a ~ are phosphorothioate.

(human): hPTENa5-d

5' *G*~G~*G*~U~*A*~A~*A*-U~*A*-C~*A*-U~*U*~C~*U*~U~*C*~A~U 3' (213)

3' C~*C*~C~*A*~U~*U*--U~*A*-U-*G*--U~*A*--A~*G*-A~*A*~G~*U*~*A* 5' (214)

Where top strand is sense and bottom strand is antisense and where bold and italics is 2'-fluoro and underlined is 2'-O-methyl and all linkages indicated by a dashes are phosphodiester and those indicated by a ~ are phosphorothioate.

Figure 43

(mouse): mPTENa6-d (Mouse version of hPTENa3-d)

5' *G*~*G*~*G*~U~*A*~A~*A*~U-*A*-C-*G*-U~*U*~C~*U*~U~*C*~A~*U* 3' (215)

3' C~*C*~C~*A*~U~*U*~U~*A*-U-*G*-C-*A*~A~*G*~A~*A*~G~*U*~A 5' (216)

Where top strand is sense and bottom strand is antisense and where bold and italics is 2'-fluoro and underlined is 2'-O-methyl and all linkages indicated by dashes are phosphodiester and those indicated by a ~ are phosphorothioate.

(mouse) mPTENa7-d (Mouse Version of hPTENa5-d)

5' *G*~G~*G*~U~*A*~A~*A*-U~*A*-C~*G*-U~*U*~C~*U*~U~*C*~A~*U* 3' (217)

3' C~*C*~C~*A*~U~*U*--U~*A*-U-*G*--C~*A*--A~*G*-A~*A*~G~*U*~A 5' (218)

Where top strand is sense and bottom strand is antisense and where bold and italics is 2'-fluoro and underlined is 2'-O-methyl and all linkages indicated by dashes are phosphodiester and those indicated by a ~ are phosphorothioate.

(mouse) mPTENa8-d (Mouse version of hPTENa2-d)

5' *G*~G~*G*~U~*A*~A-*A*-U-*A*-C-*G*-U-*U*-C~*U*~U~*C*~A~U 3' (219)

3' C~*C*~C~*A*~U~*U*-U-*A*-U-*G*-C-*A*-A-*G*~A~*A*~G~*U*~A 5' (220)

Where top strand is sense and bottom strand is antisense and where bold and italics is 2'-fluoro and underlined is 2'-O-methyl and all linkages indicated by dashes are phosphodiester and those indicated by a ~ are phosphorothioate.

(mouse) mPTENa9-d (Mouse version of hPTENa4-d)

5' *G*~G~*G*~U-*A*-A-*A*~U-*A*-C-*G*-U~*U*-C-*U*-U~*C*~A~U 3' (221)

3' C~*C*~C~*A*-U-*U*~U~*A*-U-*G*-C-*A*~A-*G*-A-*A*~G~*U*~A 5' (222)

Where top strand is sense and bottom strand is antisense and where bold and italics is 2'-fluoro and underlined is 2'-O-methyl and all linkages indicated by dashes are phosphodiester and those indicated by a ~ are phosphorothioate.

Figure 44A

(human/mouse): hmPCSK9b2-d

5' GC̲C̲UGGAGU̲U̲U̲AU̲U̲C̲GGAA 3' (223)

3' CGGAC̲C̲UCAAAU̲AAGCCUU 5' (224)

Where top strand is sense and bottom strand is antisense and where underlined is 2'-O-methyl, the rest are ribose and all linkages are phosphodiester

(human/mouse): hmPCSK9b3-d

5' *G*~C̲~C̲~U̲~*G*~G-A-G-U̲-U̲-U̲-A-U̲-U̲~C̲~*G*~*G*~A̲~A̲ 3' (225)

3' C̲~*G*~*G*~A~C̲~C-U-C-A-A-A-U̲-A-A~*G*~*C*~*C*~*U*~*U* 5' (226)

Where top strand is sense and bottom strand is antisense and where bold and italics is 2'-fluoro, underlined is 2'-O-methyl and standard letters are ribose and where all linkages indicated by dashes are phosphodiester and those indicated by a ~ are phosphorothioate.

(human/mouse): hmPCSK9b4-d

5' *G*~C̲~C̲~U̲~*G*~G~A~G-U̲-U̲-U̲-A~U̲~U̲~C̲~*G*~*G*~A̲~A̲ 3' (227)

3' C̲~*G*~*G*~A~C̲~C~U~C-A-A-A-U̲~A~A~*G*~*C*~*C*~*U*~*U* 5' (228)

Where top strand is sense and bottom strand is antisense and where bold and italics is 2'-fluoro, underlined is 2'-O-methyl and standard letters are ribose and where all linkages indicated by dashes are phosphodiester and those indicated by a ~ are phosphorothioate.

(human/mouse): hmPCSK9b5-d

5' *G*~C̲~C̲~U̲~*G*~*G*-A̲-*G*-U̲-*U*-U̲-A-U̲-*U*~C̲~*G*~*G*~A̲~A̲ 3' (229)

3' C̲~*G*~*G*~A~C̲~C̲-U-C̲-A̲-A-U̲-A-A̲~*G*~*C*~*C*~*U*~*U* 5' (230)

Where top strand is sense and bottom strand is antisense and where bold and italics is 2'-fluoro, underlined is 2'-O-methyl and standard letters are ribose and where all linkages indicated by dashes are phosphodiester and those indicated by a ~ are phosphorothioate.

Figure 44B

(human/mouse): hmPCSK9b6-d

5' *G*~C~C~U~*G*~*G*-A-*G*~U-*U*-U-A~U-U~C~*G*~*G*~A~A 3' (231)

3' C~*G*~*G*~A~C~C-U-C~A-A-A-U~A-A~*G*~C~C~U~U 5' (232)

Where top strand is sense and bottom strand is antisense and where bold and italics is 2'-fluoro, underlined is 2'-O-methyl and standard letters are ribose and where all linkages indicated by dashes are phosphodiester and those indicated by a ~ are phosphorothioate.

(human/mouse): hmPCSK9b7-d

5' *G*~C~C~U~*G*~*G*-A-*G*~U-*U*-U-A~U-U~C~*G*~*G*~A~A 3' (233)

3' C~*G*~*G*~A~C~C-U-C~A-A-A-U~A-A~*G*~C~C~U~U 5' (234)

Where top strand is sense and bottom strand is antisense and where bold and italics is 2'-fluoro, underlined is 2'-O-methyl and standard letters are ribose and where all linkages indicated by dashes are phosphodiester and those indicated by a ~ are phosphorothioate.

(human/mouse): hmPCSK9b8-d)

5' *G*~C~C~U~*G*~*G*-A-*G*~U-*U*-U-A~U-U~C~*G*~*G*~A~A 3' (235)

3' C~*G*~*G*~A~C~C-U-C~A-A-A-U~A--A--*G*~C~C~U~U 5' (236)

(human/mouse): hmPCSK9b9-d

5' *G*~C~C~U~*G*~*G*~A-*G*~U~*U*--U~A~U-U~C~*G*~*G*~A~A 3' (237)

3' C~*G*~*G*~A~C~C~U~C--A-A--A~U~A~A~*G*~C~C~U~U 5' (238)

Where for both hmPCSK9b8-d and hmPSCKb9-d, the top strand is sense and bottom strand is antisense and where bold and italics is 2'-fluoro, underlined is 2'-O-methyl and standard letters are ribose and where all linkages indicated by dashes are phosphodiester and those indicated by a ~ are phosphorothioate.

Figure 45A

(mouse): mPTP1Bc2-d

5' *G*~*A*~A~*G*~C~C-C~*A*-G-*A*-G~*G*-A~*G*~C~*U*~A~*U*~A 3' (239)

3' C~*U*~*U*~C~*G*~G-*G*~U-C-U-C-C~*U*--C~*G*~A~*U*~A~U 5' (240)

Where top strand is sense and bottom strand is antisense and where bold and italics is 2'-fluoro, underlined is 2'-O-methyl, regular type is ribose and all linkages indicated by dashes are phosphodiester and those indicated by a ~ are phosphorothioate.

(mouse): mPTP1Bc3-d

5' *G*~*A*~A~*G*~C~C-C~*A*-G-*A*-G~*G*-A~*G*~C~*U*~A~*U*~A 3' (241)

3' C~*U*~*U*~C~*G*~G-*G*--U-*C*-U-*C*--C-*U*--C~*G*~A~*U*~A~U 5' (242)

Where top strand is sense and bottom strand is antisense and where bold and italics is 2'-fluoro, underlined is 2'-O-methyl, regular type is ribose and all linkages indicated by dashes are phosphodiester and those indicated by a ~ are phosphorothioate.

(mouse): mPTP1Bc4-d

5' *G*~*A*~A~*G*~C~C-C~*A*-G-*A*-G~*G*-A~*G*~C~*U*~A~*U*~A 3' (243)

3' C~*U*~*U*~C~*G*~G-G--*U*-C-*U*-C--*C*-U--C~*G*~A~*U*~A~U 5' (244)

Where top strand is sense and bottom strand is antisense and where bold and italics is 2'-fluoro, underlined is 2'-O-methyl, regular type is ribose and all linkages indicated by dashes are phosphodiester and those indicated by a ~ are phosphorothioate.

(mouse): mPTP1Bc5-d

5' *G*~*A*~A~*G*~C~C-C~*A*-G-*A*-G~*G*-A~*G*~C~*U*~A~*U*~A 3' (245)

3' C~*U*~*U*~C~*G*~G-G--U-*C*-U-*C*--C-*U*--C~*G*~A~*U*~A~U 5' (246)

Where top strand is sense and bottom strand is antisense and where bold and italics is 2'-fluoro and underlined is 2'-O-methyl and all linkages indicated by dashes are phosphodiester and those indicated by a ~ are phosphorothioate.

Figure 45B

(mouse): mPTP1Bc6-d

5' *G*~A~<u>A</u>~*G*~<u>C</u>~*C*~<u>C</u>~A-<u>G</u>-A-<u>G</u>~*G*~<u>A</u>~*G*~<u>C</u>~*U*~<u>A</u>~*U*~<u>A</u> 3' (247)

3' <u>C</u>~*U*~*U*~<u>C</u>~*G*~<u>G</u>-*G*~<u>U</u>-C--<u>U</u>-C--<u>C</u>~*U*--<u>C</u>~*G*~<u>A</u>~*U*~<u>A</u>~*U* 5' (248)

Where top strand is sense and bottom strand is antisense and where bold and italics is 2'-fluoro and underlined is 2'-O-methyl and all linkages indicated by dashes are phosphodiester and those indicated by a ~ are phosphorothioate.

(mouse): mPTP1Bc7-d

5' *G*~A~A~*G*~*C*~*C*~*C*~A-G-A-*G*~*G*~A~*G*~*C*~U~A~U~<u>A</u> 3' (249)

3' <u>C</u>~U~*U*~C~*G*~G-*G*~U-C--U-*C*--C~*U*--C~*G*~A~*U*~A~*U* 5' (250)

Where top strand is sense and bottom strand is antisense and where bold and italics is 2'-fluoro and underlined is 2'-O-methyl and all linkages indicated by dashes are phosphodiester and those indicated by a ~ are phosphorothioate.

(mouse): mPTP1Bc8-d

5' *G*~A~*A*~*G*~<u>C</u>~*C*~<u>C</u>~A-<u>G</u>-A-<u>G</u>~*G*~<u>A</u>~*G*~<u>C</u>~*U*~<u>A</u>~*U*~<u>A</u> 3' (251)

3' <u>C</u>~*U*~*U*~<u>C</u>~*G*~<u>G</u>-*G*~<u>U</u>-C--<u>U</u>-C--<u>C</u>~*U*--<u>C</u>~*G*~<u>A</u>~*U*~<u>A</u>~<u>U</u> 5' (252)

Where top strand is sense and bottom strand is antisense and where bold and italics is 2'-fluoro and underlined is 2'-O-methyl and all linkages indicated by dashes are phosphodiester and those indicated by a ~ are phosphorothioate.

Figure 46

(human/mouse): hmPTP1Bd2-d

5' *U~C~*a ~a~a ~g-*U~C-C* ~g--a~g-a~g~*U~C*~a~g~g 3' (253)

3' A~G~*U~U~U~C*-A--G-G--*C-U--C-U-C*~A~G~*U~C~C* 5' (254)

Where top strand is sense and bottom strand is antisense and where bold and italics is 2'-fluoro, underlined is 2'-O-methyl and lower case indicates deoxyribose and all linkages indicated by dashes are phosphodiester and those indicated by a ~ are phosphorothioate..

(human/mouse): hmPTP1Bd3-d

5' *U~C~*a ~a~a ~g---*U~C-C* ~g-a~g---a~g~*U~C*~a~g~g 3' (256)

3' A~G~*U~U~U~C~*A~G-G--*C-U--C~U~C*~A~G~*U~C~C* 5' (257)

Where top strand is sense and bottom strand is antisense and where bold and italics is 2'-fluoro, underlined is 2'-O-methyl and lower case indicates deoxyribose and all linkages indicated by dashes are phosphodiester and those indicated by a ~ are phosphorothioate.

(human/mouse): hmPTP1Bd4-d

5' *U~C~*A~A~A~G~U~C-C-G~A-G--A~G~U~C~A~G~G 3' (258)

3' A~*G~*U~U~U~C--A~G-G-C--U-C~U--C~A~G~U~C~C 5' (259)

Where top strand is sense and bottom strand is antisense and where bold and italics is 2'-fluoro, underlined is 2'-O-methyl, standard type is ribose and all linkages indicated by dashes are phosphodiester and those indicated by a ~ are phosphorothioate.

(human/mouse): hmPTP1Bd5-d

5' *U~C~*A~A~A~*G~*U~C-C-*G~*A-G--A~*G~*U~C~A~G~G 3' (260)

3' A~*G~*U~*U~*U~*C*--A~*G*-G-*C*--U-*C~*U--*C~*A~*G~*U~C~C 5' (261)

Where top strand is sense and bottom strand is antisense and where bold and italics is 2'-fluoro and underlined is 2'-O-methyl and all linkages indicated by dashes are phosphodiester and those indicated by a ~ are phosphorothioate.

Figure 47A

(human): hp53E2-d

5' *U*~G~*G*~A~G~*G*-A-*G*~C-C-G-*C*~A-G-U~*C*~A~G~*A*~U 3' (262)

3' A~*C*~C~*U*~*C*~C-U-C--G-G-C-G--U--C-*A*~G~*U*~C~U~*A* 5' (263)

Where top strand is sense and bottom strand is antisense and where bold and italics is 2'-fluoro, underlined is 2'-O-methyl and simple capitals have standard ribose and all linkages indicated by dashes are phosphodiester and those indicated by a ~ are phosphorothioate.

(human): hp53E3-d

5' *U*~G~*G*~A~G~*G*-A-*G*~C-C-G-*C*~A-G-U~*C*~A~G~*A*~U 3' (264)

3' A~*C*~C~*U*~*C*~C-U-C~G-G-C-G--*U*~C-*A*~G~*U*~C~U~*A* 5' (265)

Where top strand is sense and bottom strand is antisense and where bold and italics is 2'-fluoro, underlined is 2'-O-methyl and simple capitals have standard ribose and all linkages indicated by dashes are phosphodiester and those indicated by a ~ are phosphorothioate.

(human): hp53E4-d

5' *U*~G~*G*~A~G~*G*-A-*G*~C-C--G-*C*~A-G--U~*C*~A~G~*A*~U 3' (266)

3' A~*C*~C~*U*~*C*~C~U-C~G-G-C-G~U-C~*A*~G~*U*~C~U~*A* 5' (267)

Where top strand is sense and bottom strand is antisense and where bold and italics is 2'-fluoro, underlined is 2'-O-methyl and simple capitals have standard ribose and all linkages indicated by dashes are phosphodiester and those indicated by a ~ are phosphorothioate.

(human): hp53E5-d

5' *U*~G~*G*~A~G~*G*~A~*G*~C~CXXG~*C*~A~G~U~*C*~A~G~*A*~U 3' (268)

3' A~*C*~C~*U*~*C*~C~U--C~G---G---C--G~U--C~*A*~G~*U*~C~U~*A* 5' (269)

Where top strand is sense and bottom strand is antisense and where bold and italics is 2'-fluoro, underlined is 2'-O-methyl and simple capitals have standard ribose and all linkages indicated by dashes are phosphodiester and those indicated by a ~ are phosphorothioate. XX indicates a gap in the sense strand were there us no linkage and as a result the single sense strand becomes two sense strands.

Figure 47B

(human): hp53E6-d

5' *U*~G~*G*~A~G~*G*~A~*G*~*C*~C~CXX*G*~*C*~A~*G*~U~*C*~A~G~A~U 3' (270)

3' A~*C*~C~*U*~*C*~C~U--*C*~G---G---C--G~U--C~A~*G*~U~*C*~U~A 5' (271)

Where top strand is sense and bottom strand is antisense and where bold and italics is 2'-fluoro, underlined is 2'-O-methyl and an unmodified letter is standard ribose. All linkages indicated by dashes are phosphodiester and those indicated by a ~ are phosphorothioate.

(human): hp53E7-d

5' *G*~A~*G*~*G*~A~*G*~*C*~C-G~*C*~A~*G*~U~*C*~A~G 3' (272)

3' A~*C*~C~*U*~*C*~C~U--*C*~G---G-C--G~U--C~A~*G*~U~*C*~U~A 5' (273)

Where top strand is sense and bottom strand is antisense and where bold and italics is 2'-fluoro, underlined is 2'-O-methyl and simple capitals have standard ribose and all linkages indicated by dashes are phosphodiester and those indicated by a ~ are phosphorothioate.

FIGURE 48A (human): hp53E9-d

5' *A*~U~*G*~G~*A*~U~*G*~A-*U*~*U*-U~*G*-A~*U*~G~*C*~U~G~U~C 3' (274)

3' U~*A*~C~*C*~U~*A*--C--*U*--A--*A*-*A*--C-*U*--A--*C*~G~*A*~C~*A*~G 5' (275)

Where top strand is sense and bottom strand is antisense and where bold and italics is 2'-fluoro, underlined is 2'-O-methyl and simple capitals have standard ribose and all linkages indicated by dashes are phosphodiester and those indicated by a ~ are phosphorothioate.

(human): hp53E10-d

5' *A*~U~*G*~G~*A*~U~*G*~A-*U*~*U*-U~*G*-A~*U*~G~*C*~U~G~U~C 3' (276)

3' U~*A*~C~*C*~U~*A*--C--*U*~A--*A*-*A*--C-*U*~A--*C*~G~*A*~C~*A*~G 5' (277)

Where top strand is sense and bottom strand is antisense and where bold and italics is 2'-fluoro, underlined is 2'-O-methyl and simple capitals have standard ribose and all linkages indicated by dashes are phosphodiester and those indicated by a ~ are phosphorothioate.

(human): hp53E11-d

5' *A*~U~*G*~G~*A*~*U*~*G*~A-U~*U*-U~*G*-A~*U*~G~*C*~U~G~U~C 3' (278)

3' U~*A*~C~*C*~U~*A*--C--U~*A*--A-*A*--C-*U*~A--*C*~G~*A*~C~*A*~G 5' (279)

Where top strand is sense and bottom strand is antisense and where bold and italics is 2'-fluoro, underlined is 2'-O-methyl and simple capitals have standard ribose and all linkages indicated by dashes are phosphodiester and those indicated by a ~ are phosphorothioate.

Figure 48B

(human): hp53E12-d

5' *A*~U~*G*~G~*A*~U~*G*~*A*-U~*U*-U~G-A~*U*~G~*C*~U~G~U~C 3' (280)

3' U~*A*~C~*C*~U~A--*C*--U~*A*--A-A--C~*U*--A--*C*~G~*A*~C~*A*~G 5' (281)

Where top strand is sense and bottom strand is antisense and where bold and italics is 2'-fluoro, underlined is 2'-O-methyl and simple capitals have standard ribose and all linkages indicated by dashes are phosphodiester and those indicated by a ~ are phosphorothioate.

(human): hp53E13-d

5' *G*~*C*~*A*~A~*U*~G~*G*~A-*U*~G-A-U~*U*-U~*G*~A~*U*~G~*C*~U~G~U 3' (282)

3' C~*G*~U~*U*~A~*C*--C~*U*-A~*C*-U-A--A--A--C~*U*--A~*C*~G~*A*~C~*A* 5' (283)

Where top strand is sense and bottom strand is antisense and where bold and italics is 2'-fluoro, underlined is 2'-O-methyl and simple capitals have standard ribose and all linkages indicated by dashes are phosphodiester and those indicated by a ~ are phosphorothioate.

(human): hp53E14-d

5' *G*~*C*~*A*~A~*U*~G~*G*~A~*U*-G~*A*-U~*U*-U~*G*~A~*U*~G~*C*~U 3' (284)

3' C~*G*~U~*U*~A~*C*--C~*U*--A~*C*--U--A--A-A~C~*U*~A~*C*~G~A 5' (285)

Where top strand is sense and bottom strand is antisense and where bold and italics is 2'-fluoro, underlined is 2'-O-methyl and simple capitals have standard ribose and all linkages indicated by dashes are phosphodiester and those indicated by a ~ are phosphorothioate.

Figure 49A

(human/mouse): hmAPOBf2-d

5' *G*~U~*C*~A~*U*~C~*A*~C~-A~C~-U--G-A~A-U~A~C~C~A~A~U 3' (286)

3' C~A~G~U~A~G~U--G-U--G--A--C-U-U-A~U~G~G~U~U~A 5' (287)

Where top strand is sense and bottom strand is antisense and where bold and italics is 2'-fluoro, underlined is 2'-O-methyl, standard font is ribose and all linkages indicated by dashes are phosphodiester and those indicated by a ~ are phosphorothioate.

(human/mouse): hmAPOBf3-d

5' *G*~U~*C*~A~*U*~*C*~*A*~C~-*A*~C~--U--G-*A*~A-*U*~A~*C*~C~*A*~A~U 3' (288)

3' C~*A*~G~*U*~A~G~U--G-U--G--A--C-U-U-A~*U*~G~G~U~*U*~A 5' (289)

Where top strand is sense and bottom strand is antisense and where bold and italics is 2'-fluoro, underlined is 2'-O-methyl, standard font is ribose and all linkages indicated by dashes are phosphodiester and those indicated by a ~ are phosphorothioate.

(human/mouse): hmAPOBf4-d

5' *G*~*U*~C~A~U~*C*~A~C-A~*C*--U--*G*-A~A-U~*A*~C~*C*~A~A~U 3' (290)

3' C~A~*G*~U~*A*~G~*U*--G-*U*--G--*A*--C-*U*-U-A~U~*G*~G~*U*~U~A 5' (291)

Where top strand is sense and bottom strand is antisense and where bold and italics is 2'-fluoro, underlined is 2'-O-methyl, standard font is ribose and all linkages indicated by dashes are phosphodiester and those indicated by a ~ are phosphorothioate.

(human/mouse): hmAPOBf5-d

5' *G*~U~*C*~A~*U*~*C*~*A*~C~-*A*~C~--U--G-*A*~A--*U*~A~*C*~C~*A*~A~U 3' (292)

3' C~*A*~G~*U*~A~*G*~U-G~U--G--*A*--C-U~U-A~*U*~G~G~U~*U*~A 5' (293)

Where top strand is sense and bottom stand is antisense and where bold and italics is 2'-fluoro, underlined is 2'-O-methyl, standard font is ribose and all linkages indicated by dashes are phosphodiester and those indicated by a ~ are phosphorothioate.

Figure 49B (human/mouse): hmAPOBf6-d

5' *G*~U~*C*~A~*U*~C~*A*~C~*A*-*C*--*U*--*G*-*A*~A~--*U*~A~*C*~C~*A*~A~*U* 3' (294)

3' *C*~*A*~G~*U*~A~*G*--*U*~*G*-*U*~*G*--A--*C*-*U*~*U*--A~*U*--G~*G*~U~*U*~A 5'(295)

Where top strand is sense and bottom stand is antisense and where bold and italics is 2'-fluoro, underlined is 2'-O-methyl, standard font is ribose and all linkages indicated by dashes are phosphodiester and those indicated by a ~ are phosphorothioate.

Figure 50A

(human/mouse): hmAPOBg2-d

5' *G*~<u>G</u>~U~<u>G</u>~U~<u>A</u>~U~<u>G</u>-G-<u>C</u>~U-<u>U</u>-C~<u>A</u>~A~<u>C</u>~*C*~<u>C</u>~U~<u>G</u> 3' (296)

3' <u>C</u>~*C*~<u>A</u>~*C*~<u>A</u>~U---<u>A</u>~*C*-<u>C</u>-G--<u>A</u>-A-<u>G</u>~U--<u>U</u>~*G*~<u>G</u>~*G*~<u>A</u>~*C* 5' (297)

Where top strand is sense and bottom stand is antisense and where bold and italics is 2'-fluoro, underlined is 2'-O-methyl, standard font is ribose and all linkages indicated by dashes are phosphodiester and those indicated by a ~ are phosphorothioate.

(human/mouse): hmAPOBg3-d

5' *G*~*G*~U~*G*~U~*A*~U~*G*-G-*C*~U-*U*-*C*~*A*~A~*C*~*C*~*C*~U~<u>G</u> 3' (298)

3' <u>C</u>~*C*~*A*~*C*~*A*~U---*A*~*C*-*C*-*G*--*A*-A-*G*~U--*U*~*G*~*G*~*G*~*A*~<u>C</u> 5' (299)

Where top strand is sense and bottom stand is antisense and where bold and italics is 2'-fluoro and underlined is 2'-O-methyl and all linkages indicated by dashes are phosphodiester and those indicated by a ~ are phosphorothioate.

(human/mouse): hmAPOBg4-d

5' *G*~*G*~<u>U</u>~*G*~<u>U</u>~*A*~<u>U</u>~*G*-<u>G</u>-*C*~<u>U</u>-*U*-<u>C</u>~*A*~<u>A</u>~*C*~<u>C</u>~*C*~<u>U</u>~<u>G</u> 3' (300)

3' <u>C</u>~<u>C</u>~*A*~<u>C</u>~*A*~<u>U</u>---*A*~<u>C</u>-*C*-<u>G</u>--*A*-<u>A</u>-*G*~<u>U</u>--*U*~<u>G</u>~*G*~<u>G</u>~*A*~<u>C</u> 5' (301)

Where top strand is sense and bottom stand is antisense and where bold and italics is 2'-fluoro and underlined is 2'-O-methyl and all linkages indicated by dashes are phosphodiester and those indicated by a ~ are phosphorothioate.

(human/mouse): hmAPOBg5-d

5' *G*~*G*~<u>U</u>~*G*~<u>U</u>~*A*~<u>U</u>~*G*-<u>G</u>-*C*~<u>U</u>-*U*-<u>C</u>~*A*~<u>A</u>~*C*~<u>C</u>~*C*~<u>U</u>~<u>G</u> 3' (302)

3' <u>C</u>~<u>C</u>~*A*~<u>C</u>~*A*~<u>U</u>~*A*--<u>C</u>~*C*-<u>G</u>--*A*-<u>A</u>~*G*--<u>U</u>~*U*~<u>G</u>~*G*~<u>G</u>~*A*~<u>C</u> 5' (303)

Where top strand is sense and bottom stand is antisense and where bold and italics is 2'-fluoro and underlined is 2'-O-methyl and all linkages indicated by dashes are phosphodiester and those indicated by a ~ are phosphorothioate.

Figure 50B

(human/mouse - two contiguous sense strands): hmAPOBg6-d

5' *G*~*G*~U~*G*~U~*A*~U~*G*~*G*~*C*XX*U*~*U*~*C*~*A*~A~*C*~*C*~*C*~U~*G* 3' (304)

3' C~C~*A*~C~*A*~U---*A*~C--*C*---G---*A*--A--*G*~U--*U*~G~*G*~G~*A*~C 5' (305)

Where top strand is sense and bottom stand is antisense and where bold and italics is 2'-fluoro and underlined is 2'-O-methyl and all linkages indicated by dashes are phosphodiester, those indicated by a ~ are phosphorothioate and XX indicates no linkage.

(human/mouse): hmAPOBg7-d

5' *G*~U~*A*~U~*G*~*G*~*C*~U~*U*~*C*~*A*~A~*C*~*C* 3' (306)

3' C~C~*A*~C~*A*~U---*A*~C--*C*--G--*A*---A--*G*~U--*U*~G~*G*~G~*A*~C 5' (307)

Where top strand is sense and bottom stand is antisense and where bold and italics is 2'-fluoro and underlined is 2'-O-methyl and all linkages indicated by dashes are phosphodiester and those indicated by a ~ are phosphorothioate.

(human/mouse): hmAPOBg8-d

5' *G*~*U*~*A*~*U*~*G*~*G*~*C*~*U*~*U*~*C*~*A*~*A*~*C*~*C* 3' (308)

3' C~C~*A*~C~*A*~U---*A*~C--*C*--G--*A*--A---*G*~U--*U*~G~*G*~G~*A*~C 5' (309)

Where top strand is sense and bottom stand is antisense and where bold and italics is 2'-fluoro and underlined is 2'-O-methyl and all linkages indicated by dashes are phosphodiester and those indicated by a ~ are phosphorothioate.

Figure 51

(human): hPTP1Bh2-d

5' *G*~<u>G</u>~*A*~<u>A</u>~*G*~*A*~<u>A</u>~*A*--<u>A</u>~*A*-<u>G</u>~<u>G</u>-*A*~<u>A</u>~*G*~<u>C</u>~*C*~*C*~<u>C</u> 3' (310)

3' <u>C</u>~*C*~<u>U</u>~*U*~*C*~<u>U</u>--*U*--<u>U</u>--*U*--U--C--*C*--<u>U</u>--*U*~<u>C</u>~*G*~I~I~<u>G</u> 5'     (311)

Where top strand is sense and bottom stand is antisense and where bold and italics is 2'-fluoro, underlined is 2'-O-methyl and simple capitals have standard ribose and all linkages indicated by dashes are phosphodiester and those indicated by a ~ are phosphorothioate. "I" is inosine.

(human): hPTP1Bh3-d

5' *G*~<u>G</u>~*A*~<u>A</u>~*G*~*A*~<u>A</u>~*A*--<u>A</u>~*A*-<u>G</u>~<u>G</u>-*A*~<u>A</u>~*G*~<u>C</u>~*C*~*C*~<u>C</u> 3' (312)

3' <u>C</u>~*C*~<u>U</u>~*U*~*C*~<u>U</u>--*U*~<u>U</u>--*U*--U-C--*C*~<u>U</u>--*U*--<u>C</u>~*G*~I~I~<u>G</u> 5'     (313)

Where top strand is sense and bottom stand is antisense and where bold and italics is 2'-fluoro, underlined is 2'-O-methyl and simple capitals have standard ribose and all linkages indicated by a dashes are phosphodiester and those indicated by a ~ are phosphorothioate. "I" is inosine.

(human): hPTP1Bh4-d

5' *G*~<u>G</u>~*A*~<u>A</u>~*G*~*A*~<u>A</u>~*A*~<u>A</u>XX*A*~*G*~<u>G</u>-*A*~<u>A</u>~*G*~<u>C</u>~*C*~*C*~<u>C</u> 3' (314)

3' <u>C</u>~*C*~<u>U</u>~*U*~*C*~<u>U</u>--*U*~<u>U</u>--*U*----U--<u>C</u>--*C*~<u>U</u>--*U*--<u>C</u>~*G*~I~<u>G</u>~*G* 5' (315)

Where top strand is sense and bottom stand is antisense and where bold and italics is 2'-fluoro, underlined is 2'-O-methyl and simple capitals have standard ribose and all linkages indicated by dashes are phosphodiester and those indicated by a ~ are phosphorothioate. "I" is inosine and XX is a gap in the sense strand where there is no linkage resulting in two sense strands.

(human): hPTP1Bh5-d

5' *G*~<u>G</u>~*A*~<u>A</u>~*G*~*A*~<u>A</u>~*A*~<u>A</u>~*A*~<u>G</u>XX<u>G</u>-*A*~<u>A</u>~*G*~<u>C</u>~*C*~<u>C</u>~*C*~*U*~<u>U</u> 3' (316)

3' <u>C</u>~*C*~<u>U</u>~*U*~*C*~<u>U</u>~*U*--<u>U</u>--*U*~<u>U</u>--*C*----C--*U*--<u>U</u>~*C*--<u>G</u>~I~*G*~*G*~<u>A</u>~*A* 5' (317)

Where top strand is sense and bottom stand is antisense and where bold and italics is 2'-fluoro, underlined is 2'-O-methyl and simple capitals have standard ribose and all linkages indicated by a dashes are phosphodiester and those indicated by a ~ are phosphorothioate. "I" is inosine and XX is a gap in the sense strand where there is no linkage resulting in two sense strands.

(human): hPTP1Bh6-d

5' *G*~<u>G</u>~<u>A</u>~*A*~<u>G</u>~*A*~<u>A</u>~*A*~<u>A</u>-*A*~<u>G</u>-<u>G</u>-*A*~<u>A</u>--*G*~<u>C</u>~*C*~*C*~<u>C</u>~*U*~<u>U</u> 3' (318)

3' <u>C</u>~*C*~<u>U</u>~*U*~*C*~<u>U</u>~*U*--<u>U</u>--*U*~<u>U</u>-C-C--<u>U</u>--*U*~<u>C</u>--*G*~I~*G*~*G*~<u>A</u>~*A* 5' (319)

Where top strand is sense and bottom stand is antisense and where bold and italics is 2'-fluoro, underlined is 2'-O-methyl and simple capitals have standard ribose and all linkages indicated by a dashes are phosphodiester and those indicated by a ~ are phosphorothioate. "I" is inosine.

Figure 52A

(mouse): mNOTCH1i2-d

5' *G*~G~*U*~G~*U*~*C*~*U*~U-*C*~C-*A*~G-*A*~U~*C*~C~*U*~G~*C*~U 3' (320)

3' C~*C*~A~*C*~A~*G*--A---*A*-G--*G*-U-*C*-U--*A*--G~*G*~A~*C*~G~*A* 5' (321)

Where top strand is sense and bottom stand is antisense and where bold and italics is 2'-fluoro, underlined is 2'-O-methyl, regular type is ribose and all linkages indicated by dashes are phosphodiester and those indicated by a ~ are phosphorothioate.

(mouse): mNOTCH1i3-d

5' *G*~G~*U*~G~*U*~*C*~*U*~U-*C*--C~*A*-G-*A*~U~*C*~C~*U*~G~*C*~U 3' (322)

3' C~*C*~A~*C*~A~*G*--A~*A*--G-*G*--U--*C*-U~*A*--G~*G*~A~*C*~G~*A* 5' (323)

Where top strand is sense and bottom stand is antisense and where bold and italics is 2'-fluoro, underlined is 2'-O-methyl, regular type is ribose and all linkages indicated by dashes are phosphodiester and those indicated by a ~ are phosphorothioate.

(mouse): mNOTCH1i4-d

5' *G*~G~*U*~G~*U*~*C*~*U*~U-*C*--C~*A*-G-*A*~U~*C*~C~*U*~G~*C*~U 3' (324)

3' C~*C*~A~*C*~A~*G*--A~*A*--G-*G*--U--*C*-U~*A*--G~*G*~A~*C*~G~*A* 5' (325)

Where top strand is sense and bottom stand is antisense and where bold and italics is 2'-fluoro, underlined is 2'-O-methyl, regular type is ribose and all linkages indicated by dashes are phosphodiester and those indicated by a ~ are phosphorothioate.

Figure 52B

(mouse): mNOTCH1i5-d

5' G~G~U~G~U~C~U~U~C~CXXA~G~A~U~C~C~U~G~C~U 3' (326)

3' C~C~A~C~A~G--A~A--G---G---U--C--U~A---G~G~A~C~G~A 5' (327)

Where top strand is sense and bottom stand is antisense and where bold and italics is 2'-fluoro and underlined is 2'-O-methyl and all linkages indicated by dashes are phosphodiester and those indicated by a ~ are phosphorothioate. "XX" denotes a gap in the sense strand where there is no linkage resulting in two sense strands.

(mouse): mNOTCH1i6-d

5' G~G~U~G~U~C~U~U-C--C~A-G--A~U~C~C~U~G~C 3' (328)

3' C~C~A~C~A~G--A~A--G--G-U--C~U--A~G~G~A~C~G 5' (329)

Where top strand is sense and bottom stand is antisense and where bold and italics is 2'-fluoro and underlined is 2'-O-methyl and all linkages indicated by dashes are phosphodiester and those indicated by a ~ are phosphorothioate.

(mouse): mNOTCH1i7-d

5' G~G~U~G~U~C~U~U-C--C~A~G~A~U~C~C~U 3' (330)

3' C~C~A~C~A~G---A--A--G--G-U~C~U~A~G~G~A 5' (331)

Where top strand is sense and bottom stand is antisense and where bold and italics is 2'-fluoro and underlined is 2'-O-methyl and all linkages indicated by dashes are phosphodiester and those indicated by a ~ are phosphorothioate.

Figure 53A

(mouse): mMDRj2-d

5' *G*~G~*C*~*U*~G~G~A~*C*~A-A-G~*C*~U~*G*~U~*G*~*C*~A~U 3' (332)

3' C~C~*G*~A~*C*~C--*U*---G--*U*-U-C--G-A--C~A~C~*G*~U~*A* 5' (333)

Where top strand is sense and bottom stand is antisense and where bold and italics is 2'-fluoro, underlined is 2'-O-methyl, regular type is ribose and all linkages indicated by dashes are phosphodiester and those indicated by a ~ are phosphorothioate.

(mouse): mMDRj3-d

5' *G*~G~*C*~*U*~G~G~A~*C*--A-A~G-*C*~U~*G*~U~*G*~*C*~A~U 3' (334)

3' C~C~*G*~A~*C*~C--*U*~G--*U*-U-C--G~A--C~A~C~*G*~U~*A* 5' (335)

Where top strand is sense and bottom stand is antisense and where bold and italics is 2'-fluoro, underlined is 2'-O-methyl, regular type is ribose and all linkages indicated by dashes are phosphodiester and those indicated by a ~ are phosphorothioate.

(mouse): mMDRj4-d

5' *G*~G~*C*~*U*~G~G~A~*C*-A-A~G--*C*~U~*G*~U~*G*~*C*~A~U 3' (336)

3' C~C~*G*~A~*C*~C--*U*~G--*U*-U-C--G~A--C~A~C~*G*~U~*A* 5' (337)

Where top strand is sense and bottom stand is antisense and where bold and italics is 2'-fluoro, underlined is 2'-O-methyl, regular type is ribose and all linkages indicated by dashes are phosphodiester and those indicated by a ~ are phosphorothioate.

Figure 53B

(mouse): mMDRj5-d

5' *C*~*U*~G~*G*~A~*C*~A-A~G~*C*~U~*G*~U~*G*~C 3' (338)

3' C~C~*G*~A~*C*~C--*U*~G--*U*-U--*C*--G~*A*--C~*A*~C~*G*~U~*A* 5' (339)

Where top strand is sense and bottom stand is antisense and where bold and italics is 2'-fluoro and underlined is 2'-O-methyl and all linkages indicated by dashes are phosphodiester and those indicated by a ~ are phosphorothioate.

(mouse): mMDRj6-d

5' *G*~G~*C*~*U*~G~*G*~A~*C*~AXXA~G~*C*~U~*G*~U~*G*~C~*A*~U 3' (340)

3' C~C~*G*~A~*C*~C--*U*~G--*U*----U--*C*--G~*A*--C~*A*~C~*G*~U~*A* 5' (341)

Where top strand is sense and bottom stand is antisense and where bold and italics is 2'-fluoro and underlined is 2'-O-methyl and all linkages indicated by dashes are phosphodiester and those indicated by a ~ are phosphorothioate. "XX" is a gap in the sense strand where there is no linkage resulting in two sense strands.

(mouse): mMDRj7-d

5' *G*~*G*~*C*~U~*G*~*G*~A~*C*~AXXA~G~*C*~U~*G*~*U*~*G*~*C*~*A*~U 3' (342)

3' C~C~*G*~A~*C*~C--*U*~G--*U*----U--*C*--G~*A*--C~*A*~C~*G*~U~*A* 5' (343)

Where top strand is sense and bottom stand is antisense and where bold and italics is 2'-fluoro and underlined is 2'-O-methyl and all linkages indicated by dashes are phosphodiester and those indicated by a ~ are phosphorothioate.

Figure 54A (mouse): mCOX2k2-d

5' *G*~*G*~*A*~*G*~*C*~*U*~*U*~*C*-*C*-*U*~*G*-*A*~*U*~*U*~*C*~*A*~*A*~*A*~*A* 3' (344)

3' *C*~*C*~*U*~*C*~*G*~*A*--*A*--*G*-*G*-*A*--*C*--*U*--*A*--*A*~*G*~*U*~*U*~*U*~*U* 5' (345)

Where top strand is sense and bottom stand is antisense and where bold and italics is 2'-fluoro, underlined is 2'-O-methyl, regular type is ribose and all linkages indicated by dashes are phosphodiester and those indicated by a ~ are phosphorothioate.

(mouse): mCOX2k3-d

5' *G*~*G*~*A*~*G*~*C*~*U*~*U*--*C*-*C*~*U*-*G*~*A*~*U*~*U*~*C*~*A*~*A*~*A*~*A* 3' (346)

3' *C*~*C*~*U*~*C*~*G*~*A*--*A*~*G*-*G*--*A*-*C*--*U*~*A*--*A*~*G*~*U*~*U*~*U*~*U* 5' (347)

Where top strand is sense and bottom stand is antisense and where bold and italics is 2'-fluoro, underlined is 2'-O-methyl, regular type is ribose and all linkages indicated by dashes are phosphodiester and those indicated by a ~ are phosphorothioate.

(mouse): mCOX2k4-d

5' *G*~*G*~*A*~*G*~*C*~*U*~*U*--*C*-*C*~*U*-*G*~*A*~*U*~*U*~*C*~*A*~*A*~*A*~*A* 3' (348)

3' *C*~*C*~*U*~*C*~*G*--*A*~*A*--*G*--*G*--*A*-*C*--*U*~*A*--*A*--*G*~*U*~*U*~*U*~*U* 5' (349)

Where top strand is sense and bottom stand is antisense and where bold and italics is 2'-fluoro, underlined is 2'-O-methyl, regular type is ribose and all linkages indicated by dashes are phosphodiester and those indicated by a ~ are phosphorothioate.

(mouse): mCOX2k5-d

5' *G*~*G*~*A*~*G*~*C*~*U*~*U*--*C*--*C*~*U*-*G*~*A*~*U*~*U*~*C*~*A*~*A* 3' (350)

3' *C*~*C*~*U*~*C*~*G*~*A*--*A*--*G*--*G*--*A*~*C*--*U*~*A*~*A*~*G*~*U*~*U* 5' (351)

Where top strand is sense and bottom stand is antisense and where bold and italics is 2'-fluoro and underlined is 2'-O-methyl and all linkages indicated by dashes are phosphodiester and those indicated by a ~ are phosphorothioate.

Figure 54B

(mouse): mCOX2k6-d

5' *G*~*G*~*A*~*G*~*C*~U~*U*~*C*~*C*XX*U*~*G*~A~*U*~U~*C*~*A*~*A*~*A* 3' (352)

3' C~C~U~C~G--*A*~*A*--G--*G*--A-*C*--U~*A*--*A*--G~*U*~*U*~U~*U* 5' (353)

Where top strand is sense and bottom stand is antisense and where bold and italics is 2'-fluoro and underlined is 2'-O-methyl and all linkages indicated by dashes are phosphodiester and those indicated by a ~ are phosphorothioate. "XX" represents a gap in the sense strand where there is no linkage resulting in two sense strands.

(mouse): mCOX2l2-d

5' *C*~C~*G*~C~*A*~T~*T*~*G*~*C*-C-*T*~C-*T*~*G*~*A*~A~*T*~*T*~C~*A*~A 3' (354)

3' G~*G*~C~*G*~T~*A*~A--*C*--G-*G*-A--G-A--*C*--T~*T*~A~*A*~*G*~T~*T* 5' (355)

Where top strand is sense and bottom stand is antisense and where bold and italics is 2'-fluoro, underlined is 2'-O-methyl, regular type is ribose and all linkages indicated by dashes are phosphodiester and those indicated by a ~ are phosphorothioate.

(mouse): mCOX2l3-d

5' *C*~C~*G*~C~*A*~T~*T*~*G*~*C*-C-*T*~C-*T*~*G*~*A*~A~*T*~*T*~C~*A*~A 3' (356)

3' G~*G*~C~*G*~T~*A*~A--*C*--G-*G*-A--G-A--*C*--T~*T*~A~*A*~*G*~T~*T* 5' (357)

Where top strand is sense and bottom stand is antisense and where bold and italics is 2'-fluoro, underlined is 2'-O-methyl, regular type is ribose and all linkages indicated by dashes are phosphodiester and those indicated by a ~ are phosphorothioate.

(mouse): mCOX2l4-d

5' *C*~C~*G*~C~*A*~T~*T*~*G*--*C*~C-*T*~C-*T*~*G*~*A*~A~*T*~*T*~C~*A*~A 3' (358)

3' G~*G*~C~*G*~T~*A*~A--*C*~G-*G*-A--G-A~*C*--T~*T*~A~*A*~*G*~T~*T* 5' (359)

Where top strand is sense and bottom stand is antisense and where bold and italics is 2'-fluoro, underlined is 2'-O-methyl, regular type is ribose and all linkages indicated by dashes are phosphodiester and those indicated by a ~ are phosphorothioate.

Figure 54C (mouse): mCOX2l5-d

5' C~C~G~C~A~T~T~G--C~C-T~C-T~G~A~A~T~T~C~A~A 3' (360)

3' G~G~C~G~T~A~A--C~G-G-A--G-A~C--T~T~A~A~G~T~T 5' (361)

Where top strand is sense and bottom stand is antisense and where bold and italics is 2'-fluoro and underlined is 2'-O-methyl and all linkages indicated by dashes are phosphodiester and those indicated by a ~ are phosphorothioate.

(mouse): mCOX2l6-d

5' C~C~G~C~A~T~T~G--C~CXXT~C-T~G~A~A~T~T~C~A~A 3' (362)

3' G~G~C~G~T~A~A--C~G--G---A--G-A~C--T~T~A~A~G~T~T 5' (363)

Where top strand is sense and bottom stand is antisense and where bold and italics is 2'-fluoro and underlined is 2'-O-methyl and all linkages indicated by dashes are phosphodiester and those indicated by a ~ are phosphorothioate. "XX" represents a gap in the sense stand where there is no linkage resulting in two sense strands.

(mouse): mCOX2l7-d

5' G~C~A~T~T~G~C~C~T~C~T~G~A~A~T~T 3' (364)

3' G~G~C~G~T~A~A--C~G--G--A--G--A~C--T~T~A~A~G~T~T 5' (365)

Where top strand is sense and bottom stand is antisense and where bold and italics is 2'-fluoro and underlined is 2'-O-methyl and all linkages indicated by dashes are phosphodiester and those indicated by a ~ are phosphorothioate.

Figure 55A

(mouse): mWRNm2-d

5' *C*~*C*~*U*~*C*~*U*~*G*~U~*U*~G-G~G-A-G~*U*~C~*A*~*U*~*C*~A~*A*~A 3' (366)

3' G~G~A~G~A~C~A--A--C--C--U-C--A--G~U~A~G~U~U~U 5' (367)

Where top strand is sense and bottom stand is antisense and where bold and italics is 2'-fluoro, underlined is 2'-O-methyl, regular type is ribose and all linkages indicated by dashes are phosphodiester and those indicated by a ~ are phosphorothioate.

(mouse): mWRNm3-d

5' *C*~*C*~*U*~*C*~*U*~*G*~U~*U*~G-G--G~A-G~*U*~C~*A*~*U*~*C*~A~*A*~A 3' (368)

3' G~G~A~G~A~C~A--A~C--C--U-C--A~G-U~A~G~U~U~U 5' (369)

Where top strand is sense and bottom stand is antisense and where bold and italics is 2'-fluoro, underlined is 2'-O-methyl, regular type is ribose and all linkages indicated by dashes are phosphodiester and those indicated by a ~ are phosphorothioate.

(mouse): mWRNm4-d

5' *C*~*C*~*U*~*C*~*U*~*G*~U~*U*~G-G--G~A-G--*U*~C~*A*~*U*~*C*~A~*A*~A 3' (370)

3' G~G~A~G~A~C~A--A~C--C--U-C--A-G-U~A~G~U~U~U 5' (371)

Where top strand is sense and bottom stand is antisense and where bold and italics is 2'-fluoro, underlined is 2'-O-methyl, regular type is ribose and all linkages indicated by dashes are phosphodiester and those indicated by a ~ are phosphorothioate.

(mouse): mWRNm5-d

5' *C*~*C*~*U*~*C*~*U*~*G*~U~*U*~G--I--G~A-G--*U*~C~*A*~*U*~*C*~A~*A*~A 3' (372)

3' G~G~A~G~A~C~A--A~C--C--U-C--A~G-U~A~G~U~U~U 5' (373)

Where top strand is sense and bottom stand is antisense and where bold and italics is 2'-fluoro and underlined is 2'-O-methyl and all linkages indicated by dashes are phosphodiester and those indicated by a ~ are phosphorothioate. "I' is inosine.

Figure 55B

(mouse): mWRNm6-d

5' *C*~<u>C</u>~*U*~<u>C</u>~*U*~*G*~*U*~<u>U</u>~*G*--<u>I</u>--*G*~<u>A</u>-*G*--<u>U</u>~*C*~*A*~<u>U</u>~*C*~<u>A</u>~*A*~<u>A</u> 3' (374)

3' <u>G</u>~*G*~<u>A</u>~*G*~*A*~<u>C</u>~<u>A</u>--*A*~<u>C</u>--*C*--<u>C</u>--*U*-<u>C</u>--*A*~<u>G</u>--*U*~*A*~<u>G</u>~*U*~<u>U</u>~*U* 5' (375)

Where top strand is sense and bottom stand is antisense and where bold and italics is 2'-fluoro and underlined is 2'-O-methyl and all linkages indicated by dashes are phosphodiester and those indicated by a ~ are phosphorothioate.

(mouse): mWRNm7-d

5' *C*~<u>C</u>~*U*~*C*~*U*~*G*~*U*~<u>U</u>~*G*~<u>G</u>XX*G*~*A*~*G*~<u>U</u>~*C*~*A*~<u>U</u>~*C*~<u>A</u>~*A*~<u>A</u> 3' (376)

3' <u>G</u>~*G*~<u>A</u>~*G*~*A*~<u>C</u>~<u>A</u>--*A*~<u>C</u>--*C*----<u>C</u>--*U*---<u>C</u>--*A*~<u>G</u>--*U*~*A*~<u>G</u>~*U*~<u>U</u>~*U* 5' (377)

Where top strand is sense and bottom stand is antisense and where bold and italics is 2'-fluoro and underlined is 2'-O-methyl and all linkages indicated by dashes are phosphodiester and those indicated by a ~ are phosphorothioate. "XX" is a gap in the sense strand where there is no linkage resulting in two sense strands.

ns could lead to an inhibition of antisense oligo uptake and/or to other non-antisense oligo dependent biologic effects.

METHODS AND COMPOSITIONS FOR MODULATING GENE EXPRESSION USING OLIGONUCLEOTIDE BASED DRUGS ADMINISTERED IN VIVO OR IN VITRO

CROSS REFERENCE TO RELATED APPLICATIONS

This application is a continuation application of U.S. application Ser. No. 14/148,191 filed Jan. 14, 2014, which is a continuation of Ser. No. 13/501,506 filed Dec. 3, 2012 which is a § 371 national phase entry of PCT/US10/52399, filed 12 Oct. 2010, which claims priority to U.S. Provisional Application 61/250,714, filed 12 Oct. 2009, the entire contents of each being incorporated herein by reference.

FIELD OF THE INVENTION

This invention relates to the fields of medicine and gene regulation. More specifically, the invention provides compositions and methods of use thereof which facilitate the modulation of gene expression using novel oligonucleotide based drugs.

BACKGROUND OF THE INVENTION

Numerous publications and patent documents, including both published applications and issued patents, are cited throughout the specification in order to describe the state of the art to which this invention pertains. Each of these citations is incorporated herein by reference as though set forth in full.

Conventional antisense oligonucleotides (oligos) directed to transcripts of a given target gene for the purpose of inhibiting the expression of the target gene are most often DNA analogs or are comprised of a DNA analog sequence flanked by RNA analog sequences. They are administered and function as single stranded agents. Such agents typically inhibit the expression of their target gene by a RNase H dependent mechanism and/or by sterically hindering some key process in gene expression such as ribosomal assembly or splicing.

Antisense oligos vary widely in their ability to block the expression of the target gene in cells. This appears, at least in part, to be due to: (1) variations in the availability for binding of the particular target site on the transcript that is complementary to the antisense oligo; (2) the binding affinity of the oligo for the target; and (3) the mechanism of antisense inhibition. Hence, what has been referred to as the poor uptake of oligos in part reflects the use of antisense oligos that are not properly designed and are, therefore, not optimally potent.

It is also possible that the culturing of cell lines under atmospheric oxygen conditions (which is the usual in vitro practice) produces a situation in which single stranded antisense oligos are made less active than they may be at much reduced (and more physiologically-relevant) oxygen tensions. The basis of this latter phenomenon could be due, in part, to the increased generation of reactive free oxygen radicals under ambient (atmospheric) oxygen levels by cells following treatment with any of several types of charged oligos, such as phosphorothioates. Highly reactive free oxygen radicals have been shown to have the capacity to alter the lipids in the surface membranes of cells, and to activate certain second-messenger pathways. Such altera- In general the administration of conventional antisense oligos in vivo or to freshly obtained tissues in vitro is much more effective in suppressing target gene expression compared to the administration of the same oligo in vitro to a cell line (Eckstein, Expert Opin Biol Ther 7: 1021, 2007). The likely reason for this is the more successful sequestration of oligos in endosomes or lysosomes by cell lines grown in vitro. In general, the successful treatment of cell lines in vitro with antisense oligos requires the use of a carrier.

The potential for conventional antisense oligos to be active in vivo against a wide variety of targets and a wide variety of tissues is evidenced by the many publications. Pharmacologic/toxicologic studies of phosphorothioate antisense oligos, for example, have shown that they are adequately stable under in vivo conditions, and that they are readily taken up by all the tissues in the body following systemic administration (Iversen, Anticancer Drug Design 6:531, 1991; Iversen, Antisense Res. Develop. 4:43, 1994; Crooke, Ann. Rev. Pharm. Toxicol. 32: 329, 1992; Cornish et al., Pharmacol. Comm. 3: 239, 1993; Agrawal et al., Proc. Natl. Acad. Sci. USA 88: 7595, 1991; Cossum et al., J. Pharm. Exp. Therapeutics 269: 89, 1994). In addition, these compounds readily gain access to the tissue in the central nervous system in large amounts following injection into the cerebral spinal fluid (Osen-Sand et al., Nature 364: 445, 1993; Suzuki et al., Amer J. Physiol. 266: R1418, 1994; Draguno et al., Neuroreport 5: 305, 1993; Sommer et al., Neuroreport 5: 277, 1993; Heilig et al., Eur. J. Pharm. 236: 339, 1993; Chiasson et al., Eur J. Pharm. 227: 451, 1992).

Despite the numerous documented successful treatments of animal models with conventional antisense oligos, clinical successes with these molecules to date have been few. The obstacles to clinical success with conventional antisense involve problems in the following areas: poor choice of target gene, use of inappropriate animal models for predicting clinical response, use of oligo with suboptimum mechanisms for inhibiting the selected gene target, selection of suboptimum oligo sequences and use of interfering concomitant medications.

The two principle mechanisms by which most conventional antisense oligos suppress the expression of their target gene each have positive and negative features, the net effect of which varies with the commercial purpose for which the oligo is being used. The principle advantage of the RNase H based mechanism is that it allows the conventional antisense oligo to function catalytically. Such oligos bind to the targeted RNA transcript, thereby forming a target for RNase H. This enzyme cleaves the transcript at the site hybridized to the oligo and then the oligo is released and is free to repeat the process. This approach is limited by the finding that many cells do not have adequate amounts of RNase H to provide for a robust antisense oligo response. In general, this is true for many cell types that are not stem cells.

The principle advantage to conventional antisense oligos with a steric hindrance mechanism is that they can act in any cell type since they are not dependent on RNase. This class of conventional antisense oligo includes members that have the capability of producing alternative splicing of target transcripts resulting in commercially useful effects. The principle disadvantages associated with this mechanism are (1) it is not catalytic; and (2) the choices of RNA transcript sites available for oligo binding is much more limited than for oligos based on the RNase H mechanism. These restricted target sites often provide for suboptimal binding affinity with the conventional antisense oligo on the basis of complementary base pairing.

A variant of the conventional antisense oligo approach is based on the use of RNA analogs rather than on DNA analogs that form the basis of the common approaches just described. As for the DNA based oligos these RNA based oligos are delivered and function as single strands. Specifically, the RNA analog oligo binds to its target RNA transcript by complementary base paring and as a result of the hybridization activates one or more cellular enzymes that cause the cleavage of the target transcript. These enzymes include those that attack double stranded RNA (dsRNA). These RNA analogs are chemically modified to increase their resistance to nuclease attack, improve their binding affinity to their RNA transcript target and to improve their pharmacokinetics. Typically these modifications to naturally occurring (native) RNA (i.e., RNA with normal C, G, U and A bases, ribose sugar and phosphodiester linkages) involve changes in the linkages between the subunits and/or modifications to the 2' hydroxyl of the ribose. Many but not all such RNA modifications and related modifications to such RNA analogs are described in U.S. Pat. Nos. 5,898,031, 6,107,094 and in their foreign counterparts such as WO9746570.

In one version of this approach, 17-mer oligoribonucleotides with nucleotides joined by phosphorothioate linkages with a gapmer structure have been shown to promote cleavage of the target mRNA by a double stranded RNase found in mammalian tissues (Wu et al., J Biol Chem 273: 2532, 1998). These investigators found that the center of the gapmer required a minimum of four nucleotides with native ribose sugars flanked by 2'-O-methyl modified nucleotides in order to show activity against the target.

Certain exogenously administered dsRNA molecules in the range of 16-30mers in size can also be used to suppress the expression of particular genes. Longer dsRNA have also been administered in vitro but in vivo longer dsRNA can provoke undesirable responses such as the induction of interferon. These agents include dicer substrates and siRNA. When the former are administered to cells an intracellular process converts them into shorter siRNA that are typically around 21 nucleotides in length. Exogenous siRNA can also be directly administered to cells and can be of different lengths than endogenously generated siRNA.

The general term RNA-mediated interference (RNAi) has been applied to such molecules as well as to their naturally occurring counterparts and the mechanisms behind such selective suppression of gene expression has been the focus of a substantial research effort since the discovery of the underling mechanism in the late 1990's. In brief, what appears to be the most common mechanism involves the loading of one strand of the dsRNA of an appropriate size into a naturally occurring intracellular molecular complex called the RNA-induced silencing complex ("RISC"). The loaded strand functions as an antisense oligo but is more often referred to as a "guide strand." The guide strand then directs the resultant RISC entity to its binding site on the gene target RNA transcript. Once bound, the RISC commonly directs cleavage of the RNA target by an argonaute enzyme. In some instances, translation may be inhibited by a steric hindrance mechanism. In yet another variant manifestation, the RISC may be directed to a particular gene itself where it can play an inhibitor function with respect to the expression of the gene. The intracellular mechanisms that are required for the successful suppression of particular genes by exogenously supplied siRNA are also involved in the processing of microRNA which is a normal part of the gene expression regulatory system normally found in cells.

Accordingly, RNAi based therapeutics have the capability of both having a catalytic mechanism of action and in being active in a broader range of cell types than conventional antisense oligos based on the RNase H mechanism of action or than conventional antisense oligos based on the steric hindrance mechanism where the target sequence would lead to a suboptimum inhibition. Thus, RNAi agents have the potential to complement conventional antisense oligos in a variety of commercial applications including the treatment of medical disorders.

Exogenously supplied RNAi can have the naturally occurring RNA structure (native) and be delivered to cells in vitro by means of an appropriate carrier such as certain cationic liposomes in common use for this purpose. Native dsRNA is more resistant to ribonuclease attack than native single stranded RNA, the carrier can provide more protection from ribonucleases and the tissue culture medium can be configured to reduce the levels of ribonucleases.

Chemical modifications to exogenously supplied RNAi can improve the half-life of the dsRNA and provide certain other advantages of commercial value such as biasing the selection of a particular strand in the dsRNA by RISC to function as the guide strand. Such modifications are most imperative when the RNAi is to be used in vivo where the ribonucleases present a greater obstacle than they do in vitro.

It is widely recognized that the principle drawback to double stranded RNAi agents for therapeutic and other purposes is their poor uptake by cells in a form that is bioavailable and effective to suppress gene expression both in vitro and particularly in vivo. In vitro this can be mitigated by various existing carriers such as certain cationic liposomes, such as Lipofectamine®, but these are not practical for in vivo use. There is a large and growing literature involving both patent disclosures and scientific publications providing various means of promoting the uptake of RNAi agents in vivo but to date all are complicated, difficult to utilize, have related toxicity and none has proven to have broad utility.

SUMMARY OF THE INVENTION

In accordance with the present invention, compounds which inhibit the expression of specific gene targets are disclosed. Exemplary compounds are based on SEQ ID NOS: 119-377 and duplexes thereof. Using the sequences provided in Genbank and design parameters set forth, the skilled person can readily generate novel oligo based compounds to inhibit the expression of gene targets including those provided in Table 2. An exemplary method entails contacting a cell expressing the gene target with an effective amount of an oligonucleotide, the oligo being effective to inhibit expression of the target, thereby reducing the amount of protein produced by the target gene. Oligos can include, without limitation, a single stranded siRNA, a double stranded siRNA, a dicer substrate, complementary sense and antisense oligos, an RNA analog oligo, an RNA/DNA analog oligo, and a single stranded DNA oligo.

In a particularly preferred embodiment, a two-step administration method is disclosed. An exemplary method entails administration of a first oligo strand to said cell, incubation of said cells for a suitable time period, followed by administration of a second oligo strand to said cell, said first strand and said second strand forming an intracellular duplex which is effective to catalyze degradation of target gene mRNA or inhibit translation of said mRNA. In the case of in vivo administration methods, the incubation step is omitted. Rather, administration of the second strand is delayed for an appropriate time period. After this time period elapses, the second strand is administered to those cells harboring the first strand. A duplex is then formed intracellularly which is effective to down modulate gene target expression. Preferably, this method is performed in vivo in order to inhibit gene expression associated with a particular disease state such as those listed in Table 2.

BRIEF DESCRIPTION OF THE DRAWINGS

FIG. 3: Compounds directed to Human p53 Top strand (SEQ ID NO: 119); Bottom strand (SEQ ID NO: 120)
FIG. 4: Compounds directed to Human p53 Top strand (SEQ ID NO: 121); Bottom strand (SEQ ID NO: 122)
FIG. 5: Compounds directed to Human p53 Top strand (SEQ ID NO: 123); Bottom strand (SEQ ID NO: 124)
FIG. 6: Compounds directed to Human p53 Top strand (SEQ ID NO: 125); Bottom strand (SEQ ID NO: 126)
FIG. 7: Compounds directed to Human p53 Top strand (SEQ ID NO: 127); Bottom strand (SEQ ID NO: 128)
FIG. 8: Compounds directed to Human p53 Top strand (SEQ ID NO: 129); Bottom strand (SEQ ID NO: 130)
FIG. 9: Compounds directed to Human p53 Top strand (SEQ ID NO: 131); Bottom strand (SEQ ID NO: 132)
FIG. 10: Compounds directed to Human p53 Top strand (SEQ ID NO: 133); Bottom strand (SEQ ID NO: 134)
FIG. 11: Compounds directed to Human Fas Top strand (SEQ ID NO: 135); Bottom strand (SEQ ID NO: 136)
FIG. 12: Compounds directed to Human Fas Top strand (SEQ ID NO: 137); Bottom strand (SEQ ID NO: 138)
FIG. 13: Compounds directed to Human Fas Top strand (SEQ ID NO: 139); Bottom strand (SEQ ID NO: 140)
FIG. 14: Compounds directed to Human Fas Top strand (SEQ ID NO: 141); Bottom strand (SEQ ID NO: 142)
FIG. 15: Compounds directed to Human Fas Top strand (SEQ ID NO: 143); Bottom strand (SEQ ID NO: 144)
FIG. 16: Compounds directed to Human Fas Top strand (SEQ ID NO: 145); Bottom strand (SEQ ID NO: 146)
FIG. 17: Compounds directed to Human/Murine ApoB Top strand (SEQ ID NO: 147); Bottom strand (SEQ ID NO: 148)
FIG. 18: Compounds directed to Human/Murine ApoB Top strand (SEQ ID NO: 149); Bottom strand (SEQ ID NO: 150)
FIG. 19: Compounds directed to Human/Murine ApoB Top strand (SEQ ID NO: 151); Bottom strand (SEQ ID NO: 152)
FIG. 20: Compounds directed to Human/Murine ApoB Top strand (SEQ ID NO: 153); Bottom strand (SEQ ID NO: 154)
FIG. 21: Compounds directed to Human/Murine ApoB Top strand (SEQ ID NO: 155); Bottom strand (SEQ ID NO: 156)
FIG. 22: Compounds directed to Human/Murine ApoB Top strand (SEQ ID NO: 157); Bottom strand (SEQ ID NO: 158)
FIG. 23: Compounds directed to Human/Murine ApoB Top strand (SEQ ID NO: 159); Bottom strand (SEQ ID NO: 160)
FIG. 24: Compounds directed to Human ApoB Top strand (SEQ ID NO: 161); Bottom strand (SEQ ID NO: 162)
FIG. 25: Compounds directed to Human ApoB Top strand (SEQ ID NO: 163); Bottom strand (SEQ ID NO: 164)
FIG. 26: Compounds directed to Human ApoB Top strand (SEQ ID NO: 165); Bottom strand (SEQ ID NO: 166)
FIG. 27: Compounds directed to Human ApoB Top strand (SEQ ID NO: 167); Bottom strand (SEQ ID NO: 168)
FIG. 28: Compounds directed to Human/Murine/Rat/Nonhuman Primate PCSK9 Top strand (SEQ ID NO: 169); Bottom strand (SEQ ID NO: 170)
FIG. 29: Compounds directed to Human/Murine/Rat/Nonhuman Primate PCSK9 Top strand (SEQ ID NO: 171); Bottom strand (SEQ ID NO: 172)
FIG. 30: Compounds directed to Human/Murine/Rat/Nonhuman Primate PCSK9 Top strand (SEQ ID NO: 173); Bottom strand (SEQ ID NO: 174)
FIG. 31: Compounds directed to Human/Murine/Rat/Nonhuman Primate PCSK9 Top strand (SEQ ID NO: 175); Bottom strand (SEQ ID NO: 176)
FIG. 32: Compounds directed to Human/Murine/Rat/Nonhuman Primate PCSK9 Top strand (SEQ ID NO: 177); Bottom strand (SEQ ID NO: 178)
FIG. 33: Compounds directed to Human PCSK9 Top strand (SEQ ID NO: 179); Bottom strand (SEQ ID NO: 180); Variant A: Top strand (SEQ ID NO: 181); Bottom strand (SEQ ID NO: 182); Variant B: Top strand (SEQ ID NO: 183); Bottom strand (SEQ ID NO: 184); Variant C: Top strand (SEQ ID NO: 185); Bottom strand (SEQ ID NO: 186)
FIG. 34: Compounds directed to Human PCSK9 Top strand (SEQ ID NO: 187); Bottom strand (SEQ ID NO: 188); Variant A: Top strand (SEQ ID NO: 189); Bottom strand (SEQ ID NO: 190); Variant B: Top strand (SEQ ID NO: 191); Bottom strand (SEQ ID NO: 192); Variant C: Top strand (SEQ ID NO: 193); Bottom strand (SEQ ID NO: 194)
FIG. 35: Compounds directed to Human PCSK9 Top strand (SEQ ID NO: 195); Bottom strand (SEQ ID NO: 196)
FIG. 36: Compounds directed to Human PCSK9 Top strand (SEQ ID NO: 197); Bottom strand (SEQ ID NO: 198)
FIG. 37: Compounds directed to Human PTEN Top strand (SEQ ID NO: 199); Bottom strand (SEQ ID NO: 200)
FIG. 38: Compounds directed to Human PTEN Top strand (SEQ ID NO: 201); Bottom strand (SEQ ID NO: 202)
FIG. 39: Compounds directed to Human PTEN Top strand (SEQ ID NO: 203); Bottom strand (SEQ ID NO: 204)
FIG. 40: Compounds directed to Human PTEN Top strand (SEQ ID NO: 205); Bottom strand (SEQ ID NO: 206)
FIG. 41. Sequential RNAi-mediated inhibition of PTEN in Hela cells. Fluorescent Western blotting of PTEN after lipofectamine 2000-mediated transfection of the indicated compounds (0.20 µM) in Hela cells. Mean values from 2 independent transfection experiments. Error bars represent SEM. Oligo 8 serves as a non-silencing control. Sequential addition of single strands performed as described. Values shown represent the mean PTEN protein levels (the ratio of PTEN to Erk2) after normalization to the PTEN level in the oligo 8 lysate. Fluorescent images were quantified on a Typhoon Trio variable mode imager.
FIG. 42: Compounds directed to Human PTEN are shown. SEQ ID NOS: are provided in parentheses.
FIG. 43: Compounds directed to Mouse PTEN are shown. SEQ ID NOS: are provided in parentheses.
FIGS. 44A and 44B: Compounds directed to Human/Mouse PCSK9 are shown. SEQ ID NOS: are provided in parentheses.
FIGS. 45A and 45B: Compounds directed to Mouse PTP1B are shown. SEQ ID NOS: are provided in parentheses.
FIG. 46: Compounds directed to Human/Mouse PTP1B are shown. SEQ ID NOS: are provided in parentheses.

FIGS. 47A and 47B: Compounds directed to Human p53 are shown. SEQ ID NOS: are provided in parentheses.

FIGS. 48A and 48B: Compounds directed to Human p53 are shown. SEQ ID NOS: are provided in parentheses.

FIGS. 49A and 49B: Compounds directed to Human/Mouse ApoB are shown. SEQ ID NOS: are provided in parentheses.

FIGS. 50A and 50B: Compounds directed to Human/Mouse ApoB are shown. SEQ ID NOS: are provided in parentheses.

FIG. 51: Compounds directed to Human PTP1B are shown. SEQ ID NOS: are provided in parentheses.

FIGS. 52A and 52B: Compounds directed to Mouse Notch1 are shown. SEQ ID NOS: are provided in parentheses.

FIGS. 53A and 53B: Compounds directed to Mouse MDR are shown. SEQ ID NOS: are provided in parentheses.

FIGS. 54A, 54B and 54C: Compounds directed to Mouse COX2 are shown. SEQ ID NOS: are provided in parentheses.

FIGS. 55A and 55B: Compounds directed to Mouse WRN are shown. SEQ ID NOS: are provided in parentheses.

DETAILED DESCRIPTION OF THE INVENTION

Figure 1:
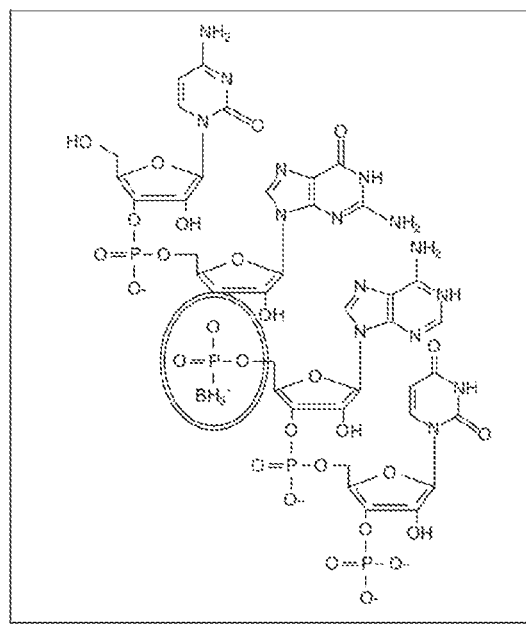
FIG. 1: Boranophosphate Linkage

A. Overview of Invention:

There have been sporadic reports in the literature of instances where a particular antisense RNA molecule has been shown to have RNAi activity when administered to cells as a single strand. Xu et al., (Biochem Biophys Res Comm 316: 680-687, 2004) conducted an in vitro study to determine how frequently such antisense RNA strands occur during screening and how active they are compared to the corresponding duplex. All the compounds tested comprised unmodified RNA. The authors found that antisense strands used alone are much less active than the corresponding duplex. Further, they determined that this difference in activity was due to an intrinsic superiority of the duplex over the antisense strand used alone rather than being do the greater nuclease stability of duplex RNA vs single stranded RNA when such compounds are transfected into cells using Lipofectamine 2000. (Such transfection agents are known to provide a degree of nuclease protection for RNA.) They demonstrated the intrinsic superiority of the duplex by showing that if cells were sequentially transfected with sense strands and followed by transfection with the complementary antisense strand that the activity was significantly higher that what was seen when the antisense RNA strand was used alone. This would not have occurred if the first strand to be transfected had been degraded.

A key feature of the present invention are methods for designing sense and antisense RNA (RNA analogs) that have sufficient nuclease resistance to be administered in vivo as naked compounds (no protective carrier) and survive at least long enough to enter cells and to be present for combining with their subsequently administered complementary partner while at the same time being able to function as RNAi after forming a duplex. This ability which provides for in vivo applications which were not achievable based on Xu et al.

Accordingly, the present invention provides compositions and methods that largely overcome the in vivo uptake problems that are widely recognized as the single greatest obstacle to the broad use of exogenously administered RNAi for purposes such as the treatment of medical conditions, advancing the understanding of functional genomics and drug target validation studies.

In brief, the present inventor has made the surprising discovery that the individual complementary antisense and sense stands can be sequentially administered to cells, taken up by the cells and then form the active dsRNA agent within the cells that subsequently fulfills the intended function of suppressing the expression of the particular gene to which the antisense strand is directed. Thus, the administered sense and antisense oligo strands come to function as passenger and guide strands respectively inside of cells. This method can be applied to many functional siRNA sequences (such as but not limited to those described in PCT/US09/02365). Such sequences, however, typically must be combined with methods that render the resulting individual oligo strands sufficiently stable with respect to nuclease attack under the conditions they are being administered. Thus, this method provides a generally applicable method for achieving RNAi activity in vivo using compounds in the form of complementary sense and antisense oligos in numerous cell and tissue types without the necessity of having a carrier or the use of potentially traumatic methods such as hydrodynamic injection. This method is also generally useful for increasing the activity of single oligo strands that have ss-siRNA activity.

When the method is applied in vitro, carriers for the individual strands are needed for most cell lines. However, when freshly obtained tissue samples are contacted, carriers frequently can be avoided. The smaller size of the individual sense and antisense strands compared to dsRNA, reduces the burden on the cell penetrating peptide (CPP) and/or other carriers and thus allows for more efficient delivery of individual strands when compared to dsRNA, and for the use of a broader range of carriers reducing the likelihood of carrier induced side effects.

The present invention also provides for compositions that can be utilized with the novel methods provided for herein. Specifically, the said compositions include the following: (1) sense strands that can be administered as single stranded agents to cells in vitro or in vivo and subsequently bind to the corresponding antisense strand intracellularly where they combine to form an RNAi structure capable of promoting the suppression of the gene target; and (2) antisense strands that can be administered as single stranded agents to cells in vitro or in vivo and subsequently loaded into RISC either being presented to RISC as a dsRNA with its sense strand partner or as a ss-siRNA Such RNA strands can be appropriately modified relative to the native RNA for in vivo use and typically but not necessarily modified for in vitro use.

B. Definitions:

The following definitions and terms are provided to facilitate an understanding of the invention.

"Antisense oligos or strands" are oligos that are complementary to sense oligos, pre-mRNA, RNA or sense strands of particular genes and which bind to such genes and gene products by means of base pairing. When binding to a sense oligo, the antisense oligo need not base pair with every nucleoside in the sense oligo. All that is necessary is that there be sufficient binding to provide for a Tm of greater than or equal to 40° C. under physiologic salt conditions at submicromolar oligo concentrations.

"Sense oligos or strands" are oligos that are complementary to antisense oligos or antisense strands of particular genes and which bind to such genes and gene products by means of base pairing. When binding to an antisense oligo, the sense oligo need not base pair with every nucleoside in the antisense oligo. All that is necessary is that there be sufficient binding to provide for a Tm of greater than or equal to 40° C. under physiologic salt conditions at submicromolar oligo concentrations.

"Conventional antisense oligos" are single stranded oligos that inhibit the expression of the targeted gene by one of the following mechanisms: (1) steric hindrance—e.g., the antisense oligo interferes with some step in the sequence of events leading to gene expression resulting in protein production by directly interfering with the step. For example, the antisense oligo may bind to a region of the RNA transcript of the gene that includes a start site for translation which is most often an AUG sequence (other possibilities are GUG, UUG, CUG, AUA, ACG and CUG) and as a result of such binding, the initiation of translation is inhibited; (2) Induction of enzymatic digestion of the RNA transcripts of the targeted gene by RNase H. RNase H recognizes DNA/RNA or certain DNA analog/RNA duplexes (not all oligos that are DNA analogs will support RNase H activity) and digests the RNA adjacent to the DNA or DNA analog hybridized to it; (3) Induction of enzymatic digestion of the RNA transcripts of the targeted gene by RNase L; (4) Induction of enzymatic digestion of the RNA transcripts of the targeted gene by RNase P: (5) Induction of enzymatic digestion of the RNA transcripts of the targeted gene by double stranded RNase. Double stranded RNase recognizes RNA/RNA or certain RNA analog/RNA duplexes (not all oligos that are RNA analogs will support RNase H activity) and digests the gene target transcript adjacent to the antisense RNA or RNA analog containing oligo hybridized to it; and (6) combined steric hindrance and the capability for inducing gene target transcript digestion.

"Native RNA" is naturally occurring RNA (i.e., RNA with normal C, G, U and A bases, ribose sugar and phosphodiester linkages).

"RNAi" or RNA-mediated interference (or just RNA interference) makes use of cellular mechanisms involved in processing of endogenous RNAi. In brief, this mechanism includes the loading of an antisense oligo often referred to as a "guide strand" into a molecular complex called the RNA-induced silencing complex ("RISC"). The guide strand then directs the resultant RISC entity to its binding site on the target gene RNA transcript. Once bound, the RISC directs cleavage of the RNA target by an argonaute enzyme or in the alternative, translation may be inhibited by a steric hindrance mechanism. In a variant manifestation, the RISC may be directed to the gene itself where it can play an inhibitor function. Such exogenously supplied RNAi conventionally has been administered in one of three forms. These are the following: (a) dicer substrates, (b) double stranded siRNA (siRNA) and (c) single stranded siRNA (ss-siRNA). With the exception of ss-siRNA, RNAi is a double stranded structure with one or more so-called passenger strand(s) hybridized to the guide strand.

For convenience, the monomers comprising the oligo sequences will be termed herein "nucleotides" or "nucleosides" but it is to be understood that the normal sugar moiety (deoxyribose or ribose) and/or the normal base (adenine, guanine, thymine, cytosine and uracil) moieties may be substantially modified or even replaced by functionally similar analogs, for example, the normal sugar may have a fluorine inserted in the 2' position or be entirely replaced by a different ring structure as is the case with piperazine or morpholino oligos. Further, in particular embodiments, the nucleotides or nucleosides within an oligo sequence may be abasic. In addition, the linkers between the monomers will often be varied from the normal phosphodiester structure and can include one or more of several other possibilities depending on such considerations as the need for nuclease resistance, high target sequence binding affinity, pharmacokinetics and preferential uptake by particular cell types. The alternating linker/sugar or sugar substitute structure of oligos is referred to as the "backbone" while the normal bases or their substitutes occur as appendages to the backbone.

"Cell penetrating peptides" (CPPs) are peptides that promote cell penetration of molecules to which they are attached. CPPs may be naturally occurring protein domains or they may be designed based on the naturally occurring versions. CPPs typically share a high density of basic charges and are usually 6-30 amino acids in length. CPPs useful in the single and double stranded oligos of the invention are described further hereinbelow. "Endosomolytic and lysosomotropic agents" are agents that can be used in combination with an oligo to promote its release from endosomes, lysosomes or phagosomes. The former are agents that are attached to oligos or incorporated into particular oligo delivery systems while the latter agents may be so attached or incorporated or be administered as separate agents from, but in conjunction with, any such oligo used with, or without, a delivery system. Lysosomotropic agents have other desirable properties and can exhibit antimicrobial activity.

"Endosomolytic agent" refers to an agent that possesses at least endosomal lytic activity. In certain embodiments, an endosomal lytic moiety also exhibits lysosomolytic, phagosomolytic or lysosmotropic activity.

A "specific binding pair" comprises a specific binding member and a binding partner that have a particular specificity for each other and which in normal conditions bind to each other in preference to other molecules. Such members and binding partners are also referred to as targeting molecules herein. Examples of specific binding pairs include but are not limited to ligands and receptor, antigens and antibodies, and complementary nucleic acid molecules. The skilled person is aware of many other examples. Further the term "specific binding pair" is also applicable to where either or both of the specific binding pair member and the binding partner comprise a part of a larger molecule.

"Tm" or melting temperature is the midpoint of the temperature range over which the oligo separates from the target nucleotide sequence. At this temperature, 50% helical (hybridized) versus coiled (unhybridized) forms are present. Tm is measured by using the UV spectrum to determine the formation and breakdown (melting) of hybridization. Tm can be determined using techniques that are well known in the art. There are also formulas available for estimating Tm on the basis of sequence and common chemical modifications if any.

"Gene target" or "target gene" refers to either the DNA sequence of a gene or its RNA transcript (processed or unprocessed) that is targeted by any given RNAi for suppression of the expression of the gene in question.

A "stem cell" is a rare cell type in the body that exhibits a capacity for self-renewal. Specifically when a stem cell divides the resulting daughter cells are either committed to undergoing a particular differentiation program (along with any progeny) or they are a replica of the parent cell. In other words, the replica cells are not committed to undergo a differentiation program. When the division of a stem cell produces daughter cells that are replicas of the parent cell, the division is called "self-renewal." Accordingly, stem cells are able to function as the cellular source material for the maintenance and/or expansion of a particular tissue or cell type.

There are many types of stem cells and often any given type exists in a hierarchy with respect to the differentiation potential of any daughter cells committed to undergoing a differentiation program. For example, a more primitive hematopoietic stem cell could have the capacity to produce committed daughter cells that in turn have the capacity to give rise to progeny that include any myelopoietic cell type while a less primitive hematopoietic stem cell might be only capable of producing committed daughter cells that can give rise to monocytes and granulocytes.

Induced pluripotent (iPS or iPSC) stem cells" are created (induced) from somatic cells by human manipulation. Such manipulation has typically involved the use of expression vectors to cause altered (increased or decreased) expression of certain genes in the somatic cells. "Pluripotent" refers to the fact that such stem cells can produce daughter cells committed to one of several possible differentiation programs.

"dsRNA" refers to a ribonucleic acid based oligo having a duplex structure comprising two anti-parallel oligos with sufficient complementarity between adjacent bases on opposite strands to have a Tm of greater than or equal to 40° C. under physiologic salt conditions and submicromolar oligo concentrations. In a variant design one oligo may be hybridized to two complementary strands where the former acts as the guide stand and the latter as passenger strands in an RNAi agent.

"Upstream" and "Downstream" respectively refer to moving along a nucleotide strand in a 3' to 5' direction or a 5' to 3' direction.

"Introducing into" means uptake or absorption in the cell, as is understood by those skilled in the art. Absorption or uptake of oligos can occur through cellular processes, or via the use of auxiliary agents or devices.

A "two-step administration or method" is where cells are treated with one strand of a complementary sense and antisense oligo pair and after cellular uptake of this strand, the cells are treated with the other strand in a manner that also provides for its uptake into the cells. The two strands then form a functional RNAi duplex intracellularly to inhibit target gene expression in the cells containing the RNAi duplex. In a variant of the two-step method a conventional antisense oligo is administered first followed by the administration of a complementary sense oligo with the intent of blocking the activity of the antisense oligo.

The term "identity" as used herein and as known in the art, is the relationship between two or more oligo sequences, and is determined by comparing the sequences. Identity also means the degree of sequence relatedness between oligo sequences, as determined by the match between strings of such sequences. Identity can be readily calculated (see, e.g., Computation Molecular Biology, Lesk, A. M., eds., Oxford University Press, New York (1998), and Biocomputing: Informatics and Genome Projects, Smith, D. W., ed., Academic Press, New York (1993), both of which are incorporated by reference herein). While a number of methods to measure identity between two polynucleotide sequences are available, the term is well known to skilled artisans (see, e.g., Sequence Analysis in Molecular Biology, von Heinje, G., Academic Press (1987); and Sequence Analysis Primer, Gribskovm, M. and Devereux, J., eds., M. Stockton Press, New York (1991)). Methods commonly employed to determine identity between oligo sequences include, for example, those disclosed in Carillo, H., and Lipman, D., Siam J. Applied Math. (1988) 48:1073.

"Substantially identical," as used herein, means there is a very high degree of homology preferably >90% sequence identity.

As used herein, the term "treatment" refers to the application or administration of a single or double stranded oligo(s) or other therapeutic agent to a patient, or application or administration of an oligo or other drug to an isolated tissue or cell line from a patient, who has a medical condition, e.g., a disease or disorder, a symptom of disease, or a predisposition toward a disease, with the purpose to cure, heal, alleviate, relieve, alter, remedy, ameliorate, improve, or affect the disease, the symptoms of disease, or the predisposition toward disease. In an alternative embodiment, tissues or cells or cell lines from a normal donor may also be "treated".

As used herein, the terms "modulate", "modulating" or "modulation" refer to changing the rate at which a particular process occurs, inhibiting a particular process, reversing a particular process, and/or preventing the initiation of a particular process. Accordingly, if the particular process is tumor growth or metastasis, the term "modulation" includes, without limitation, decreasing the rate at which tumor growth and/or metastasis occurs; inhibiting tumor growth and/or metastasis; reversing tumor growth and/or metastasis (including tumor shrinkage and/or eradication) and/or preventing tumor growth and/or metastasis.

A "pharmaceutical composition" comprises a pharmacologically effective amount of a single or double stranded oligo(s), optionally other drug(s), and a pharmaceutically acceptable carrier. As used herein, "pharmacologically effective amount," "therapeutically effective amount" or simply "effective amount" refers to that amount of an agent effective to produce a commercially viable pharmacological, therapeutic, preventive or other commercial result.

"Pharmaceutically acceptable carrier" refers to a carrier or diluent for administration of a therapeutic agent. Pharmaceutically acceptable carriers for therapeutic use are well known in the pharmaceutical art, and are described, for example, in Remington's Pharmaceutical Sciences, AR Gennaro (editor), 18$^{th}$ edition, 1990, Mack Publishing, which is hereby incorporated by reference herein. Such carriers include, but are not limited to, saline, buffered saline, dextrose, water, glycerol, ethanol, and combinations thereof. The term specifically excludes cell culture medium. For drugs administered orally, pharmaceutically acceptable carriers include, but are not limited to pharmaceutically acceptable excipients such as inert diluents, disintegrating agents, binding agents, lubricating agents, sweetening agents, flavoring agents, coloring agents and preservatives. Suitable inert diluents include sodium and calcium carbonate, sodium and calcium phosphate, and lactose, while corn starch and alginic acid are suitable disintegrating agents. Binding agents may include starch and gelatin, while the lubricating agent, if present, will generally be magnesium stearate, stearic acid or talc. If desired, the tablets may be coated with a material such as glyceryl monostearate or glyceryl distearate, to delay absorption in the gastrointestinal tract. The compounds of the invention may also be admixed, encapsulated, conjugated or otherwise associated with other molecules, molecule structures or mixtures of compounds, as for example, liposomes, receptor targeted molecules, oral, rectal, topical or other formulations, for assisting in uptake, distribution and/or absorption. Representative United States patents that teach the preparation of such uptake, distribution and/or absorption assisting formulations include, but are not limited to, U.S. Pat. Nos. 5,108,921; 5,354,844; 5,416,016; 5,459,127; 5,521,291; 5,543,158; 5,547,932; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756. The single or double stranded oligos of the present invention encompass any pharmaceutically acceptable salts, esters, or salts of such esters, or any other compound which, upon administration to an animal including a human, is capable of providing (directly or indirectly) the biologically active metabolite or residue thereof. Accordingly, for example, prodrugs and pharmaceutically acceptable salts of the compounds of the invention, pharmaceutically acceptable salts of such prodrugs, and other bioequivalents are also encompassed by the present invention. In addition, single stranded oligos may be formulated for oral delivery (Tillman et al., J Pharm Sci 97: 225, 2008; Raoof et al., J Pharm Sci 93: 1431, 2004; Raoof et al., Eur J Pharm Sci 17: 131, 2002; U.S. Pat. No. 6,747,014; US 2003/0040497; US 2003/0083286; US 2003/0124196; US 2003/0176379; US 2004/0229831; US 2005/0196443; US 2007/0004668; US 2007/0249551; WO 02/092616; WO 03/017940; WO 03/018134; WO 99/60012). Such formulations may incorporate one or more permeability enhancers such as sodium caprate that may be incorporated into an enteric-coated dosage form with the oligo.

C. The Embodiments:

In one embodiment, complementary sense and antisense oligo compounds are administered to cells or organisms in a two-step procedure (two-step administration or method) whereby one strand is administered to and taken up by a cell expressing the gene target, followed by administration of the second complementary strand which binds to the first strand to form a double stranded RNAi compound intracellularly, thereby triggering inhibition of gene target expression.

In a related embodiment, complementary sense and antisense oligo compounds are administered to cells or organisms in a two-step procedure whereby the antisense strand of a conventional antisense oligo is administered to and taken up by a cell expressing the gene target, followed by administration of the second complementary sense strand which binds to the first strand to form an inactive duplex; the effect being the inactivation of the antisense activity.

In another related embodiment, methods and designs are provided for modifying known functional double stranded RNAi molecules such that they are more broadly suitable for use in the two-step administration method described above. In particular these methods and designs provide for the creation of novel complementary sense and antisense strands that can be individually delivered to cells. Specifically, the modifications described provide increased nuclease resistance thereby facilitating use of the two-step method inhibition of target gene expression in cells without the necessity of having an additional component, such as a carrier, that provides increased nuclease resistance. Such reconfigured compounds have the following properties: (1) they are comprised of individual strands with sufficient nuclease resistance to withstand administration as single strands; (2) they are capable of forming a duplex intracellularly with their partner strand; and (3) the duplex formed intracellularly exhibits enhanced gene target modulatory function relative to effects seen when the strands are administered alone or compared to conventional siRNA directed to the same gene target. The chemical modifications to oligos provided by these methods and designs are not ones that must be reversed intracellularly in order for the individual strands to be able to form a duplex with their partner strands and/or subsequently function as a RNAi compound. This feature provides an advantage in that the compounds provided herein are not dependent on cell to cell variations in the ability of cells or cell products to process the strands into their functional forms.

In still another related embodiment, the nuclease resistance of one, or both, of the individual strands (sense and antisense) is further increased by designing or selecting strand(s) having the potential to form hair pins in accordance with the methods and designs provided herein. This approach has the advantage of allowing for less chemical modification in the central region of the strands. This can improve gene target suppressor activity in some circumstances. For example, the region of the antisense strand that is adjacent to the argonaute 2 cleavage site of the target is particularly adversely sensitive, with respect to its ability to induce argonaute 2 activity, to many types of chemical modifications that improve nuclease sensitivity. Thus, the use of a hair pin can provide a means of protecting that region of the strand allowing for less chemical modification.

In another embodiment, the designs and methods provided herein can be used to generate complementary sense and antisense oligos that form intracellular RNAi compounds that are not modifications or reconfigurations of existing RNAi compounds. This approach can be applied to generating inhibitors of any eukaryotic gene target and for any commercial purpose where RNAi is a suitable technology. In a preferred version of this embodiment the antisense strand that ultimately functions as RNAi after combining with its partner strand is directed to a hot spot in gene target transcripts where the hot spot is determined using the hotspots and methods for identifying hotspots described in U.S. Pat. No. 7,517,644. A related embodiment comprises the sense and antisense oligos as compositions of matter that form the functional RNAi in cells as well as the dsRNA composition of matter that results from the duplexing of such oligos and that result from the methods described herein.

In another embodiment, the present invention provides the means to convert active conventional antisense oligos to compounds with RNAi activity, when combined with a sense oligo partner, without the accompanying problem of inadequate uptake very frequently seen with the administration of double stranded RNAi compounds.

The present invention also provides methods and designs applicable to adapting conventional antisense oligos for use as the antisense strand in the two-step method that obviate many of the requirements imposed by the many algorithms well known in the art that have been developed to select active conventional RNAi compounds. This approach confers a number of new useful features to conventional antisense oligos that include but are not limited to: (1) extending the duration of inhibition of gene target expression; (2) extending the range of cell types in which conventional antisense oligos with an RNase H mechanism of action are active since many cells have inadequate levels of RNase H to support a robust antisense response based on this mechanism; (3) increasing the activity level of conventional antisense oligos with a steric hindrance mechanism of action, as RNAi typically have a catalytic activity whereby a given guide strand loaded into a RISC complex can lead to the successive cleavage of RNA transcripts of the gene target.

Conversely, in another embodiment, the antisense strands useful for the creation of RNAi agents in cells can be reconfigured as conventional antisense oligos as discussed herein and as summarized in Table 1.

In other embodiments, specific compositions of matter, based on the designs and properties just mentioned are provided for a number of gene targets including those listed in Table 2. While these sense and antisense compositions of matter are designed for administration as individual strands they can also be administered as a duplex with or without a carrier. The importance of such administrations includes but is not limited to mechanism of action studies where, for example, the relative efficiencies of duplex verses sequential single strand administration are compared. In addition, the double stranded RNAi compositions of the present invention and their administration to cells provide advantages over their conventional RNAi counter parts in addition to their delivery advantages, including but not limited, to the advantage of more prolonged activity.

In a preferred embodiment, the sense strand that is destined to become a passenger strand is administered first followed by the antisense strand destined to become a guide strand when duplexed with its partner within cells. Alternatively, the sense strand can be administered as two oligos that form a contiguous duplex with the antisense strand.

In yet another embodiment the antisense strand has significant ss-siRNA activity which is substantially enhanced when it forms a duplex with a complementary sense strand and where such strands are administered by the two-step method.

In a related embodiment, each of the individual complementary strands administered by the two-step method lack sufficient RNAi activity of their own to produce the desired commercial result such as the treatment of a medical condition. These strands only gain sufficient RNAi activity after they form an intracellular duplex with each other.

In another embodiment, methods and designs are provided that can be used to modify existing or newly developed double stranded or single stranded RNAi to provide sufficient nuclease resistance and RNAi activity suitable for use in accordance with the novel methods just described. In still another embodiment, the novel ss-siRNA disclosed can be used in vitro or in vivo without a second strand. In yet another embodiment carriers are provided that are useful for the purposes described herein.

The two-step administration and the oligo compounds provided can be used in vitro or in vivo. In general, a carrier will be required for the efficient introduction of each individual strand into cell lines grown in vitro. Such carriers can provide protection against nucleases which are typically less problematic for in vitro uses. The methods and designs provided herein provide the option for less stringently modified oligos capable of providing intracellular RNAi activity for in vitro and/or carrier associated use. Indeed, the strands of many conventional RNAi compounds can be delivered by the two-step administration in vitro or in vivo when a carrier or other delivery mechanism is used. Specifically, the use of conventional RNAi (that is RNAi with a native RNA structure or minimal chemical modification defined as the individual strands having a half life of less than two hours in the relevant biological fluids such as plasma) will require the concomitant use of a carrier that protects the single strands from nuclease attack long enough that they can penetrate cells and form a duplex with their partner strand so that they can function as RNAi within cells. The principle advantage of the two-step administration for carrier associated in vitro or in vivo use is that it reduces the burden on the carrier or other delivery method and thus allows a more efficient and a less traumatic transfer of the oligo components of RNAi agents into cells.

The principle advantage of the two-step administration method is that for in vivo use in most instances, a carrier or other mechanism such as hydrodynamic injection will not be needed. This is a substantial improvement over the prior art where poor in vivo uptake of RNAi compounds by the majority of cell types is a great problem. Further, the enhanced nuclease stability of the compounds provided for herein for use in vivo use also provide for extended activity in cells. The present approach is surprisingly robust in being applicable to many gene targets, commercial applications and established RNAi compounds.

Carriers or other uptake mechanisms may be desirable for use in promoting the uptake of individual strands in vivo in accordance with the two-step administration method in certain circumstances including the following: (1) situations where a carrier is used to direct the oligos to particular types of cells to the exclusion of others, for example, to reduce side effects by avoiding tissues involved in such side effects by means of a carrier not well suited for delivering molecules to the non-suitable tissues; (2) situations involving cells that are sequestered behind natural barriers to charged molecules in the size range of 16-30-mer oligonucleotides including but not limited to the central nervous system, the testis and the interior of the eye; (3) where the RNAi is a dicer substrate that of necessity must be subject to a nuclease attack that will convert the dicer substrate into siRNA intracellularly and as a result may require the added nuclease protection that can be provided by some carriers; and (4) in addition to increasing nuclease resistance certain carriers, such as cholesterol (cholesterol also can be linked to the 3'-end of a passenger or guide strand using a variety of know linkers such as pyrrolidine), may also be used to prolong the half-life of the oligos in serum by promoting binding to plasma proteins and, thereby, reducing the rate of renal clearance. This can also be achieved by using a predominance of phosphorothioate linkages in a given strand. These methods provide more time for tissue uptake of individual strands to occur.

D. Methods for Reconfiguring Guide Strands for Use as Conventional Antisense Oligos Guide or antisense strands that have been configured for use in the present invention can also be reconfigured as conventional antisense oligos. The details of the reconfiguration will depend on the desired mechanism of action, the level of nuclease resistance required and on the commercial goal of the treatment. These same types of considerations are also important when choosing an RNAi vs. conventional antisense oligo approach. One such mechanism of action requires RNase H activity. Stem cells possess sufficient RNAase H levels to support the action of conventional antisense oligos dependent on this activity. However, levels of RNAse H activity can be reduced in more differentiated cells to levels that are insufficient (Crooke, S T (1995) Therapeutics Applications of Oligonucleotides, pp. 1-25, RG Landes. Publishers, Austin Tx). An established way to gain susceptibility to RNase H action is to produce oligos which are gapmers wherein the central nucleosides in the oligo have deoxyribose as the preferred sugar moiety, combined with a linkage such as boranophosphate or phosphorothioate that can support RNase H when used as part of a DNA analog. LNA, FANA or 2'fluoro gapmer oligos are preferably 16-22mers with phosphorothioate or boranophosphate linkages and a 4-18 nucleoside core flanked by sequences that do not readily support RNase H activity (those containing LNA, FANA or 2'fluoro containing nucleosides) wherein flanking sequences are no more than two nucleosides different in length. The 4-18 nucleoside core uses normal deoxyribose or a suitable analog as the sugar that will support RNase H cleavage of the target RNA to which the oligo is hybridized. Phosphodiester linkages also may be used for in vitro applications where nuclease activity is reduced. Most preferred are 20-mer 2'fluoro gapmers with an 8 nucleoside core and phosphorothioate linkages throughout as illustrated below. The lower case "x"s represent different bases (A, G, U/T or C comprising deoxyribose sugars) that are part of a series of linked nucleosides while the uppercase "X"s represent nucleosides with 2'fluoro modifications to the sugar. The ~ symbol represents nuclease resistant linkages including, without limitation phosphorothioate or boranophosphate. RNA analogs (e.g., 2'fluoro) oligos are typically but not necessarily produced using uracil rather than thymine bases.

5'-X~X~X~X~X~X~x~x~x~x~x~x~x~X~X~X~X~X-3'

Variant gapmers with sugars containing 2'-O-methyl, 2'-O-ethyl, 2'-O-methoxyethoxy or 2'-O-methoxyethyl groups in the flanking sequences can also be used but are less preferred than LNA, FANA or 2'fluoro modifications with the 2'fluoro modification being most preferred. In addition to the documents provided above, synthetic processes for generating oligos with variable combinations of nucleoside linkages including, but not limited to phosphodiester, phosphorothioate, phosphoramidate and boranophosphate including those for promoting RNase H activity against the RNA target are also presented in WO2004/044136, WO0047593, WO0066609, WO0123613, U.S. Pat. Nos. 6,207,819 and 6,462,184.

In another approach to improve the ability of conventional antisense oligos to promote RNase H activity against their target, nucleosides with certain base modifications can be inserted at a single position near the center (within 4 nucleosides of either the 5' or 3' end) of oligos that do not significantly support RNase H activity such as FANA, LNA, 2'fluoro or piperazine oligos. In addition, such nucleosides can be placed at the junction between a series of RNA or RNA-analog nucleoside and a series of DNA or DNA analog nucleosides making up an oligo (such as occurs in oligos with a gapmer design) with insufficient RNase H activity in order to further promote this activity. This approach can be applied, for example, to FANA, LNA, 2'fluoro, 2'-O-ethyl 2'-O-methoxyethoxy or 2'-O-methoxyethyl gapmer antisense oligos. The promotion of RNase H activity by this means appears to be due to added flexibility to the strand that is needed for promoting RNase H activity without interfering with the recognition of the oligo:RNA hybrid as a suitable substrate. The specific base modifications that can be used for this purpose and inserted either at gapmer junctions or near the center of the oligo are selected from the group consisting 4'-C-hydroxymethyl-DNA, 3'-C-hydroxymethyl-ANA, or piperazino-functionalized C3', O2'-linked-ANA where ANA refers to an arabinonucleic acid. Modified nucleotides or nucleotides that can be inserted at gapmer junctions for the purpose of promoting RNase H activity are selected from the group consisting of 2'fluoro-arabinonucleotides, abasic, tetrahydrofuran (THF).

Conventional antisense oligos can also be configured to support the activity of double stranded RNases. Such oligos are described in Wu et al., J Biol Chem 273: 2532, 1998, U.S. Pat. Nos. 5,898,031; 6,737,512; 7,491,524; 7,432,249; 7,432,250; and 2004/0191773. Wu et al. (J Biol Chem 275:

36957, 2000) have cloned a human double stranded RNase (RNase III) capable of supporting this mechanism of action for conventional antisense oligos. The enzyme is ubiquitously expressed in the nucleus in human tissues and cell lines.

One of numerous oligo designs disclosed in the literature capable of supporting double strand RNase activity makes use of the gapmer design and a small subset have been tested by Wu et al., 1998 (vide supra). In this design, a set of at least four contiguous nucleosides and linkages which together support double stranded RNase activity against gene target transcripts are flanked on both sides by nucleosides and linkages that do not support such activity but do provide other advantages such as increased affinity for the target transcript. Wu et al. tested the ability of a series of gapmers to suppress mutated Harvey Ras expression in T24 cells. All the linkages were phosphorothioate and the central nucleosides contained native ribose while the two flanking regions contained 2'methyoxy modified ribose. Seventeen-mer oligos with 5, 7 or 9 native ribose nucleoside centers as well as those with just native ribose were active in supporting double stranded RNase activity against the gene target. Oligos with 3 native ribose nucleoside centers were not active. Oligos where the linkages between the nucleosides with native ribose were replaced with phosphodiester linkages were cleaved along with the gene target confirming the RNase involved was a double strand RNase.

A third mechanism whereby conventional antisense oligos can inhibit the expression of a particular gene is through steric hindrance which is applicable to any cell type. RNA and DNA target sites suitable for conventional antisense oligo attack of this type include (1) primary and secondary translational start sites; (2) 5'-end untranslated sites involved in ribosomal assembly; and (3) sites involved in the splicing of pre-mRNA. A primary translational start site is the one most often used by a particular cell or tissue type. A secondary translational start site is one that is used less often by a particular cell or tissue type. The use of the latter may be determined by natural cellular processes or may be the result of inhibition of the use of the primary translational start site such as would occur when the such cells are treated with an oligo directed to the primary translational start site in question. Thus, when taking this approach, the complete inhibition of the expression of a particular gene could require the use of two or more oligos where one is directed to the primary translational start site and one or more additional oligos are directed to secondary translational start sites.

Oligo backbone configurations that demonstrate particularly high binding affinities to the target (measured by melting temperature or Tm) are preferred for implementing the steric hindrance mechanism. LNA, FANA, 2'-fluoro, morpholino and piperazine containing backbones are particularly well suited for this purpose. Most preferred are 22-mer 2'fluoro oligos with phosphorothioate linkages throughout as illustrated below. The "x"s represent different bases (A, G, U/T or C) that are part of a series of linked nucleosides with 2'fluoro modifications to the sugar. The ~ symbol represents nuclease resistant linkages, such as phosphorothioate, phosphordiaminidate, boranophosphate and others well know in the art. In RNA analogs 2'fluoro oligos typically, but not necessarily, are produced with uracil rather than thymine bases.

5'-X~X~X~X~X~X~X~X~X~X~X~X~X~X~X~X~X~X~X~X~X~X-3'

Phosphorothioate linkages typically lead to a reduction in binding affinity with the target RNA but they may improve pharmacokinetics of an oligo by causing it to bind to plasma proteins. The potential pharmacokinetic advantages provided by these linkages, however, are not necessary in the case of backbones containing morpholino or piperazine substitutions for the sugar.

In the case of oligos with other nucleoside chemistries and linkages than phosphorothioate, or boranophosphate, plasma protein binding, however, can be improved by covalently attaching to it, or to a carrier associated with it, a molecule that binds a plasma protein such as serum albumin. Such molecules include, but are not limited, to an arylpropionic acid, for example, ibuprofen, suprofen, ketoprofen, pranoprofen, tiaprofenic acid, naproxen, flurpibrofen and carprofen (U.S. Pat. No. 6,656,730).

oligo functions requiring this activity. Stem cells and early progenitor cells have adequate levels of RNase H for this purpose while cells that have differentiated beyond the stem or progenitor cell stage typically do not. When functional, however, oligos that support the RNase H based mechanism have the potential advantage over steric hindrance based mechanism of working catalytically since the same oligo is capable of inactivating numerous target RNA molecules. As discussed elsewhere herein, it is also possible to modify LNA, FANA, 2'-fluoro, morpholino and piperazine containing backbones to enable or increase their potential to catalyze the cleavage of their target RNA by RNase H by inserting certain linkers, acyclic nucleosides or by using the gapmer approach. Thus, conventional antisense oligos with both potent steric hindrance and RNase H promoting activity can be generated and used for the practice of this invention.

TABLE 1

Reconfiguration of Guide Strands For Use As Conventional Antisense Oligos

POTENTIAL FEATURES OF GUIDE STRAND TO BE MODIFIED

| AS OLIGO MECHANISM | URACIL THYMINE | HAIR PIN | MISMATCHES WITH GENE TARGET | RNase H SUPPORTING DESIGN | OVER HANGS |
|---|---|---|---|---|---|
| RNase H | Thymine required in RNase H supporting region | Not required for nuclease resistance | Preferably removed | Required | Preferably removed |
| Double-stranded RNase | Uracil required in double strand RNase supporting region | Required when double strand RNase supporting region is not nuclease resistant | Preferably removed | Not required | Preferably removed unless involved in generating a potential hair pin where one is required |
| Steric Hindrance | Uracil preferred for RNA or RNA-analogs - Thymine preferred for DNA or DNA-analogs | Not required for nuclease resistance | Preferably removed | Not required | Preferably removed |

Morpholino oligos are commercially available from Gene Tools LLC. Morpholino oligo characteristics and synthesis include but are not limited to those presented in the following: Summerton and Weller, Antisense Nucleic Acid Drug Dev 7: 187, 1997; Summerton, Biochim Biophys Acta 1489: 141, 1999; Iversen, Curr Opin Mol Ther 3: 235, 2001; U.S. Pat. Nos. 6,784,291, 5,185,444, 5,378,841, 5,405,938, 5,034,506, 5,142,047, 5,235,033. Morpholino oligos for the purposes of the present invention may have the uncharged and/or at least one cationic linkage between the nucleoside analogs made up of a morpholino ring and a normal base (guanine, uracil, thymine, cytosine or adenine) or a unnatural base as described herein. The preferred linkage for morpholino oligos is phosphorodiamidate which is an uncharged linkage. In some embodiments it may be modified as discussed below to provide a positive charge.

Since the steric hindrance mechanism is not dependent on RNase H activity, oligos which function via this mechanism have the potential to be active in cells where RNase H levels are too low to adequately support conventional antisense E. Methods for Design, Production and Synthesis of the Oligos of the Invention Any functional double strand dicer substrates or single or double strand siRNA sequences can be used for the practice of this invention. They may be found in the prior art (such as but not limited to those described in PCT/US09/02365) or may be designed using the design parameters set forth herein. Reconfiguration of a number of specific sequences is exemplified herein. Most commonly such functional RNAi will inhibit the expression of the target gene by causing the degradation of its RNA transcripts. Alternatively, RNAi can also promote translation arrest or directly inhibit the expression of the target gene. The examples and illustrations provided involve siRNA but it is to be understood that such siRNA may be derived from dicer substrates that will be processed to the siRNA form by intracellularly. It is also to be understood that the antisense strands in the designs provided for use in the present invention can also be used as ss-siRNA which are up to 30-mers in length in contrast to double stranded RNAi longer than 23-24mers in length that are shortened by an enzyme before being loaded into RISC. Most preferred are compounds that meet the design requirements provided herein that allow for in vivo administration of the individual strands of a complementary sense and antisense oligo pair according to the two-step administration method. Employment of the two-step method, particularly when combined with the design principles provided herein, can be used to increase cellular uptake and effectiveness when compared to the single step administration method of conventional duplexed siRNA.

Modifications:

The basic requirements primarily to be considered for compositions of matter suitable for use in the present invention are (1) the individual oligo strands of the agents must be sufficiently stable with respect to nuclease attack that they have the potential to fulfill their intended intracellular RNAi function; and (2) any modifications made to the native RNA structure must be consistent with the maintenance of the RNAi function. The three principle factors that affect nuclease resistance of individual strands are the following: (1) the chemical structure of the nucleoside particularly with respect to the ribose: (2) the nature of the internucleoside linkages; and (3) the presence or absence of a hair pin.

The problem of nuclease degradation of individual oligo strands can have somewhat different solutions depending on whether the agents are to be used in vitro or in vivo and whether or not a carrier will be used as carriers often provide a degree of protection from nucleases.

The general problem of achieving such single strand nuclease resistance without the loss of the intended intracellular RNAi activity is consistent between in vitro vs. in vivo use but the degree of the problem is affected by parameters such as the following: (1) which strand is being modified (antisense vs. sense); (2) strand length; (3) the binding affinity (Tm) of the terminal 4 nucleosides of each end of the antisense strand (exclusive of any over hang) with the corresponding nucleosides of the sense strand in the case of compounds designed to produce intracellular double stranded RNAi with blunt ended or conventional overhangs (this language is meant to exclude designs where the sense strand does not extend far enough to pair with both ends of the antisense strand); and (4) the positioning of any covalently linked carriers or carrier components with respect to the oligos.

Pharmacokinetics is also an important consideration for in vivo use, however, the agents described for use with the present invention will not have dramatically different pharmacology from conventional antisense oligos except for those agents where a carrier is employed. Accordingly the structural variants discussed below will not require the development of fundamentally new pharmacologic principles.

One key consideration with respect to the chemical modification of oligos designed to produce an intracellular double stranded RNAi agent and the promotion of its RNAi activity is the relative Tms of the four adjacent nucleosides on each end of the duplex. The lower the relative Tm of one end with respect to the other, the higher the likelihood that the strand with its 5'-end involved in the lower Tm will be loaded into RISC and function as the guide strand. The Tm effect is not evenly distributed across the four terminal nucleosides because the most terminal is the most important with the successive nucleosides being progressively less important. Violations to this rule do not render a particular siRNA non functional but they may exhibit suboptimum activity because there will be more passenger strand loading into RISC and/or off-target effects may occur.

Thus, nucleosides and/or linkage modifications to complementary sense and antisense oligos that affect the terminal four nucleotides of either end of a resulting double strand RNAi agent must also be designed such that the loading of the desired antisense stand into RISC is promoted over loading of the intended sense strand. With respect to the naturally occurring bases G-C pairs on opposing strands bind more tightly than A-U pairs. Tms can be decreased through the use of mismatches, universal bases and abasic nucleosides. Tms are also affected by the nature of the linkages that bind nucleosides together. These factors are well known in the art.

A ranking of relative affinities between nucleosides from higher to lower typically has the following order: (1) 2'-fluoro/2'-fluoro; (2) 2'-fluoro/2'-O-methyl; (3) 2'-fluoro/native ribose; (4) 2'-O'methyl/native ribose; (5) 2'-O'methyl/2'-O-methyl. Variations can occur as a result of the nature of the adjacent nucleosides.

The relative Tms of the two duplexed ends of an siRNA weighted for nucleotide position can be determined as follows: (1) prepare a full length dsRNA duplex along with additional duplexes that are missing 1, 2, 3 or 4 nucleosides from either the left side or right side as shown in Prototype 1; (2) determine the change in Tm for each deletion compared to the full length siRNA; (3) weight the Tm contribution of each of the four nucleosides by multiplying the outer most by 4 the next by 3 the next by 2 and the last by 1.5 and then adding the totals; (4) the total Tm for the left side should be at least 4 degrees Centigrade higher than the total for the right side as shown in Prototype 1; and (5) make any needed adjustments in the nucleosides to achieve this asymmetry in Tm. The latter can be achieved in a number of ways as discussed herein but most preferred are changes in the distribution of 2'-fluoro and 2'-O-methyl nucleosides among the terminal four nucleosides on each end as shown in Prototype 1. Any of the novel compounds described herein, including those shown in FIGS. 3-40 may optionally comprise cytosines methylated at the C5 position.

Prototype 1: Tm of Opposing Ends of Double Stranded siRNA

```
16-24-mer dsRNA
5' I-I-I-I-N-I-I-I-I-I-I-I-I-I-I-I 3'

3' I-I-I-I-N-I-I-I-I-I-I-I-I-I-I-I 5'
   Higher Tm                Lower Tm
```

Where:
1) the upper strand is the passenger strand (lower Tm between its 5'-end and 3'-end of the lower guide strand compared to Tm of other end);
2) I is an individual nucleoside;
3) a dash (-) is an internucleoside linkage;
4) N is a number of nucleosides between 0 and 10 depending on the selected strand length (16-24-mer) and where the number represents additional nucleosides in the passenger and guide strands
5) the nucleosides involved in the guide strand selection process (as described in the text) are shown in bold and italics
6) The addition of 1 to 4 nucleoside 5'-end or 3'-end overhangs found in some siRNA designs do not alter the preferred design illustrated in this Prototype. The composition of these overhangs does not affect the Tm requirements for the terminal duplexed regions illustrated here. Accordingly, it follows from this that in the reconfiguring of existing siRNA compounds with low Tm nucleosides (A and U) at the 3'-end of the guide stand that are adjacent to high Tm nucleosides (G and C), for example, can be converted to overhangs by deleting any corresponding low Tm nucleosides in the passenger strand so that the high Tm nucleosides are now the terminal duplexed nucleosides at the left end of the compound. Similar maneuvers can be performed on the right end of the compound, for example, where there are high Tm nucleosides (G and C) at the 3'-end of the passenger stand or 5'-end of the guide strand that are adjacent to low Tm nucleosides (A and U). This high Tm duplex can be eliminated by converting the high Tm nucleosides in one of the strands to overhangs by deleting the corresponding nucleosides in the other strand so that the low Tm nucleosides make up the terminal duplex at the right end of the compound.

7) The effect of this design is to increase the proportion of intended guide strands that get loaded into RISC. There are other designs described herein that have the same goal. The designs shown in Prototype 8, for example, reduce the importance of the design consideration shown here.

Another key consideration with respect to the chemical modification of antisense oligos intended to function as guide strands is the position of the two nucleosides that will be adjacent to the argonaute 2 cleavage site of the target RNA (Prototype 2). These nucleosides are in positions 10 and 11 counting downstream from the 5'end of the guide strand (shown in bold in Prototype 2). Some modifications that can be tolerated other places in the guide strand or in the passenger strand are not well tolerated at this site or in the one to three adjacent nucleosides and the associated linkages on each side (underlined region in Prototype 2 that delineates 8 nucleosides and 7 linkages) with the nature of the proximal nucleosides and linkages (to the two in italics) having the most impact on the level of Argonaute 2 activity. The positions of these most sensitive sites are nucleotides 9-12 (shown in italics in Prototype 2) counting from the 5'end and their linkages. This is illustrated in the following diagram for 16-23-mers. Longer RNAi guide strands are generally limited to dicer substrates so they will be shortened by intracellular processes such that the resulting siRNA will be 21-23-mers or possibly to ss-siRNA. Ss-siRNA will have the design considerations shown in Prototype 2 while double stranded siRNA will have the design considerations in both Prototypes 1 and 2 except the double stranded siRNA designs shown in Prototype 8 and those described in Designs 1b, 2b and 3b will not have the design considerations shown in Prototype 1 (see detailed description of Prototype 8). The designs shown in Prototype 8 are most preferred for converting conventional antisense oligos to RNAi compounds because it simplifies the design constraints illustrated in Prototype 1. All of the single and double stranded siRNA designs provided herein are compatible with the hair pin designs shown in Prototypes 3 and 4.

Prototype 2: Guide Strand Regions Adjacent to Argonaute 2 Cleavage Site

```
16-24-mer
5' I-I-I-I-I-I-I-I-I-I-I-I-I-I-I-N 3'
``` where:
1) I is an individual nucleoside;
2) dash (-) is an internucleoside linkages;

3) N=0 to 10 depending on the guide strand length where the number represents additional nucleosides (in the case of ss-siRNA N=0-15 for the guide strand);
4) the nucleosides adjacent to the argonaute 2 cleavage site are shown in bold and italics while the adjacent two nucleosides are shown in italics only;
5) the nucleotides and linkages that can effect the activity of argonaute 2 are underlined (see Prototype 2). This region requires special consideration in the design of chemically modified RNAi as discussed elsewhere herein Hair pins can be designed into oligos in a way that both promotes nuclease resistance and allows for subsequent RNAi functioning for dicer substrates, double stranded siRNA and ss-siRNA (Prototypes 3 and 4). This approach can be applied to either the sense or the antisense stand, to both or to neither. It can also be applied to ss-siRNA.

The hair pin approach allows a greater range of chemical modifications to the 6 nucleosides adjacent to the argonaute 2 cleavage region and to the linkages between these nucleosides. Specifically, the nuclease protection provided by the hair pin allows the chemical modifications to the 6 underlined nucleosides and their linkages (Prototype 2) to have a lower degree of nuclease resistance than would be the case without the hair pin design. Accordingly, considering the two strands of an intended RNAi duplex, the hair pin approach is most preferred for the antisense strand.

The higher affinity of the guide strand with its target and/or passenger strand compared to its self-interaction in the form of the hair pin provided for herein allows this approach to work. Such hair pins are most preferred for oligoribonucleotides with more than two phosphodiester linkages that are to be systemically administered without the use of a protective carrier.

In one version of this approach the guide or passenger strand sequence can be selected such that it forms a hair pin under physiologic conditions (pH, salt concentration and temperature) with the desired thermodynamic (free energy or Tm) properties (Prototype 3). This design, however, substantially reduces the number of suitable guide strand binding sites for any given gene target.

Prototype 3: General Hair Pin Design for Individual siRNA Strand Stabilization to Nuclease Attack

```
8-24-mer
5' W-A-X-B-I-I-N-I-I-C-Y-D-Z 3'
```

Where:
1) The strand illustrated is either a passenger or a guide strand that will form a double or single stranded siRNA; while this design can be applied to strands with overhangs these are specifically considered in Prototype 4;
2) I is an individual nucleoside;
3) A is a nucleoside capable of base pairing with nucleoside D and nucleoside B is capable of base pairing with nucleoside C;
4) X and Y represent equal numbers of nucleosides (possibly 0) such that the pairings A:D and B:C can contribute to the formation of a hair pin under physiological conditions (other base pairs can also contribute to the formation of the hair pin Prototype and may be necessary in order to meet the free energy requirement described herein);
5) W, N and Z are represent numbers of nucleosides where they are not necessarily equivalent numbers (and may be zero) such that when they are added together with all the other nucleosides in the oligo, the result is a total number between 8 and 24 where in the case of guide strands, the length will be at least 16; In the case of single passenger strands they will have a length of 12 or greater with shorter passenger strands being limited to those continuous passenger strands described in. Designs 1b, 2b and 3b.

6) In the case of guide strands a limited number of mismatches with the sequence of the gene target can be tolerated in certain regions of the strand. Such mismatches with the target can be used to obtain a strand with the desired hair pin characteristics. As shown in Prototype 2 nucleosides 10 and 11 counting from the 5' end lie opposite the argonaute 2 cleavage site on the gene target RNA sequence. These nucleosides cannot have mismatches with the target and it is preferred that there be no mismatches in any of the five nucleosides on either side of these. It is also preferred that no more than one-third of the remaining nucleosides in the guide strand have mismatches with the gene target.

7) there are preferably no linkages, such as phosphodiester, that are susceptible to exonuclease attack that extend beyond the hair pin particularly where the RNAi is being used in vivo and/or where there is no carrier that provides protection from nucleases Greater flexibility (more gene target binding site choices) can be achieved by adjusting the one or more of the bases in the terminal 1-5 bases on the 5' or 3' ends of a given passenger or guide strand with up to 4 mismatches total (for both ends of the oligo) with the binding site for the target are allowed and where the result is that such changes result in the formation of a hair pin with the properties described herein. In general, the shorter the duplex the shorter the length of the terminal region that will tolerate mismatches with the target binding site. Thus, no more than two such terminal nucleosides with such mismatches are preferred for a 19-mer duplex and 5 for a 22-mer or larger duplex with no more than a total of 4 of such mismatches. Accordingly no mismatches of this type should occur in the central 14 (even numbered oligos) or 15 (odd numbered oligos) nucleosides if the objective is to achieve cleavage of the target. Mismatches in this area can lead to translational arrest of targeted mRNA or to inhibition of gene expression at the transcriptional level. For the large majority of applications cleavage of target RNA is preferred due to its catalytic nature and the lack of direct attack on the encoding gene.

Such adjustments to the ends of oligos so that they can form siRNA duplexes can be achieved without consideration of the sequence of the guide strand binding site on the gene target. This approach is limited by the need to make corresponding adjustments in the partner strand (so that complementary base pairing between the duplex partners is maintained) in any double stranded RNAi and by the design consideration illustrated in Prototype 1 above.

The greatest flexibility with this approach in the case of designs for double stranded siRNA with a 3'-end overhang design (involving 1-5 nucleosides in the overhang with 2 or 3 being most preferred) is illustrated in Prototype 4. Since the nature of the bases in an overhang is irrelevant to siRNA function per se they can be selected to form a hair pin with the desired characteristics in either or both of the component strands. In a variant of this design, an overhang used in the formation of a hair pin can involve the 5'end although 3' overhangs are preferred. Although ss-siRNA does not have overhangs per se the related hair pin design considerations regarding overhangs can still be applied to ss-siRNA because 5' and 3' end nucleoside mismatches with the binding site in the gene target can be tolerated in ss-siRNA as well as in double stranded siRNA.

In yet another variant, the formation of a hair pin involving either 5' or 3' overhangs can be further supported by adjustments to one or more of the bases in the terminal 1-5 bases on the 5' or 3' ends as described above where the terminal bases are not in any overhang but are involved in the duplex formation between the passenger and guide strands. In the case of 5' overhangs in a guide strand, however, the number of nucleosides in the overhang that are to be included in the count determines which nucleosides will be adjacent to the argonaute 2 cleavage site (as shown in Prototype 2 and elsewhere herein).

Hair pins suitable for use in the present invention exhibit negative free energy ranges of 2-15 kcal/mol. As a rule of thumb, the negative free energy of the hair pin is preferred to be no more than one third of the negative free energy of the binding of the strand to its partner strand. The free energy of hair pins can be adjusted in several ways including but not limited to the following: (1) the proportion of G:C vs. A:U base pairings involved in forming the hair pin (T may replace U in an overhang) with the former pairing providing the higher free energy; and (2) the selection of the nucleoside chemistry as described herein, for example, 2' fluoro modified nucleotides have a higher free energy of binding with the target RNA than 2'-O-methyl modified ribonucleotides.

Prototype 4: Overhang Hair Pin Design for Individual siRNA Strand Stabilization to Nuclease Attack A) Illustrated with Two Overhangs on Each Strand

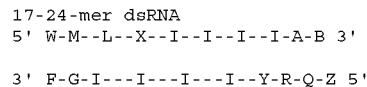

B) Illustrated with Five Overhangs on Each Strand

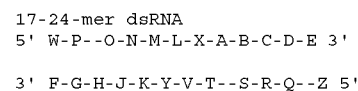

Where:
1) The top strand is a passenger strand and the bottom strand is a guide strand;
2) I is an individual nucleoside;
3) A, B, C, D and E are passenger strand overhangs that respectively pair with L, M, N, O and P;
4) W is some number of nucleosides that may be zero;
5) the passenger strand has at least one over hang A and as many as five A-E;
6) X is some number of nucleosides that gives a sum of at least 4 when added to the number of nucleosides represented by I (so X can be 0 in the top illustration and it must be at least 4 in the bottom illustration);
7) all of the nucleotides in the passenger strand add up to a number between 17 and 24 where at least 16 nucleotides are not over hangs;
8) nucleosides in the passenger strand that are not found in overhangs also may contribute to the formation of the hairpin under physiologic conditions by pairing with another nucleoside that is also not in a hairpin;
9) F, G, H, J and K are passenger strand overhangs that respectively pair with Q, R, S, T and V;
10) Z is some number of nucleosides that may be zero;

11) the guide strand has at least one over hang F and as many as five F-K; Y is some number of nucleosides that gives a sum of at least 4 when added to the number of nucleosides represented by I (so Y can be 0 in the top illustration and must be at least 4 in the bottom illustration);
12) all of the nucleotides in the guide strand add up to a number between 17 and 24 where at least 16 nucleotides are not over hangs;
13) nucleosides in the guide strand that are not found in overhangs also may contribute to the formation of the hairpin under physiologic conditions by pairing with another nucleoside that is also not in a hairpin;
14) the passenger and guide strands for a given siRNA may have different numbers of nucleosides in their overhangs;
15) there are preferably no linkages, such as phosphodiester, that are susceptible to exonuclease attack that extend beyond the hair pin particularly where the RNAi is being used in vivo and/or where there is no carrier that provides protection from nucleases;
16) not every base in an overhang must pair with another base that is in the oligo but it is preferred that they do with a limited number of exceptions e.g., when adjusting the binding affinity of the hair pin so that it fits within the preferred free energy range and avoiding runs of guanines that are greater than three;
17) In the case of guide strands and excluding the 3' overhangs described for this design (these need not base pair with the gene target) a limited number of mismatches with the sequence of the gene target can be tolerated in certain regions of the strand. Such mismatches with the target can be used to obtain a strand with the desired hair pin characteristics. As shown in Prototype 2 nucleosides 10 and 11 counting from the 5' end lie opposite the argonaute 2 cleavage site on the gene target RNA sequence. These nucleosides cannot have mismatches with the target and it is preferred that there be no mismatches in any of the five nucleosides on either side of these. It is also preferred that no more than one-third of the remaining nucleosides in the guide strand have mismatches with the gene target.
18) one or more contiguous dashes (-, -- or ---) represent single linkages between nucleosides.

Modifications for In Vitro Use:

For in vitro applications, native RNA structures may be used in the practice of the present invention. At least some modifications to provide protection from nuclease attack are desirable. Such modifications are the same as those described herein for in vivo use, however, they can be reduced in number. So, for example, rather than all the nucleotides outside the region adjacent to the argonaute 2 cleavage site comprise 2'-ribose modifications, a smaller number may be so modified. As another example, rather than having all the linkages outside the region adjacent to the argonaute 2 cleavage site be boranophosphates some smaller number may be so modified.

Modifications for In Vivo Use:

The preferred complementary sense and antisense oligos intended for use in the present invention produce double stranded RNAi agents that are 16-21-mers without 3'-overhangs or 5'-phosphates added to the guide strand terminal ribose sugar. These are illustrated below as 18-mers. The corresponding shorter or longer oligos will simply have longer or shorter 3'-ends on the intended guide strand where the sequence for the added nucleotides is determined by the RNA target with a corresponding increase or decrease in the 5'-end of the passenger strand. As discussed elsewhere herein these length changes do not affect the position of the nucleosides in the guide strand that are adjacent to the argonaute 2 cleavage site for the target RNA.

The preferred ss-siRNA are 19-23-mers and have the designs shown in Prototypes 9, 10 and 11 where 20-mers are illustrated. As for dsRNA the changes in length come at the 3'-end and follow the target sequence according to the principles of complementary base pairing. These are illustrated as 20-mers.

The preferred oligos have the following modifications in various configurations often in combination with native RNA nucleosides or phosphodiester linkages: (1) 2'-fluoro or 2'-O-methyl modifications of the ribose sugar; and (2) boranophosphate linkages. In the case of the 2'fluoro modification, it is understood that the fluorine has the same stereochemical orientation as the hydroxyl in ribose. (In instances where the fluorine has the opposite orientation, the associated nucleoside will be referred to as FANA or 2'-deoxy-2'fluoro-arabinonucleic acid). Other modifications, as described elsewhere herein are also suitable for use in the present invention but they are less preferred.

The key to the design illustrations is as follows: I represents an individual nucleotide; a dash - represents an internucleoside linkage; an underline extending under multiple nucleosides and their linkages indicates the nucleosides adjacent to the argonaute 2 cleavage site and the continuous nucleosides singled out for special consideration as provided for below. The passenger strands are shown on the top and the guide strands on the bottom. Special features of each design are presented with the corresponding illustration. For longer or shorter dsRNA the strands are extended or shortened by adding to the 3'-end of the guide strand and the 5'-end of the passenger strand. In any case the nucleosides shown in italics on the left ends remain at the ends although the associated sequences will change.

Prototype 5: Design #1 for Double Stranded siRNA

```
16-24-mer siRNA
5' I-I-I-I-N-I-I-I-I-I-I-I-I-I-I 3'

3' I-I-I-I-N-I-I-I-I-I-I-I-I-I-I 5'
```

Features of Design #1a:
1) This Design is most suitable for use with a carrier that provides nuclease resistance to the strand and/or with the hair pin approach for increasing nuclease resistance as disclosed herein.
2) The terminal 4 nucleosides in each strand (shown in italics) are made up of 2'-fluoro or 2'-O-methyl modified nucleosides or a combination of 2'-fluoro, 2'-O-methyl modified nucleosides and possibly including native nucleosides meeting the criteria illustrated in Prototype 1 and discussed in the associated text. 2%-O-(2-methoxyethyl) modified ribose can also be used in combination with one or both of these other ribose analogs or native ribose. Native nucleosides are preferably not used in the terminal positions. Other nucleosides, such as LNA or FANA may be used as described elsewhere herein but 2'-fluoro and 2'-O-methyl are preferred.
3) The underlined nucleosides and linkages in the guide strand (see Prototype 2) preferably have one of the following alternating configurations: (a) 2'-fluoro with 2'-O-methyl with no more than 3 contiguous nucleosides having the same type of 2'-moiety with contiguous nucleotides not being identical most preferred; (b)

2'-fluoro with native RNA nucleotides with no more than 3 contiguous nucleosides having the same type of 2'-moiety with contiguous nucleotides not being identical most preferred unless they are native ribose; or (c) 2'-O-methyl with native RNA nucleotides with no more than 3 contiguous nucleosides having the same type of 2'-moiety with contiguous nucleotides not being identical most preferred unless they are native ribose.

4) Preferably, the rest of the ribonucleotides in the guide or passenger strand are 2'-fluoro, 2'-O-(2-methoxyethyl) and/or native ribose. The exact mix can be adjusted to increase or decrease the overall Tm of the duplex and the Tm of the guide strand with its RNA target. Higher Tms for the guide strand with its target are preferred. Native ribose is preferably not used in terminal nucleosides and preferably there are no more than 3 contiguous native ribose containing nucleosides. Other nucleosides such as locked nucleic acids (LNA) and FANA can be used as described elsewhere herein. A minority of deoxyribonucleosides can be used in the passenger strand.

5) The linkages in both strands are phosphodiester

6) N represents some number of nucleosides between 0 and 8 and when 0 in the guide strand the next nucleoside downstream is considered to be underlined for the purposes of understanding the design Features of Design #1b:

In a variant of Design 1 a above, the passenger strand is missing one of the central linkages such that it occurs as two continuous oligos. Each of these oligos must have a Tm of at least 40 degrees Centigrade with the corresponding section of the guide strand. The Tm can be increased by using more 2'-fluoro modified nucleosides or other nucleosides discussed elsewhere herein such as LNAs. Any such adjustments for Tm considerations in the terminal 4 nucleosides of the duplex must continue to respect the principles illustrated in Prototype 1 and discussed in the associated text.

Prototype 6: Design #2 for Double Stranded siRNA

```
16-24-mer siRNA
5' I-I-I-I-N-I--I--I--I--I-I-I-I-I-I-I 3'

3' I-I-I-I-N~I~I~I~I~I-I-I-I-I-I-I-I 5'
```

Features of Design #2a:

1) The terminal 4 nucleosides in each strand (shown in italics) are made up of 2'-fluoro or 2'-O-methyl modified nucleosides or a combination of 2'-fluoro, 2'-O-methyl and/or native ribonucleosides organized as shown in Prototype 1 and as discussed in the associated text. 2'-O-(2-methoxyethyl) modified ribose can also be used in combination with one or both of these other ribose analogs or native ribose. Native nucleosides are preferably not used in the terminal positions. Other nucleosides, such as LNA or FANA may be used as described elsewhere herein but 2'-fluoro and 2'-O-methyl are preferred.

2) The underlined nucleosides in the guide strand (see Prototype 2) have one of the following alternating configurations: (a) 2'-fluoro with 2'-O-methyl with no more than 3 contiguous nucleosides having the same type of 2'-moiety with contiguous nucleotides not being identical most preferred; (b) 2'-fluoro with native RNA nucleotides with no more than 3 contiguous nucleosides having the same type of 2% moiety with contiguous nucleotides not being identical most preferred unless they are native ribose; or (c) 2'-O-methyl with native RNA nucleotides with no more than 3 contiguous nucleosides having the same type of 2'-moiety with contiguous nucleotides not being identical most preferred unless they are native ribose. Added nuclease protection for this region of the guide strand may be obtained by use of a hair pin design as described herein. This approach allow for a greater use of native ribose in this region.

3) Preferably, the rest of the ribonucleotides in the guide or passenger strand are 2'-fluoro, 2'-O-methyl, 2'-O-(2-methoxyethyl) and/or native ribose. The exact mix can be adjusted to increase or decrease the overall Tm of the duplex and the Tm of the guide strand with its RNA target. Higher Tms for the guide strand with its target are preferred. Native ribose is preferably not used in terminal nucleosides and preferably there are no more than 3 contiguous native ribose containing nucleosides. Other nucleosides such as LNA and FANA can be used as described elsewhere herein. A minority of deoxyribonucleosides can be used in the passenger strand.

4) Single or multiple dashes represent either boranophosphate or phosphodiester linkages.

5) The linkages in the guide strand are a mixture of boranophosphate and phosphodiester according to the following scheme; (a) no more than three of the five linkages indicated by the symbol ~ in the guide strand can be boranophosphate with the Sp stereoisomer configuration being most preferred and no more than two can be contiguous; Added nuclease protection for this region of the guide strand may be obtained by use of a hair pin design as described herein. Such an approach allows for the greater use of phosphodiester linkages in this region; (b) The majority of the linkages outside the underlined sequence in the guide strand will be boranophosphate with all of them being boranophosphate being most preferred.

6) The linkages in the passenger strand are preferentially boranophosphate although they may be phosphorothioate or a mixture that includes no more than three contiguous phosphodiester linkages. These phosphorothioate linkages can consistently have the Sp or Rp stereochemistry, be a mixture of Sp and Rp or be phosphorodithioate.

7) N represents some number of nucleosides between 0 and 8 and when 0 in the guide strand the next nucleoside downstream is considered to be underlined for the purposes of understanding the design The frequency of boranophosphate linkages and certain other parameters depend, in part, on the synthesis method for establishing boranophosphate linkages as discussed herein.

Features of Design #2b:

In a variant of design #2 above, the passenger strand is missing one of the central linkages such that it occurs as two continuous oligos. Each of these oligos must have a Tm of at least 40 degrees Centigrade with the corresponding section of the guide strand. The Tm can be increased by using more 2'-fluoro modified nucleosides or other nucleosides in either strand as discussed elsewhere herein (such as the use of locked nucleic acids). Any such adjustments for Tm considerations in the terminal 4 nucleosides of the duplex must continue to respect the principle illustrated in Prototype 1 and discussed in the associated text.

Prototype 7: Design #3 for Double Stranded siRNA

```
16-24-mer siRNA
5' I-I-I-I-N--I-I---I---I-I-I-I-I-I-I 3'
3' I-I-I-I-N~I~I~I~I-I-I-I-I-I-I-I 5'
```

Features of Design #3a:
1) The terminal 4 nucleosides in each strand (shown in italics) are made up of 2'-fluoro or 2'-O-methyl modified nucleosides or a combination of 2'-fluoro, 2'-O-methyl and/or native ribonucleosides organized as shown in Prototype 1 and as discussed in the associated text. 2'-0-(2-methoxyethyl) modified ribose can also be used in combination with one or both of these other ribose analogs or native ribose. Native nucleosides are preferably not used in the terminal positions. Other nucleosides, such as LNA or FANA may be used as described elsewhere herein but 2'-fluoro and 2'-O-methyl are preferred.
2) The underlined nucleosides in the guide strand (see Prototype 2) have one of the following alternating configurations: (a) 2'-fluoro with 2'-O-methyl with no more than 3 contiguous nucleosides having the same type of 2'-moiety with contiguous nucleotides not being identical most preferred; (b) 2'-fluoro with native RNA nucleotides with no more than 3 contiguous nucleosides having the same type of 2'-moiety with contiguous nucleotides not being identical most preferred unless they are native ribose; or (c) 2'-O-methyl with native RNA nucleotides with no more than 3 contiguous nucleosides having the same type of 2'-moiety with contiguous nucleotides not being identical most preferred unless they are native ribose. Added nuclease protection for this region of the guide strand may be obtained by use of a hair pin design as described herein. This approach allow for a greater use of native ribose in this region.
3) Preferably, the rest of the ribonucleotides in the guide or passenger strand are 2'-fluoro, 2'-O-methyl, 2'-O-(2-methoxyethyl) and/or native ribose. The exact mix can be adjusted to increase or decrease the overall Tm of the duplex and the Tm of the guide strand with its RNA target. Higher Tms for the guide strand with its target are preferred. Native ribose is preferably not used in terminal nucleosides and preferably there are no more than 3 contiguous native ribose containing nucleosides. Other nucleosides such as LNA and FANA can be used as described elsewhere herein. A minority of deoxyribonucleosides can be used in the passenger strand.
4) Single or multiple dashes represent either phosphorothioate or phosphodiester linkages.
5) The linkages in the guide strand are a mixture of phosphorothioate and phosphodiester according to the following scheme; (a) no more than three of the five linkages indicated by the symbol ~ in the guide strand can be phosphorothioate with the Sp stereoisomer configuration being most preferred and no more than two can be contiguous; Added nuclease protection for this region of the guide strand may be obtained by use of a hair pin design as described herein. This approach allow for a greater use of phosphodiester linkages in this region; (b) The majority of the linkages outside the underlined sequence in the guide strand will be phosphorothioate with all of them being phosphorothioate being most preferred. These phosphorothioate linkages can consistently have the Sp or Rp stereochemistry, be a mixture of Sp and Rp or be phosphorodithioate.
6) The linkages in the passenger strand are preferably a phosphorothioate plus phosphodiester mixture that includes no more than three contiguous phosphodiester linkages and a predominance of phosphorothioates in the terminal five linkages on both ends of the strand.
7) N represents some number of nucleosides between 0 and 8 and when 0 in the guide strand the next nucleoside downstream is considered to be underlined for the purposes of understanding the design.

Features of Design #3b:
In a variant of design #2 above, the passenger strand is missing one of the central linkages such that it occurs as two continuous oligos. Each of these oligos must have a Tm of at least 40 degrees Centigrade with the corresponding section of the guide strand. The Tm can be increased by using more 2'-fluoro modified nucleosides or other nucleosides in either strand as discussed elsewhere herein (such as the use of locked nucleic acids). Any such adjustments for Tm considerations in the terminal 4 nucleosides of the duplex must continue to respect the principle illustrated in Prototype 1 and discussed in the associated text.

Prototype 8: Design #4 for Double Stranded siRNA
16-24-Mer Guide Strand siRNA
Features of Design 4a:

```
5' A-I--I-I-I-X--I-I-I-I-B 3'
3' I-I-I-I-Y-I-I-I--I---I-I-I-I--I-I-I 5'
```

Features of Design 4b and 4c:

```
16-24-mer guide strand siRNA
5' A-I--I---I-I-X-I-I-I-I-B 3'
3' I-I-I-I-Y~I~I~I~I-I-I-I-I--I-I-I 5'
```

Where for Designs 4a, 4b and 4c:
1) the top strand is the passenger strand and the bottom strand is the guide strand;
2) one or more contiguous dashes (- or --) or waves (~) represent internucleoside linkages;
3) I represents a nucleoside;
4) A, B, X and Y each represent some number of nucleosides (the number may be zero) where the sum of A plus X plus B plus the number of nucleosides represented by the letter I add up to a sum number between 12 and a larger number which is two less than the length of the guide strand (a sum of 14 or is preferred with 15 being most preferred);
5) Y is some number between zero and 8;
6) "A" represents a number of nucleosides such that the 3' end of the guide strand has at least 1 and as many as 7 nucleosides that are not paired with nucleosides in the passenger strand;
7) "B" represents a number of nucleosides such that the 5' end of the guide strand has at least 1 and as many as 5 nucleosides that are not paired with nucleosides in the passenger strand;
8) designs involving hair pins can be applied to either or both the passenger and/or guide strands;
9) the Tm rules described in Prototype 1 and the related text do not apply here if there are two or more nucleosides overhangs extending from both ends of the guide strand if there are one or two nucleosides in these overhangs then the number of duplexed nucleosides that are relevant (4 terminal nucleosides in Prototype 1) are reduced to 3 or 2 respectively;

10) the passenger strand and the guide strand can be but are not necessarily stabilized by one of the hair pin designs as described herein;

Where for Design 4a:
1) This design is most suitable for use with a carrier that provides nuclease resistance to the strand and/or with the hair pin approach disclosed herein.
2) The underlined nucleosides in the guide strand (see Prototype 2) have one of the following alternating configurations: (a) 2'-fluoro with 2'-O-methyl with no more than 3 contiguous nucleosides having the same type of 2'-moiety with contiguous nucleotides not being identical being most preferred; (b) 2'-fluoro with native RNA nucleotides with no more than 3 contiguous nucleosides having the same type of 2'-moiety with contiguous nucleotides not being identical being most preferred unless they are native ribose; or (c) 2'-O-methyl with native RNA nucleotides with no more than 3 contiguous nucleosides having the same type of 2'-moiety with contiguous nucleotides not being identical most preferred unless they are native ribose. Added nuclease protection for this region of the guide strand may be obtained by use of a hair pin design as described herein. Such an approach allows for the greater use of native ribose in this region.
3) Preferably, the rest of the ribonucleotides in the guide or passenger strand are 2'-fluoro, 2'-O-methyl, 2'-O-(2-methoxyethyl) and/or native ribose. The exact mix can be adjusted to increase or decrease the overall Tm of the duplex and the Tm of the guide strand with its RNA target. Higher Tms for the guide strand with its target are preferred. Native ribose is preferably not used in terminal nucleosides and preferably there are no more than 3 contiguous native ribose containing nucleosides. Other nucleosides such as locked nucleic acids (LNA) and FANA can be used as described elsewhere herein. A minority of deoxyribonucleosides can be used in the passenger strand but ribonucleosides (native ribose, 2'-fluoro etc.) are preferred of all positions
4) The linkages in both strands are phosphodiester
5) Y represents some number of nucleosides and when 0 in the guide strand the next nucleoside downstream is considered to be underlined for the purposes of understanding the design Where for Design 4b:
1) The underlined nucleosides in the guide strand (see Prototype 2) have one of the following alternating configurations: (a) 2'-fluoro with 2'-O-methyl with no more than 3 contiguous nucleosides having the same type of 2'-moiety with contiguous nucleotides not being identical being most preferred; (b) 2'-fluoro with native RNA nucleotides with no more than 3 contiguous nucleosides having the same type of 2'-moiety with contiguous nucleotides not being identical most preferred unless they are native ribose; or (c) 2'-O-methyl with native RNA nucleotides with no more than 3 contiguous nucleosides having the same type of 2'-moiety with contiguous nucleotides not being identical most preferred unless they are native ribose. Added nuclease protection for this region of the guide strand may be obtained by use of a hair pin design as described herein. Such an approach allows for the greater use of native ribose in this region.
2) Preferably, the rest of the ribonucleotides in the guide or passenger strand are 2'-fluoro, 2'-O-(2-methoxyethyl) and/or native ribose. The exact mix can be adjusted to increase or decrease the overall Tm of the duplex and the Tm of the guide strand with its RNA target. Higher Tms for the guide strand with its target are preferred. Native ribose is preferably not used in terminal nucleosides and preferably there are no more than 3 contiguous native ribose containing nucleosides. Other nucleosides such as LNA and FANA can be used as described elsewhere herein. A minority of deoxyribonucleosides can be used in the passenger strand but ribonucleosides such as 2'-fluoro are preferred at all positions.
3) The linkages in the guide strand are a mixture of boranophosphate and phosphodiester according to the following scheme; (a) no more than three of the five linkages indicated by the symbol ~ in the guide strand can be boranophosphate with the Sp stereoisomer configuration being most preferred and no more than two can be contiguous; Added nuclease protection for this region of the guide strand may be obtained by use of a hair pin design as described herein. Such an approach allows for the greater use of phosphodiester linkages in this region; (b) The majority of the linkages outside the underlined sequence in the guide strand will be boranophosphate with all of them being boranophosphate being most preferred.
4) The linkages in the passenger strand are preferentially boranophosphate although they may be phosphorothioate or a mixture that includes no more than three contiguous phosphodiester linkages. These phosphorothioate linkages can consistently have the Sp or Rp stereochemistry, be a mixture of Sp and Rp or be phosphorodithioate.
5) Y represents some number of nucleosides and when 0 in the guide strand the next nucleoside downstream is considered to be underlined for the purposes of understanding the design Where for Design 4c:
1) The underlined nucleosides in the guide strand (see Prototype 2) have one of the following alternating configurations: (a) 2'-fluoro with 2'-O-methyl with no more than 3 contiguous nucleosides having the same type of 2'-moiety with contiguous nucleotides not being identical being most preferred; (b) 2'-fluoro with native RNA nucleotides with no more than 3 contiguous nucleosides having the same type of 2'-moiety with contiguous nucleotides not being identical most preferred unless they are native ribose; or (c) 2'-O-methyl with native RNA nucleotides with no more than 3 contiguous nucleosides having the same type of 2'-moiety with contiguous nucleotides not being identical most preferred unless they are native ribose. Added nuclease protection for this region of the guide strand may be obtained by use of a hair pin design as described herein. Such an approach allows for the greater use of native ribose in this region.
2) Preferably, the rest of the ribonucleotides in the guide or passenger strand are 2'-fluoro, 2'-O-methyl, 2'-O-(2-methoxyethyl) and/or native ribose. The exact mix can be adjusted to increase or decrease the overall Tm of the duplex and the Tm of the guide strand with its RNA target. Higher Tms for the guide strand with its target are preferred. Native ribose is preferably not used in terminal nucleosides and preferably there are no more than 3 contiguous native ribose containing nucleosides. Other nucleosides such as LNA and FANA can be used as described elsewhere herein. A minority of deoxyribonucleosides can be used in the passenger strand although ribonucleosides such as 2'-fluoro are preferred in all variant positions.

3) The linkages in the guide strand are a mixture of phosphorothioate and phosphodiester according to the following scheme; (a) no more than three of the five linkages indicated by the symbol ~ in the guide strand can be phosphorothioate with the Sp stereoisomer configuration being most preferred and no more than two can be contiguous; Added nuclease protection for this region of the guide strand may be obtained by use of a hair pin design as described herein. Such an approach allows for the greater use of phosphodiester linkages in this region; (b) The majority of the linkages outside the underlined sequence in the guide strand will be phosphorothioate with each being phosphorothioate most preferred. These phosphorothioate linkages can consistently have the Sp or Rp stereochemistry, be a mixture of Sp and Rp or be phosphorodithioate.

4) The linkages in the passenger strand can be all phosphorothioate although they preferably are a phosphorothioate plus phosphodiester mixture that includes no more than three contiguous phosphodiester linkages. The phosphorothioate linkages can consistently have the Sp or Rp stereochemistry, be a mixture of Sp and Rp or be phosphorodithioate.

5) Y represents some number of nucleosides and when 0 in the guide strand the next nucleoside downstream is considered to be underlined for the purposes of understanding the design.

Prototype 9: Design Illustration #1 for ss-siRNA

```
20-mer
5' I-I-I-I-I-I-I-I-I-I-I-I-I-I-I-I-I-I-I-I 3'
```

Features of Design #1:
1) This Design is most suitable for use with a carrier that provides nuclease resistance to the strand and/or with the hair pin approach disclosed herein. Carriers covalently linked to the strand are preferably attached to the 3'-end.
2) The underlined nucleosides in the guide strand (see Prototype 2) have one of the following alternating configurations: (a) 2'-fluoro with 2'-O-methyl with no more than 3 contiguous nucleosides having the same type of 2'-moiety with contiguous nucleotides not being identical most preferred; (b) 2'-fluoro with native RNA nucleotides with no more than 3 contiguous nucleosides having the same type of 2'-moiety with contiguous nucleotides not being identical most preferred unless they are native ribose; or (c) 2'-O-methyl with native RNA nucleotides with no more than 3 contiguous nucleosides having the same type of 2'-moiety with contiguous nucleotides not being identical most preferred unless they are native ribose. Added nuclease protection for this region of the guide strand may be obtained by use of a hair pin design as described herein. Such an approach allows for the greater use of native ribose in this region.
3) The rest of the ribonucleotides are 2'-fluoro, 2'-O-methyl and/or native where the exact mix can be adjusted to increase or decrease the overall Tm of the guide strand with its RNA target. Higher Tms with the target RNA are more preferred (2'-fluoro>2'-O-methyl>native) and 2'-fluoro modifications to the 3'end are more preferred particularly for the terminal ribonucleotide.
4) The linkages are phosphodiester
5) A 5' phosphate is preferred over a 5'hydroxyl in the terminal ribose or ribose analog.

Prototype 10: Design Illustration #2 for ss-siRNA

```
20-mer
5' I-I-I-I-I-I-I~I~I~I~I~I-I-I-I-I-I-I 3'
```

Features of Design #2:
1) The underlined nucleosides in the guide strand (see Prototype 2) have one of the following alternating configurations: (a) 2'-fluoro with 2'-O-methyl with no more than 3 contiguous nucleosides having the same type of 2'-moiety with contiguous nucleotides not being identical most preferred; (b) 2'-fluoro with native RNA nucleotides with no more than 3 contiguous nucleosides having the same type of 2'-moiety with contiguous nucleotides not being identical most preferred unless they are native ribose; or (c) 2'-O-methyl with native RNA nucleotides with no more than 3 contiguous nucleosides having the same type of 2'-moiety with contiguous nucleotides not being identical most preferred unless, they are native ribose. Added nuclease protection for this region of the guide strand may be obtained by use of a hair pin design as described herein. Such an approach allows for the greater use of native ribose in this region.
2) The rest of the nucleotides are 2'-fluoro, 2'-O-methyl and/or native where the exact mix can be adjusted to increase or decrease the overall Tm of the guide strand with its RNA target. Higher Tms are most preferred (2'-fluoro>2'-O-methyl>native) and 2'-fluoro modifications to the 3'end are preferred particularly the terminal nucleotide.
3) The linkages are a mixture of boranophosphate and phosphodiester according to the following scheme; (a) no more than three of the five linkages indicated by the symbol ~ in the guide strand can be boranophosphate with the Sp stereoisomer configuration being most preferred and no more than two of these can be contiguous; Added nuclease protection for this region of the guide strand may be obtained by use of a hair pin design as described herein. Such an approach allows for the greater use of phosphodiester linkages in this region; (b) The majority of the other linkages in the guide strand will be boranophosphate with all of these being boranophosphate being most preferred.
4) A 5'phosphate is preferred over a 5'hydroxyl in the terminal ribose or ribose analog.

The frequency of boranophosphate linkages and certain other parameters depend, in part, on the synthesis method for establishing boranophosphate linkages as discussed herein.

Prototype 11: Design Illustration #3 for ss-siRNA

```
20-mer
5' I-I-I-I-I-I-I~I~I~I~I~I-I-I-I-I-I-I 3'
```

Features of Design #3:
1) The underlined nucleosides in the guide strand (see Prototype 2) have one of the following alternating configurations: (a) 2'-fluoro with 2'-O-methyl with no more than 3 contiguous nucleosides having the same type of 2'-moiety with contiguous nucleotides not being identical most preferred; (b) 2'-fluoro with native RNA nucleotides with no more than 3 contiguous nucleosides having the same type of 2'-moiety with contiguous nucleotides not being identical most preferred unless they are native ribose; or (c) 2'-O-methyl with native RNA nucleotides with no more than 3 contiguous nucleosides having the same type of 2'-moiety with contiguous nucleotides not being identical most preferred, unless they are native ribose. Added nuclease protection for this region of the guide strand may be obtained by use of a hair pin design as described herein. Such an approach allows for the greater use of native ribose in this region.

2) The rest of the nucleotides are 2'-fluoro, 2'-O-methyl and/or native where the exact mix can be adjusted to increase or decrease the overall Tm of the guide strand with its RNA target. Higher Tms are most preferred (2'-fluoro>2'-O-methyl>native) and 2'-fluoro modifications to the 3'end are preferred particularly the terminal nucleotide.

3) The linkages are a mixture of phosphorothioate and phosphodiester according to the following scheme; (a) no more than three of the five linkages indicated by the symbol ~ in the guide strand can be phosphorothioate with the Sp stereoisomer configuration being most preferred of boranophosphate with the Sp stereoisomer configuration being most preferred and no more than two of these non-phosphodiester linkages can be contiguous; Added nuclease protection for this region of the guide strand may be obtained by use of a hair pin design as described herein. Such an approach allows for the greater use of phosphodiester in this region; (b) The majority of the other linkages in the guide strand will be phosphorothioate with all of these being phosphorothioate being most preferred. These phosphorothioate linkages can consistently have the Sp or Rp stereochemistry, be a mixture of Sp and Rp or be phosphorodithioate.

4) A 5'phosphate is preferred over a 5'hydroxyl in the terminal ribose or ribose analog.

Boranophosphate linkages, (FIG. 1) differ from native DNA and RNA in that a borane ($BH_3^-$) group replaces one of the non-bridging oxygen atoms in the native phosphodiester linkage. Such linkages can be inserted in oligos via two general methods: (1) template directed enzymatic polymerization; and (2) chemical synthesis using solid supports. Synthetic schemes for solid support methods that have been worked out using deoxyribonucleotides can also be applied to RNA. However, for native ribonucleotides, the 2'hydroyl on the ribose must be protected and then deprotected during synthesis. This does not apply to ribonucleotides with 2' ribose modifications such as 2'-fluoro or 2'-O-methyl. Protection and deprotection of the 2'-hydroxyl of native ribonucleotides can be achieved by a wide variety of means that are well known in the art.

In template directed enzymatic polymerization stereoregular boranophosphate linkages are used in oligos and can be inserted by means of an enzymatic process (Hall et al., Nucl Acids Res 32: 5991, 2004; Wan and Shaw, Nucleosides, Nucleotides & Nucleic Acids, 24: 943, 2005; Wan, Enzymatic synthesis, properties and functions of boranophosphate RNA, PhD Dissertation, Duke University, Durham N.C., 2005; Li et al., Chem Rev 107: 4746, 2007; U.S. Pat. No. 5,859,231). Here boranophosphate containing guide and passenger strands are generated in separate reactions from DNA templates by transcription using an RNA polymerase such as bacteriophage T7 and native or modified ribonucleoside 5' triphosphates.

As a group such RNA polymerases usually preferentially produce boranophosphate linkages in oligoribonucleotides that have the Sp stereoisomer configuration. As in the case of T7 they may achieve this by starting with Rp ribonucleoside 5'(alpha-P-borano)triphosphates. The stereochemical configuration of such linkages can impact the ability of the oligoribonucleotide to interact with other enzymes, for example nucleases. The synthesis and purification of specific Rp or Sp diastereomers of ribonucleoside 5'(alpha-P-Borano)triphosphates useful for the practice of this invention is described in He et al., J Org Chem 63: 5769, 1998; He, "Synthesis and properties of boranophosphate nucleic acids" PhD Dissertation, Duke University, Durham N.C., 2000 and Li et al., Chem Rev 107: 4766, 2007.

Figure 2:
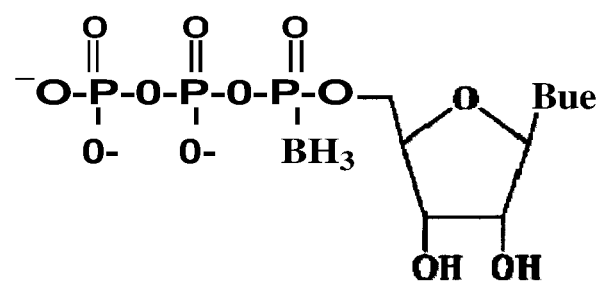
FIG. 2: Boranophosphate Monomer with Native Ribose

Using this enzymatic approach facilitates production of an oligo having mixed boranophosphate and phosphodiester linkages. One can convert one or more of the type(s) of ribonucleosides (G, C, A or U) into 5'-(alpha-P-borano) triphosphates as illustrated in FIG. 2 and alternate these with ribonucleosides having native 5' triphosphates. This approach thus limits the sequences that can be used with this method when the design principles described in Prototypes 6, 8 (Design 4b) and 10 are to be followed. Similarly, this approach limits the selection of native, 2'-fluoro or 2'-O-methyl ribose to some types of ribonucleosides (G, C, A or U) to the exclusion of others in order to meet these same design principles because any given type of ribonucleotide (G, C, A or U) must only have one type of ribose. Further, T7 based synthesis is most efficient when the first ribonucleoside has a guanine base and this enzyme catalyzes the formation of RNA in the 5' to 3' direction. Specific illustrations of using this synthesis method and meeting the indicated design criteria are provided in the Example section.

In a variant of this method the guide and passenger strands can each be synthesized as two pieces in a manner such that after annealing of each piece with its partner there will be over hangs that can be used to align each duplex pair for ligation so that a complete double stranded si-RNA is formed by the ligation step. In this way the specific combinations of ribonucleosides with borano triphosphates vs. native triphosphates can be different for each of the four starting oligos. This allows for greater flexibility in meeting the illustrated design requirements.

Boranophosphate oligonucleotide production can be achieved by a variety of solid phase chemical synthetic schemes including methods that involve modifications to the very commonly used approaches employing phosphoramidites or H-phosphonates in the production of phosphodiesters, phosphorothioates and phosphorodithioates among other chemistries (Li et al., Chem Rev 107: 4746, 2007). Other solid phase synthesis techniques more precisely directed to boranophosphates have also been developed over the last few years. Wada and his colleagues, for example, have developed what they call the boranophosphotriester method that can make use of H-phosphonate intermediates (Shimizu et al., J Org Chem 71: 4262, 2006; Kawanaka et al., Bioorg Med Chem Lett 18: 3783, 2008). This method can also be applied to the synthesis of diastereometically pure boranophosphates (Enya et al., Bioorg Med Chem 16: 9154, 2008).

The generation of oligos with mixed linkages such as boranophosphate and phosphate linkages has been accomplished by several solid phase methods including one involving the use of bis(trimethylsiloxy)cyclododecyloxysilyl as the 5'-O-protecting group (Brummel and Caruthers, Tetrahedron Lett 43: 749, 2002). In another example the 5'-hydroxyl is initially protected with a benzhydroxybis (trimethylsilyloxy)silyl group and then deblocked by $Et_3N$:HF before the next cycle (McCuen et al., J Am Chem Soc 128: 8138, 2006). This method can result in a 99% coupling yield and can be applied to the synthesis of oligos with pure boranophosphate linkages or boranophosphate mixed with phosphodiester, phosphorothioate, phosphorodithioate or methyl phosphonate linkages.

The boranophosphorylating reagent 2-(4-nitrophenyl) ethyl ester of boranophosphoramidate can be used to produce boranophosphate linked oligoribonucleosides (Lin, Synthesis and properties of new classes of boron-containing nucleic acids, PhD Dissertation, Duke University, Durham N.C., 2001). This reagent readily reacts with a hydroxyl group on the nucleosides in the presence of 1H-tetrazole as a catalyst. The 2-(4-nitrophenyl)ethyl group can be removed by 1,4-diazabicyclo[5.4.0]undec-7-ene (DBU) through beta-elimination, producing the corresponding nucleoside boranomonophosphates (NMPB) in good yield.

The stereo-controlled synthesis of oligonucleotide boranophosphates can be achieved using an adaptation of the oxathiaphospholane approach originally developed for the stereo-controlled synthesis of phosphorothioates (Li et al., Chem Rev 107: 4746, 2007). This method involves a tricoordinate phosphorus intermediate that allows for the introduction of a borane group.

Other approaches include stereo-controlled synthesis by means of chiral indole-oxazaphosphorine or chiral oxazaphospholidine. Both of these approaches initially use used for the stereocontrolled synthesis of phosphorothioates and have been successfully adapted to boranophosphates (Li et al., Chem Rev 107: 4746, 2007).

The main difference between oligoribonucleotide and oligodeoxyribonucleotide synthesis is the need to protect the 2'-hydroxyl found on native ribose during synthesis followed by deprotection. Such methods are well established and allow oligodeoxyribonucleotides containing native ribose to be synthesized by basically the same methods that are used to synthesize oligodeoxyribonucleotides.

Carriers

The carriers contemplated for use in accordance with the present invention are divided into various categories below, but it is to be understood by the one skilled in the art that some components of these carriers can be mixed and matched. For example, various linkers can be used to attach various peptides of the type described herein to any given oligo and various peptides can be incorporated into particular nanoparticle-based carriers depending on the commercial or clinical purpose to be served.

Carriers and/or endosomolytic agents can be used to advantage for delivering adequate amounts of oligos in vitro or in vivo to certain intracellular compartments such as the nucleus or the cytoplasm and/or in delivering adequate amounts of such agents in vivo to certain tissues such as the following: (1) delivery to the brain, an organ that typically takes up relatively small amounts of oligos following systemic administration; (2) preferentially concentrating oligos in particular target organs, such as heart; and (3) increasing the levels of active oligos in tissues more resistant to oligo uptake due to certain conditions, such as poor vascularization in tumors and disrupted blood supply in ischemia reperfusion injuries; and (4) reducing the dose needed for oligo action, while reducing potential side effect risk(s) in non-target tissues.

For the purposes of this invention, the preferred carriers, particularly for in vivo use, make use of peptides that promote cell penetration. These cell penetrating peptides (CPPs) typically share a high density of basic charges and are approximately 10-30 amino acids in length. Such peptides may be part of a complex carrier composition, including but not limited to nanoparticles. Alternatively, such CPP peptides may be conjugated to the oligo directly or by means of a linker. Further, CPPs can be fused to, or otherwise associated with peptides that provide other features to oligo carriers such as increasing homing to particular organs, or to particular subcellular compartments. For example, certain peptides described herein may enhance nuclear localization or provide an endosomolytic function (i.e., they function to enhance the escape of oligos or other drugs from endosomes, lysosomes or phagosomes). CPPs and peptides with other useful carrier functions may be derived from naturally occurring protein domains or synthetic versions may be designed which retain the activity of the naturally occurring versions. Those of human origin include peptide-mimetics such as polyethylenimines. The naturally occurring peptides discussed below have sequence variants, such as those observed in different strains or species or as a result of polymorphisms within species. Thus, the representative peptide sequences provided cannot be considered to be exact and variations in peptide sequences exist between some of the documents referenced. These variants are fully functional and may be used interchangeably.

Given the relatively small size of most cell penetrating peptides compared to the large size of siRNA, it is often preferable to employ such peptides in larger carrier structures such as nanoparticles rather than use direct conjugation of the peptide to these oligo types. This approach typically improves the charge ratio and cellular uptake for oligo/carrier complexes. However, an example of a CPP that has been directly and covalently attached to siRNA and shown to promote its uptake by cells is TAT (Chiu et al., Chem Biol 11: 1165, 2004; Davidson et al., J Neurosci 24: 10040, 2004). Delivery of antisense oligos contained within expression vectors generally will require a viral vector or one of the siRNA or dicer substrate delivery mechanisms as provided for herein.

Targeting molecules may be operably linked to CPPs thus providing improved oligo uptake in particular cell types. One example of targeting molecules useful for this purpose are those directed to G-protein coupled receptors. Other examples of targeting molecules are ligands to IL-13, GM-CSF, VEGF and CD-20. Other examples of complex structures involved in targeting include nucleic acid aptamers or spiegelmers directed to particular cell surface structures. Characteristics, production uses and methods related to these targeting molecules and complex structures are provided in the following documents: (Nolte et al., Nat Biotech 14: 1116, 1996; McGown et al., Anal Chem 67: 663A, 1995; Pestourie et al., Biochimie 87: 921, 2005; Brody and Gold, J Biotechnol 74: 5, 2000; Mayer and Jenne, BioDrugs 18: 351, 2004; Wolfl and Diekmann, J Biotechnol 74: 3, 2000; Ferreira et al., Tumour Biol 27: 289, 2006; Stoltenburg et al., Anal Bioanal Chem 383: 83, 2005; Rimmele, Chembiochem 4: 963, 2003; Ulrich Handb Exp Pharmacol 173: 305, 2006; Drabovich et al., Anal Chem 78: 3171, 2006; Eulberg and Klussmann, Chembiochem 4: 979, 2003; Vater and Klussmann, Curr Opin Drug Discov Devel 6: 253, 2003; Binkley et al., Nucleic Acids Res 23: 3198, 1995; U.S. Pat. No. 7,329,638, US 2005/0042753, US 2007/0148449, US 2002/0076755, US 2006/0166274, US 2007/0179090, WO 01/81408, WO 2006/052723, WO 2007/137117, WO 03/094973, WO 2007/048019, WO 2007/016507, WO 2008/039173).

Methods and agents that can be used to bypass endosomal, lysosomal or phagosomal sequestration or used to promote the escape of oligos from endosomes, lysosomes or phagosomes are optionally administered with the oligo based therapeutics described herein. Such methods include, but are not limited to three approaches that are not mutually exclusive. First, endosomolytic or lysosomotropic agents may be attached to oligos or included in oligo carrier compositions. Second, lysosomotropic agents may be administered as separate agents at about the time the oligo or carrier/oligo complex is administered in vivo or in vitro. Such lysosomotropic agents include, but are not limited to, the following agents: chloroquine, omeprazole and bafilomycin A. Third, agents that inhibit vacuolar proton ATPase activity (promotes acidification of endosomes, lysosomes or phagosomes) or acidic organelle function may be utilized to sensitize cells to oligo action. Such agents and methods for their administration are provided in U.S. Pat. No. 6,982,252 and WO 03/047350. Such compounds include but are not limited to the following: (1) a bafilomycin such as bafilomycin A1; (2) a macrolide antibiotic such as concanamycin; (3) a benzolacton enamide such as salicilyhalamide A, oximidine or lobatamide; (4) inhibitors of rapamycin, bFGF, TNF-alpha, and/or PMA activated pathways; (5) inhibitors of the class III phosphatidylinositol 3'-kinase signal transduction pathway; and/or (6) antisense oligos directed to the gene or RNA encoding vacuolar proton ATPase protein.

Certain lysosomotropic agents such as chloroquine and omeprazole have been used medically, but not as agents for the promotion of oligo activity. These agents exhibit lysosomotropic activity at established doses and treatment regimens both in vivo and in vitro, and thus such studies provide a dosing guide for their use in combination with oligos to promote oligo activity (Goodman & Gilman's The Pharmacologic Basis of Therapeutics 11$^{th}$ edition Brunton et al., editors, 2006, McGraw-Hill, New York). Other lysosomotropic agents are suitable for in vitro use and dosing studies can be performed according to well established methods known in the art to optimize efficacy when used in combination with oligo therapeutics in vivo. Methods have also been devised that allow chloroquine to be incorporated into carriers or directly conjugated to oligos for boosting the intended antisense activity of oligos on cells. These include but are not limited to, those found in US 2008/0051323 and WO2007/040469.

The molecules listed below are useful as carriers and/or as components of complex carriers for transporting the oligos of the present invention into cells and into subcellular compartments (in accordance with the guidance provided herein) where they can express their inhibitory functions. Unless otherwise noted these molecules: (1) are CPPs; and/or (2) are useful for achieving oligo function in a wide variety of cell types. Certain of the molecules have been shown to work well in particular cell types or tissues and/or to selectively work with particular cell types or tissues. Such tissues and cell types for which certain of the following molecules have proved to be particularly useful as targeting ligands, carriers or as members of complex carriers include but are not limited to brain, CNS, liver, heart, endothelium, pancreatic islet cells, retina, etc. The biochemical features of the following disclosed peptides and other molecules listed (e.g., increased target cell membrane penetration activity, promotion of endosomolytic activity, activation by to exposure to low pH environments and coding sequence information) are provided in detail below.

(1) TAT and TAT variants—See the following references:
(Astriab-Fisher et al., Pharmaceutical Res 19: 744, 2002; Zhao and Weissleder, Med Res Rev 24: 1, 2004; Jensen et al., J Controlled Release 87: 89, 2003; Hudecz et al., Med Res Rev 25: 679, 2005; Meade et al., Adv Drug Delivery Rev 59: 134, 2007; Meade and Dowdy Adv Drug Delivery Rev 60: 530, 2008; Jones et al., Br J Pharmacol 145: 1093, 2005; Gupta et al., Oncology Res 16: 351, 2007; Kim et al., Biochimie 87: 481, 2005; Klein et al., Cell Transplantation 14: 241, 2005; U.S. Pat. Nos. 6,316,003, 7,329,638, US 2005/0042753, US 2007/0105775, US 2006/0159619, WO 99/55899, WO 2007/095152, WO 2008/008476, WO 2006/029078, WO 2006/0222657, WO 2008/022046, WO 2006/053683, WO 2004/048545, WO 2008/093982, WO 94/04686)—Tat includes the HIV TAT protein transduction domain and sequences that have been used for this purpose, such as: KRRQRRR (SEQ ID NO: 1), GYGRKKRRQRRR (SEQ ID NO:2), YGRKKRRQRRR (SEQ ID NO: 3), CYGRKKRRQRRR (SEQ ID NO:4), RKKRRQRRRPPQC (SEQ ID NO: 5), CYQRKKRRQRRR (SEQ ID NO: 6) and RKKRRQRRR (SEQ ID NO: 7). In addition, various amino acid substitutions in TAT have been shown to promote the CPP activity of TAT as disclosed in the referenced documents. TAT can be used as a fusion peptide with enhanced CPP activity where the fusion partner is selected from peptides derived from the following group: (a) HEF from influenza C virus; (b) HA2 and its analogs, see below; (c) transmembrane glycoproteins from filovirus, rabies virus, vesicular stomatitis virus or Semliki Forest virus; (d) fusion polypeptide of sendai virus, human respiratory syncytial virus, measles virus, Newcastle disease virus, visna virus, murine leukemia virus, human T-cell leukemia virus, simian immunodeficiency virus; or (e) M2 protein of influenza A virus.

TAT and TAT variants have been used successfully to facilitate delivery of therapeutic agents to a wide variety of tissue and cell types that include but are not limited to the following: (a) the CNS and increase penetration of the blood brain barrier. See Kilic et al., Stroke 34: 1304, 2003; Kilic et al., Ann Neurol 52: 617, 2002; Kilic et al., Front Biosci 11: 1716, 2006; Schwarze et al., Science 285, 1569, 1999; Banks et al., Exp Neurol 193: 218, 2005; and WO 00/62067; (b) TAT peptides have also been shown to effectively penetrate heart tissue. See Gustafsson et al., Circulation 106: 735, 2002; (c) TAT or TAT/PDT are described in Embury et al., Diabetes 50: 1706, 2001; and Klein et al., Cell Transplantation 14: 241, 2005. These investigators disclose that such peptides are useful for delivery of desired agents to pancreatic islet cells; (d) Schorderet et al., Clin Exp Ophthalmology 33: 628, 2005 describe the use of D-TAT which is the retro-inverso form of TAT for delivery of agents to the retina and thus this peptide is also useful in the methods disclosed herein.

(2) MPG peptide—See the following references. (Morris et al., Nucleic Acids Res 25: 2730, 1997; Simeoni et al., Nucleic Acids Res 31: 2117, 2003; Hudecz et al., Med Res Rev 25: 679, 2005; Deshayes et al., Adv Drug Delivery Rev 60: 537, 2008; WO 2006/053683, WO 2004/048545)—Delivery systems using this CPP make combined use of a sequence that is derived from the fusion sequence of the HIV protein gp41, the sequence including for example, GALFLGF(or W)LGAAGSTMGA (SEQ ID NO:8) or the longer peptide sequence GALFLGF(or W)LGAAGSTMGAWSQPKKKRKV (SEQ ID NO:9) when the goal is to achieve higher levels nuclear transport of the oligo. Nuclear concentration is most suitable for conventional antisense oligos that have an RNase H mechanism of action or those that interfere with splicing by means of a steric hindrance mechanism as well as for siRNA that functions as a transcriptional inhibitor and for expression vectors. An alternative form of the longer MPG peptide where the second lysine is replaced by a serine (GALFLGF(or W)LGAAGSTMGAWSQPK-SKRKV; (SEQ ID NO: 10) causes the transported oligo to preferentially localize in the cytoplasm. This is most suitable for conventional antisense oligos that interfere with translation by a steric hindrance mechanism or for siRNA that function via interfering with translation, as well as for most dicer substrates or siRNA. In the MPG delivery system, these peptides are incorporated into nanoparticles that combine with oligos by charge/charge interaction.

(3) Penetratin and EB1—See the following references. (Astriab-Fisher et al., Pharmaceutical Res 19: 744, 2002; Hudecz et al., Med Res Rev 25: 679, 2005; Lindgren et al., Bioconjugate Chem 11: 619, 2000; Meade et al., Adv Drug Delivery Rev 59: 134, 2007; Meade and Dowdy Adv Drug Delivery Rev 60: 530, 2008; Jones et al., Br J Pharmacol 145: 1093, 2005; Lundberg et al., FASEB J 21: 2664, 2007; U.S. Pat. No. 7,329,638, US 2005/0042753, US 2007/0105775, WO 2007/095152, WO 2008/008476, WO 2006/029078, WO 2006/0222657, WO2008/022046, WO 2006/053683, WO 2004/048545, WO 2008/093982)—Penetratin sequences include but are not limited to the following: RQIKIWFQNRRMKWKK (SEQ ID NO: 11) and RQIKIWFQNRRMKWKKGGC (SEQ ID NO:12). EB1 which has been modified from penetratin in part by inserting histidine residues in strategic spots in the peptide in order to add increased endosomolytic activity to the parent CPP. EB1 sequences include but are not limited to the following: LIRLWSHLIHIWFQN-RRLKWKKK (SEQ ID NO:13) Penetratin or EB1 can be used as a fusion peptide with enhanced CPP activity where the fusion partner is selected from peptides derived from the following group: (a) hemagglutinin esterase fusion protein (HEF) from influenza C virus; (b) HA2 and its analogs, see below and as an example of such a fusion peptide the following sequence: GLFGAIAGFIEN-GWEGMIDGRQIKIWFQNRRMKWKK (SEQ ID NO: 14); (c) transmembrane glycoproteins from filovirus, rabies virus, see below, vesicular stomatitis virus or Semliki Forest virus; (d) fusion polypeptide of sendai virus, FFGAVIGTIALGVATA SEQ ID NO: 15) human respiratory syncytial virus, FLGFLLGVGSAIASGV (SEQ ID NO: 16), HIV gp41, GVFVLGFLGFLATAGS (SEQ ID NO: 17), ebola GP2, GAAIGLAWIPYFGPAA, (SEQ ID NO: 18) See WO 2008/022046), measles virus, Newcastle disease virus, visna virus, murine leukemia virus, human T-cell leukemia virus, simian immunodeficiency virus; or (e) M2 protein of influenza A virus.

(4) VP22—See the following references. (Suzuki et al., J Mol Cell Cardiology 36: 603, 2004; Hudecz et al., Med Res Rev 25: 679, 2005; Meade et al., Adv Drug Delivery Rev 59: 134, 2007; Meade and Dowdy Adv Drug Delivery Rev 60: 530, 2008; Jones et al., Br J Pharmacol 145: 1093, 2005; Xiong et al., BMC Neuroscience 8: 50, 2007; Lemken et al., Mol Ther 15: 310, 2007; Bamdad and Bell, Iran Biomed J 11: 53, 2007; Greco et al., Gene Ther 12: 974, 2005; Aints et al., J Gene Med 1: 275, 1999; U.S. Pat. No. 7,329,638, US 2005/0042753, US 2007/0105775, WO 2007/095152, WO 2008/008476, WO 2006/029078, WO 2006/0222657, WO2008/022046, WO 2006/053683, WO 2004/048545)—VR22 sequences include for example: DAATATRGRSAASRPTERPRAPARSASR-PRRPVD (or E) (SEQ ID NO: 19). In addition to being a potent CPP suitable for use with a wide variety of tissue and cell types, VP22 has the added ability to shuttle the oligo to secondary cells after having delivered it to an initial set of cells. VP22 can be used as a fusion peptide with enhanced CPP activity where the fusion partner is selected from peptides derived from the following group: (a) HEF from influenza C virus; (b) HA2 and its analogs; (c) transmembrane glycoproteins from filovirus, rabies virus, vesicular stomatitis virus or Semliki Forest virus; (d) fusion polypeptide of sendai virus, human respiratory syncytial virus, measles virus, Newcastle disease virus, visna virus, murine leukemia virus, human T-cell leukemia virus, simian immunodeficiency virus; or (e) M2 protein of influenza A virus.

VP22 has been shown to facilitate penetration of the blood brain barrier. See Kretz et al., Mol Ther 7: 659, (2003). VP22 can also be employed to deliver oligos to heart tissue. See Suzuki et al., J Mol Cell Cardiology 36: 603, 2004. Xiong et al., Hum Gene Ther 18: 490, 2007 report that VP22 peptides also have utility for targeting skeletal muscle. Kretz et al., Mol Ther 7: 659, 2003 have described the use of VP22 peptides for facilitating delivery to the retina.

(5) Model amphipathic peptide (MAP)—See the following references. (Hudecz et al., Med Res Rev 25: 679, 2005; Meade et al., Adv Drug Delivery Rev 59: 134, 2007; Meade and Dowdy Adv Drug Delivery Rev 60: 530, 2008; Jones et al., Br J Pharmacol 145: 1093, 2005; Drin et al., AAPS PharmSci 4: 1, 2002, WO2008/022046, WO 2004/048545, WO 2008/093982)—MAP has broad application as a CPP and its peptide sequences include, but are not limited to, KLAKLLALKALKAALKLA (SEQ ID NO: 20) and KLALKLALKALKAALKLA (SEQ ID NO: 21).

(6) Pep-1—See the following references. (Morris et al., Nature Biotech 19: 1173, 2001; Kim et al., J Biochem Mol Biol 39: 642, 2006; Choi et al., Mol Cells 20: 401, 2005; An et al., Mol Cells 25: 55, 2008; Munoz-Morris et al., Biochem Biophys Res Commun 355: 877, 2007; Choi et al., Free Radic Biol Med 41: 1058, 2006; Cho et al., Neurochem Int 52: 659, 2008; An et al., FEBS J 275: 1296, 2008; Lee et al., BMB Rep 41: 408, 2008; Yune et al., Free Radic Biol Med published online ahead of print Jul. 27, 2008; Eum et al., Free Radic Biol Med 37: 1656, 2004; Weller et al., Biochem 44: 15799, 2005; Choi et al., FEBS Lett 580: 6755, 2006; Gros et al., Biochim Biophys Acta 1753: 384, 2006; US 2003/0119725, U.S. Pat. No. 6,841,535, US 2007/0105775, WO 2008/093982)—Pep-1 sequences include, but are not limited to, KETWWETW-WTEWSQPKKKRKV (SEQ ID NO: 22). Pep-1 is a CPP that can be operably linked to nanoparticles capable of delivery of oligos to the cytoplasm of cells. In addition to numerous other tissues and cell types, Pep-1 can be successfully used as a CPP for the delivery of oligos and other large charged molecules to intracellular compartments of brain and spinal cord and cells. Such uses include the oligo treatment of various neurological disorders including but not limited to the following: ischemia-reperfusion injury (including stroke), spinal cord injury amyotrophic lateral sclerosis and Parkinson's Disease.

(7) Pep-1 Related Peptides—See the following US Patent Applications and issued patent. (US 2003/0119725, U.S. Pat. No. 6,841,535, US 2007/0105775)—Pep-1 belongs to a series of related CPPs that are effective carriers or carrier components for the delivery of potent oligos into intracellular compartments. Pep-2 has the sequence KETWFETWFTEWSQPKKKRKV (SEQ ID NO: 23).

Two amino acid sequence patterns have been observed in closely related peptides with CPP activity. In these peptides, the term Xaa refers to a position in the sequence where either any amino acid or no amino acid is acceptable. The sequence pattern that includes Pep-1 is the following: KXaaXaaWWETWWXaaXaaXaaSQPKKXaaRKXaa (SEQ ID NO: 24). Additional peptides in this family include the following sequences: KETWWETWWTEWSQPKKRKV (SEQ ID NO: 25), KETWWETWWTEASQPKKRKV (SEQ ID NO: 26), KETWWETWWETWSQPKKKRKV (SEQ ID NO: 27), KETWWETWTWSQPKKKRKV (SEQ ID NO: 28) and KWWETWWETWSQPKKKRKV (SEQ ID NO: 29). The closely related pattern is as follows: KETWWETWWXaaXaaWSQPKKKRKV (SEQ ID NO: 30).

(8) Fusion sequence-based protein (FBP)—See the following references. (Hudecz et al., Med Res Rev 25: 679, 2005; Drin et al., AAPS PharmSci 4: 1, 2002; WO 2004/048545)—FBP peptide sequences include but are not limited to GALFLGWLGAAGSTM (SEQ ID NO: 31) and GALFLGWLGAAGSTMGAWSQPKKKRKV (SEQ ID NO: 32) where the second sequence ends with a nuclear localization sequence from SV40 T antigen.

(9) bPrPp—See Hudecz et al., Med Res Rev 25: 679, 2005; Magzoub et al., Biochim Biophys Acta 1716: 126, 2005; Magzoub et al., Biochem 44: 14890, 2005; Magzoub et al., Biochem Biophys Res Commun 348: 379, 2006; and Biverstahl et al., Biochem 43: 14940, 2004). bPrPp is a CPP based on peptides that are found in bovine prions and includes the following sequence: MVKSKIGSWILVLFVAMWSDVGLCKKRPKP (SEQ ID NO: 33). This peptide has endosomolytic as well as CPP activity.

(10) PG-1—(peptide protegrin)—See Drin et al., AAPS PhannSci 4: 1, 2002 Adenot et al., Chemotherapy 53: 73, 2007; U.S. Pat. No. 7,399,727).—PG-1 is a CPP originally isolated from porcine leukocytes. Use of PG-1 peptides to deliver the oligos of the invention enhances intracellular delivery thereof. Such PG-1 containing molecules are sometimes referred to as SynB vectors. These vectors typically employ protegrin based peptides of varying lengths, for example, SynB1 (RGGRLSYSRRRFSTSTGR; (SEQ ID NO: 34) and SynB3 (RRLSYSRRRF; (SEQ ID NO:35). In addition to numerous other tissue and cell types, PG-1 and SynB vectors comprising CPPs based on Syn B family peptides can be used to increase transport of oligos across the blood brain barrier.

(11) Transportan and analogues such as TP-7, TP-9 and TP-10—See the following references. (Soomets et al., Biochim Biophys Acta 1467: 165, 2000; Hudecz et al., Med Res Rev 25: 679, 2005; Fisher et al., Gene Ther 11: 1264, 2004; Rioux, Curr Opin Investig Drugs 2: 364, 2001; El-Andaloussi et al., J Control Release 110: 189, 2005; Lindgren et al., Bioconjugate Chem 11: 619, 2000; Pooga et al., FASEB J 12: 67, 1998, WO2008/022046, WO 2006/053683, WO 2004/048545, WO 2008/093982)—Transportin is approximately 27 amino acids in length and contains approximately 12 functional amino acids from the neuropeptide galanin and approximately 14 amino acids from the mast cell degranulating peptide mastoparan, a CPP in its own right. Typically these peptides are connected by a lysine. Transportan sequences include but are not limited to the following: GWTLNSAGYLLGKINLKALAALAKKIL (SEQ ID NO: 36). The TP-10 sequence is the shortest of the transportan group, TP-7, TP-9 and TP-10 and is as follows: AGYLLGKINLKALAALAKKIL (SEQ ID NO: 37).

(12) Protamine and Protamine-fragment/SV40 peptides—See Benimetskaya et al., Bioconjugate Chem 13: 177, 2002; U.S. Pat. No. 5,792,645, U.S. Pat. No. 7,329,638, and US 2005/0042753. Protamine-fragment/SV40 peptides are bifunctional CPPs composed of a C-terminal protamine-fragment that contains a DNA binding domain and an N-terminal nuclear localization signal derived from SV40 large T-antigen. One variant is called s-protamine-NLS and has sequences that include but are not limited to, R6WGR6-PKKKRKV (SEQ ID NO: 38) while another, 1-protamine-NLS, has sequences that include R4SR6FGR-6VWR4-PKKKRKV (SEQ ID NO: 39). In addition to being combined with peptides from SV40, protamine itself has the capacity to promote uptake of oligos into intracellular compartments.

(13) Polyethylenimine (PEI)—See the following references. (Intra and Salem, J Controlled Release 130: 129, 2008; Ogris et al., J Biol Chem 276: 47550, 2001; Breunig et al., J Gene Med 7: 1287, 2005; Loftus et al., Neurosci 139: 1061, 2006; Wang et al., Mol Therapy 3: 658, 2001; Boeclde et al., J Control Release 112: 240, 2006; U.S. Pat. No. 5,792,645, US 2003/0027784, US 2004/0185564, US 2008/0207553, WO 9602655, WO 00/59548, WO 2006/041617, WO 2004/029213, WO 03/099225, WO 2007/0135372, WO 94/01448)—PEI comes in linear and branched forms as well as in a low molecular weight form (<50,000 Daltons). It is a CPP-mimetic that has a particular advantage over other CPPs in that it is not subject to proteolysis. In addition to iv and im routes of administration, oligos associated with a PEI containing carrier can be administered by aerosol delivery via the respiratory tract. Conjugation of PEI to certain melittin analogs provides added endosomolytic activity and, therefore, enhanced oligo delivery to intracellular sites where oligos can carry out their intended function. PEI, as for most if not all CPPs, can be incorporated into nanoparticles to further promote the efficiency of oligo delivery to intracellular compartments. The specific methods for such CPP incorporation depend on the type of nanoparticle and are discussed in the reference documents provided herein for each type of nanoparticle. PEI can also be used to facilitate delivery of a oligo to the brain following intranasal administration. Also see Bhattacharya et al., Pharmaceut Res 25: 605, 2007; Zhang et al., J Gene Med 4: 183, 2002; Boado et al., Biotechnol Bioeng 96: 381, 2007; Coloma et al., Pharm Res 17: 266, 2000; US 2008/0051564, WO 94/13325, WO 99/00150, WO 2004/050016).

(14) Insulin and insulin-like growth factor receptor ligands—See Basu and Wickstrom, Bioconjugate Chem 8: 481, 1997; Zhang et al., J Gene Med 4: 183, 2002; Boado et al., Biotechnol Bioeng 96: 381, 2007; Coloma et al., Pharm Res 17: 266, 2000; Soos et al., Biochem J 235: 199, 1986; US 2008/0051564, WO 99/00150, WO 2004/050016 and U.S. Pat. No. 7,388,079)—Human Insulin receptor (HIR) monoclonal antibodies (MAbs) are directed to the human insulin receptor. Other suitable ligands include but are not limited to insulin, IGF-1 and IGF-2 or functional fragments thereof. Examples of IGF-1 binding peptides that can be used for this purpose include but are not limited to JB3 (D-C-S-K-A-P-K-L-P-A-A-Y-C (SEQ ID NO: 40) where D denotes the D stereoisomer of C and where all the other stereoisomers are L) and JB9 (G-G-G-G-G-C-S-K-C; SEQ ID NO: 41). Amide bond linked oligos can be inserted between the first and second Gs of JB9. When incorporated into a carrier, these ligands can be used to deliver oligos into cells that express this receptor. Such cells include but are not limited to liver, adipose tissue, skeletal muscle, cardiac muscle, brain, kidney and pancreas.

Insulin and insulin-like growth factor receptor ligands as described U.S. Pat. No. 4,801,575, WO 99/00150, WO 2004/050016, WO 2008/022349, WO 2005/035550, WO 2007/044323) are useful in methods targeting the CNS for delivery of oligos specific for desired CNS targets. HIR monoclonal antibodies (HIR MAbs) are able to both cross the blood brain barrier as well as brain cell membranes. When conjugated to an oligo or incorporated into a carrier, such molecules facilitate transport of oligos across the blood brain barrier. Other suitable ligands include IGF-1 and IGF-2 molecules and functional fragments thereof.

(15) Poly-Lysine—See Zhu et al., Biotechnol Appl Biochem 39: 179, 2004; Parker et al., J Gene Med 7: 1545, 2005; Stewart et al., Mol Pharm 50: 1487, 1996; U.S. Pat. Nos. 5,547,932, 5,792,645, WO 2006/053683, WO 2004/029213, and WO 93/04701. Poly-lysine consisting of approximately 3-20 amino acids can be used (D and L lysine stereoisomers both work) as carriers or as part of more complex carriers to transport oligos into intracellular compartments where they can express their intended therapeutic effects. The CPP activity of poly-lysine can also be enhanced by glycosylation.

(16) Histidine-Lysine Peptides—See the following references. (Leng et al., Drug News Perspect 20: 77, 2007; U.S. Pat. Nos. 7,070,807, 7,163,695, US 2008/0171025, WO 01/47496, WO 2004/048421, WO 2006/060182)—Histidine-Lysine Peptides useful for the practice of the present invention come in both linear and branched forms. They may also be conjugated to polyethylene glycol and vascular specific ligands where they are particularly useful for delivering oligos to the intracellular compartments of cells in solid tumors.

(17) Poly-Arginine—See Meade et al., Adv Drug Delivery Rev 59: 134, 2007; Meade and Dowdy Adv Drug Delivery Rev 60: 530, 2008; Jones et al., Br J Pharmacol 145: 1093, 2005; WO 2007/095152, WO 2008/008476, WO 2006/029078, WO 2006/0222657, WO 2006/053683, and WO 2004/029213. Poly-Arginine consisting of approximately 3-20 amino acids can be used (D and L lysine stereoisomers both work) as a fusion peptide with enhanced CPP activity where the fusion partner is selected from peptides derived from the following group: (a) HEF from influenza C virus; (b) HA2 and its analogs; (c) transmembrane glycoproteins from filovirus, rabies virus, vesicular stomatitis virus or Semliki Forest virus; (d) fusion polypeptide of sendai virus, human respiratory syncytial virus, measles virus, Newcastle disease virus, visna virus, murine leukemia virus, human T-cell leukemia virus, simian immunodeficiency virus; or (e) M2 protein of influenza A virus.

(18) NL4-10K—This molecule is described in Zeng et al., J Gene Med 6: 1247, 2004 and US 2005/0048606.—The NL4-10K peptide is based on nerve growth factor and has the sequence CTTTHTFVKALTMDGKQAAWRFIRID-TAC (SEQ ID NO: 42) and is typically used in a hairpin configuration. It facilitates uptake of oligos into cells and tissues that express the nerve growth factor receptor TrkA. Alternative peptides based on nerve growth factor suitable for this purpose include, the following: TTAT-DIKGKEVMV (SEQ ID NO: 43), EVNINNSVF (SEQ ID NO: 44), RGIDSKHWNSY (SEQ ID NO: 45) and TTTHTFVKALTMDGKQAAWRFIRIDTA (SEQ ID NO: 46). Cells expressing TrkA include but are not limited to hepatocellular carcinoma, prostate cancer, neuroblastoma, melanoma, pancreatic cancer as well as non-malignant lung, pancreas, smooth muscle and prostate. NL4-10K peptides are suitable for getting oligos across the blood brain barrier and into brain cells. US 2005/0048606 also provides CPPs suitable for promoting oligo uptake into cells that express the TrkB and TrkC receptors.

(19) $S4_{13}$-PV—See Mano et al., Biochem J 390: 603, 2005 and Mano et al., Biochimica Biophysica Acta 1758: 336, 2006.—$S4_{13}$-PV is a CPP that has a pronounced capacity to transport substances such as oligos into cells without passing through endosomes. An exemplary sequence is ALWKTLLKKVLKAPKKKRKVC (SEQ ID NO: 47).

(20) Sweet Arrow Peptide (SAP)—Foerg et al., Biochem 44: 72, 2005 described the SAP.—An exemplary SAP sequence is VRLPPPVRLPPPVRLPPP (SEQ ID NO: 48).

(21) Human Calcitonin Derived Peptide hCT(9-32)—See Foerg et al., Biochem 44: 72, 2005.—hCT(9-32) has the following sequence LGTYTQDFNKFHTFPQTAIGV-GAP, (SEQ ID NO: 49).

(22) ARF based CPPs—See WO 2008/063113.—ARF based CPPs are 15-26 amino acids long comprising at least amino acids 1-14 of a mature mammalian ARF protein or a scrambled or partially inverted sequence thereof, optionally linked to one or more members of the group consisting of a cell-homing peptide, a receptor ligand, a linker and a peptide spacer comprising a selective protease cleavage site coupled to an inactivating peptide. A scrambled or partially inverted sequence of ARF defines a sequence wherein the same amino acids in the ARF sequence are included but one or several amino acids are in different positions so that part of the sequence is inverted or the whole sequence is scrambled. ARF sequences suitable for this use include but are not limited to human p14ARF and murine p19ARF. Suitable peptides for this use include but are not limited to M918 (MVT-VLFRRLRIRRACGPPRVRV; (SEQ ID NO: 50), M917 (MVRRFLVTLRIRRACGPPRVRV; (SEQ ID NO: 51) and M872 (FVTRGCPRRLVARLIRVMVPRR; (SEQ ID NO: 52).

(23) Kaposi FGF signal sequences—See Hudecz et al., Med Res Rev 25: 679, 2005; WO 2008/022046, and WO 2008/093982.—Kaposi FGF signal sequences include but are not limited to: AAVALLPAVLLALLAP (SEQ ID NO: 53) and AAVLLPVLLPVLLAAP (SEQ ID NO: 54).

(24) Human beta3 integrin signal sequence—See WO 2008/022046.—Human beta3 integrin signal sequences include: VTVLALGALAGVGVG, (SEQ ID NO: 55).

(25) gp41 fusion sequence—See WO 2008/022046, and WO 2006/053683.)—gp41 fusion sequences include: GALFL-GWLGAAGSTMGA (SEQ ID NO: 56) which can be used as a CPP or combined with other CPPs to increase their endosomolytic function.

(26) *Caiman crocodylus* Ig(v) light chain—See the following references (Drin et al., AAPS PharmSci 4: 1, 2002; WO 2008/022046, WO 2006/053683, and WO 2004/048545.—*Caiman crocodylus* Ig(v) light chain sequences include: MGLGLHLLVLAAALQ (SEQ ID NO: 57) and MGLGLHLLVLAAALQGAWSQPKKKRKV (SEQ ID NO: 58) where the second sequence ends with a nuclear localization sequence from SV40 T antigen.

(27) hCT-derived peptide—See WO 2008/022046.—hCT-derived peptide sequences include: LGTYTQDFNKFHT-FPQTAIGVGAP (SEQ ID NO: 59).

(28) Loligomer—See WO 2008/022046.—An exemplary loligomer has the following sequence: TPPKKKRKVED-PKKKK (SEQ ID NO: 60).

(29) Anthrax toxin derivatives—See the following references. (Arora and Leppla, 3 Biol Chem 268: 3334, 1993; Arora and Leppla, Infect Immun 62: 4955, 1994; Bradley et al., Nature 414: 225, 2001; Kushner et al., Proc Natl Acad Sci USA 100: 6652, 2003; Ballard et al., Proc Natl Acad Sci USA 93: 12531, 1996; Zhang et al., Proc Natl Acad Sci USA 101: 16756, 2004; Blanke et al., Proc Natl Acad Sci USA 93: 8437, 1996; Melnyk and Collier, Proc Natl Acad Sci USA 103: 9802, 2006; Krantz et al., Science 309: 777, 2005; Liu et al., Cell Microbiol 9: 977, 2007; U.S. Pat. No. 5,677,274, US 2003/0202989, US 2005/0220807, WO 97/23236, WO 03/087129, WO 2006/091233, and WO 94/18332)—Receptors for anthrax toxin are broadly found on the surfaces of various cell types. Anthrax toxin protective antigen (PA) is the portion of the anthrax toxin that is normally responsible for delivering the toxin to the cytoplasm of cells. PA functions both as a CPP and as an endosomolytic agent, is nontoxic, and can be used to promote the delivery of oligos to the cytoplasm of cells. While PA is suitable, engineered peptides based on those regions of the PA domains directly involved in CPP and endosomolysis, along with certain other anthrax toxin sequences which augment these functions are most preferred. Anthrax lethal factor and fragments thereof also can be used to deliver oligos into the cytoplasm of cells. Suitable engineered peptides based on anthrax sequences include, but are not limited to, ligation of a portion of the lethal factor sequence that contains the PA binding site with a sequence called the entry motif as provided by WO 2006/091233. Such engineered peptides can optionally be attached to a nuclear localization sequence. Oligos linked to polycationic tracts, e.g., polylysine, polyarginine and/or polyhistidine can further potentiate delivery of oligos into the cytoplasm of cells.

(30) Ligands for transferrin receptor—See the following references. (U.S. Pat. No. 4,801,575, U.S. Pat. No. 5,547,932, U.S. Pat. No. 5,792,645, WO 2004/020404, WO 2004/020405, WO 2004/020454, WO 2004/020588, WO 2005/121179, WO 2006/049983, WO 2006/096515, WO 2008/033395, WO 2008/072075, WO 2008/022349, WO 2005/035550, WO 2007/044323 and WO 91/04753)— Ligands for transferrin receptor can be used to transport oligos into cells which express this receptor. Such ligands include but are not limited to transferrin based peptides but can include other molecules such as peptides based on melanocortin, an integrin or glucagon-like peptide 1. Ligands for the transferrin receptor can therefore be operably linked to the oligos of the invention to facilitate transport of the therapeutic across the blood brain barrier in disorders where delivery to the CNS is desirable.

(31) Ligands for transmembrane domain protein 30A—See WO 2007/036021—Ligands for transmembrane domain protein 30A can be used to transport oligos into cells that express this protein such as brain endothelium and can also be used to advantage to transport oligo across the blood brain barrier. Such ligands include antibodies and antibody fragments that bind the TMEM30A antigen as well as any one of several peptide ligands set forth in WO 2007/036021.

(32) Ligands for asialoglycoprotein receptor—See the following references. (Li et al., Sci China C Life Sci 42: 435, 1999; Huang et al., Int J Pharm 360: 197, 2008; Wang et al., J Drug Target 16: 233, 2008; Khorev et al., Bioorg Med Chem 16: 5216, 2008; WO 93/04701)—Ligands for asialoglycoprotein receptor can be used to transport oligos into cells that express them, such as liver cells.

(33) Actively Transported Nutrients—See U.S. Pat. No. 6,528,631.—Actively transported nutrients can be directly conjugated to oligos or associated with more complex carrier structures for the purpose of transporting said oligo into intracellular compartments. Exemplary nutrients for this purpose include, but are not limited to, folic acid, vitamin B6, vitamin B12, and cholesterol.

(34) UTARVE—See the following references. (Smith et al., International J Oncology 17: 841, 2000; WO 99/07723, WO 00/46384)—UTARVE refers to a vector for the delivery of oligos into the cytoplasm of cells where the vector comprises a CPP or a ligand for a cell surface receptor that is internalized with the receptor and an influenza virus hemagglutinin peptide with endosomolytic activity. The CPP or cell surface receptor ligand can include any of those described herein. In addition, the ligand can be adenovirus penton peptide, epidermal growth factor receptor or the GM1 ganglioside receptor for cholera toxin B subunit. In addition, the vector may also include a polylysylleucyl peptide to provide additional oligo attachment sites and/or a nuclear localization signal. Adenovirus penton base proteins contain a receptor binding site motif (RGD) for attachment to integrins. Integrins are ubiquitous cell receptors. As used herein adenovirus penton base protein refers to the entire adenovirus penton base protein or to fragments thereof that include at least amino acids 1-354 that contain the receptor binding motif. The particular adenovirus from which the adenovirus penton base protein is derived is not critical and examples of such adenoviruses include but are not limited to Ad2, Ad3 and Ad5. These sequences are well known in the art. The influenza hemagglutinin peptide with endosomolytic activity is described elsewhere herein. The polylysylleucyl peptide has the sequence (KL)m where the lysine residues interact with the oligo while the leucine residues decrease the potential steric hindrance resulting from adjacent lysine residues. The value of m is not critical but generally represents from 1 to 300 alternating residues and preferably from 3 to 100. Should nuclear localization be desirable, a nuclear localization sequence, such as those discussed above, or otherwise well known in the art, may be employed.

(35) Antimicrobial peptides and their analogs—See the following references. (Sandgren et al., J Biol Chem 279: 17951, 2004; US 2004/0132970; US 2002/0082195, US 2004/0072990, US 2006/0069022, US 2007/0037744, US 2007/0065908, US 2007/0149448, US 2006/0128614, WO 2005/040201, WO 2006/011792, WO 2006/067402, WO 2006/076742, WO 2007/076162, WO 2007/148078, WO 2008/022444, WO 2006/050611, WO 2008/0125359)—Numerous antimicrobial peptides are naturally occurring and are involved in innate immunity. These peptides are typically cationic and function as CPPs and therefore can be harnessed to assist in the delivery of oligos. The receptors for antimicrobial peptides are the cell surface proteoglycans, a major source of cell surface polyanions. While they are cytotoxic to microbes, antimicrobial peptides typically are much less toxic to mammalian cells. One such peptide is LL-37 which has the following sequence: LLGDFFRKSKEKIG-KEFKRIVQRIKDFLRNLVPRTES (SEQ ID NO: 61). Other examples involve peptides based on the dermaseptin family of antimicrobial peptides found on the skin of frogs of the Phylloinedusinae genus. Such peptides include, for example: ALWKTLLKKVLKA (SEQ ID NO: 62), ALWKTLLKKVLKAPKKKRKV, (SEQ ID NO: 63), PKKKRKVALWKTLLKKVLKA, (SEQ ID NO: 64) and RQARRNRRRALWKTLLKKVLKA, (SEQ ID NO: 65). Other suitable antimicrobial peptides or their analogs with CPP activity include but are not limited to novispirins, MUC7-12, CRAMP, PR-39, cryptdin-4, HBD-2, dermcidin, cecropin P1, maganin-2, granulysin and FALL-39. Such antimicrobial peptides are being developed as antimicrobial agents but also can be employed to enhance oligo delivery into cells. Analogs of antimicrobial peptides include but are not limited to those with D amino acid substitutions for their L stereoisomer counterparts for the purpose of reducing protease attack.

(36) Screened products of peptide and MAb fragment display libraries—See the following references. (Thomas et al., Pharmaceutical Res 24: 1564, 2007; WO 01/15511, WO 03/068942, WO 2007/143711, WO 97/17613, WO 97/17614)—A series of CPPs and MAb fragments with the capacity to transport oligos into a broad range of cell types in a manner that promotes their biological activity have been identified through a series of screening steps starting with peptide or MAb fragment libraries. Indeed, a series of antibody single chain variable fragments (scFvs) with the capacity to bind to endothelial cells have been developed. Such scFvs can be used to advantage to facilitate transport oligos into the endothelium. It is clear from such work that a wide range of effective CPP for the purposes of the present invention are readily available. A series of scFvs with the capacity to bind to endothelial cells and to cause the transport oligos across the blood brain barrier have been developed and are described in the references provided.

(37) Designer CPPs—See the following references. (Rhee and Davis J Biol Chem 281: 1233, 2006; Kim et al., Exp Cell Res 312: 1277, 2006; Kaihatsu et al., Biochem 43: 14340, 2004; Hudecz et al., Med Res Rev 25: 679, 2005; Adenot et al., Chemotherapy 53: 73, 2007; U.S. Pat. Nos. 5,547,932, 7,329,638, 7,101,844, 6,200,801, 5,972,901, US 2005/0154188, US 2006/0228407, US 2004/0152653, US 2005/0042753, US 2003/0119725, US 2005/0239687, US 2005/0106598, US 2007/0129305, U.S. Pat. No. 6,841,535, US 2008/0182973, US 2009/0029387, WO 2007/069090, WO 00/34308, WO 00/62067, WO 2007/095152, WO 2007/056153, WO 2008/022046, US 2008/0234183, WO 2005/007854, WO 2007/053512, WO 20081093982, WO 03/106491, WO 2004/016274, WO 03/097671, WO 01/08708, WO 97/46100, WO 06126865)—A large number of CPPs have been rationally designed based on the following: (i) a substantial number of potent CPPs have been identified beginning with those of natural origin; and (ii) effective CPPs typically can function as a prototype for other CPPs that share a set of similar properties related to amino acid composition, sequence patters and size. Such CPPs have subsequently been screened for activity and particularly active CPPs identified and tested in various carrier arrangements of the types provided herein. In addition, Hallbrink et al., have studied a broad range of CPPs and have developed comprehensive rules that describe CPP structure and function. They then applied these rules to generate a large number of Designer CPPs as described in US 2008/0234183 which claims priority to WO 03/106491. Design features that can be individually or in some instances in combination with one or more other such features can be used to generate designer CPPs are provided below:

(a) The design parameters disclosed in US 2008/0234183 include a bulk property value $Z_\Sigma$, a term called $Bulk_{ha}$ that reflects the number of non-hydrogen atoms (e.g. C, N, S and O) in the side chains of the amino acids and a term hdb standing for the number of accepting hydrogen bonds for the side chains of the amino acids. Some examples of these Designer CPPs include the peptide sequenced IVIAKLKA (SEQ ID NO: 66) and IVIAKLKANLMCKTCRLAK (SEQ ID NO: 67);

(b) Those that include the peptide sequence KVKKQ (SEQ ID NO:68);

(c) Those that include the D-amino acid peptide sequence $D(AAKK)_4$ (SEQ ID NO: 69);

(d) Those that include the sequence PFVYLI (SEQ ID NO: 70) including but not limited to the sequence CSIPPEVKFNKPFVYLI (SEQ ID NO: 71) that has been termed the C105Y peptide;

(e) polycations consisting of various combinations of amines, substituted amines, guanidinium, substituted guanidinium, histidyl or substituted histidyl and organized into one of 60 different patters where a specific patterns repeats one to about 20 times (WO 2005/007854). These polycations can be directly attached to an oligo, attached to an oligo through a linker or indirectly associated through pRNA, nanoparticles, nanoparticles based on dendrimers, nanolattices, nanovesicles or micelles;

(f) An arginine-rich peptide of 8-16 subunits selected from X subunits, Y subunits and optional Z subunits including at least six X subunits, at least two Y subunits and at most three Z subunits where >50% of said subunits are X subunits and where (i) each X subunit independently represents arginine or an arginine analog said analog being a cationic alpha-amino acid comprising a side chain of the structure $R^1N=C(NH_2)R^2$ where $R^1$ is H or R; $R^2$ is R $NH_2$, NHR or $NR_2$ where R is lower alkyl or lower alkenyl and may further include oxygen or nitrogen; $R^1$ and $R^2$ may together from a ring; and the side chain is linked to said amino acid via $R^1$ or $R^2$; (ii) each Y subunit independently represents a neutral amino acid —C(O)—(CHR)n-NH— where either n is 2 to 7 and each R is independently H or methyl or n is 1 and R is a neutral side chain selected from substituted or unsubstituted alkyl, alkenyl, alkynyl, aryl and aralkyl wherein said neutral side chain selected from substituted alkyl, alkenyl and alkynyl, includes at most one heteroatom for every four carbon atoms; and (iii) each Z subunit independently represents an amino acid selected from alanine, asparagine, cysteine, glutamine, glycine, histidine, lysine, methionine, serine and threonine.

(g) Sequences with the one of the following patterns were the term Xaa denotes either any amino acid or a position where an amino acid is not necessary with the noted preferred exceptions: XaaXaaXaaKKRRXaaXaaXaaXaaXaaXaaTWXaaETWWXaaXaaXaa (SEQ ID NO: 72) (preferably at least one of the positions eight through thirteen is P, Q or G), YGFKKRRXaaXaaQXaaXaaXaaTWXaaETWWTE (SEQ ID NO: 73) (preferably Xaa of position 16 is not omitted and preferably is an aromatic hydrophobic amino acid and is most preferably W) and YGFKKXRRPWTWWETWWTEX (SEQ ID NO: 74) (preferably Xaa in position six is a hydrophobic amino acid, more preferably an aromatic hydrophobic amino acid and that the Xaa in position twenty is preferably omitted.

(h) A CPP comprising an amino acid sequence according to the general formula $(X_1X_2B_1B_2X_3B_3X_4)n$ (SEQ ID NO:

75) wherein $X_1$-$X_4$ are independently any hydrophobic amino acid; where in $B_1$, $B_2$ and $B_3$ are independently any basic amino acid; and wherein n is between 1 and 10.

(i) A CPP comprising an amino acid sequence according to either the general formula $Q_1$-$X^1$-$(X^2)_2$-$(X^3)_2$-$X^2$-$X^4$-$X^3$-$X^4$-$X^2$-$X^4$-$X^3$-$(X^2)_2$-$Q_2$ (SEQ ID NO: 76) or $Q_1$-$(X^2)_2$-$X^3$-$X^4$-$X^2$-$X^4$-$X^3$-$X^4$-$X^2$-$(X^3)_2$-$(X^2)_2$-$X^1$-$Q_2$ (SEQ ID NO: 77) where in one of $Q_1$ and $Q_2$ is H and the other of $Q_1$ and $Q_2$ is a covalent attachment to a linking moiety further attached to an oligo or to a carrier complex associated with an oligo; each $X^1$ is, independently, a naturally occurring or non-naturally occurring amino acid; each $X^2$, is independently, a D or L amino acid selected from lysine, histidine, homolysine, diaminobutyric acid, arginine, ornithine or homoarginine; each $X^3$ is, independently, a D or L amino acid selected from alanine, valine, leucine, isoleucine, phenylalanine, tyrosine, tryptophan, cysteine, or methionine; and each $X^4$ is, independently, a D or L amino acid selected from lysine, histidine, homolysine, diaminobutyric acid, arginine, ornithine, homoarginine, alanine, valine, leucine, isoleucine, phenylalanine, tyrosine, tryptophan, cysteine, methionine, glycine, serine, threonine, aspartate, glutamate, asparagine or glutamine.

(j) Those based on Syn B family peptides and generated using a computational model of cellular uptake followed by demonstrated ability to transport large charge molecules into intracellular compartments.

(k) CPPs have been designed that preferentially deliver oligos to the cytoplasm of cells rather than to the nucleus. The CPP sequences useful for this purpose include but are not limited to the following sequence A-$X_1$-$X_2$-B-$X_3$-$X_4$-$X_5$-$X_6$-$X_7$-$X_8$ (SEQ ID NO: 78) wherein A is an amino acid exhibiting relatively high freedom at the Φ and ω rotations of a peptide unit such as G or A, B is a basic amino acid and at least 3 residues of $X_1$-$X_2$-B-$X_3$-$X_4$-$X_5$-$X_6$-$X_7$-$X_8$ are R or K. CPP sequences useful for this purpose also include but are not limited to the following related sequences: YGRRARRRRRR (SEQ ID NO: 79), YGRRARRRARR (SEQ ID NO: 80) and YGRRRRRRRRR (SEQ ID NO: 81).

For example, designer ligands and CPPs have been described in the following references. See Costantino et al., J Controlled Release 108: 84, (2005), WO 2006/061101; WO 2007/143711 and WO 2005/035550. Exemplary ligands include those with one of the following sequences: HAIYPRH (SEQ ID NO: 82) or THRPPMWSPVWP (SEQ ID NO: 83). A designer CPP with the sequence $H_2$N-G-F-D-T-G-F-L-S-CONH$_2$ (SEQ ID NO: 84), where D denotes the D stereoisomer of T and where all the other stereoisomers are L, that can be incorporated into nanoparticles suitable for transporting oligos across the blood brain barrier. A designer CPP with the sequence $H_2$N-GF (specifically Phe-D)TG-FLS-CONH$_2$ (SEQ ID NO: 85) is well suited to carry oligos into the cytoplasm of endothelial cells.

(38) Designer polycations that are not peptides—See U.S. Pat. No. 6,583,301; WO 99/02191. Designer polycations that are not peptides have been produced and shown to transport large charged molecules into intracellular compartments. These include but are not limited to structures that contain bipolar lipids with cationic heads, a hydrophobic backbone and a hydrophilic tail with a detailed structure as described in U.S. Pat. No. 6,583,301.

(39) Rabies virus glycoprotein (RVG) peptide—(U.S. Pat. No. 7,329,638, US 2005/0042753, WO 2008/054544)—The RVG peptide has sequences that include but are not limited to YTIWMPENPRPGTPCDIFTNSRGKRASNG (SEQ ID NO: 86). When this peptide or a derivative or variant of it is used in a carrier for an oligo, it facilitates transport of the carrier/oligo complex across the blood brain barrier and into brain cells. In some embodiments the RVG peptide functions as a targeting agent and is conjugated to a carrier particle and an agent termed an effector agent (as defined by WO 2008/054544) that is associated with the carrier particle. In one embodiment said effector agent is a oligo. RVG may be used as the sole targeting agent or be used in combination with other targeting agents that include but are not limited to insulin, transferrin, insulin like growth factor, leptin, low density lipoprotein and fragments or peptidomimetics thereof. In some embodiments, the carrier particle is a lysosomal or polymeric nanoparticle, for example a liposome, polyarginine, protamine or a cyclodextrin-based nanoparticle. In alternative embodiments, the carrier particle is a CPP such as 11dR, 9dR, 7dR, 5dR or TAT or fragments thereof. 11dR, 9dR, 7dR and 5dR are polymeric arginine residues of varying length in these cases 11, 9, 7 and 5 arginines respectively.

(40) Ligands for leptin receptor—(WO 2008/022349, WO 2005/035550, WO 2007/044323)—Ligands for leptin receptor can be used to transport oligos across the blood brain barrier.

(41) Ligands for lipoprotein receptor—(U.S. Pat. No. 5,547,932, WO 2008/022349, WO 2007/044323)—Ligands for lipoprotein receptor can be used to transport oligos across the blood brain barrier.

(42) Hemagglutinating virus of Japan (HVJ) envelope. See the following references. Zhang et al., Biochem Biophys Res Commun 373: 345, 2008; Yamada et al., Am J Physiol 271: R1212, 1996; Bai et al., Ann Thorac Surg 66: 814, 1998; Ogata et al., Curr Eye Res 18: 261, 1999; Matsuo et al., J Drug Target 8: 207, 2000; Tomita et al., J Gene Med 4: 527, 2002; Okano et al., Gene Ther 10: 1381, 2003; Parveen et al., Virology 314: 74, 2003; Ferrari et al., Gene Ther 11: 1659, 2004; Sasaki et al., Gene Ther 12: 203, 2005; Griesenbach et al., Biomaterials 29: 1533, 2008; Kaneda et al., Mol Ther 6: 219, 2002; Kaneda et al., Expert Opin Drug Deliv 5: 221, 2008; Mima et al., J Gene Med 7: 888, 2005; Shimbo et al., Biochem Biophys Res Commun 364: 423, 2007; Kaneda et al., Adv Genet 53: 307, 2005; Shimamura et al., Biochem Biophys Res Commun 300: 464, 2003; Morishita et al., Biochem Biophys Res Commun 334: 1121, 2005; Kotani et al., Curr Gene Ther 4: 183, 2004; Hagihara et al., Gene Ther 7: 759, 2000; Ohmori et al., Eur J Cardio-thoracic Surg 27: 768, 2005; Tsujie et al., Kidney Inter 59: 1390, 2001; Yonemitsu et al., Gene Ther 4: 631, 1997; U.S. Pat. No. 6,913,923, US 2003/0013195, US 2004/0219674, US 2005/0239188, US 2006/0002894, WO 95/30330. Tissues where improved oligo uptake can be achieved by HVJ containing delivery systems include but are not limited to CNS, cardiovascular, uterus, liver, spleen, periodontal, skin, lung, retina, kidney, lymphoid tissues, embryonic stem cells and various solid tumors. In addition, carriers based on the HVJ envelope can be used to transfer oligos across the blood brain barrier. Delivery has been via numerous routes including but not limited to topical, iv, intranasal, direct tissue injections including injection into amniotic fluid. This delivery system is particularly versatile and optionally includes nanoparticles and liposomes.

(43) Heart homing peptides are described in WO 00/75174 and include: GGGVFWQ (SEQ ID NO: 87), HGRVRPH (SEQ ID NO: 88), VVLVTSS (SEQ ID NO: 89), CLHRGNSC (SEQ ID NO: 90) and CRSWNKADNRSC (SEQ ID NO: 91). These peptides can be directly conjugated to oligos or be incorporated into more complex carriers. Further, they can be conjugated to or indirectly associated with other CPPs provided herein. The CRSWNKADNRSC (SEQ ID NO: 92) peptide is particularly well suited to targeting regions of ischemia-reperfusion injury in the heart such as occurs in the treatment of heart attacks when the blood supply is medically restored.

(44) Peptides that target the LOX-1 receptor as described in White et al., Hypertension 37: 449, 2001) are particularly suitable for targeting oligos to the endothelium. These peptides were initially selected from peptide libraries and then further screened for CPP activity. Examples include but are not limited to the following peptides: LSIPPKA (SEQ ID NO: 93), FQTPPQL (SEQ ID NO: 94) and LTPATAI (SEQ ID NO: 95). LOX-1 is up-regulated on dysfunctional endothelial cells such as those involved in hypertension, diabetes, inflammation, restenosis, septic shock, ischemia-reperfusion injury and atherosclerosis and thus such peptides are particularly well suited for concentrating oligos into this subset of cells to treat these and related medical conditions;

(45) Peptide for ocular delivery (POD) is described in Johnson et al., Mol Ther 16: 107, 2008)—POD has the following sequence GGG(ARKKAAKA)$_4$ (SEQ ID NO: 96) and is suitable for transporting oligos into the retina.

(46) LFA-1 targeting moieties are described in U.S. Pat. No. 7,329,638, US patent application 2005/0042753, International application WO 2007/127219. Preferred targeting moieties are selected from the group consisting of an antibody or a functional fragment thereof having immunospeciflcity for LFA-2 or protamine or a functional fragment thereof such as a peptide with the sequence RSQSRSRYYRQRQRSRRRRRRS (SEQ ID NO: 97). Cells susceptible to LAF-1 targeting of oligos include leukocytes and nerve cells as well as a variety of cancer cell types including but not limited to breast, colon and pancreas.

(47) P11-50—is described in WO 03/082213 and can be cross-linked and milled to generate nanoparticles to deliver oligos to cells such as phagocytes involved in inflammation such as but not limited to those involved in ischemia reperfusion injury, arthritis and in atherosclerotic plaques.

(48) HA2 peptides are described in Dopheide et al., J Gen Virol 50: 329, 1980; Wang and El-Deiry, Trends Biotech 22: 431, 2004, Pichon et al., Antisense Nucleic Acid Drug Dev 7: 335, 1997; Daniels et al., Cell 40: 431, 1985; Navarro-Quiroga et al., Brain Res Mol Brain Res 105: 86, 2002; Cho et al., Biotechnol Appl Biochem 32: 21, 2000; Bailey et al., Biochim Biophys Acta 1324: 232, 1997; Steinhauer et al., J Virol 69: 6643, 1995; Sugita et al., Biochem Biophys Res. Comm 363: 107, 2007; U.S. Pat. No. 5,547,932, WO 00/46384, WO 99/07723, and WO2008/022046. HA2 peptides can be employed in the compositions and methods of the invention to enhance endosomolysis to facilitate increased levels of oligo delivery. Influenza virus hemagglutinin (HA) is a trimer of identical subunits each of which contains two polypeptide chains HA1 and HA2. Functional HA2 sequences include but are not limited to: GLFGAIAGFIENGWEG (SEQ ID NO: 98), GLFGAIAGFIGN(or G)GWGGMI(or V)D (SEQ ID NO: 99) or GDIMGEWGNEIFGAIAGFLG (SEQ ID NO: 100). In some instances, HA2 has been fused to the TAT CPP as described briefly above, to produce the dTAT-HA2 peptide. Such sequences include: RRRQRRKKRGGDIMGEWGNEIFGAIAGFLG (SEQ ID NO: 101). dTAT-HA2 can more effectively deliver a bioactive oligo than TAT in instances where endosomal/lysosomal sequestration of the oligo reduces activity significantly.

(49) Poly-histidine and histidine requiring peptides See the following references. (Leng et al., Drug News Perspect 20: 77, 2007; McKenzie et al., Bioconjug Chem 11: 901, 2000; Reed et al., Nucleic Acids Res 33: e86, 2005; Lee et al., J Control Release 90: 363, 2003; Lo and Wang, Biomaterials 29: 2408, 2008, and WO 2006/053683)—Poly-histidine is hydrophobic at physiological pH but ionized at endosomal pH resulting in destabilization of the endosomal membrane. Polyhistidine can be operably linked to various CPPs to promote endosomolysis following cellular uptake. In some manifestations histidine is conjugated to poly(2-hydroxyethyl aspartamide) to produce an endosomolytic molecule capable of promoting the release of oligos from endosomes, lysosomes or phagosomes. In another manifestation, approximately 10 histidines (preferred range 3 to 20 His) are conjugated to the C-terminus of TAT. In yet another embodiment, the aforementioned molecule comprises two cysteine residues which are incorporated into the molecule with a preferred distribution being cysteine-5 histidines-TAT-5 histidines-cysteine. Other histidine requiring peptides suitable for this purpose include but are not limited to the following: CHKKKKKKHC (SEQ ID NO: 102), CHHHHHHKKKHHHHHHC (SEQ ID NO: 103) and HHHHHWYG (SEQ ID NO: 104).

(50) Sendi F1—(WO 2008/022046)—has the following sequence: FFGAVIGTIALGVATA (SEQ ID NO: 105) which can be incorporated into fusion CPPs to increase their endosomolytic activity.

(51) Respiratory Syncytial Virus F1—(WO 2008/022046)—has the following sequence: FLGFLLGVGSAIASGV (SEQ ID NO: 106) and can be incorporated into fusion CPPs to increase their endosomolytic activity.

(52) HIV gp41—(WO 2008/022046, WO 2006/053683)—has the following sequence: GVFVLGFLGFLATAGS (SEQ ID NO: 107) can be incorporated into fusion CPPs to increase their endosomolytic activity.

(53) Ebola GP2—(WO 2008/022046)—has the following sequence: GAAIGLAWIPYFGPAA (SEQ ID NO: 108) and can be incorporated into fusion CPPs to increase their endosomolytic activity.

(54) pH Triggered Agents See the following references (Ogris et al., J Biol Chem 276: 47550, 2001; Meyer et al., J Gene Med 9: 797, 2007; Chen et al., Bioconjug Chem 17: 1057, 2006; Boeckle et al., J Control Release 112: 240, 2006; Schreier, Pharm Acta Helv 68: 145, 1994; Martin and Rice, AAPS J 9: E18, 2007; Plank et al., Adv Drug Delivery Rev 34:21, 1998; Wagner, Adv Drug Deliv Rev 38: 279, 1999; Eliyahu et al., Biomaterials 27: 1646, 2006; Eliyahu et al., Gene Therapy 12: 494, 2005; Provoda et al., J Biol Chem 278: 35102, 2003; Choi and Lee, J Controlled Release 131: 70, 2008; Parente et al., Biochem 29: 8720, 1990; Wyman et al., Biochem 36: 3008, 1997; Rittner et al., Mol Therapy 5: 104, 2002; US 2007/0036865, US 2004/0198687, US 2005/0244504, US 2003/0199090, US 2008/0187998, US 2006/0084617, U.S. Pat. No. 7,374,778, WO 2004/090107, WO 96/00792, WO 03/093449, WO 2006/053683, WO 94/01448)—pH Triggering Agents are agents that respond to the acidic pH found in endosomes/lysosomes or phagosomes in a manner that causes them to become endosomolytic. Such agents include certain viral proteins listed elsewhere herein but also include other peptides and small molecules that can be incorporated into a larger carrier molecule in multiple copies to concentrate their effect on endosomes/lysosomes (endosomolytic polymer). Endosomolytic polymers can be conjugated directly to oligos by stable or by means of pH labile bonds or incorporated into nanoparticles carriers. Maleamates suitable for use as pH triggering agents include, but are not limited to, carboxydimethylmaleic anhydride, carboxydimethylmaleic anhydride-thioester and carboxydimethylmaleic anhydride-polyethylene glycol. In a preferred embodiment, a multiplicity of such maleamates (e.g., disubstituted maleic anhydride derivatives) are reversibly linked to polyamine as an endosomolytic polymer. Alternative pH triggering agents include but are not limited to the following:

(a) poly(beta-amino ester) as well as salts, derivatives, co-polymers and blends thereof;
(b) oligo sulfonamides including those with sulfamethizole, sulfadimethoxine, sulfadiazine or sulfamerazine moieties. Such oligo sulfonamides can be used without a separate endosomolytic polymer;
(c) Spermine where said spermine may include a cholesterol and/or fatty acid that may be bonded directly to a secondary amine in the spermine and said spermine may be further linked to a carbohydrate such as dextran or arabinogalactan;
(d) Peptides based on certain bacterial pore forming proteins such as listeriolysin O where the damage caused to cellular membranes around neutral pH is not unacceptably toxic. Listeriolysin O also can be beneficially combined with low molecular weight PEI to promote delivery of oligos.
(e) Peptides and conjugates based on melittin (also called mellitin) of GIGAVLKVLTTGLPALISWIKRKRQQ (SEQ ID NO: 109). Certain melittin analogues are better suited to this purpose than native melittin. Melittin-PEI conjugates are particularly preferred and are well suited as pH triggering agents. Exemplary conjugates include those where the N-terminus of melittin is conjugated to PEI. Further, modification of the C-terminally linked melittin peptide by replacement of the two neutral Q residues with E residues can increase the membrane lytic activity of melittin-PEI conjugates at endosomal pH. A preferred peptide structure with CPP and endosomolytic activity is a dimethylmaleic acid-melittin-polylysine conjugate. Melittin has also been developed into a gene delivery peptide capable of condensing and cross-linking DNA. This involves addition of lysine residues to increase the positive charge and terminal cysteine residues to promote polymerization.
(f) Alternative endosomolytic polymers include but are not limited to polyesters, polyanhydrides, polyethers, polyamides, polyacrylates, polymethacrylates, polycarbamates, polycarbonates, polyureas, poly(beta-amino esters) polythioesters and poly(alkyl)acrylic acids.
(g) The endosomolytic/pH triggering agents include but are not limited to peptides that contain imidazole groups or peptides having a repeating glutamate, alanine, leucine, alanine structure such as the EALA peptide (SEQ ID NO: 110) (also known as GALA; SEQ ID NO: 111) with a sequence that includes but is not limited to WEAALAEA-LAEALAEHLAEALAEALEALAA (SEQ ID NO: 112) as well as the following: KALA (SEQ ID NO:113) with a sequence that includes but is not limited to WEAK-LAKALAKALAKHLAKALAKALKACEA (SEQ ID NO: 114), EGLA (SEQ ID NO: 115), JTS-1 with a sequence that includes but is not limited to GLFEAL-LELLESLWELLLEA (SEQ ID NO: 116), gramicidin S, ppTG1 with a sequence that includes but is not limited to GLFKALLKLLKSLWKLLLKA (SEQ ID NO: 117) and ppTG20 with a sequence that includes but is not limited to GLFRALLRLLRSLWRLLLRA (SEQ ID NO: 118).
(h) Any polymer which is not hydrophobic at physiologic pH but which becomes hydrophobic at pH (5.0-6.5) can be useful to promote endosomolysis and increase delivery of the oligo described herein. Further examples include: (a) Polymers that contain multiple carboxylic acid groups; and (b) Random, block and graft copolymers that include acrylate groups and alkyl substituted acrylate groups where preferably the alkyl group is a 1-6 carbon straight, branched or cyclic alkane. Preferred monomers for use in polymeric materials include poly(ethylacrylic acid), poly (propylacrylic acid) and poly(butylacrylic acid). Copolymers of these monomers by themselves or including acrylic acid can be used. Alternatively, or in addition, the carrier composition can include ligands such as polylysine or chitosan that can be associated with the oligo.

The ability of the molecules described above to move oligos across cell membranes may be further enhanced by combining them with certain lipophilic domains and then combining the product with an oligo as described, for example, in Koppelhus et al., Bioconjugate Chem 19: 1526, 2008 and WO 2008/043366. Such lipophilic domains that may be conjugated to the CPP or to the oligo include but are not limited to the following: (1) an alkyl, alkenyl or alkynyl chain comprising 5-20 carbon atoms with a linear arrangement or including at least one cycloalkyl or heterocycle; or (2) a fatty acid containing 4 to 20 carbon atoms.

In certain embodiments of the invention, CPP, linkers, nanoparticles, nanoparticles based on dendrimers, nanolattices, nanovesicles, nanoribbons, liposomes or micelles used to associate such peptides to oligos may be employed in the therapeutically beneficial compositions described herein. Such liposome applications include the use of heat delivery systems to promote targeting of heat labile liposomes carrying oligos to particular tissues. Such compositions are described in Najlah and D'Emanuele, Curr Opin Pharmacol 6: 522, 2006; Munoz-Morris et al., Biochem Biophys Res Commun 355: 877, 2007; Lim et al., Angew Chem hit Ed 46: 3475, 2007; Zhu et al., Biotechnol Appl Biochem 39: 179, 2004; Huang et al., Bioconjug Chem 18: 403, 2007; Kolhatkar et al., Bioconjug Chem 18: 2054, 2007; Najlah et al., Bioconjug Chem 18: 937, 2007; Desgates et al., Adv Drug Delivery Rev 60: 537, 2008; Meade et al., Adv Drug Delivery Rev 59: 134, 2007; Albarran et al., Protein Engineering, Design & Selection 18: 147, 2005; Hashida et al., Br J Cancer 90: 1252, 2004; Ho et al., Cancer Res 61: 474, 2001; U.S. Pat. No. 7,329,638, US 2005/0042753, US 2006/0159619, US 2007/0077230, WO 2008/106503, WO 2008/073856, WO 2008/070141, WO 2008/045486, WO 2008/042686, WO 2008/003329, WO 2008/026224, WO 2008/037463, WO 2008/039188, WO2007/056153, WO2008/022046, WO 2007/131286, WO 2007/048019, WO 2004/048545, WO 2008/033253, WO 2005/035550, WO 0610247, and WO 2007/133182.

In certain embodiments, CPP are not employed to enhance uptake of the oligo of the invention. Compositions suitable for this embodiment are provided in the following references: Najlah and D'Emanuele, Curr Opin Pharmacol 6: 522, 2006; Huang et al., Bioconjug Chem 18: 403, 2007; Kolhatkar et al., Bioconjug Chem 18: 2054, 2007; Najlah et al., Bioconjug Chem 18: 937, 2007; US 2005/0175682, US 2007/0042031, U.S. Pat. No. 6,410,328, US 2005/0064595, US 2006/0083780, US 2006/0240093, US 2006/0051405, US 2007/0042031, US 2006/0240554, US 2008/0020058, US 2008/0188675, US 2006/0159619, WO 2008/096321, WO 2008/091465, WO 2008/073856, WO 2008/070141, WO 2008/045486, WO 2008/042686, WO 2008/003329, WO 2008/026224, WO 2008/037463, WO 2007/131286, WO 2007/048019, WO 2004/048545 WO 2007/0135372, WO 2008/033253, WO 2007/086881, WO 2007/086883, and WO 2007/133182.

In certain embodiments, it is preferable to deliver oligos topically (e.g., to skin (e.g., for the treatment of psoriasis), mucus membranes, rectum, lungs and bladder). The following references describe compositions and methods that facilitate topical oligo delivery. See US 2005/0096287, US 2005/0238606, US 2008/0114281, U.S. Pat. No. 7,374,778, US 2007/0105775, WO 99/60167, WO 2005/069736, and WO 2004/076674. Exemplary methods and compositions include: (1) instruments that deliver a charge by means of electrodes to the skin with the result that the stratum corneum in an area beneath the electrodes is ablated thereby generating at least one micro-channel, the oligos being administered optionally being associated with any of the oligo carriers described herein; (2) the use of ultrasound to both cross the skin and to assist in getting carrier/oligo complexes into cells; and (3) use of a carrier including but not limited to emulsions, colloids, surfactants, microscopic vesicles, a fatty acid, liposomes and transfersomes. The methods and compositions just provided in (2) and (3) and where the oligo has phosphodiester and/or phosphorothioate linkages may be further abetted by the use of reversible Charge Neutralization Groups of the type described in WO 2008/008476.

Polyampholyte complexes can be used to promote oligo uptake following topical application or following intravascular, intramuscular, intraperitoneal administration or by direct injections into particular tissues. In a preferred embodiment the polyampholyte complexes contain pH-labile bonds such as those described in US 2004/0162235, and WO 2004/076674.

Additional agents, CPPs and endosomolytic agents may be directly linked to oligos or to carriers non-covalently associated with oligos to improve the intracellular bioavailability of the oligo. Such agents include but are not limited to the compositions, methods and uses described in the following: Kubo et al., Org Biomol Chem 3: 3257, 2005; U.S. Pat. No. 5,574,142, U.S. Pat. No. 6,172,208, U.S. Pat. No. 6,900,297, US 2008/0152661, US 2003/0148928, WO 01/15737, WO 2008/022309, WO 2006/031461, WO 02/094185, WO 03/069306, WO 93/07883, WO 94/13325, WO 92/22332, WO 94/01448.

In order to cross intact mammalian skin, lipid vesicles must pass through a series of fine pores, each with a diameter less than 50 nm, under the influence of a suitable transdermal gradient. Therefore, it is desirable to use a liposome that is highly deformable and able to pass through such fine pores.

Liposomes obtained from natural phospholipids are biocompatible and biodegradable; liposomes can incorporate a wide range of water and lipid soluble drugs; liposomes can protect encapsulated drugs in their internal compartments from metabolism and degradation (Rosoff, in Pharmaceutical Dosage Forms, Lieberman, Rieger and Banker (Eds.), 1988, Marcel Dekker, Inc., New York, N.Y., volume 1, p. 245). Important considerations in the preparation of liposome formulations are the lipid surface charge, vesicle size and the aqueous volume of the liposomes.

Liposomes are useful for the transfer and delivery of active ingredients to the site of action. Because the liposomal membrane is structurally similar to biological membranes, when liposomes are applied to a tissue, the liposomes start to merge with the cellular membranes. As the merging of the liposome and cell progresses, the liposomal contents are emptied into the cell where the active agent may act.

Liposomal formulations have been the focus of extensive investigation as the mode of delivery for many drugs. There is growing evidence that for topical administration, liposomes present several advantages over some other formulations. Such advantages include reduced side-effects related to high systemic absorption of the administered drug, increased accumulation of the administered drug at the desired target, and the ability to administer a wide variety of drugs, both hydrophilic and hydrophobic, into the skin.

Several reports have detailed the ability of liposomes to deliver agents including high-molecular weight DNA into the skin. Compounds including analgesics, antibodies, hormones and high-molecular weight DNAs have been administered to the skin. The majority of applications resulted in the targeting of the upper epidermis.

Liposomes fall into two broad classes. Cationic liposomes are positively charged liposomes that interact with the negatively charged DNA molecules to form a stable complex. The positively charged DNA/liposome complex binds to the negatively charged cell surface and is internalized into an endosome. Due to the acidic pH within the endosome, the liposomes are ruptured, releasing their contents into the cell cytoplasm (Wang et al., Biochem Biophys Res Commun, 1987, 147, 980-985).

Liposomes which are pH-sensitive or negatively-charged, entrap DNA rather than complex with it. Since both the DNA and the lipid are similarly charged, repulsion rather than complex formation occurs. Nevertheless, some DNA is entrapped within the aqueous interior of these liposomes. pH-sensitive liposomes have been used to deliver DNA encoding the thymidine kinase gene to cell monolayers in culture. Expression of the exogenous gene was detected in the target cells (Thou et al., J Controlled Release, 1992, 19, 269-274).

One major type of liposomal composition includes phospholipids other than naturally-derived phosphatidylcholine. Neutral liposome compositions, for example, can be formed from dimyristoyl phosphatidylcholine (DMPC) or dipalmitoyl phosphatidylcholine (DPPC). Anionic liposome compositions generally are formed from dimyristoyl phosphatidylglycerol, while anionic fusogenic liposomes are formed primarily from dioleoyl phosphatidylethanolamine (DOPE). Another type of liposomal composition is formed from phosphatidylcholine (PC) such as, for example, soybean PC, and egg PC. Another type is formed from mixtures of phospholipid and/or phosphatidylcholine and/or cholesterol.

Several studies have assessed the topical delivery of liposomal drug formulations to the skin. Application of liposomes containing interferon to guinea pig skin resulted in a reduction of skin herpes sores while delivery of interferon via other means (e.g., as a solution or as an emulsion) were ineffective (Weiner et al., Journal of Drug Targeting, 1992, 2, 405-410). Further, an additional study tested the efficacy of interferon administered as part of a liposomal formulation to the administration of interferon using an aqueous system, and concluded that the liposomal formulation was superior to aqueous administration (du Plessis et al., Antiviral Research, 1992, 18, 259-265).

Non-ionic liposomal systems have also been examined to determine their utility in the delivery of drugs to the skin, in particular systems comprising non-ionic surfactant and cholesterol. Non-ionic liposomal formulations comprising Novasome® I (glyceryl dilaurate/cholesterol/polyoxyethylene-10-stearyl ether) and Novasome® II (glyceryl distearate/cholesterol/polyoxyethylene-10-stearyl ether) were used to deliver cyclosporin-A into the dermis of mouse skin. Results indicated that such non-ionic liposomal systems were effective in facilitating the deposition of cyclosporin-A into different layers of the skin (Hu et al. S.T.P. Pharma. Scid., 1994, 4, 6, 466).

Liposomes also include "sterically stabilized" liposomes, a term which, as used herein, refers to liposomes comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome (A) comprises one or more glycolipids, such as monosialoganglioside GM1, or (B) is derivatized with one or more hydrophilic polymers, such as a polyethylene glycol (PEG) moiety. While not wishing to be bound by any particular theory, it is thought in the art that, at least for sterically stabilized liposomes containing gangliosides, sphingomyelin, or PEG-derivatized lipids, the enhanced circulation half-life of these sterically stabilized liposomes derives from a reduced uptake into cells of the reticuloendothelial system (RES) (Allen et al., FEBS Letters, 1987, 223, 42; Wu et al., Cancer Research, 1993, 53, 3765). Various liposomes comprising one or more glycolipids are known in the art. Papahadjopoulos et al. (Ann. N.Y. Acad. Sci., 1987, 507, 64) reported the ability of monosialoganglioside GM1, galactocerebroside sulfate and phosphatidylinositol to improve blood half-lives of liposomes. These findings were expounded upon by Gabizon et al. (Proc. Natl. Acad. Sci. U.S.A., 1988, 85, 6949). U.S. Pat. No. 4,837,028 and WO 88/04924, both to Allen et al., who disclose liposomes comprising (1) sphingomyelin and (2) the ganglioside GM1 or a galactocerebroside sulfate ester. U.S. Pat. No. 5,543,152 (Webb et al.) discloses liposomes comprising sphingomyelin. Liposomes comprising 1,2-sn-dimyristoylphosphatidylcholine are disclosed in WO 97/13499 (Lim et al.).

Many liposomes comprising lipids derivatized with one or more hydrophilic polymers, and methods of preparation thereof, are known in the art. Sunamoto et al. (Bull. Chem. Soc. Jpn., 1980, 53, 2778) described liposomes comprising a nonionic detergent, 2C1215G, that contains a PEG moiety. Ilium et al. (FEBS Lett., 1984, 167, 79) noted that hydrophilic coating of polystyrene particles with polymeric glycols results in significantly enhanced blood half-lives. Synthetic phospholipids modified by the attachment of carboxylic groups of polyalkylene glycols (e.g., PEG) are described by Sears (U.S. Pat. Nos. 4,426,330 and 4,534,899). Klibanov et al. (FEBS Lett., 1990, 268, 235) described experiments demonstrating that liposomes comprising phosphatidylethanolamine (PE) derivatized with PEG or PEG stearate have significant increases in blood circulation half-lives. Blume et al. (Biochimica et Biophysica Acta, 1990, 1029, 91) extended such observations to other PEG-derivatized phospholipids, e.g., DSPE-PEG, formed from the combination of distearoylphosphatidylethanolamine (DSPE) and PEG. Liposomes having covalently bound PEG moieties on their external surface are described in European Patent No. EP 0 445 131 B1 and WO 90/04384. Liposome compositions containing 1-20 mole percent of PE derivatized with PEG, and methods of use thereof, are described by Woodle et al. (U.S. Pat. Nos. 5,013,556 and 5,356,633) and Martin et al. (U.S. Pat. No. 5,213,804 and European Patent No. EP 0 496 813 B1). Liposomes comprising a number of other lipid-polymer conjugates are disclosed in WO 91/05545 and U.S. Pat. No. 5,225,212 (both to Martin et al.) and in WO 94/20073 (Zalipsky et al.) Liposomes comprising PEG-modified ceramide lipids are described in WO 96/10391 (Choi et al.). U.S. Pat. No. 5,540,935 (Miyazaki et al.) and U.S. Pat. No. 5,556,948 (Tagawa et al.) describe PEG-containing liposomes that can be further derivatized with functional moieties on their surfaces.

A limited number of liposomes comprising nucleic acids are known in the art. WO 96/40062 to Thierry et al. discloses methods for encapsulating high molecular weight nucleic acids in liposomes. U.S. Pat. No. 5,264,221 to Tagawa et al. discloses protein-bonded liposomes and asserts that the contents of such liposomes may include an antisense RNA. U.S. Pat. No. 5,665,710 to Rahman et al. describes certain methods of encapsulating oligos in liposomes. WO 97/04787 to Love et al. discloses liposomes comprising antisense oligos targeted to the raf gene.

Transfersomes are yet another type of liposomes, and are highly deformable lipid aggregates which are attractive candidates for drug delivery vehicles. Transfersomes may be described as lipid droplets that are so highly deformable that they are easily able to penetrate through pores which are smaller than the droplet. Transfersomes are adaptable to the environment in which they are used, e.g., they are self-optimizing (adaptive to the shape of pores in the skin), self-repairing, frequently reach their targets without fragmenting, and often self-loading. To make transfersomes, it is possible to add surface edge-activators, usually surfactants, to a standard liposomal composition. Transfersomes have been used to deliver serum albumin to the skin. The transfersome-mediated delivery of serum albumin has been shown to be as effective as subcutaneous injection of a solution containing serum albumin.

Surfactants find wide application in formulations such as emulsions (including microemulsions) and liposomes. The most common way of classifying and ranking the properties of the many different types of surfactants, both natural and synthetic, is by the use of the hydrophile/lipophile balance (HLB). The nature of the hydrophilic group (also known as the "head") provides the most useful means for categorizing the different surfactants used in formulations (Rieger, in Pharmaceutical Dosage Forms, Marcel Dekker, Inc., New York, N.Y., 1988, p. 285).

If the surfactant molecule is not ionized, it is classified as a nonionic surfactant. Nonionic surfactants find wide application in pharmaceutical products and are usable over a wide range of pH values. In general their HLB values range from 2 to about 18 depending on their structure. Nonionic surfactants include nonionic esters such as ethylene glycol esters, propylene glycol esters, glyceryl esters, polyglyceryl esters, sorbitan esters, sucrose esters, and ethoxylated esters. Nonionic alkanolamides and ethers such as fatty alcohol ethoxylates, propoxylated alcohols, and ethoxylated/propoxylated block polymers are also included in this class. The polyoxyethylene surfactants are the most popular members of the nonionic surfactant class.

If the surfactant molecule carries a negative charge when it is dissolved or dispersed in water, the surfactant is classified as anionic. Anionic surfactants include carboxylates such as soaps, acyl lactylates, acyl amides of amino acids, esters of sulfuric acid such as alkyl sulfates and ethoxylated alkyl sulfates, sulfonates such as alkyl benzene sulfonates, acyl isethionates, acyl taurates and sulfosuccinates, and phosphates. The most important members of the anionic surfactant class are the alkyl sulfates and the soaps.

If the surfactant molecule carries a positive charge when it is dissolved or dispersed in water, the surfactant is classified as cationic. Cationic surfactants include quaternary ammonium salts and ethoxylated amines. The quaternary ammonium salts are the most used members of this class.

E. Methods of Administration of the Oligo Based Compounds of the Invention

Clinical Applications

RNAi has the potential to form the basis of a broadly applicable drug platform for the treatment of a very wide range of diseases. The principal barrier to the wide use of this technology is the lack of the means for achieving cellular uptake of sufficient amounts of compound for adequate biologic activity in vivo by a wide range of cells. The present invention provides a basic approach that can be widely applied to overcome this basic problem. By separately administering complementary sense and antisense oligos capable of double stranded RNAi and allowing them to assemble into a functional double stranded RNAi intracellularly, uptake can be achieved in may cell types in vivo without the necessity of a carrier. This approach requires that the individual strands have sufficient resistance to nuclease attack while retaining the capacity to function as siRNA following hybridization to their partner in cells. These requirements can be achieved in a number of ways and several of these have been disclosed here in. In the case of ss-siRNA with high activity, administration of a second strand will not be necessary. However, second strand administration will boost the activity of a guide strand that is active by itself. These methods can also be applied in vitro but here carriers will be needed for most cell lines in order to get the individual strands into cellular compartments where they can exhibit their biologic activity.

The present invention further provides pharmaceutical kits. Exemplary kits of the invention comprise a first pharmaceutical composition comprising an effective amount of at least one passenger strand and a second pharmaceutical composition comprising at least one guide strand together in a package. Such kits may also comprise conventional agents which are effective to treat the medical condition targeted by RNAi based therapy. For example, when cancer is the underlying medical condition, additional agents known to have efficacy for the treatment of the disease may be included in the kit. For example, in a subtherapeutic dose for the individual agent, the agents being effective in combination with the RNAi and providing reduced side effects while maintaining efficacy. Alternatively, each agent can be provided at a higher dose, such as those found for the agent in the Physician's Desk Reference.

The pharmacology of conventional antisense oligos with a variety of backbone chemistries with and without the use of carriers has been extensively studied in multiple species, including humans. These oligos include those with various backbone modifications including those with 2'-O modifications to the sugar (e.g., 2'-O-methyl) where most often the modification is intermittent and with various linkages such as phosphorothioate. The pharmacokinetics of these oligos are similar and they behave in a similar manner to many other drugs that are used systemically. As a result, the basic pharmacologic principals that have been established over the years apply to the oligos of the invention as well.

The ss-siRNA or separate complementary sense and antisense oligos intended to form intracellular RNAi which are designed and administered in accordance with the present invention are, from a pharmacokinetic point of view, the same as conventional antisense oligos. As a result the same pharmacokinetic principles and analysis methods apply.

By way of reference the standard general textbooks include the following: "Principles of Drug Action: the Basis of Pharmacology", W B Pratt and P Taylor, (editors), $3^{rd}$ edition, 1990, Churchill Livingston, 1990; Principles of Pharmacology: The Pathophysiologic Basis of Drug Therapy, D E Golan, A H Tashjian, E J Armstrong and A W Armstrong (editors) $2^{nd}$ edition, 2007, Lippincott Williams & Wilkins.

References that summarize much of pharmacology for a range of different types of oligo therapeutics includes the following: Encyclopedia of Pharmaceutical Technology,—6 Volume Set, J Swarbrick (Editor) 3rd edition, 2006, Informa HealthCare; Pharmaceutical Perspectives of Nucleic Acid-Based Therapy, R I Mahato and S W Kim (Editora) I edition, 2002, CRC press; Antisense Drug Technology: Principles, Strategies, and Applications, S T Crooke (Editor) 2nd edition, 2007, Pharmaceutical Aspects of Oligonucleotides, P Couvreur and C Malvy (Editors) 1st edition, 1999, CRC press; Therapeutic Oligonucleotides (RSC Biomolecular Sciences) (RSC Biomolecular Sciences) (Hardcover) by Jens Kurreck (Editor) Royal Society of Chemistry; 1 edition, 2008, CRC press; Clinical Trials of Genetic Therapy with Antisense DNA and DNA Vectors, E Wickstrom (Editor) 1st edition, 1998, CRC press.

For the purposes of this invention, oligos can be administered intravenously (i.v.), intraperitoneally (i.p.), subcutaneously (s.c.), topically, or intramuscularly (i.m.) intrathecally, orally or used in combination with agents that interrupt or permeate the blood-brain barrier in order to treat conditions involving the central nervous system.

In certain embodiments, (e.g., for the treatment of lung disorders, such as pulmonary fibrosis or asthma or to allow for self administration) it may desirable to deliver the oligos described herein in aerosolized form. A pharmaceutical composition comprising at least one oligo can be administered as an aerosol formulation which contains the oligos in dissolved, suspended or emulsified form in a propellant or a mixture of solvent and propellant. The aerosolized formulation is then administered through the respiratory system or nasal passages.

An aerosol formulation used for nasal administration is generally an aqueous solution designed to be administered to the nasal passages as drops or sprays. Nasal solutions are generally prepared to be similar to nasal secretions and are generally isotonic and slightly buffered to maintain a pH of about 5.5 to about 6.5, although pH values outside of this range can also be used. Antimicrobial agents or preservatives can also be included in the formulation.

An aerosol formulation for use in inhalations and inhalants is designed so that the oligos are carried into the respiratory tree of the patient. See (WO 01/82868; WO 01/82873; WO 01/82980; WO 02/05730; WO 02/05785. Inhalation solutions can be administered, for example, by a nebulizer. Inhalations or insufflations, comprising finely powdered or liquid drugs, are delivered to the respiratory system as a pharmaceutical aerosol of a solution or suspension of the drug in a propellant.

An aerosol formulation generally contains a propellant to aid in disbursement of the oligos. Propellants can be liquefied gases, including halocarbons, for example, fluorocarbons such as fluorinated chlorinated hydrocarbons, hydrochlorofluorocarbons, and hydrochlorocarbons as well as hydrocarbons and hydrocarbon ethers (Remington's Pharmaceutical Sciences 18th ed., Gennaro, A. R., ed., Mack Publishing Company, Easton, Pa. (1990)).

Halocarbon propellants useful in the invention include fluorocarbon propellants in which all hydrogens are replaced with fluorine, hydrogen-containing fluorocarbon propellants, and hydrogen-containing chlorofluorocarbon propellants. Halocarbon propellants are described in Johnson, U.S. Pat. No. 5,376,359, and Purewal et al., U.S. Pat. No. 5,776,434.

Hydrocarbon propellants useful in the invention include, for example, propane, isobutane, n-butane, pentane, isopentane and neopentane. A blend of hydrocarbons can also be used as a propellant. Ether propellants include, for example, dimethyl ether as well as numerous other ethers.

The oligos can also be dispensed with a compressed gas. The compressed gas is generally an inert gas such as carbon dioxide, nitrous oxide or nitrogen.

An aerosol formulation of the invention can also contain more than one propellant. For example, the aerosol formulation can contain more than one propellant from the same class such as two or more fluorocarbons. An aerosol formulation can also contain more than one propellant from different classes. An aerosol formulation can contain any combination of two or more propellants from different classes, for example, a fluorohydrocarbon and a hydrocarbon.

Effective aerosol formulations can also include other components, for example, ethanol, isopropanol, propylene glycol, as well as surfactants or other components such as oils and detergents (Remington's Pharmaceutical Sciences, 1990; Purewal et al., U.S. Pat. No. 5,776,434). These aerosol components can serve to stabilize the formulation and lubricate valve components.

The aerosol formulation can be packaged under pressure and can be formulated as an aerosol using solutions, suspensions, emulsions, powders and semisolid preparations. A solution aerosol consists of a solution of an active ingredient such as oligos in pure propellant or as a mixture of propellant and solvent. The solvent is used to dissolve the active ingredient and/or retard the evaporation of the propellant. Solvents useful in the invention include, for example, water, ethanol and glycols. A solution aerosol contains the active ingredient peptide and a propellant and can include any combination of solvents and preservatives or antioxidants.

An aerosol formulation can also be a dispersion or suspension. A suspension aerosol formulation will generally contain a suspension of an effective amount of the oligos and a dispersing agent. Dispersing agents useful in the invention include, for example, sorbitan trioleate, oleyl alcohol, oleic acid, lecithin and corn oil. A suspension aerosol formulation can also include lubricants and other aerosol components.

An aerosol formulation can similarly be formulated as an emulsion. An emulsion can include, for example, an alcohol such as ethanol, a surfactant, water and propellant, as well as the active ingredient, the oligos. The surfactant can be nonionic, anionic or cationic. One example of an emulsion can include, for example, ethanol, surfactant, water and propellant. Another example of an emulsion can include, for example, vegetable oil, glyceryl monostearate and propane.

Oligos may be formulated for oral delivery (Tillman et al., J Pharm Sci 97: 225, 2008; Raoof et al., J Pharm Sci 93: 1431, 2004; Raoof et al., Eur J Pharm Sci 17: 131, 2002; U.S. Pat. No. 6,747,014; US 2003/0040497; US 2003/0083286; US 2003/0124196; US 2003/0176379; US 2004/0229831; US 2005/0196443; US 2007/0004668; US 2007/0249551; WO 02/092616; WO 03/017940; WO 03/018134; WO 99/60012). Such formulations may incorporate one or more permeability enhancers such as sodium caprate that may be incorporated into an enteric-coated dosage form with the oligo.

There are also delivery mechanisms applicable to oligos with or without carriers that can be applied to particular parts of the body such as the CNS. These include the use of convection-enhanced delivery methods such as but not limited to intracerebral clysis (convection-enhanced microinfusion into the brain—Jeffrey et al., Neurosurgery 46: 683, 2000) to help deliver the cell-permeable carrier/NABT complex to the target cells in the CNS as described in WO 2008/033285.

Drug delivery mechanisms based on the exploitation of so-called leverage-mediated uptake mechanisms are also suitable for the practice of this invention (Schmidt and Theopold, Bioessays 26: 1344, 2004). These mechanisms involve targeting by means of soluble adhesion molecules (SAMs) such as tetrameric lectins, cross-linked membrane-anchored molecules (MARMs) around lipoproteins or bulky hinge molecules leveraging MARMs to cause a local inversion of the cell membrane curvature and formation of an internal endosome, lysosome or phagosome. More specifically leverage-mediated uptake involves lateral clustering of MARMs by SAMs thus generating the configurational energy that can drive the reaction towards internalization of the oligo carrying complex by the cell. These compositions, methods, uses and means of production are provided in WO 2005/074966.

As for many drugs, dose schedules for treating patients with oligos can be readily extrapolated from animal studies. The extracellular concentrations that must be generally achieved with highly active conventional antisense or complementary sense and antisense oligos for use in the two-step method is in the 1-200 nanomolar (nM) range. Higher extracellular levels, up to 1.5 micromolar, may be more appropriate for some applications as this can result in an increase in the speed and the amount of the oligos driven into the tissues. Such levels can readily be achieved in the plasma.

For in vivo applications, the concentration of the oligos to be used is readily calculated based on the volume of physiologic balanced-salt solution or other medium in which the tissue to be treated is being bathed. With fresh tissue, 1-1000 nM represents the concentration extremes needed for oligos with moderate to excellent activity. Two hundred nanomolar (200 nM) is a generally serviceable level for most applications. With most cell lines a carrier will typically be needed for in vitro administration. Incubation of the tissue with the oligos at 5% rather than atmospheric (ambient) oxygen levels may improve the results significantly.

Pharmacologichoxicologic studies of phosphorothioate oligos, for example, have shown that they are adequately stable under in vivo conditions, and that they are readily taken up by all the tissues in the body following systemic administration with a few exceptions such as the central nervous system (Iversen, Anticancer Drug Design 6:531, 1991; Iversen, Antisense Res. Develop. 4:43, 1994; Crooke, Ann. Rev. Pharm. Toxicol. 32: 329, 1992; Cornish et al., Pharmacol. Comm. 3: 239, 1993; Agrawal et al., Proc. Natl. Acad. Sci. USA 88: 7595, 1991; Cossum et al., J. Pharm. Exp. Therapeutics 269: 89, 1994). These compounds readily gain access to the tissue in the central nervous system in large amounts following injection into the cerebral spinal fluid (Osen-Sand et al., Nature 364: 445, 1993; Suzuki et al., Amer J. Physiol. 266: R1418, 1994; Draguno et al., Neuroreport 5: 305, 1993; Sommer et al., Neuroreport 5: 277, 1993; Heilig et al., Eur. J. Pharm. 236: 339, 1993; Chiasson et al., Eur J. Pharm. 227: 451, 1992). Phosphorothioates per se have been found to be relatively non-toxic, and the class specific adverse effects that are seen occur at higher doses and at faster infusion rates than is needed to obtain a therapeutic effect with a well chosen sequence. In addition to providing for nuclease resistance, one potential advantage of phosphorothioate and boranophosphate linkages over the phosphodiester linkage is the promotion of binding to plasma proteins and albumin in particular with the resulting effect of an increased plasma half-life. By retaining the oligo for a longer period of time in plasma the oligo has more time to enter tissues as opposed to being excreted by the kidney. Oligos with primarily or exclusively phosphodiester linkages have a plasma half-life of only a few minutes. Thus, they are of little use for in vivo applications when used without a carrier. In the case of oligos with a preponderance or exclusively phosphodiester linkages, plasma protein binding can be improved by covalently attaching the oligo a molecule that binds a plasma protein such as serum albumin. Such molecules include, but are not limited to, an arylpropionic acid, for example, ibuprofen, suprofen, ketoprofen, pranoprofen, tiaprofenic acid, naproxen, flurpibrofen and carprofen (U.S. Pat. No. 6,656,730). As for other moieties that might be linked to the oligos suitable for use with the present invention the preferred site is the 3'-end of the oligo. Intravenous administrations of oligos can be continuous for days or be administered over a period of minutes depending on the particular oligos and the medical indication. Phosphorothioate-containing oligos have been tested containing 18 nucleotides (e.g., oblimersen) to 20 nucleotides (e.g., cenersen, alicaforsen, aprinocarsen, ISIS 14803, ISIS 5132 and ISIS 2503) in length. When so administered such oligos show an alpha and a beta phase of elimination from the plasma. The alpha phase oligo half-life is 30 to 60 minutes while the beta phase is longer than two weeks for oligos with both phosphorothioate linkages and 2'-O substitutions in at least the terminal four nucleosides on each end of the oligo.

The most prominent toxicities associated with intravenous administration of phosphorothioates have been related to the chemical class and generally independent of the mRNA target sequence and, therefore, independent of hybridization. The observed and measured toxicities have been consistent from drug to drug pre-clinically and clinically, with non-human primates being most similar to humans for certain key toxicities.

The class-related toxicities that have been most compelling in choosing dose and schedule for pre-clinical and clinical evaluation occur as a function of binding to specific plasma proteins and include transient inhibition of the clotting cascade and activation of the complement cascade. Both of these toxicities are thought to be related to the polyanionic nature of the molecules.

The effect of phosphorothioates on the clotting cascade results in plasma concentration-related prolongation of the activated partial thromboplastin (aPPT) time. Maximum prolongation of the aPTT correlates closely with the maximum plasma concentration so doses and schedules that avoid high peak concentrations can be selected to avoid significant effects on the aPTT. Because the plasma half-life of these drugs is short (30 to 60 minutes), the effect on clotting is transient. Several of these drugs have been evaluated in the clinic with prolonged intravenous infusions lasting up to 3 weeks. Shorter IV infusions (e.g., 2 hours) have also been studied. For example, aprinocarsen (ISIS 3521) and ISIS 5132 were studied with both 2 hour and 3-week continuous infusion schedules. At a dose of 3 mg/kg/dose over 2 hours, transient prolongation of the aPTT was observed. When 3 mg/kg was given daily by continuous infusion for 21 days, there was no effect on aPTT. The effect of antisense molecules of this chemical class on the clotting cascade is consistent.

Similarly, the activation of complement is a consistent observation; however, the relationship between plasma concentration of oligonucleotides and complement activation is more complex than the effect on clotting. Also, while the effect on clotting is found in rats as well as monkeys, the effect on the complement cascade has only been observed in monkeys and humans.

When these drugs are given to cynomolgus monkeys by 2-hour infusion, increases in complement split products (i.e., C3a, C5a, and Bb) occur only when plasma concentrations exceed a threshold value of 40-50 µg/mL. In monkeys, there is a low incidence of cardiovascular collapse associated with increases in these proteins. For the most part, clinical investigations of phosphorothioates have been designed to avoid these high plasma concentrations.

Cenersen has been evaluated in Rhesus monkeys using a 7-day continuous infusion schedule with a maximum dose of 27 mg/kg/day. In this study, minor Bb increases were noted in the highest dose group of 27 mg/kg/day with mean steady state plasma concentrations of cenersen measured in the 14-19 µg/mL range. Continuous intravenous schedules have not been evaluated in non-human primates with other oligonucleotides.

However, continuous infusions have been studied in clinical trials. Cenersen has been evaluated in a Phase I study at doses up to 0.25 mg/kg/hour for up to 10 days in patients with AML/MDS. ISIS 3521 was evaluated at doses up to 0.125 mg/kg/hour for 3 weeks and ISIS 5132 was evaluated at doses up to 0.21 mg/kg/hour for 3 weeks. In cancer patients treated with intermittent short infusions of ISIS 3521 and ISIS 5132 (2 hour infusions, given three times per week.) complement activation was not observed with doses up to 6 mg/kg (3 mg/kg/hour×2 hours) where mean peak plasma concentrations up to 30 µg/mL were recorded.

When ISIS 3521 was given as a weekly 24 hour infusion at doses as high as 24 mg/kg (1 mg/kg/hour×24 hours), the steady state plasma concentrations reached approximately 12 µg/mL at the high dose. On this schedule, however, there were substantial increases in C3a and Bb even though these plasma levels were much lower than those seen with the shorter infusions. Thus, activation of complement may be associated with both dose and schedule where plasma concentrations that are well tolerated over shorter periods of time (e.g. 2 hours), are associated with toxicity when the plasma concentrations are maintained for longer. This likely provides the explanation for the findings with cenersen in rhesus monkeys where complement activation was observed at concentrations of 14-19 µg/mL.

When ISIS 3521 was given at 1.0 and 1.25 mg/kg/hour×2 hours, the mean peak plasma concentrations were 11.1±0.98 and 6.82±1.33 ug/mL, respectively. There was no complement activation at these or other higher doses and no other safety issues. It is expected that the maximum peak plasma concentrations for similarly sized phosphorothioate given at 1.2 mg/kg/hour×1 hour would be similar to that observed with ISIS 3521.

Thus, limiting infusion rates for phosphorothioates to 3.6 mg/kg/h or less is highly preferred. With somewhat higher infusion rates the effects of complement activation can be expected. Decisions made about the sequential shortening of the infusion below one hour using a constant total dose of approximately 22 mg/kg should be readily achieved based on review of the safety information, including evaluation of complement split products.

These considerations set a range of dose and scheduling parameters particularly for in vivo use of the oligos of the present invention in situations where a carrier is not used.

Methods for Administering the Oligos of the Invention for the Treatment of Disease For most systemic in vivo purposes a daily intravenous administration over one hour for a given oligo or pair of passenger oligos (See Prototypes 5, 6 and 7 designs 1b, 2b and 3b respectively) at an infusion rate of up to 3.6 mg/kg/h are appropriate. The timing of the administration of the second oligo in accordance with the two-step method is primarily dictated by the plasma half-life of the first oligo, the speed at which an RNAi effect is needed for a given medical or other commercial purpose and the frequency of the courses of treatment.

In general for in vivo uses, the preferred delay between a single two-step administrations is between 4 and 24 hours for the passenger (may be a pair) and guide strand oligos where it is preferred that the passenger strand(s) is administered first. When multiple courses are to be given the delay between the administration of the second oligo of the first course and the first oligo of the second course is preferably at least 4 hours. Particularly for non-dividing cells the delay between the first and second oligo administrations for a single course can be quite long and up to a few weeks. This time frame is a function of the tissue residence time for the first oligo.

In general for in vitro uses, the second strand can be administered within minutes of the first strand or after a longer period that is primarily dependent on the growth rate of the target cells and the intracellular levels of the first strand. In most instances the second strand will be given within three days. For non-proliferating cells the period of time that the first strand remains at functional levels can be readily determined empirically, however, in most instances the second strand will be administered in less than 7 days from the administration of the first.

The methods provided herein can be applied to essentially any conventional antisense oligo and to any active RNAi compound based on ss-siRNA or on a double stranded siRNA where the strands hybridize by complementary base pairing. Such RNAi compounds can target any gene in eukaryotic cells. Many such genes are useful targets for a wide variety of medical conditions some of which are presented in Table 2.

The nucleic acid sequence information for the genes listed herein and in Table 2 are either provided or are available from sources such as GenBank. Using the design parameters set forth herein oligos effective to down modulate target gene expression can be generated. Diseased cells expressing such genes can then be contacted with an oligo in an amount which is effective to down modulate expression of the desired gene target. Such oligos can be applied alone or with other oligos or in combination with other agents typically used for treating the disease in question. Methods for treating cells in vitro are well within the skill of the artisan in this art area. Methods for in vivo delivery to targeted tissues are provided herein.

When the two-step method is employed, cells are contacted with a single stranded oligo under conditions which facilitate uptake of the oligo into the cells. The cells are contacted with the complementary single stranded such that a duplexed structure forms intracellularly, the duplex being effective to catalyze destruction of or inhibition of mRNA functions.

TABLE 2

Gene Targets and Particular Medical Conditions or Other Commercial Purposes Which Can Be Modulated Using the Disclosed Oligo Based Compounds

| Gene Targets (alternative names) | Medical Conditions to be Treated or Other Commercial Objectives to be Achieved using the Oligo Based Compounds of the Invention and Directed to the Indicated Gene Target to Inhibit (unless otherwise stated) the Following |
|---|---|
| 5-alpha reductase | Benign prostatic hyperplasia; Evolution of benign prostatic hyperplasia to prostate cancer; Prostate cancer; Male androgenic alopecia; Endometriosis |
| A-myb | Cancers expressing this gene |
| Androgen receptor | Androgen dependent cancers; Diabetes mellitus type 1; Atherosclerosis; Promote wound healing; Endometriosis |
| AP-2 (TFAP2A; BOFS) | Neuroblastoma |
| AP-4 (TFAP4) | Cancer |
| Apoliprotein B (Apo B) | Atherosclerosis; Congestive heart failure; Familial hypercholesterolemia; Statin resistant hypercholesterolemia; HDL/LDL cholesterol imbalance; dyslipidemias; Acquired hyperlipidemia; Coronary artery disease; Thrombosis |
| Apolipoprotein epsilon 4 | Alzheimer's Disease |
| ATF-3 | Medical conditions where a pathologic apoptosis program plays a key role; Medical disorders mediated by Toll-like receptors; Hodgkin's disease; Insulin-resistant or type 2 diabetes |
| B-myb | Cancers expressing this gene; Cancers expressing this gene and SGP2 (clusterin) |
| β-amyloid precursor protein | Alzheimer's Disease; Amyloidosis; Prostate cancer, Lung cancer; Pancreatic cancer; Head & neck cancer; Thyroid cancer |
| BCL-2 alpha (Bcl-2) | Cancers expressing reduced amounts of TR3 and/or defective TR3 induced programmed cell death |
| BCL-2 beta (Bcl-2) | Cancers expressing reduced amounts of TR3 and/or defective TR3 induced programmed cell death |
| BCL-X (Bcl-2-like 1; BCL2L1; BCL2L: Bcl-xS) Pro-apoptotic form of gene product | Hepatic ischemia and ischemia-reperfusion injury; Heart failure; Prevent atherosclerotic plaque rupture; Liver allograft rejection |

TABLE 2-continued

Gene Targets and Particular Medical Conditions or Other Commercial Purposes Which
Can Be Modulated Using the Disclosed Oligo Based Compounds

| Gene Targets (alternative names) | Medical Conditions to be Treated or Other Commercial Objectives to be Achieved using the Oligo Based Compounds of the Invention and Directed to the Indicated Gene Target to Inhibit (unless otherwise stated) the Following |
|---|---|
| BCL-xL (Bcl-2-like 1; BCL2L1; BCL2L) Anti-apoptotic form of gene product | Lung cancer; Mesothelioma; Colorectal cancer; Malignant melanoma; Head and neck cancer; Ovarian cancer; Transitional cell carcinoma; Esophageal cancer; Pancreatic cancer; Glioblastoma; Breast cancer; Psoriasis |
| BSAP (Pax5) | B cell malignancies |
| C/EBP (C/EBPdelta; CEBPD; NF-IL6beta) | Cancers expressing this gene; Inflammation; Kidney damage secondary to disseminated intravascular coagulation or ischemia reperfusion injury |
| c-fos | Cancers expressing this gene; Rheumatoid arthritis; Heart failure |
| c-jun | Osteosarcoma; Fatty Liver Disease; Fulminant hepatitis; Endometriosis; Heart failure |
| c-myb | Colon and breast cancer; Atherosclerosis |
| c-myc | Malignant melanoma; Cancers over-expressing this gene (compared to corresponding normal tissue) |
| CDK-1 (p34; cdc2) | Cancers expressing this gene; Graft coronary artery disease; Cancers with deficient wild type p53 expression (defined as lacking p53-dependent cell cycle checkpoints) |
| CDK-2 | Alzheimer's Disease; Pemphigus vulgaris |
| CDK-3 | Cancers expressing this gene |
| CDK-4 | Obesity; Cancers with mutated ras gene |
| CDK-4 Inhibitor (Arf) | Expand normal stem cell numbers for applications such as transplantation; Promote reprogramming of stem cells including iPS; Protection of normal tissue from toxic effects of cancer chemotherapy or radiation; Alopecia; Wound healing; Diabetes mellitus; Lymphomas with mutant p53; Cancers with deficient wild type p53 expression (defined as lacking p53-dependent cell cycle checkpoints) |
| cHF.10 (ZNF35; HF10) | Male contraception; Cancers expressing this gene |
| COX-2 | Inflammation; Cancer; Alzheimer's Disease; Parkinson's Disease; Heterotopic ossification; Endometriosis; Autoimmune disease; Multiple sclerosis; Allergic encephalomyelitis; Insulin-dependent diabetes mellitus; Proteinuria; Age-related macular degeneration; Schizophrenia; Depression; Myocardial infarction; Stromal keratitis; Peutz-Jeghers polyposis |
| cp19 (Hox C4) | Cancers expressing this gene; Lung cancer |
| CREB | Malignant melanoma; Leukemia; Cerebral ischemia; Bipolar disorder; Major depressive disorder; Cocaine addiction; Insulin-resistant or type 2 diabetes |
| CREBP-1 (ATF-2) | Block side effects due to interferon production in response to systemic administration of double stranded oligo therapeutics; Endometriosis; Cancer; Alzheimer's Disease |
| CREM | Systemic lupus erythematosus; High cholesterol; Achieve male contraception |
| Cyclin A | Prostate cancer; Acute leukemia; Squamous cell carcinoma; Renal cell carcinoma; Soft tissue sarcoma; Chronic ulcers such as might occur on legs; Psoriasis |
| Cyclin B | Breast cancer; Head and neck squamous cell cancer; Gastric cancer; Alzheimer's Disease; Vascular dementia; Psoriasis; Hereditary tyrosinemia type I |
| Cyclin D1 | Endometriosis; Inflammation; Cancer angiogenesis; Maintaining self-renewal capabilities of non-malignant stem cells for applications such as expanding their number for transplantation; Promoting toxicity of chemotherapy and radiation to non-malignant cells |
| Cyclin D2 | Maintaining self-renewal capabilities of non-malignant stem cells for applications such as expanding their number for transplantation; B-cell malignancies |
| Cyclin D3 | Prostate cancer; T cell malignancies; Transplant rejection |
| DB-1 (ZNF161; VEZF1) | Cancers expressing this gene; Atherosclerosis; Hypertension including that associated with type 2 diabetes; Cardiac hypertrophy; Congestive heart failure |
| Dopamine D2 Receptors | Psychosis; Erectile dysfunction; Neuroendocrine tumors |
| DP-1 | Atherosclerosis; Promote stem cell proliferation for applications such as expanding their number for transplantation in the case of normal stem cells or to put malignant stem cells in cycle in order to sensitized them to cell cycle dependent therapies; Medical conditions where a pathologic apoptosis program plays a key role; Cancers with mutated p53; Cancers with over-expressed c-myc |

TABLE 2-continued

Gene Targets and Particular Medical Conditions or Other Commercial Purposes Which
Can Be Modulated Using the Disclosed Oligo Based Compounds

| Gene Targets (alternative names) | Medical Conditions to be Treated or Other Commercial Objectives to be Achieved using the Oligo Based Compounds of the Invention and Directed to the Indicated Gene Target to Inhibit (unless otherwise stated) the Following |
|---|---|
| E12 | Cancers expressing this gene |
| E2A | Cancers expressing this gene |
| E2F-1 (RBAP-1) | Atherosclerosis; Promote stem cell proliferation; Medical conditions where a pathologic apoptosis program plays a key role; Cancers with mutated p53; Cancers with over-expressed c-myc; Prostate cancer; Obesity; Fat induced diabetes; Parkinson's Disease |
| E2F-2 | Essential hypertension; Put quiescent cancer cells in cycle |
| E47 | Cancers expressing this gene |
| E4BP4 (NFIL3) | Osteoporosis |
| ELK-1 | Liver cancer; Neurodegeneration |
| Epidermal growth factor receptor | Cancers that over-express this receptor and/or have activating mutations of this receptor |
| ERM (ETV5) | Breast cancer |
| Estrogen receptor | Hormone dependent gynecologic cancers |
| ERG-1 | Atherosclerosis; Cancer; Restenosis; Ischemia reperfusion injury; Allograft rejection; Inflammation; Autoimmune disease |
| ERK-1 and 3; ERK subunits a and b | Cancers expressing at least one of these genes; Alzheimer's Disease; Chronic obstructive pulmonary disease; Renal failure; Inflammation; Graft vs host disease |
| Ets-1 | Cancers expressing this gene; Pancreatic cancer; Vascular inflammation; Arthritis; Prevent Fas mediated death of liver cells (see FAS/APO-1 below) |
| Ets-2 | Down's Syndrome; Hormone independent gynecologic cancers |
| FAS/APO-1 (CD-95; Tnfrsf6) | Myocardial infarction; Fatty liver disease; Fulminant hepatitis; Cirrhosis of the liver; Alcoholic hepatitis; Cholestatic liver injury; Acute liver failure; Cystic fibrosis; Systemic lupus erythematosus; Arthritis; Parkinson's Disease; Autoimmune diabetes; Central nervous system injuries, Demyelinating diseases; Stroke; Chemotherapy-induced neuropathy; Neurodegenerative diseases; Spinal cord injury; Ischemia -reperfusion injury |
| FLT-1 (VEGFR-1) | Cancers expressing this gene; Psoriasis; Rheumatoid arthritis; Corneal neovascularization; Degenerative achilles tendon disease |
| FLT-4 (VEGFR-3) | Cancers expressing this gene; Prevent atherosclerotic plaque rupture |
| Fra-1 | Cancers expressing this gene |
| Fra-2 | Pulmonary fibrosis; Breast cancer; Cocaine addiction |
| GADD-153 (CHOP) | Medical conditions where a pathologic apoptosis program plays a key role; Parkinson's Disease |
| GADD-45 | Medical conditions where a pathologic apoptosis program plays a key role; Sensitize cancers to cytotoxic treatments dependent on cell proliferation and/or DNA replication; Diamond-Blackfan syndrome; Shwachman Diamond Syndrome and other disorders involving defective ribosomes |
| GATA-2 | Blast crisis CML with altered GATA-2 |
| GATA-3 | Allergic responses; Breast cancer; Pancreatic cancer |
| GATA-4 | Ovarian cancer; Testicular cancer; Retard differentiation of embryonic or iPS cells |
| HB9 (MNX-1; HLXB9) | Cancers expressing this gene |
| HB24 (HLX-1) | Cancers expressing this gene |
| h-plk (ERV3) | Cancers expressing this gene |
| Hox1.3 (HoxA5) | Cancers expressing this gene |
| Hox 2.3 (HoxB7) | Cancers expressing this gene |
| Hox2.5 (HoxB9) | Cancers expressing this gene |
| Hox 5.4 (Hox D8) | Cancers expressing this gene; Lung cancer |
| Hox4A (HoxD3) | Cancers expressing this gene |
| Hox 4D (HoxD10) | Cancers expressing this gene; Lung cancer |
| Hox 7 (MSX-1) | Cancers expressing this gene |
| HoxA1 | Cancers expressing this gene |
| HoxA10 | Cancers expressing this gene |
| HoxC6 | Cancers expressing this gene; Gastrointestinal carcinoids |

TABLE 2-continued

Gene Targets and Particular Medical Conditions or Other Commercial Purposes Which
Can Be Modulated Using the Disclosed Oligo Based Compounds

| Gene Targets (alternative names) | Medical Conditions to be Treated or Other Commercial Objectives to be Achieved using the Oligo Based Compounds of the Invention and Directed to the Indicated Gene Target to Inhibit (unless otherwise stated) the Following |
|---|---|
| HS1 (14-3-3 beta/alpha; YWHAB) | Chronic lymphocytic leukemia; Systemic lupus erythematosus |
| HTF4a (TCF12; HEB) | Autoimmunity; Transplant rejection; Graft verses host disease |
| I-Rel (RelB) | Leukemia; Lymphoma; Prostate cancer; Breast cancer |
| ICE (CASP1; Caspase-1) | Autoimmune disease; Psoriasis; Inflammation; Septic shock; ARDS; Gouty arthritis; Melvalonate kinase deficiency syndrome; Myocardial infarction; Neurodegenerative diseases; Ischemia reperfusion injury; Heart failure; Diabetic retinopathy; Age-related cognitive dysfunction; Retinitis pigmentosa; Convulsions; Pancreatitis; Pancreatic cancer; Amyotrophic lateral sclerosis |
| ICH-1L (CASP2L; Caspase-2L) | Protect tissues from toxic effects of chemotherapy or radiation; Epilepsy; High levels of cholesterol and/or triacylglycerol; Prevent atherosclerotic plaque rupture; Alzheimer's Disease |
| ICH-1S (CASP2S; Caspase-2S) | Promote toxic effects of chemotherapy or radiation; Prevent survival of cells giving rise to atherosclerotic plaques |
| ID-1 | Cancers expressing this gene; Acquired cholesteatoma; Improve hematopoietic stem cell transplant conditioning regimens; Differentiation of iPS or ES cells into nerve cells; Psoriasis; Ischemia-reperfusion injury |
| ID-2 | Colon cancer; Pancreatic cancer; Uveal melanoma; Vasculoproliferative disorders; B-cell lymphoma; Neuroblastoma; Brain cancers expressing this gene; Ewing sarcoma; Neurodegenerative diseases |
| ID-3 | Medical conditions where a pathologic apoptosis program plays a key role; Vasculoproliferative disorders |
| IRF-1 | Block interferon production in response to double stranded oligo therapeutics; Anemia associated with medical conditions involving interferon production or treatment with interferon; Sensitize cancers expressing EGRF to cytotoxic treatments dependent on cell proliferation and/or DNA replication; Myelodysplasis and cancers expressing alternatively spliced IRF-1 |
| IRF-2 | Esophageal cancer; Leukemia |
| ISGF3 (Stat1) | Conditions where a pathologic apoptosis program plays a key role; Asthma; Psoriasis; Ischemia-reperfusion injury; Rheumatoid arthritis; Atherosclerosis; Inflammation; Renal cell carcinoma; Transplant rejection; Cancers with phosphorylated ISGF3 |
| junB | Sensitize cancers to cytotoxic treatments dependent on cell proliferation and/or DNA replication; Allergic responses; Psoriasis vulgaris; CD 30 expressing lymphomas; Cutaneous T-cell lymphoma |
| junD | Cancers expressing this gene; Inflammation; Osteoporosis; Liver fibrosis |
| KDR/FLK-1 (VEGFR-2) | Cancers expressing this gene; Rheumatoid arthritis: Macular degeneration; Stroke; Edema; Degenerative Achilles tendon disease |
| L-myc | Merkel cell carcinoma; Ovarian cancer |
| Lyl-1 | Leukemia |
| MAD-1 (MXD-1; MAD) | Cancers expressing this gene; Sensitize cancers to anti-cancertreatments dependent on cell proliferation and/or DNA replication |
| MAD-3 (NFKBIA; NFKBI; IKBA; IkappaBalpha) | Ectodermal dysplasia with immune deficiency; Medical disorders promoted by activated NF-kappaB |
| MADS/MEF-2 (MEF2C) | Cardiac hypertrophy; B-cell malignancies; Myeloid leukemias; Inflammation |
| MAX | C-myc over-expressing cancers (compared to corresponding normal tissue) |
| Mcl-1 | Cancers expressing this gene; Rheumatoid arthritis |
| MDR-1 | Cancers expressing this gene; Drug resistant epilepsy |
| MRP | Cancers expressing this gene |
| MSX-2 | Pancreatic cancer; Vascular calcification |
| MTF-1 | Prion disease |
| mts1 (S100A4) | Cancers expressing this gene; Pulmonary vascular disease; Disorders characterized by fibrosis and inflammation such as: cardiac hypertrophy with fibrosis; Arthritis; Neurodegenerative disease |
| MTS-2 (CDKN2B; p15; INK4B) | Actinic keratosis; Expansion of normal stem cells for purposes such as transplantation; Protection of normal tissue from toxic effects of cancer chemotherapy or radiation; Alopecia; Wound healing; Diabetes mellitus type 1 |
| Mxi1 | Renal cell carcinoma; Sensitize cancers to anti-cancertreatments dependent on cell proliferation and/or DNA replication; Hypoxic cancers |

TABLE 2-continued

Gene Targets and Particular Medical Conditions or Other Commercial Purposes Which Can Be Modulated Using the Disclosed Oligo Based Compounds

| Gene Targets (alternative names) | Medical Conditions to be Treated or Other Commercial Objectives to be Achieved using the Oligo Based Compounds of the Invention and Directed to the Indicated Gene Target to Inhibit (unless otherwise stated) the Following |
|---|---|
| MZF-1 | Liver cancer |
| NET (ELK3; ERP) | Cancers expressing the gene |
| NF-ATC (NFAT2; NFATC1) | Autoimmune disease; Rheumatoid arthritis; Ulcerative colitis; Inflammation; Restenosis |
| NF-IL6 (C/EBPbeta; CEBPB) | AIDS; Inflammation; Cancers expressing this gene; Sensitize cancers with wild type p53 to chemotherapy radiation or other genotoxic anti-cancer agents; Atherosclerosis; Fibrosis of liver; Fatty liver disease; Fulminant hepatitis; Cirrhosis of the liver; Alcoholic hepatitis; Cholestatic liver Injury; Acute liver failure; Rheumatoid arthritis |
| NF-IL6beta (C/EBPdelta; CEBPD) | Cancers expressing this gene; Inflammation; Kidney damage secondary to disseminated intravascular coagulation or ischemia reperfusion injury; Rheumatoid arthritis |
| NF-kappaB Includes 51 KD, 65 KD and A subunits as well as intron 15. | Cancers expressing this gene; Interferon production in response to double stranded oligo therapeutics; Autoimmune disease; Psoriasis; Osteoarthritis; Rheumatoid arthritis; Ulcerative colitis; Osteoporosis; Cerebral ischemia; Inflammation; Acute pancreatitis; Heart failure; Cardiac hypertrophy; Cerebral aneurysm; Type 2 diabetes; Allergic asthma; Prevent deep vein thrombosis |
| N-myc | Neuroblastoma; Hepatocellular carcinoma |
| OCT-1 (POU2F1; NF-A1; OTF-1) | Atherosclerosis; Manifestations of Herpes simplex infections; Cancer; Carcinogenesis; Sensitize cancers to anti-cancertreatments dependent on cell proliferation and/or DNA replication; Rheumatoid arthritis; Beta-globin disorders characterized by reduced expression of gamma-globin gene(s); Sickle cell anemia; Beta-thalassemia |
| OCT-2 (POU2F2; NF-A2; OTF-2) | Cancers expressing this gene; t(14; 18) lymphoma |
| OTF-3 (POU5F1; OCT-3; OCT-4; OTF4; Oct-3/4) | Cancers expressing this gene particularly cancer stem cells; Inducing differentiation of stem cells including for tissue repair |
| Oct-T1 (POU4F1; Brn-3a) | Cancers expressing both this gene and wild type p53; Cervical cancer; Prostate cancer; Neuroendocrine cancers; Systemic lupus erythematosus |
| Oct-T2 (POU4F2; Brn-3b) | Disorders characterized by expression of this gene and by pathologic expression of p53-dependent apoptosis (see p53 below); Breast cancer |
| OTF-3C (POU5F1P1) | Cancers expressing this gene |
| OZF (Znf146) | Pancreatic cancer; Colon cancer |
| p40 | Crohn's disease; Arthritis |
| PTEN (MMAC1; TEP1) | Cancers with mutated p53; Activate cell proliferation including hematopoietic stem cells; Regeneration of damaged nerves |
| p53 | Sensitize cancers with wild type p53 to cytotoxic therapies; Cancers with mutant p53; Sensitize cancers with mutant p53 to the induction of apoptosis by anyapoptosis inducer; Stem cell quiescence including malignant stem cells (expand normal stem cells and progeny or put malignant stem cells in cycle so they can be attacked by cell cycle dependent anti-cancer agents; Heart failure; Medical conditions where apoptosis is promoted; Inhibiting apoptosis in non-malignant stem cells; Huntington's disease; Diamond-Blackfan syndrome; Shwachman Diamond Syndrome and other disorders involving defective ribosomes; Fatty liver disease; Stress induced immunosuppression; Sequellae associated with subarachnoid hemorrhage; Pathologic hyperpigmentation; Hyperkeratosis; Toxic effects of cancer chemotherapy and radiation including but not limited to the following: hair loss, mucositis, myelosupression, hearing loss, peripheral nerve damage, impaired brain function and kidney damage; Inflammatory bowel disease; Crohn's disease; ARDS; Multiple organ failure; Sensitize cancers to cytotoxic treatments dependent on cell proliferation and/or DNA replication; Amyloid deposition; Neurodegenerative diseases; Ischemia-reperfusion injury; Avoidance of effects of cytotoxic therapy due to quiescence of malignant stem cells; Reduced expansion of non-malignant tissue due to stem cell quiescence; Prevent demyelination; |
| p53 (continued) | Multiple sclerosis; Alzheimer's Disease; Parkinson's disease; Prevent cell death associated with diabetic ischemia; Spontaneous apoptosis, cell cycle arrest, senescence and differentiation in stem cells including embryonic stem cells and iPS such as reduces the efficiency of preparing such cells for transplantation organ generation, the generation of animals or for use in scientific research; |

TABLE 2-continued

Gene Targets and Particular Medical Conditions or Other Commercial Purposes Which Can Be Modulated Using the Disclosed Oligo Based Compounds

| Gene Targets (alternative names) | Medical Conditions to be Treated or Other Commercial Objectives to be Achieved using the Oligo Based Compounds of the Invention and Directed to the Indicated Gene Target to Inhibit (unless otherwise stated) the Following |
|---|---|
| | Prevent cell death associated with cerebral ischemia; Prevent cell death associated with myocardial infarction including consequent heart wall rupture; Schizophrenia; Psoriasis; AIDS; Prevent rupture of atherosclerotic plaques; Prevent aneurysm rupture; Graft vs host disease; Systemic lupus erythematosus; Promote healing of hard to heal wounds; Capillary leak syndrome; Emphysema; Reduce endosomal, lysosomal or phagosomal sequestration of oligo therapeutics with the effect of increasing their biologic activity; Promote proliferation of stem cells such as hematopoietic or neural; Diabetes mellitus including insulin resistant diabetes; Ribosomopathies |
| p107 (RBL1; PRB1; cp107) | Obesity; Sensitize cancer cells to chemotherapy, radiation or other genotoxic anti-cancer agents |
| PDEGF (Platelet-derived endothelial growth factor) | Cancers expressing this gene; Atherosclerosis; Restenosis; Pulmonary hypertension; Renal diseases; Fibrotic diseases including pulmonary fibrosis, liver cirrhosis, scleroderma, glomerulosclerosis and cardiac fibrosis; Rheumatoid arthritis |
| PDGFR (Platelet-derived growth factor receptor) | Cancers expressing this gene; Atherosclerosis; Restenosis; Pulmonary hypertension; Renal diseases; Fibrotic diseases including pulmonary fibrosis, liver cirrhosis, scleroderma, glomerulosclerosis and cardiac fibrosis; Rheumatoid arthritis |
| PES (Prostaglandin Endoperoxide Synthase 1; Cox-1) | Inflammation; Platelet Aggregation; Cancer; Asthma |
| Pim-1 | Cancers expressing this gene; Hypoxic cancers; Prostate cancer; Leukemia; Lymphoma; Head and neck squamous cell carcinoma |
| PKC alpha | Cancers expressing this gene; Heart failure |
| PKC beta | B cell lymphoma; Restenosis; Type 2 diabetes; Diabetic retinopathy |
| PKC delta | Cancers expressing this gene; Neurodegenerative disease; Diabetes |
| PKC epsilon | Acute myelogenous leukemia; Prostate cancer; Ischemia-reperfusion injury; Graft rejection; Allergic responses |
| PKC gamma | Parkinson's Disease; Retinitis pigmentosa |
| PKC iota (PKC lambda) | Allergic airway inflammation; Glioblastoma |
| PKC mu (PRKD1; Protein kinase D1) | Pathological cardiac remodeling |
| PKC theta | Insulin resistance; Autoimmune diseases; Rheumatoid arthritis; Breast cancer |
| PKC zeta | Autoimmune diseases; Inflammation; Allergic responses; Follicular lymphoma; Sepsis mediated tissue injury; Restenosis |
| PCSK9 (NARC-1) | Atherosclerosis; Hypercholesterolemia; Statin resistant hypercholesterolemia; HDL/LDL cholesterol imbalance; dyslipidemias; Acquired hyperlipidemia; Coronary artery disease |
| Rb (RB1; pRb, Retinoblastoma 1; OSRC; pp110; p105-Rb) | Sensitize cancers to chemotherapy, radiation or other genotoxic anti-cancer agents; Bladder cancer; Lung cancer; Uveal melanoma |
| Rb-2 (RBL2; p130; RBR-2) | Induce cell proliferation for various purposes including replacement of damaged tissues |
| Ref-1 (APEX1; APE; APE1; HAP1; APEN; AP endonuclease 1) | Cancers expressing this gene; Malignant melanoma; Pancreatic cancer; Ovarian cancer; Prostate cancer; Sensitize cancers to chemotherapy, radiation or other genotoxic anti-cancer agents; Cancer chemoprevention; Inflammation; Asthma; Ischemia-reperfusion injury; Induction of cardiac differentiation by stem cells such as for use in cardiac repair |
| REL (c-Rel) | Inflammatory bowel disease; Breast cancer; B-cell malignancies; Islet allograft rejection; Allergic asthma |
| SAP-1 (ELK4; SRF accessory protein 1) | Prostate cancer |
| SCL (TAL-1; TCL5; Stem cell protein) | T-cell acute lymphocytic leukemia |
| SGP2 (clusterin; CLU; TRPM-2; Apolipoprotein J; APOJ; Complement associated protein SP-40,40; Complement cytolysis inhibitor; KUB1; CLI; Testosterone-repressed prostate message 2) | Cancers expressing this gene; Sensitizing cancers to chemotherapy, radiation or other genotoxic anti-cancer agents; Cervical cancer; Laryngeal squamous cell carcinoma; Osteosarcoma; Liver cancer; Colorectal cancer; Ovarian cancer; Bladder cancer; Breast cancer including sensitizing breast cancer to biologics in the case of breast cancers responsive to hormonal-pathway manipulation including sensitizing them to the use of estrogen antagonists; Prostate cancer including sensitizing this cancer to biologics in the case of prostate cancers responsive to hormonal-pathway manipulation including the use of estrogen therapy, androgen deprivation therapy including gonadotropin-releasing hormone antagonists and luteinizing hormone-releasing hormone agonists (LHRH analogs) as well as |

TABLE 2-continued

Gene Targets and Particular Medical Conditions or Other Commercial Purposes Which Can Be Modulated Using the Disclosed Oligo Based Compounds

| Gene Targets (alternative names) | Medical Conditions to be Treated or Other Commercial Objectives to be Achieved using the Oligo Based Compounds of the Invention and Directed to the Indicated Gene Target to Inhibit (unless otherwise stated) the Following |
|---|---|
| | cytochrome P450(17alpha)/C17-20 lyase inhibitors such as abiraterone; Preeclampsia; Early stage atherosclerosis; Fuch's endothelial dystrophy |
| Sp-1 | Prevent Fas mediated death of liver cells; Prevent rupture of atherosclerotic plaques; Cancers expressing the nerve growth factor receptor p75NTR; Neuroblastoma; Hepatocellular cancer; Esophageal cancer; Breast cancer; Pancreatic cancer; Airway inflammatory disease including asthma; Prevent death of non-malignant brain cells as a result of hypo-osmolar stress which is a common complication of traumatic brain injury, stroke, epileptic sezures, microbial infections and brain cancer; Neuropathic pain following nerve injury; Alzheimer's Disease; Prevent hair follicle regression; Psoriasis; Prion disease; Prevent keloid formation; Preventlung fibrosis |
| Sp-3 | Cancers that express this gene; Neuroblastoma; Hepatocellular carcinoma |
| Sp-4 | Alzheimer's Disease; Pancreatic cancer |
| Spi-1 (PU.1) | Promote retention of self-renewal capacity of hematopoietic stem cells in order to expand their numbers for various purposes including stem cell transplant; Anemia; Osteoporosis |
| Spi-B (PU.1 related) | B-cell Cancers; Autoimmunity |
| SRF | Alzheimer's Disease; Pulmonary fibrosis; Liver cancer; Prostate cancer; Heart failure |
| TGFβ (TGFβ1: TGFB1; TGFB) | Lung cancer; Prostate cancer; Breast cancer; Colorectal cancer; Chronic obstructive pulmonary disease; Chronic graft rejection |
| TNFα | Multiple sclerosis; Multiple-systems organ failure syndrome; Rheumatoid arthritis; Toxic shock syndrome; Crohn's disease; Psoriasis; Ankylosing spondylitis; Endothelial cell inflammation; Chronic obstructive pulmonary disease; Asthma; Uveitis; Graft rejection |
| TR3 (NUR77; NR4A1; NAK-1) | Inflammation; Medical indications characterized by pathologic expression of apoptosis |
| TR4 (NR2C2; TR2R1) | Cancers expressing this gene and expressing reduced amounts of TR3 and/or expressing defective TR3 induced programmed cell death |
| USF (USF1; MLTF) | Familial combined hyperlipidemia |
| VEGF | Cancers expressing this gene; Psoriasis; Rheumatoid arthritis; Macular degeneration; Inflammatory bowel disease; Periodontal disease |
| Waf-1 (p21; CAP20; CDKN1; CIP1; MDA6) | Cancers expressing this gene; Obesity; Protection of gastrointestinal tract from radiation toxicity; Insulin resistance; Duchenne muscular dystrophy; Sarcoidosis; Fatty liver disease; Emphysema; Diamond-Blackfan syndrome; Shwachman-Diamond Syndrome and other disorders involving mutant and defective ribosomes; Tissue damage due to influenza infection; Tissue damage due to Ebola infection |
| WRN | Treatment of Werner syndrome via inhibition of Wrn |
| WT-1 (GUD; WAGR; WIT-2; WT33; Wilms' tumor protein; WT1) | Brain cancer; Osteogenic sarcoma; Hepatocellular cancer; Promote cancer cell proliferation by cancers that express the gene to sensitize them to cell cycle dependent anti-cancer treatments |
| YY-1 (YY1; NF-E1; Yin-Yang-1; UCRBP; INO80S) | Cancer (but contraindicated for use in combination with chemotherapeutic agents that act on microtubules such as taxanes); Cancer cell resistance to TRAIL induced apoptosis |

The gene targets in Table 2 include a number of genes that are subject to alternative splicing and/or to alternative translational start sites. The medical disorders and other commercial uses associated with these gene targets take this fact into consideration and not all such homologs of a given gene will be appropriate for the indicated use. Such differences are well established in the art and form the basis for differential targeting of homologs of the same gene by oligos targeting structurally and/or functionally variable portions of the transcripts of such genes, for example, the alpha and beta forms of Bcl-2 or Bcl-X and bcl-XL or SGP2 for which distinguishing oligos are provided for herein. The phrases "cancers expressing this gene" or cancers expressing one or more of these genes" are to be interpreted as including both normal and structurally abnormal forms of the gene and to include all of the supporting cell types (fibroblasts, stroma, blood vessels etc.) within the definition of the cancer. Oligos to be used to treat cancer will typically be used in combination with other anti-cancer agents with established activity in the disease in order to improve outcomes.

Representative functional siRNA or conventional antisense oligo compounds known in the art and directed to one of several examples of gene targets are provided below. A variety of medical applications for inhibitors of these exemplified gene targets are provided in Table 2. The non-limiting reconfigured established RNAi and conventional antisense oligos shown in the examples are not meant to provide an exhaustive set of illustrations of how the designs presented herein can be applied in general or in particular to the siRNA or conventional antisense oligos provided in each of the examples. One skilled in the art can readily use the design principles and the examples provided herein to arrive at a very limited set of compounds that can be generated in accordance with the present invention using any given RNAi or conventional antisense oligo.

The following examples are provided to illustrate certain embodiments of the present invention. They are not intended to limit the invention in any way. In these examples siRNA compounds with previously established activity to a particular gene target are included along with their novel reconfigured counterparts designed for use in the two-step method as provided by the present invention. These established siRNAs, however, could be used in the two-step method if carriers are used to deliver each strand intracellularly where the carriers provide sufficient nuclease protection to maintain the strand prior to its forming a duplex with its partner stand intracellularly.

EXAMPLE 1

Compounds for Down-Regulating p53 Expression p53 is involved in the regulation of a variety of cellular programs including those involving stem cell self-renewal, cellular proliferation and viability such as proliferation, differentiation, apoptosis, senescence, mitotic catastrophe and autophagy. The pathological expression or failure of expression of such programs, and the death programs in particular, underlie many of the morbidities associated with a wide variety of medical conditions where blocking p53 function can prevent much if not all of such morbidity (Table 2).

In cancer, for example, both wild type and mutant p53 play key roles in tumor maintenance that include increasing the threshold for the induction of programs that can lead to the death of the cancer cells. Typically the use of a p53 inhibitor, such as an siRNA directed to the p53 gene target, in combination with an inducer of a cell death program, such as a DNA damaging agent, can be used to promote the death of cancer cells. At the same time inhibition of p53 protects many normal tissues from the toxic effects of many such second agents including chemotherapy and radiation.

Further, the present inventor has found that Boron Neutron Capture Therapy (BNCT) can be used in combination with ss-siRNA, double stranded siRNA or conventional antisense oligos that inhibit p53 (such as but not limited to those described in PCT/US09/02365) as a method for treating cancer (Brownell et al., "Boron Neutron Capture Therapy" In; "Therapy of Nuclear Medicine," RP Spencer (ed), Grune and Stratton, N Y, 1978; Barth et al. Cancer Res 50: 1061, 1990; Summers and Shaw, Curr Med Chem 8: 1147, 2001). Specifically, the $^{10}$B atom undergoes fission to generate $^7$Li and energetic alpha (helium) particles following capturing a thermal neutron. Within their 10-14 mm path, such particles cause DNA and other types of damage that enhance apoptosis and other inactivating effects on cancer cells when wild type or mutated p53 is inhibited.

The use of conventional antisense oligos which function using an RNAse H mechanism of action and directed to the p53 gene target have been studied in vitro and in patients. These oligos have been shown to promote the anti-cancer effects of certain conventional treatments and to protect normal tissues from genome damaging agents. Few cell types, with the exception of stem cells, possess sufficient levels of RNase H to support conventional antisense oligos dependent on this enzyme for their activity. Consequently, RNAi directed to the p53 gene target which are not dependent on RNAse H activity for function offer the potential advantage of being active in vivo in a broader range of cell types. As for RNAi, generally this potential is severely limited by the well known problems associated with the poor uptake of conventional double stranded RNAi uptake in vivo.

Molitoris et al. (J Am Soc Nephrol 20: 1754, 2009) presents data showing that double stranded siRNA directed to the p53 gene target can attenuate cisplatin induced kidney damage in rats. The siRNA described was a blunt ended 19-mer with alternating 2'O-methy/native ribose nucleosides. A carrier was not needed because the proximal tubule cells in the kidney are both a major site of kidney injury associated with ischemia or nephrotoxicity such as that caused by cisplatin and is the site of oligo reabsorption by the kidney. Thus, this carrier free approach with conventional siRNA is of very limited use for preventing the pathologic effects of p53-dependent programs that kill cells or otherwise incapacitate them, but it does illustrate the potential usefulness of inhibiting p53 for this medical indication.

Zhao et al. (Cell Stem Cell 3: 475, 2008) demonstrated that inhibiting p53 expression with siRNA can be used to enhance the production of iPSC. Human fibroblasts, for example, were converted to iPSC by using expression vectors for several genes to gain their expression in the cells. The efficiency of iPSC production was very low but was increased approximately two logs when shRNA directed to the p53 gene target was installed in the cells using a lentiviral vector. The approach described herein provides the means to transiently suppress p53 compared to the long term suppression provided by shRNA. This is important when the iPSC are to be induced to differentiate into particular cell type such as would be needed in tissue repair applications. As described herein the two-step administration approach combined with the linkage of a short peptide CPP to each strand provides an efficient way to obtain RNAi activity in stem cells in vitro with minimal carrier related toxicity.

RNAi compounds directed to the human p53 gene target that can be reconfigured for use in the two-step method provided by the present invention are found in WO 2006/035434, US 2009/0105173 and US 2004/0014956. FIGS. 3-10 provide novel compositions of matter which include many of the features heretofore described for increasing cellular uptake and/or stability for down modulating p53 expression in target cells. The sequence used for human p53 is provided in GenBank, Accession No. NM_000546.4.

Table 2 lists a variety of disorders which would benefit with treatment of the p53 directed compounds described herein. For example, heart failure is a serious condition that results from various cardiovascular diseases. p53 plays a significant role in the development of heart failure. Cardiac angiogenesis directly related to the maintenance of cardiac function as well as the development of cardiac hypertrophy induced by pressure-overload. Upregulated p53 induced the transition from cardiac hypertrophy to heart failure through the suppression of hypoxia inducible factor-1 (HIF-1), which regulates angiogenesis in the hypertrophied heart. In addition, p53 is known to promote apoptosis, and apoptosis is thought to be involved in heart failure. Thus, p53 is a key molecule which triggers the development of heart failure via multiple mechanisms.

Accordingly, the p53 directed compounds of the invention can be employed to diminish or alleviate the pathological symptoms associated with cardiac cell death due to apoptosis of heart cells. Initially the compound(s) will be incubated with a cardiac cell and the ability of the oligo to modulate p53 gene function (e.g., reduction in production p53, apoptosis, improved cardiac cell signaling, Ca++ transport, or morphology etc) can be assessed. For example, the H9C2 cardiac muscle cell line can be obtained from American Type Culture Collection (Manassas, Va., USA) at passage 14 and cultured in DMEM complete culture medium (DMEM/F12 supplemented with 10% fetal calf serum (FCS), 2 mM α-glutamine, 0.5 mg/l Fungizone and 50 me gentamicin). This cell line is suitable for characterizing the inhibitory functions of the p53 directed compounds of the invention and for characterization of modified versions thereof. HL-1 cells, described by Clayton et al. (1998) PNAS 95:2979-2984, can be repeatedly passaged and yet maintain a cardiac-specific phenotype. These cells can also be used to further characterize the effects of the oligos described herein.

It appears that expression of the apoptosis regulator p53 is governed, in part, by a molecule that in mice is termed murine double minute 2 (MDM2), or in man, human double minute 2 (HDM2), an E3 enzyme that targets p53 for ubiquitination and proteasomal processing, and by the deubiquitinating enzyme, herpesvirus-associated ubiquitin-specific protease (HAUSP), which rescues p53 by removing ubiquitin chains from it. Birks et al. (Cardiovasc Res. 2008 Aug. 1; 79(3):472-80) examined whether elevated expression of p53 was associated with dysregulation of ubiquitin-proteasome system (UPS) components and activation of downstream effectors of apoptosis in human dilated cardiomyopathy (DCM). In these studies, left ventricular myocardial samples were obtained from patients with DCM (n=12) or from non-failing (donor) hearts (n=17). Western blotting and immunohistochemistry revealed that DCM tissues contained elevated levels of p53 and its regulators HDM2, MDM2 or the homologs thereof found in other species, and HAUSP (all $P<0.01$) compared with non-failing hearts. DCM tissues also contained elevated levels of polyubiquitinated proteins and possessed enhanced 20S-proteasome chymotrypsin-like activities ($P<0.04$) as measured in vitro using a fluorogenic substrate. DCM tissues contained activated caspases-9 and -3 ($P<0.001$) and reduced expression of the caspase substrate PARP-1 ($P<0.05$). Western blotting and immunohistochemistry revealed that DCM tissues contained elevated expression levels of caspase-3-activated DNAse (CAD; $P<0.001$), which is a key effector of DNA fragmentation in apoptosis and also contained elevated expression of a potent inhibitor of CAD (ICAD-S; $P<0.01$). These investigators concluded that expression of p53 in human DCM is associated with dysregulation of UPS components, which are known to regulate p53 stability. Elevated p53 expression and caspase activation in DCM was not associated with activation of both CAD and its inhibitor, ICAD-S. These findings are consistent with the concept that apoptosis may be interrupted and therefore potentially reversible in human HF.

In view of the foregoing, it is clear that the p53 directed compounds provided herein should exhibit efficacy for the treatment of heart failure. Accordingly, in one embodiment of the invention, p53 directed compounds are administered to patients to inhibit cardiac cell apoptosis, thereby reducing the incidence of heart failure.

Cellular transformation during the development of cancer involves multiple alterations in the normal pattern of cell growth regulation and dysregulated transcriptional control. Primary events in the process of carcinogenesis can involve the activation of oncogene function by some means (e.g., amplification, mutation, chromosomal rearrangement) or altered or aberrant expression of transcriptional regulator functions, and in many cases the removal of anti-oncogene function. One reason for the enhanced growth and invasive properties of some tumors may be the acquisition of increasing numbers of mutations in oncogenes and anti-oncogenes, with cumulative effect (Bear et al., Proc. Natl. Acad. Sci. USA 86:7495-7499, 1989). Alternatively, insofar as oncogenes function through the normal cellular signalling pathways required for organismal growth and cellular function (reviewed in McCormick, Nature 363:15-16, 1993), additional events corresponding to mutations or deregulation in the oncogenic signalling pathways may also contribute to tumor malignancy (Gilks et al., Mol. Cell Biol. 13:1759-1768, 1993), even though mutations in the signalling pathways alone may not cause cancer.

p53 provides a powerful target for efficacious anti-cancer agents. Combination of the p53 directed compounds with one or more therapeutic agents that promote apoptosis effectively induces cell death in cancer cells. Such agents include but are not limited to conventional chemotherapy, radiation and biologic agent such as monoclonal antibodies and agents that manipulate hormone pathways.

p53 protein is an important transcription factor which plays a central role in cell cycle regulation mechanisms and cell proliferation control. Baran et al. performed studies to identify the expression and localization of p53 protein in lesional and non-lesional skin samples taken from psoriatic patients in comparison with healthy controls (Acta Dermatovenerol Alp Panonica Adriat. (2005) 14:79-83). Sections of psoriatic lesional and non-lesional skin (n=18) were examined. A control group (n=10) of healthy volunteers with no personal and family history of psoriasis was also examined. The expression of p53 was demonstrated using the avidin-biotin complex immunoperoxidase method and the monoclonal antibody DO7. The count and localization of cells with stained nuclei was evaluated using a light microscope in 10 fields for every skin biopsy. In lesional psoriatic skin, the count of p53 positive cells was significantly higher than in the skin samples taken from healthy individuals ($p<0.01$) and non-lesional skin taken from psoriatic patients ($p=3.02$). No significant difference between non-lesional psoriatic skin and normal skin was observed ($p=0.1$). A strong positive correlation between mean count and mean percent of p53 positive cells was found ($p<0.0001$). p53 positive cells were located most commonly in the basal layer of the epidermis of both healthy skin and non-lesional psoriatic skin. In lesional psoriatic skin p53 positive cells were present in all layers of the epidermis. In view of these data, it is clear that p53 protein appears to be an important factor in the pathogenesis of psoriasis. Accordingly, compounds which effectively down regulate p53 expression in the skin used alone or in combination with other agents used to treat psoriasis should alleviate the symptoms of this painful and unsightly disorder.

EXAMPLE 2

Compounds for Down-Regulating FAS (APO-1 or CD95) Expression

Fas (APO-1 or CD95) is a cell surface receptor that controls a pathway leading to cell death via apoptosis. This pathway is involved in a number of medical conditions where blocking fas function can provide a clinical benefit. See Table 2. Fas-mediated apoptosis, for example, is a key contributor to the pathology seen in a broad spectrum of liver diseases where inhibiting hepatocyte death can be life saving.

Lieberman and her associates have studied the effects of siRNA directed to the murine fas receptor gene target in murine models of fulminant hepatitis and renal ischemia-reperfusion injury (Song et al., Nature Med 9: 347, 2003; Hamar et a., Proc Natl Acad Sci USA 101: 14883, 2004). siRNA delivered by a hydrodynamic transfection method showed that such siRNA protects mice from concanavalin A generated hepatocyte apoptosis as evidenced by a reduction in liver fibrosis or from death associated with injections of a more hepatotoxic fas specific antibody. In the second study, siRNA was shown to protect mice from acute renal failure after clamping of the renal artery.

RNAi compounds directed to the human fas (apo-1 or CD95) receptor or ligand gene target are provided in WO 2009/0354343, US 2005/0119212, WO 2005/042719 and US 2008/0227733. FIGS. 11-16 provide novel compositions of matter which include many of the features heretofore described for increasing cellular uptake and/or stability for down modulating fas expression in target cells. The sequence used for human fas is provided in GenBank, Accession No. NM_000043.

Recently, Feng et al. reported that during myocardial ischemia, cardiomyocytes can undergo apoptosis or compensatory hypertrophy (Coron Artery Dis. 2008 November; 19(7):527-34). Fas expression is upregulated in the myocardial ischemia and is coupled to both apoptosis and hypertrophy of cardiomyocytes. Some reports suggested that Fas might induce myocardial hypertrophy. Apoptosis of ischemic cardiomyocytes and Fas expression in the nonischemic cardiomyocytes occurs during the early stage of ischemic heart failure. Hypertrophic cardiomyocytes easily undergo apoptosis in response to ischemia, after which apoptotic cardiomyocytes are replaced by fibrous tissue. In the late stage of ischemic heart failure, hypertrophy, apoptosis, and fibrosis are thought to accelerate each other and might thus form a vicious circle that eventually results in heart failure. Based on these observations, it is clear that Fas directed compounds provide useful therapeutic agents for ameliorating the pathological effects associated with myocardial ischemia and hypertrophy. Accordingly, fas directed oligos will be administered cardiac cells and their effects on apoptosis assessed. As discussed above, certain modifications of the fas directed compounds will also be assessed. These include conjugation to heart homing peptides, alterations to the phosphodiester backbone to improve bioavailability and stability, inclusion of CPPs, as well as encapsulation in liposomes or nanoparticles as appropriate.

In their article entitled, "Fas Pulls the Trigger on Psoriasis", Gilhar et al. describe an animal model of psoriasis and the role played by Fas mediated signal transduction (2006) Am. J. Pathology 168:170-175). Fas/FasL signaling is best known for induction of apoptosis. However, there is an alternate pathway of Fas signaling that induces inflammatory cytokines, particularly tumor necrosis factor alpha (TNF-α) and interleukin-8 (IL-8). This pathway is prominent in cells that express high levels of anti-apoptotic molecules such as Bcl-xL. Because TNF-α is central to the pathogenesis of psoriasis and psoriatic epidermis has a low apoptotic index with high expression of Bcl-xL, these authors hypothesized that inflammatory Fas signaling mediates induction of psoriasis by activated lymphocytes. Non-involved skin from psoriasis patients was grafted to beige-severe combined immunodeficiency mice, and psoriasis was induced by injection of FasL-positive autologous natural killer cells that were activated by IL-2. Induction of psoriasis was inhibited by injection of a blocking anti-Fas (ZB4) or anti-FasL (4A5) antibody on days 3 and 10 after natural killer cell injection. Anti-Fas monoclonal antibody significantly reduced cell proliferation (Ki-67) and epidermal thickness, with inhibition of epidermal expression of TNF-α, IL-15, HLA-DR, and ICAM-1. Fas/FasL signaling is an essential early event in the induction of psoriasis by activated lymphocytes and is necessary for induction of key inflammatory cytokines including TNF-α and IL-15.

Such data provide the rationale for therapeutic regimens entailing topical administration of Fas directed compounds and/or BCL-xL directed compounds for the treatment and alleviation of symptoms associated with psoriasis.

EXAMPLE 3

Compounds for Down-Regulating APO-B Expression

Apolipoprotein B (apoB) is an essential protein for the formation of low-density lipoproteins (LDL) and is the ligand for LDL receptor. LDL is responsible for carrying cholesterol to tissues. High levels of apoB can lead to plaques that cause atherosclerosis. Accordingly, blocking apo B expression is a useful treatment modality for a variety of medical disorders including those listed in Table 2.

Soutschek et al. (Nature 432: 173, 2004) have described two siRNA compounds simultaneously directed to both the murine and human apoB gene targets suitable for use in the present invention (FIGS. 27 and 29). These compounds have 21-mer passenger and 23-mer guide strands with cholesterol conjugated to the 3'-ends of the passenger strand. The cholesterol promoted both nuclease resistance and cellular uptake into the target tissues. The reductions in apoB expression in liver and jejunum were associated with reductions in plasma levels of apoB-100 protein and LDL. The authors indicated that the unconjugated compounds (lacking cholesterol) were inactive and concluded that the conjugated compounds need further optimization to achieve improved in vivo potency at doses and dose regimens that are clinically acceptable.

The same group of investigators filed US20060105976, WO06036916 and U.S. Pat. No. 7,528,118 that also provide siRNA compounds suitable for down modulating both human and mouse APO-B gene expression. Eighty-one distinct RNAi compounds with demonstrated activity in the human HepG2 and/or the murine liver cell line NmuLi that expresses apoB were described. Twenty-seven of these double stranded siRNA compounds were found to reduce apoB protein expression in HepG2 cells to less than 35% of control. One of these siRNA was tested in human apoB-100 transgenic mice where following three daily tail vein injections, the siRNA reduced mouse apoB mRNA levels 43+/−10% in liver and 58+/−12% in jejunum and also reduced human apoB mRNA in livers to 40+/−10%. Other siRNA compounds directed to apoB suitable for use in the present invention have been disclosed in US 2006/0134189. These have been described for use in combination with the SNALP (stable nucleic acid lipid particles) delivery technology. FIGS. 17-23 provide novel compositions of matter which include many of the features heretofore described for increasing cellular uptake and/or stability of siRNA for down modulating ApoB expression in target cells.

Conventional antisense oligos directed to gene targets such as the apoB can be converted to RNAi compounds in accordance with the present invention and used as described herein. A series of conventional antisense oligos directed to apoB and suitable for use with the present invention have been described in Merki et al., Circulation 118: 743, 2008; Crooke et al., J Lipid Res 46: 872, 2005; Kastelein et al., Circulation 114: 1729, 2006; U.S. Pat. No. 7,407,943, US 2006/0035858 and WO 2007/143315.

The conventional antisense oligos described in filing WO 2007/143315 are 8-16-mers. It is known that guide strands shorter than 15-mers are not active. Further 16-mer guide strands are the shortest suggested for use with the present invention. Thus, the compounds listed in this filing that are suitable for use with the present invention are limited to 16-mers or to 15-12-mers that are extended to 16-mers using the human ApoB sequence. Such 16-mers can be further lengthened by the use of overhangs which as described herein do not necessarily need to base pair with the gene target.

A number of treatment regimens suitable for use with such conventional antisense oligos or for use with the two-step administration described by the present invention are provided in WO 2008/118883. FIGS. 24-27 provide novel compositions of matter which include many of the features heretofore described for increasing cellular uptake and/or stability for down modulating ApoB expression in target cells. The sequence used for human ApoB is provided in GenBank, Accession No. X04714.1.

Atherosclerosis is a condition in which vascular smooth muscle cells are pathologically reprogrammed. Fatty material collects in the walls of arteries and there is typically chronic inflammation. This leads to a situation where the vascular wall thickens, hardens, forms plaques, which may eventually block the arteries or promote the blockage of arteries by promoting clotting. The latter becomes much more prevalent when there is a plaque rupture.

If the coronary arteries become narrow due to the effects of the plaque formation, blood flow to the heart can slow down or stop, causing chest pain (stable angina), shortness of breath, heart attack, and other symptoms. Pieces of plaque can break apart and move through the bloodstream. This is a common cause of heart attack and stroke. If the clot moves into the heart, lungs, or brain, it can cause a stroke, heart attack, or pulmonary embolism.

Risk factors for atherosclerosis include: diabetes, high blood pressure, high cholesterol, high-fat diet, obesity, personal or family history of heart disease and smoking. The following conditions have also been linked to atherosclerosis: cerebrovascular disease, kidney disease involving dialysis and peripheral vascular disease. Down modulation of apoB s can have a beneficial therapeutic effect for the treatment of artherosclerosis and associated pathologies. WO/2007/030556 provides an animal model for assessing the effects of apoB directed compounds on the formation of atherosclerotic lesions.

EXAMPLE 4

Compounds for Down-Regulating PCSK9 Expression

Protein convertase subtilisin-like kexin type 9 (PCSK9) is a serine protease that destroys LDL receptors in liver and consequently the level of LDL in plasma. PCSK9 mutants can have gain-of-function attributes that promote certain medical disorders associated with alterations in the proportions of plasma lipids. Agents that inhibit PCSK9 function have a role to play in the treatment of such medical disorders including those listed in Table 2.

Frank-Kamenetsky et al. (Proc Natl Acad Sci USA 105: 11915, 2008) have described four siRNA compounds suitable for use in the present invention with three different sequences directed to the PCSK9 gene targets of human, mouse, rats, and nonhuman primates (and have characterized their activity in model systems. These siRNA were selected from a group of 150 by screening for activity using HepG2 cells. These compounds were formulated in lipidoid nanoparticles for in vivo testing. These compounds reduced PCSK9 expression in the livers of rats and mice by 50-70% and this was associated with up to a 60% reduction in plasma cholesterol levels. In transgenic mice carrying the human PCSK9 gene siRNA compounds were shown to reduce the levels of the transcripts of this gene in livers by >70%. In nonhuman primates after a single bolus injection of PCSK9 siRNA the negative effect on PCSK9 expression lasted 3 weeks. During this time apoB and LDL cholesterol (LDLc) levels were reduced. There were no detectable effects on HDL cholesterol or triglycerides.

US2008/0113930 and WO 2007/134161 disclose additional PCSK9 RNAi compounds which can be modified as disclosed herein. FIGS. 28-32 provide novel compositions of matter which include many of the features heretofore described for increasing cellular uptake and/or stability of siRNA for down modulating PCSK9 expression in target cells.

Conventional antisense oligos directed to the PCSK9 gene target provide another example showing how conventional antisense oligos can be reconfigured to provide novel compositions of matter suitable for use in the present invention. Such a reconfiguration is useful in situations where siRNA has advantages over conventional antisense oligos as described herein. A series of conventional antisense oligos directed to human PCSK9 and suitable for use with the present invention have been described in WO 2007/143315. The novel compositions of matter that result from the reconfiguration of these compounds in accordance with the present invention are provided in the Figures. These sequences were among the most active of those that were screened for PCSK9 inhibiting activity in vitro using the Hep3B cell line. The conventional antisense oligos described in this filing are 8-16-mers. It is known that guide strands shorter than 15-mers are not active. Further 16-mer guide strands are the shortest suggested for use with the present invention. Thus, the compounds in this filing that are suitable for use with the present invention are limited to 16-mers or to 15-12-mers that are extended to 16-mers using the PCSK9 sequence provided by Genbank accession number NM_174936.2. Such 16-mers can be further lengthened by the use of overhangs which as described herein do not necessarily need to base pair with the gene target in the case of the guide strand.

A number of treatment regimens suitable for use with such conventional antisense oligos or for use with the two-step administration of strands capable of forming siRNA in cells and where the guide strand is directed to PCSK9 are described in WO 2008/118883. The conventional antisense oligos in this filing are targeted to apoB but the tissues involved and the therapeutic purposes involving PCSK9 are the same and thus essentially the same treatment regimens can be used.

This protein plays a major regulatory role in cholesterol homeostasis. PCSK9 binds to the epidermal growth factor-like repeat A (EGF-A) domain of the low-density lipoprotein receptor (LDLR), inducing LDLR degradation. Reduced LDLR levels result in decreased metabolism of low-density lipoproteins, which could lead to hypercholesterolemia. Inhibition of PSCK9 function provides a means of lowering cholesterol levels. PCSK9 may also have a role in the differentiation of cortical neurons.

Further, the usefulness of conventional antisense oligos directed to the murine PCSK9 gene target for the treatment of hypercholesterolemia has been demonstrated by Graham et al. (J lipid Res 48: 763, 2007). A series of antisense oligos were screened for activity and the most active (ISIS 394814) selected for in vivo studies. Administration of ISIS 394814 to high fat fed mice for 6 weeks resulted in a 53% reduction in total plasma cholesterol and a 38% reduction in plasma LDL. This was accompanied by a 92% reduction in liver PCSK9 expression. FIGS. 33-36 provide novel compositions of matter which include many of the features heretofore described for increasing cellular uptake and/or stability for down modulating PCSK9 expression in target cells. The sequence used for human PCSK9 was NM_174936.2.

EXAMPLE 5

Compounds for Down-Regulating Phosphatase and Tensin Homolog (PTEN) Expression

PTEN is a phosphatase (phosphatidylinositol-3, 4, 5-trisphosphate 3-phosphatase) that is frequently mutated in cancers with wild type p53 where the effect or the mutation is to inhibit its enzymatic activity. In this context, PTEN is thought to function as a tumor suppressor. In cancers with mutated p53, however, PTEN supports the viability and growth of the tumor in part by increasing the levels of gain-of-function p53 mutants (Li et al., Cancer Res 68: 1723, 2008). PTEN also modulates cell cycle regulatory proteins with the effect of inhibiting cell proliferation. Thus, PTEN inhibitors have a role in the treatment of some cancers and in promoting cell proliferation such as expanding cell populations for purposes such as transplantation.

In vivo regeneration of peripheral neurons is constrained and rarely complete, and unfortunately patients with major nerve trunk transections experience only limited recovery. Intracellular inhibition of neuronal growth signals may be among these constraints. Christie et al. investigated the role of PTEN (phosphatase and tensin homolog deleted on chromosome 10) during regeneration of peripheral neurons in adult Sprague Dawley rats (J. Neuroscience 30:9306-9315 (2010). PTEN inhibits phosphoinositide 3-kinase (PI3-K)/Akt signaling, a common and central outgrowth and survival pathway downstream of neuronal growth factors. While PI3-K and Akt outgrowth signals were expressed and activated within adult peripheral neurons during regeneration, PTEN was similarly expressed and poised to inhibit their support. PTEN was expressed in neuron perikaryal cytoplasm, nuclei, regenerating axons, and Schwann cells. Adult sensory neurons in vitro responded to both graded pharmacological inhibition of PTEN and its mRNA knockdown using siRNA. Both approaches were associated with robust rises in the plasticity of neurite outgrowth that were independent of the mTOR (mammalian target of rapamycin) pathway. Importantly, this accelerated outgrowth was in addition to the increased outgrowth generated in neurons that had undergone a preconditioning lesion. Moreover, following severe nerve transection injuries, local pharmacological inhibition of PTEN or siRNA knockdown of PTEN at the injury site accelerated axon outgrowth in vivo. The findings indicated a remarkable impact on peripheral neuron plasticity through PTEN inhibition, even within a complex regenerative milieu. Overall, these findings identify a novel route to propagate intrinsic regeneration pathways within axons to benefit nerve repair. In view of these findings, it is clear that the PTEN directed compounds of the invention may be useful for the treatment of nerve injury and damage. In a preferred embodiment, such agents would be administered intrathecally as described for insulin in Toth et al., *Neuroscience*. (2006) 139:429-49. Czaudema et al. (Nuc Acids Res 31: 2705, 2003) have described an active siRNA compound that is directed to the human PTEN gene target which is suitable for use in accordance with the present invention as described herein. Allerson et al. (J Med Chem 48: 901, 2005) have described two siRNA compounds suitable for use in the present invention that are targeted to human PTEN. FIGS. 37-40 and FIG. 42 provide novel compositions of matter which include many of the features heretofore described for increasing cellular uptake and/or stability for down modulating PTEN expression in target cells. The sequence used for human PTEN was BC005821.2.

EXAMPLE 6

Inhibition of PTEN Expression in HELA Cells

In order to demonstrate the effects of sequential administration of the compositions of the invention on down modulation of gene expression, double and single stranded oligos were transfected into cells and protein production monitored by Western Blot. While antisense to PTEN is demonstrated herein, any of the compounds disclosed herein should exhibit inhibitory effects on target gene expression. The results reveal that sequential administration of sense and antisense strands that have been modified to possess substantial nuclease resistance as single strands results in down modulation of the target gene to a degree comparable to the corresponding siRNA duplex. In addition, duplexes comprised of such stabilized individual sense and antisense strands exhibit as good or better activity than the corresponding conventional siRNA that is not comprised of strands with sufficient stability for sequential in vivo administration in accordance with the present invention.

The following materials and methods are provided to facilitate the practice of the present example.
Cells.
NIH3T3 cells, HELA cells and HepG2 cells were obtained from the ATCC.
Tranfection Reagent
Lipofectamine 2000 transfection reagent was obtained from Invitrogen. It was used for in vitro screening of compounds for activity.
Sequential Transfection Protocol
The sense oligo (0.20 µM) was transfected first. After a four hour incubation, the lipofectamine-oligonucleotide mixture was removed and the cells were washed 3x in culture medium. The antisense oligo (0.20 µM) was then added and incubated with cells for an additional 4 hours. Culture medium was then added and the cells incubated for 20 to 48 hours prior to harvest and preparation of lysates for ECL-Western (fluorescent) blotting. Fluorescent images were quantified on a Typhoon Trio variable mode imager. Erk2 serves as a loading control on Western blots.
Duplex Transfection Protocol
For screening purposes, duplex siRNAs directed to particular targets such as PTEN were tested at 0.05 µM, 0.20 µM, and 0.80 µM. Controls include: (i) non-silencing control ds RNAs prepared by TriLink Inc; (ii) untransfected cells. The non-silencing control (oligo 8) has the following structure:

Oligo 8. ds RNA/2'OMe RNA where the 2'-O-methyl containing nucleosides are underlined

```
5' AAUUCUCCGAACGUGUCACG 3'

3' UUAAGAGGCUUGCACAGUGC 5'
```

Mean values from at least 2 independent transfection experiments are determined and the error bars representing standard error of the mean (SEM) are generated. Target protein level values are shown in the histogram of FIG. 41 where each bar represents the mean protein level (the ratio of Target to Erk2) for given treatment condition after normalization to the Target protein level in the oligo 8 lysate.

Results

Figure 41:
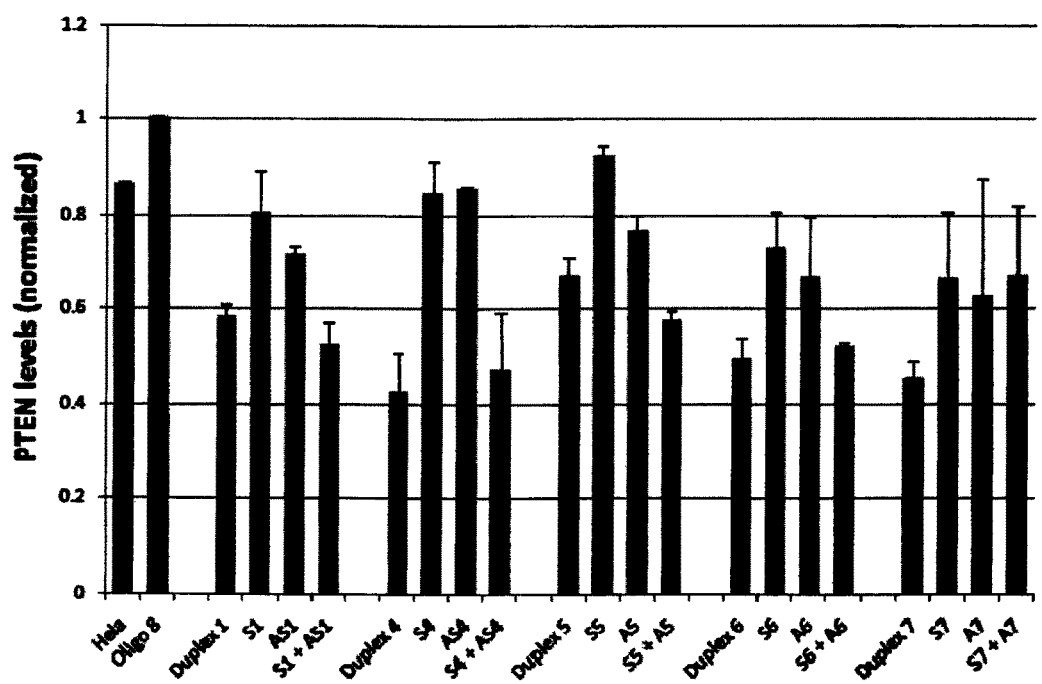

The data for the human PTEN compounds are shown in FIG. 41 which is based on ECL-Western blotting of PTEN after lipofectamine 2000-mediated transfection of siRNA (0.20 μM) in Hela cells as described above. The bar labeled Hela represents the PTEN levels in mock transfected cells while Oligo 8 is the non-silencing control. Five siRNA (duplexes) were tested along with the corresponding sense (S), antisense (A or AS) strands or sequentially administered sense and then antisense strands (S+A or AS). The numbers 1, 4-7 distinguish each of the five sets of compounds. All the sense and antisense stands have the same sequence. The SEQ ID NOS: for Duplex 4 are (SEQ ID NOS: 207-208) Duplex 5 (SEQ ID NOS: 209-210) Duplex 6 (SEQ ID NOS: 211-212) and Duplex 7 (SEQ ID NOS: 213-214). Duplex 1 does not have strands that have been stabilized for unprotected (for example by a carrier) individual in vivo administration in accordance with the present invention.

These data show that all of the four duplexes (4, 5 6 and 7) stabilized for individual strand administration in vivo had activity against PTEN as evidenced by reduced levels of expression. When the corresponding sense and antisense strands of these duplexes were sequentially administered the level of suppression for duplexes 4, 5 and 6 were as good as or slightly better than the result obtained when the duplex itself was used. In the case of duplex 7 the sequentially administered stands were suppressive compared to the non-silencing control but they were not as active as the parent duplex 7. The error bars for duplex 7 components are large and the experiment will be repeated.

Conclusion

Using the design methods of the present invention it is possible to readily generate complementary sense and antisense strands that are sufficiently nuclease resistant to effect single strand administration in vivo and at the same time be able to form a duplex within cells with their partner strand following sequential administration and thereafter have the intended suppressor activity against the target.

EXAMPLE 7

PTP1B Down-Modulation for the Treatment of Cancer, Diabetes and Obesity

PTP1B, a non-transmembrane protein tyrosine phosphatase that has long been studied as a negative regulator of insulin and leptin signaling, has received renewed attention as an unexpected positive factor in tumorigenesis. These dual characteristics make PTP1B a particularly attractive therapeutic target for diabetes, obesity, and perhaps breast cancer.

In the case of insulin signaling, PTP1B dephosphorylates the insulin receptor (IR) as well as its primary substrates, the IRS proteins; by contrast, in leptin signaling a downstream element, the tyrosine kinase JAK2 (Janus kinase 2), is the primary target for dephosphorylation. However, hints that PTP1B might also play a positive signaling role in cell proliferation began to emerge a few years ago, with the finding by a number of groups that PTP1B dephosphorylates the inhibitory Y529 site in Src, thereby activating this kinase. Other PTP1B substrates might also contribute to pro-growth effects. Indeed, the idea that PTP1B can serve as a signaling stimulant in some cases received key confirmation in previous work that showed PTP1B plays a positive role in a mouse model of ErbB2-induced breast cancer. See Yip et al. Trends in Biochemical Sciences 35:442-449 (2010). For these reasons, PTP1B has attracted particular attention as a potential therapeutic target in obesity, diabetes, and now, cancer.

Accordingly, the compounds directed at PTP1B can be used to advantage for the treatment of such disorders.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A preparation which inhibits expression of at least one target ribonucleic acid (RNA) sequence of interest in a cell, comprising an ss-siRNA ribonucleic acid strand in a pharmaceutically acceptable vehicle for in vitro or in vivo administration, said strand being a 19 to 23 mer and comprising modifications effective to promote stability and activity of said strand in target tissue; and having the structure 5' I-I-I-I-I-I-<u>I-*I*~*I*~*I*~*I*~*I*~*I*-I</u>-I-I-N 3' where:
a) I is an individual nucleoside;
b) dash (-) is an internucleoside linkage;
c) N=3 to 7 of additional nucleosides;
d) nucleosides adjacent to the argonaute 2 cleavage site on the target RNA are shown in bold and italics while the adjacent two nucleosides are shown in italics only;
e) nucleotides and linkages which modulate activity of argonaute 2 are in the underlined central region of the strand;

wherein the underlined nucleosides have one of the following configurations:
(ia) alternating 2'-fluoro and 2'-O-methyl sugar modifications; or
(ib) 1, 2, or 3, 2'-fluoro sugar modifications alternating with 1, 2 or 3, 2' O-methyl group sugar modifications, with no more than 3 contiguous nucleosides having the same type of 2' sugar modification;
(ii) 2'-fluoro with ribose with no more than 3 contiguous nucleosides having the 2'-fluoro moiety; or
(iii) 2'-O-methyl with ribose with no more than 3 contiguous nucleosides having the 2'-O-methyl moiety;
(iv) nucleosides flanking the underlined region comprising one or modifications selected from the group consisting of 2'-fluoro, 2'-O-methyl, or is native ribose;
v) linkages are a mixture of phosphorothioate and phosphodiester wherein no more than three of the five linkages indicated by ~ in the strand are phosphorothioate and no more than two of said phosphorothioate linkages are contiguous;
vi) the majority of the linkages flanking the underlined sequence in the strand, or all are phosphorothioate; and
vii) wherein the hydroxyl group in the nucleoside at the 5' end is optionally replaced with a 5'phosphate, said strand being effective to induce degradation of said target ribonucleotide acid within said cell, wherein said target RNA is PTEN and said ss-RNA has the sequence of SEQ ID NO: 221.

2. A preparation which inhibits expression of at least one target ribonucleic acid (RNA) sequence of interest in a cell, comprising an ss-siRNA ribonucleic acid strand in a pharmaceutically acceptable vehicle for in vitro or in vivo administration, said strand being a 19 to 23 mer and comprising modifications effective to promote stability and activity of said strand in target tissue; and having the structure

5' I-I-I-I-I-I-I-/-/-*I*~*I*~*I*-/-/-I-I-I-N 3' where:
a) I is an individual nucleoside;
b) dash (-) is an internucleoside linkage;
c) N =3 to 7 of additional nucleosides;
d) nucleosides adjacent to the argonaute 2 cleavage site on the target RNA are shown in bold and italics while the adjacent two nucleosides are shown in italics only;
e) nucleotides and linkages which modulate activity of argonaute 2 are in the underlined central region of the strand;

wherein the underlined nucleosides have one of the following configurations:
(ia) alternating 2'-fluoro and 2'-O-methyl sugar modifications; or
(ib) 1, 2, or 3, 2'-fluoro sugar modifications alternating with 1, 2 or 3, 2' O-methyl group sugar modifications, with no more than 3 contiguous nucleosides having the same type of 2' sugar modification;
(ii) 2'-fluoro with ribose with no more than 3 contiguous nucleosides having the 2'-fluoro moiety; or
(iii) 2'-O-methyl with ribose with no more than 3 contiguous nucleosides having the 2'-O-methyl moiety;
(iv) nucleosides flanking the underlined region comprising one or modifications selected from the group consisting of 2'-fluoro, 2'-O-methyl, or is native ribose;
v) linkages are a mixture of phosphorothioate and phosphodiester wherein no more than three of the five linkages indicated by ~ in the strand are phosphorothioate and no more than two of said phosphorothioate linkages are contiguous;
vi) the majority of the linkages flanking the underlined sequence in the strand, or all are phosphorothioate; and
vii) wherein the hydroxyl group in the nucleoside at the 5' end is optionally replaced with a 5'phosphate, said strand being effective to induce degradation of said target ribonucleotide acid within said cell, wherein said target RNA is PTEN and said ss-RNA has the sequence of SEQ ID NO: 222.

3. The preparation as claimed in claim 2, that is delivered to a cell in vivo by a carrier which promotes uptake of said composition into a cell.

4. The preparation of claim 3, wherein said carrier provides protection from ribonucleases.

5. The preparation of 3, wherein said carrier is linked to the 3' end of said ss-RNA.

6. The preparation of claim 3, wherein said carrier is cholesterol.

7. The preparation of claim 2, wherein the hydroxyl group at the 5' end is replaced with a 5' phosphate.

8. The preparation as claimed in claim 1, that is delivered to a cell in vivo by a carrier which promotes uptake of said composition into a cell.

* * * * *

SEQUENCE LISTING

```
<160> NUMBER OF SEQ ID NOS: 378

<210> SEQ ID NO 1
<211> LENGTH: 40
<212> TYPE: RNA
<213> ORGANISM: Artificial Sequence
<220> FEATURE:
<223> OTHER INFORMATION: Synthetic Sequence

<400> SEQUENCE: 1
cagaccuaug gaaacuacuu aaguaguuuc cauaggucug                          40

<210> SEQ ID NO 2
```

```
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 2

Gly Tyr Gly Arg Lys Lys Arg Arg Gln Arg Arg Arg
1               5                   10

<210> SEQ ID NO 3
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 3

Tyr Gly Arg Lys Lys Arg Arg Gln Arg Arg Arg
1               5                   10

<210> SEQ ID NO 4
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 4

Cys Tyr Gly Arg Lys Lys Arg Arg Gln Arg Arg Arg
1               5                   10

<210> SEQ ID NO 5
<211> LENGTH: 13
<212> TYPE: PRT
<213> ORGANISM: Artificial Sequence
<220> FEATURE:
<223> OTHER INFORMATION: Synthetic Sequence

<400> SEQUENCE: 5

Arg Lys Lys Arg Arg Gln Arg Arg Arg Pro Pro Gln Cys
1               5                   10

<210> SEQ ID NO 6
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 6

Cys Tyr Gln Arg Lys Lys Arg Arg Gln Arg Arg Arg
1               5                   10

<210> SEQ ID NO 7
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 7

Arg Lys Lys Arg Arg Gln Arg Arg Arg
1               5

<210> SEQ ID NO 8
<211> LENGTH: 17
```

```
<212> TYPE: PRT
<213> ORGANISM: Artificial Sequence
<220> FEATURE:
<223> OTHER INFORMATION: Synthetic Sequence
<220> FEATURE:
<221> NAME/KEY: VARIANT
<222> LOCATION: 7
<223> OTHER INFORMATION: Xaa = Phe or Trp

<400> SEQUENCE: 8

Gly Ala Leu Phe Leu Gly Xaa Leu Gly Ala Ala Gly Ser Thr Met Gly
1               5                   10                  15

Ala

<210> SEQ ID NO 9
<211> LENGTH: 27
<212> TYPE: PRT
<213> ORGANISM: Artificial Sequence
<220> FEATURE:
<223> OTHER INFORMATION: Synthetic Sequence
<220> FEATURE:
<221> NAME/KEY: VARIANT
<222> LOCATION: 7
<223> OTHER INFORMATION: Xaa = Phe or Trp

<400> SEQUENCE: 9

Gly Ala Leu Phe Leu Gly Xaa Leu Gly Ala Ala Gly Ser Thr Met Gly
1               5                   10                  15

Ala Trp Ser Gln Pro Lys Lys Lys Arg Lys Val
            20                  25

<210> SEQ ID NO 10
<211> LENGTH: 27
<212> TYPE: PRT
<213> ORGANISM: Artificial Sequence
<220> FEATURE:
<223> OTHER INFORMATION: Synthetic Sequence
<220> FEATURE:
<221> NAME/KEY: VARIANT
<222> LOCATION: 7
<223> OTHER INFORMATION: Xaa = Phe or Trp

<400> SEQUENCE: 10

Gly Ala Leu Phe Leu Gly Xaa Leu Gly Ala Ala Gly Ser Thr Met Gly
1               5                   10                  15

Ala Trp Ser Gln Pro Lys Ser Lys Arg Lys Val
            20                  25

<210> SEQ ID NO 11
<211> LENGTH: 16
<212> TYPE: PRT
<213> ORGANISM: Artificial Sequence
<220> FEATURE:
<223> OTHER INFORMATION: Synthetic Sequence

<400> SEQUENCE: 11

Arg Gln Ile Lys Ile Trp Phe Gln Asn Arg Arg Met Lys Trp Lys Lys
1               5                   10                  15

<210> SEQ ID NO 12
<211> LENGTH: 19
<212> TYPE: PRT
<213> ORGANISM: Artificial Sequence
<220> FEATURE:
<223> OTHER INFORMATION: Synthetic Sequence

<400> SEQUENCE: 12
```

```
Arg Gln Ile Lys Ile Trp Phe Gln Asn Arg Arg Met Lys Trp Lys Lys
1               5                   10                  15

Gly Gly Cys
```

<210> SEQ ID NO 13
<211> LENGTH: 23
<212> TYPE: PRT
<213> ORGANISM: Artificial Sequence
<220> FEATURE:
<223> OTHER INFORMATION: Synthetic Sequence

<400> SEQUENCE: 13

```
Leu Ile Arg Leu Trp Ser His Leu Ile His Trp Phe Gln Asn Arg
1               5                   10                  15

Arg Leu Lys Trp Lys Lys Lys
            20
```

<210> SEQ ID NO 14
<211> LENGTH: 36
<212> TYPE: PRT
<213> ORGANISM: Artificial Sequence
<220> FEATURE:
<223> OTHER INFORMATION: Synthetic Sequence

<400> SEQUENCE: 14

```
Gly Leu Phe Gly Ala Ile Ala Gly Phe Ile Glu Asn Gly Trp Glu Gly
1               5                   10                  15

Met Ile Asp Gly Arg Gln Ile Lys Ile Trp Phe Gln Asn Arg Arg Met
            20                  25                  30

Lys Trp Lys Lys
        35
```

<210> SEQ ID NO 15
<211> LENGTH: 16
<212> TYPE: PRT
<213> ORGANISM: Artificial Sequence
<220> FEATURE:
<223> OTHER INFORMATION: Synthetic Sequence

<400> SEQUENCE: 15

```
Phe Phe Gly Ala Val Ile Gly Thr Ile Ala Leu Gly Val Ala Thr Ala
1               5                   10                  15
```

<210> SEQ ID NO 16
<211> LENGTH: 16
<212> TYPE: PRT
<213> ORGANISM: Artificial Sequence
<220> FEATURE:
<223> OTHER INFORMATION: Synthetic Sequence

<400> SEQUENCE: 16

```
Phe Leu Gly Phe Leu Leu Gly Val Gly Ser Ala Ile Ala Ser Gly Val
1               5                   10                  15
```

<210> SEQ ID NO 17
<211> LENGTH: 16
<212> TYPE: PRT
<213> ORGANISM: Artificial Sequence
<220> FEATURE:
<223> OTHER INFORMATION: Synthetic Sequence

<400> SEQUENCE: 17

```
Gly Val Phe Val Leu Gly Phe Leu Gly Phe Leu Ala Thr Ala Gly Ser
1               5                   10                  15
```

```
<210> SEQ ID NO 18
<211> LENGTH: 16
<212> TYPE: PRT
<213> ORGANISM: Artificial Sequence
<220> FEATURE:
<223> OTHER INFORMATION: Synthetic Sequence

<400> SEQUENCE: 18

Gly Ala Ala Ile Gly Leu Ala Trp Ile Pro Tyr Phe Gly Pro Ala Ala
1               5                   10                  15

<210> SEQ ID NO 19
<211> LENGTH: 34
<212> TYPE: PRT
<213> ORGANISM: Artificial Sequence
<220> FEATURE:
<223> OTHER INFORMATION: Synthetic Sequence
<220> FEATURE:
<221> NAME/KEY: VARIANT
<222> LOCATION: 34
<223> OTHER INFORMATION: Xaa = Asp or Glu

<400> SEQUENCE: 19

Asp Ala Ala Thr Ala Thr Arg Gly Arg Ser Ala Ala Ser Arg Pro Thr
1               5                   10                  15

Glu Arg Pro Arg Ala Pro Ala Arg Ser Ala Ser Arg Pro Arg Arg Pro
                20                  25                  30

Val Xaa

<210> SEQ ID NO 20
<211> LENGTH: 18
<212> TYPE: PRT
<213> ORGANISM: Artificial Sequence
<220> FEATURE:
<223> OTHER INFORMATION: Synthetic Sequence

<400> SEQUENCE: 20

Lys Leu Ala Lys Leu Leu Ala Leu Lys Ala Leu Lys Ala Ala Leu Lys
1               5                   10                  15

Leu Ala

<210> SEQ ID NO 21
<211> LENGTH: 18
<212> TYPE: PRT
<213> ORGANISM: Artificial Sequence
<220> FEATURE:
<223> OTHER INFORMATION: Synthetic Sequence

<400> SEQUENCE: 21

Lys Leu Ala Leu Lys Leu Ala Leu Lys Ala Leu Lys Ala Ala Leu Lys
1               5                   10                  15

Leu Ala

<210> SEQ ID NO 22
<211> LENGTH: 21
<212> TYPE: PRT
<213> ORGANISM: Artificial Sequence
<220> FEATURE:
<223> OTHER INFORMATION: Synthetic Sequence

<400> SEQUENCE: 22

Lys Glu Thr Trp Trp Glu Thr Trp Trp Thr Glu Trp Ser Gln Pro Lys
1               5                   10                  15

Lys Lys Arg Lys Val
```

20

<210> SEQ ID NO 23
<211> LENGTH: 21
<212> TYPE: PRT
<213> ORGANISM: Artificial Sequence
<220> FEATURE:
<223> OTHER INFORMATION: Synthetic Sequence

<400> SEQUENCE: 23

Lys Glu Thr Trp Phe Glu Thr Trp Phe Thr Glu Trp Ser Gln Pro Lys
1               5                   10                  15

Lys Lys Arg Lys Val
            20

<210> SEQ ID NO 24
<211> LENGTH: 21
<212> TYPE: PRT
<213> ORGANISM: Artificial Sequence
<220> FEATURE:
<223> OTHER INFORMATION: Synthetic Sequence
<220> FEATURE:
<221> NAME/KEY: VARIANT
<222> LOCATION: 2, 3, 10-12, 18, 21
<223> OTHER INFORMATION: Xaa = any or no amino acid

<400> SEQUENCE: 24

Lys Xaa Xaa Trp Trp Glu Thr Trp Trp Xaa Xaa Xaa Ser Gln Pro Lys
1               5                   10                  15

Lys Xaa Arg Lys Xaa
            20

<210> SEQ ID NO 25
<211> LENGTH: 20
<212> TYPE: PRT
<213> ORGANISM: Artificial Sequence
<220> FEATURE:
<223> OTHER INFORMATION: Synthetic Sequence

<400> SEQUENCE: 25

Lys Glu Thr Trp Trp Glu Thr Trp Trp Thr Glu Trp Ser Gln Pro Lys
1               5                   10                  15

Lys Arg Lys Val
            20

<210> SEQ ID NO 26
<211> LENGTH: 20
<212> TYPE: PRT
<213> ORGANISM: Artificial Sequence
<220> FEATURE:
<223> OTHER INFORMATION: Synthetic Sequence

<400> SEQUENCE: 26

Lys Glu Thr Trp Trp Glu Thr Trp Trp Thr Glu Ala Ser Gln Pro Lys
1               5                   10                  15

Lys Arg Lys Val
            20

<210> SEQ ID NO 27
<211> LENGTH: 21
<212> TYPE: PRT
<213> ORGANISM: Artificial Sequence
<220> FEATURE:
<223> OTHER INFORMATION: Synthetic Sequence

<400> SEQUENCE: 27

```
Lys Glu Thr Trp Trp Glu Thr Trp Trp Glu Thr Trp Ser Gln Pro Lys
1               5                   10                  15

Lys Lys Arg Lys Val
            20

<210> SEQ ID NO 28
<211> LENGTH: 19
<212> TYPE: PRT
<213> ORGANISM: Artificial Sequence
<220> FEATURE:
<223> OTHER INFORMATION: Synthetic Sequence

<400> SEQUENCE: 28

Lys Glu Thr Trp Trp Glu Thr Trp Thr Trp Ser Gln Pro Lys Lys
1               5                   10                  15

Arg Lys Val

<210> SEQ ID NO 29
<211> LENGTH: 19
<212> TYPE: PRT
<213> ORGANISM: Artificial Sequence
<220> FEATURE:
<223> OTHER INFORMATION: Synthetic Sequence

<400> SEQUENCE: 29

Lys Trp Trp Glu Thr Trp Trp Glu Thr Trp Ser Gln Pro Lys Lys
1               5                   10                  15

Arg Lys Val

<210> SEQ ID NO 30
<211> LENGTH: 21
<212> TYPE: PRT
<213> ORGANISM: Artificial Sequence
<220> FEATURE:
<223> OTHER INFORMATION: Synthetic Sequence
<220> FEATURE:
<221> NAME/KEY: VARIANT
<222> LOCATION: 10, 11
<223> OTHER INFORMATION: Xaa = any or no amino acid

<400> SEQUENCE: 30

Lys Glu Thr Trp Trp Glu Thr Trp Trp Xaa Xaa Trp Ser Gln Pro Lys
1               5                   10                  15

Lys Lys Arg Lys Val
            20

<210> SEQ ID NO 31
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 31

Gly Ala Leu Phe Leu Gly Trp Leu Gly Ala Ala Gly Ser Thr Met
1               5                   10                  15

<210> SEQ ID NO 32
<211> LENGTH: 27
<212> TYPE: PRT
<213> ORGANISM: Artificial Sequence
<220> FEATURE:
<223> OTHER INFORMATION: Synthetic Sequence

<400> SEQUENCE: 32
```

```
Gly Ala Leu Phe Leu Gly Trp Leu Gly Ala Ala Gly Ser Thr Met Gly
1               5                   10                  15

Ala Trp Ser Gln Pro Lys Lys Arg Lys Val
            20                  25

<210> SEQ ID NO 33
<211> LENGTH: 30
<212> TYPE: PRT
<213> ORGANISM: Artificial Sequence
<220> FEATURE:
<223> OTHER INFORMATION: Synthetic Sequence

<400> SEQUENCE: 33

Met Val Lys Ser Lys Ile Gly Ser Trp Ile Leu Val Leu Phe Val Ala
1               5                   10                  15

Met Trp Ser Asp Val Gly Leu Cys Lys Lys Arg Pro Lys Pro
            20                  25                  30

<210> SEQ ID NO 34
<211> LENGTH: 18
<212> TYPE: PRT
<213> ORGANISM: Artificial Sequence
<220> FEATURE:
<223> OTHER INFORMATION: Synthetic Sequence

<400> SEQUENCE: 34

Arg Gly Gly Arg Leu Ser Tyr Ser Arg Arg Phe Ser Thr Ser Thr
1               5                   10                  15

Gly Arg

<210> SEQ ID NO 35
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 35

Arg Arg Leu Ser Tyr Ser Arg Arg Arg Phe
1               5                   10

<210> SEQ ID NO 36
<211> LENGTH: 27
<212> TYPE: PRT
<213> ORGANISM: Artificial Sequence
<220> FEATURE:
<223> OTHER INFORMATION: Synthetic Sequence

<400> SEQUENCE: 36

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 37
<211> LENGTH: 21
<212> TYPE: PRT
<213> ORGANISM: Artificial Sequence
<220> FEATURE:
<223> OTHER INFORMATION: Synthetic Sequence

<400> SEQUENCE: 37

Ala Gly Tyr Leu Leu Gly Lys Ile Asn Leu Lys Ala Leu Ala Ala Leu
1               5                   10                  15
```

```
Ala Lys Lys Ile Leu
            20

<210> SEQ ID NO 38
<211> LENGTH: 21
<212> TYPE: PRT
<213> ORGANISM: Artificial Sequence
<220> FEATURE:
<223> OTHER INFORMATION: Synthetic Sequence

<400> SEQUENCE: 38

Arg Arg Arg Arg Arg Arg Trp Gly Arg Arg Arg Arg Arg Pro Lys
1               5                   10                  15

Lys Lys Arg Lys Val
            20

<210> SEQ ID NO 39
<211> LENGTH: 32
<212> TYPE: PRT
<213> ORGANISM: Artificial Sequence
<220> FEATURE:
<223> OTHER INFORMATION: Synthetic Sequence

<400> SEQUENCE: 39

Arg Arg Arg Arg Ser Arg Arg Arg Arg Arg Phe Gly Arg Arg
1               5                   10                  15

Arg Arg Arg Val Trp Arg Arg Arg Pro Lys Lys Arg Lys Val
            20                  25                  30

<210> SEQ ID NO 40
<211> LENGTH: 13
<212> TYPE: PRT
<213> ORGANISM: Artificial Sequence
<220> FEATURE:
<223> OTHER INFORMATION: Synthetic Sequence
<220> FEATURE:
<221> NAME/KEY: MOD_RES
<222> LOCATION: 1
<223> OTHER INFORMATION: Xaa = D-isomer of Cys

<400> SEQUENCE: 40

Xaa Cys Ser Lys Ala Pro Lys Leu Pro Ala Ala Tyr Cys
1               5                   10

<210> SEQ ID NO 41
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 41

Gly Gly Gly Gly Gly Cys Ser Lys Cys
1               5

<210> SEQ ID NO 42
<211> LENGTH: 39
<212> TYPE: PRT
<213> ORGANISM: Artificial Sequence
<220> FEATURE:
<223> OTHER INFORMATION: Synthetic Sequence

<400> SEQUENCE: 42

Cys Thr Thr Thr His Thr Phe Val Lys Ala Leu Thr Met Asp Gly Lys
1               5                   10                  15
```

Gln Ala Ala Trp Arg Phe Ile Arg Ile Asp Thr Ala Cys Lys Lys
            20                  25                  30

Lys Lys Lys Lys Lys Lys Lys
        35

<210> SEQ ID NO 43
<211> LENGTH: 13
<212> TYPE: PRT
<213> ORGANISM: Artificial Sequence
<220> FEATURE:
<223> OTHER INFORMATION: Synthetic Sequence

<400> SEQUENCE: 43

Thr Thr Ala Thr Asp Ile Lys Gly Lys Glu Val Met Val
1               5                   10

<210> SEQ ID NO 44
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 44

Glu Val Asn Ile Asn Asn Ser Val Phe
1               5

<210> SEQ ID NO 45
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 45

Arg Gly Ile Asp Ser Lys His Trp Asn Ser Tyr
1               5                   10

<210> SEQ ID NO 46
<211> LENGTH: 27
<212> TYPE: PRT
<213> ORGANISM: Artificial Sequence
<220> FEATURE:
<223> OTHER INFORMATION: Synthetic Sequence

<400> SEQUENCE: 46

Thr Thr Thr His Thr Phe Val Lys Ala Leu Thr Met Asp Gly Lys Gln
1               5                   10                  15

Ala Ala Trp Arg Phe Ile Arg Ile Asp Thr Ala
            20                  25

<210> SEQ ID NO 47
<211> LENGTH: 21
<212> TYPE: PRT
<213> ORGANISM: Artificial Sequence
<220> FEATURE:
<223> OTHER INFORMATION: Synthetic Sequence

<400> SEQUENCE: 47

Ala Leu Trp Lys Thr Leu Leu Lys Lys Val Leu Lys Ala Pro Lys Lys
1               5                   10                  15

Lys Arg Lys Val Cys
            20

<210> SEQ ID NO 48

```
<211> LENGTH: 18
<212> TYPE: PRT
<213> ORGANISM: Artificial Sequence
<220> FEATURE:
<223> OTHER INFORMATION: Synthetic Sequence

<400> SEQUENCE: 48

Val Arg Leu Pro Pro Pro Val Arg Leu Pro Pro Pro Val Arg Leu Pro
1               5                   10                  15

Pro Pro

<210> SEQ ID NO 49
<211> LENGTH: 24
<212> TYPE: PRT
<213> ORGANISM: Artificial Sequence
<220> FEATURE:
<223> OTHER INFORMATION: Synthetic Sequence

<400> SEQUENCE: 49

Leu Gly Thr Tyr Thr Gln Asp Phe Asn Lys Phe His Thr Phe Pro Gln
1               5                   10                  15

Thr Ala Ile Gly Val Gly Ala Pro
            20

<210> SEQ ID NO 50
<211> LENGTH: 22
<212> TYPE: PRT
<213> ORGANISM: Artificial Sequence
<220> FEATURE:
<223> OTHER INFORMATION: Synthetic Sequence

<400> SEQUENCE: 50

Met Val Thr Val Leu Phe Arg Arg Leu Arg Ile Arg Arg Ala Cys Gly
1               5                   10                  15

Pro Pro Arg Val Arg Val
            20

<210> SEQ ID NO 51
<211> LENGTH: 22
<212> TYPE: PRT
<213> ORGANISM: Artificial Sequence
<220> FEATURE:
<223> OTHER INFORMATION: Synthetic Sequence

<400> SEQUENCE: 51

Met Val Arg Arg Phe Leu Val Thr Leu Arg Ile Arg Arg Ala Cys Gly
1               5                   10                  15

Pro Pro Arg Val Arg Val
            20

<210> SEQ ID NO 52
<211> LENGTH: 22
<212> TYPE: PRT
<213> ORGANISM: Artificial Sequence
<220> FEATURE:
<223> OTHER INFORMATION: Synthetic Sequence

<400> SEQUENCE: 52

Phe Val Thr Arg Gly Cys Pro Arg Arg Leu Val Ala Arg Leu Ile Arg
1               5                   10                  15

Val Met Val Pro Arg Arg
            20

<210> SEQ ID NO 53
```

```
<211> LENGTH: 16
<212> TYPE: PRT
<213> ORGANISM: Artificial Sequence
<220> FEATURE:
<223> OTHER INFORMATION: Synthetic Sequence

<400> SEQUENCE: 53

Ala Ala Val Ala Leu Leu Pro Ala Val Leu Leu Ala Leu Leu Ala Pro
1               5                   10                  15

<210> SEQ ID NO 54
<211> LENGTH: 16
<212> TYPE: PRT
<213> ORGANISM: Artificial Sequence
<220> FEATURE:
<223> OTHER INFORMATION: Synthetic Sequence

<400> SEQUENCE: 54

Ala Ala Val Leu Leu Pro Val Leu Leu Pro Val Leu Leu Ala Ala Pro
1               5                   10                  15

<210> SEQ ID NO 55
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 55

Val Thr Val Leu Ala Leu Gly Ala Leu Ala Gly Val Gly Val Gly
1               5                   10                  15

<210> SEQ ID NO 56
<211> LENGTH: 17
<212> TYPE: PRT
<213> ORGANISM: Artificial Sequence
<220> FEATURE:
<223> OTHER INFORMATION: Synthetic Sequence

<400> SEQUENCE: 56

Gly Ala Leu Phe Leu Gly Trp Leu Gly Ala Ala Gly Ser Thr Met Gly
1               5                   10                  15

Ala

<210> SEQ ID NO 57
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 57

Met Gly Leu Gly Leu His Leu Leu Val Leu Ala Ala Ala Leu Gln
1               5                   10                  15

<210> SEQ ID NO 58
<211> LENGTH: 27
<212> TYPE: PRT
<213> ORGANISM: Artificial Sequence
<220> FEATURE:
<223> OTHER INFORMATION: Synthetic Sequence

<400> SEQUENCE: 58

Met Gly Leu Gly Leu His Leu Leu Val Leu Ala Ala Ala Leu Gln Gly
1               5                   10                  15

Ala Trp Ser Gln Pro Lys Lys Lys Arg Lys Val
```

20                  25

<210> SEQ ID NO 59
<211> LENGTH: 24
<212> TYPE: PRT
<213> ORGANISM: Artificial Sequence
<220> FEATURE:
<223> OTHER INFORMATION: Synthetic Sequence

<400> SEQUENCE: 59

Leu Gly Thr Tyr Thr Gln Asp Phe Asn Lys Phe His Thr Phe Pro Gln
1               5                   10                  15

Thr Ala Ile Gly Val Gly Ala Pro
            20

<210> SEQ ID NO 60
<211> LENGTH: 16
<212> TYPE: PRT
<213> ORGANISM: Artificial Sequence
<220> FEATURE:
<223> OTHER INFORMATION: Synthetic Sequence

<400> SEQUENCE: 60

Thr Pro Pro Lys Lys Lys Arg Lys Val Glu Asp Pro Lys Lys Lys Lys
1               5                   10                  15

<210> SEQ ID NO 61
<211> LENGTH: 37
<212> TYPE: PRT
<213> ORGANISM: Artificial Sequence
<220> FEATURE:
<223> OTHER INFORMATION: Synthetic Sequence

<400> SEQUENCE: 61

Leu Leu Gly Asp Phe Phe Arg Lys Ser Lys Glu Lys Ile Gly Lys Glu
1               5                   10                  15

Phe Lys Arg Ile Val Gln Arg Ile Lys Asp Phe Leu Arg Asn Leu Val
            20                  25                  30

Pro Arg Thr Glu Ser
        35

<210> SEQ ID NO 62
<211> LENGTH: 13
<212> TYPE: PRT
<213> ORGANISM: Artificial Sequence
<220> FEATURE:
<223> OTHER INFORMATION: Synthetic Sequence

<400> SEQUENCE: 62

Ala Leu Trp Lys Thr Leu Leu Lys Lys Val Leu Lys Ala
1               5                   10

<210> SEQ ID NO 63
<211> LENGTH: 20
<212> TYPE: PRT
<213> ORGANISM: Artificial Sequence
<220> FEATURE:
<223> OTHER INFORMATION: Synthetic Sequence

<400> SEQUENCE: 63

Ala Leu Trp Lys Thr Leu Leu Lys Lys Val Leu Lys Ala Pro Lys Lys
1               5                   10                  15

Lys Arg Lys Val
        20

```
<210> SEQ ID NO 64
<211> LENGTH: 20
<212> TYPE: PRT
<213> ORGANISM: Artificial Sequence
<220> FEATURE:
<223> OTHER INFORMATION: Synthetic Sequence

<400> SEQUENCE: 64

Pro Lys Lys Lys Arg Lys Val Ala Leu Trp Lys Thr Leu Leu Lys Lys
1               5                   10                  15

Val Leu Lys Ala
            20

<210> SEQ ID NO 65
<211> LENGTH: 22
<212> TYPE: PRT
<213> ORGANISM: Artificial Sequence
<220> FEATURE:
<223> OTHER INFORMATION: Synthetic Sequence

<400> SEQUENCE: 65

Arg Gln Ala Arg Arg Asn Arg Arg Ala Leu Trp Lys Thr Leu Leu
1               5                   10                  15

Lys Lys Val Leu Lys Ala
            20

<210> SEQ ID NO 66
<211> LENGTH: 8
<212> TYPE: PRT
<213> ORGANISM: Artificial Sequence
<220> FEATURE:
<223> OTHER INFORMATION: Synthetic Sequence

<400> SEQUENCE: 66

Ile Val Ile Ala Lys Leu Lys Ala
1               5

<210> SEQ ID NO 67
<211> LENGTH: 19
<212> TYPE: PRT
<213> ORGANISM: Artificial Sequence
<220> FEATURE:
<223> OTHER INFORMATION: Synthetic Sequence

<400> SEQUENCE: 67

Ile Val Ile Ala Lys Leu Lys Ala Asn Leu Met Cys Lys Thr Cys Arg
1               5                   10                  15

Leu Ala Lys

<210> SEQ ID NO 68
<211> LENGTH: 5
<212> TYPE: PRT
<213> ORGANISM: Artificial Sequence
<220> FEATURE:
<223> OTHER INFORMATION: Synthetic Sequence

<400> SEQUENCE: 68

Lys Val Lys Lys Gln
1               5

<210> SEQ ID NO 69
<211> LENGTH: 16
<212> TYPE: PRT
<213> ORGANISM: Artificial Sequence
<220> FEATURE:
```

```
<223> OTHER INFORMATION: Synthetic Sequence
<220> FEATURE:
<221> NAME/KEY: MOD_RES
<222> LOCATION: (1)...(16)
<223> OTHER INFORMATION: D-amino acids

<400> SEQUENCE: 69

Ala Ala Lys Lys Ala Ala Lys Lys Ala Ala Lys Lys Ala Ala Lys Lys
1               5                   10                  15

<210> SEQ ID NO 70
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 70

Pro Phe Val Tyr Leu Ile
1               5

<210> SEQ ID NO 71
<211> LENGTH: 17
<212> TYPE: PRT
<213> ORGANISM: Artificial Sequence
<220> FEATURE:
<223> OTHER INFORMATION: Synthetic Sequence

<400> SEQUENCE: 71

Cys Ser Ile Pro Pro Glu Val Lys Phe Asn Lys Pro Phe Val Tyr Leu
1               5                   10                  15

Ile

<210> SEQ ID NO 72
<211> LENGTH: 23
<212> TYPE: PRT
<213> ORGANISM: Artificial Sequence
<220> FEATURE:
<223> OTHER INFORMATION: Synthetic Sequence
<220> FEATURE:
<221> NAME/KEY: VARIANT
<222> LOCATION: 1-3, 8-13, 16, 21-23
<223> OTHER INFORMATION: Xaa = any or no amino acid

<400> SEQUENCE: 72

Xaa Xaa Xaa Lys Lys Arg Arg Xaa Xaa Xaa Xaa Xaa Xaa Thr Trp Xaa
1               5                   10                  15

Glu Thr Trp Trp Xaa Xaa Xaa
            20

<210> SEQ ID NO 73
<211> LENGTH: 22
<212> TYPE: PRT
<213> ORGANISM: Artificial Sequence
<220> FEATURE:
<223> OTHER INFORMATION: Synthetic Sequence
<220> FEATURE:
<221> NAME/KEY: VARIANT
<222> LOCATION: 8, 9, 11-13, 16
<223> OTHER INFORMATION: Xaa = any or no amino acid

<400> SEQUENCE: 73

Tyr Gly Phe Lys Lys Arg Arg Xaa Xaa Gln Xaa Xaa Xaa Thr Trp Xaa
1               5                   10                  15

Glu Thr Trp Trp Thr Glu
            20
```

```
<210> SEQ ID NO 74
<211> LENGTH: 20
<212> TYPE: PRT
<213> ORGANISM: Artificial Sequence
<220> FEATURE:
<223> OTHER INFORMATION: Synthetic Sequence
<220> FEATURE:
<221> NAME/KEY: VARIANT
<222> LOCATION: 6, 20
<223> OTHER INFORMATION: Xaa = any or no amino acid

<400> SEQUENCE: 74

Tyr Gly Phe Lys Lys Xaa Arg Arg Pro Trp Thr Trp Trp Glu Thr Trp
1               5                   10                  15

Trp Thr Glu Xaa
            20

<210> SEQ ID NO 75
<211> LENGTH: 7
<212> TYPE: PRT
<213> ORGANISM: Artificial Sequence
<220> FEATURE:
<223> OTHER INFORMATION: Synthetic Sequence
<220> FEATURE:
<221> NAME/KEY: VARIANT
<222> LOCATION: 1, 2, 5, 7
<223> OTHER INFORMATION: Xaa = hydrophobic amino acid
<220> FEATURE:
<221> NAME/KEY: VARIANT
<222> LOCATION: 3, 4, 6
<223> OTHER INFORMATION: Xaa = basic amino acid
<220> FEATURE:
<221> NAME/KEY: VARIANT
<222> LOCATION: 1-7
<223> OTHER INFORMATION: amino acids 1-7 are optionally repeated 1 to 9
      times

<400> SEQUENCE: 75

Xaa Xaa Xaa Xaa Xaa Xaa Xaa
1               5

<210> SEQ ID NO 76
<211> LENGTH: 14
<212> TYPE: PRT
<213> ORGANISM: Artificial Sequence
<220> FEATURE:
<223> OTHER INFORMATION: Synthetic Sequence
<220> FEATURE:
<221> NAME/KEY: VARIANT
<222> LOCATION: 1
<223> OTHER INFORMATION: Xaa = any amino acid
<220> FEATURE:
<221> NAME/KEY: VARIANT
<222> LOCATION: 2, 3, 6, 10, 13, 14
<223> OTHER INFORMATION: Xaa = D or L lysine, histidine, homolysine,
      diaminobutyric acid, arginine, ornithine, or
      homoarginine
<220> FEATURE:
<221> NAME/KEY: VARIANT
<222> LOCATION: 4, 5, 8, 12
<223> OTHER INFORMATION: Xaa = D or L alanine, valine, leucine,
      isolecucine, phenylalanine, tyrosine, tryptophan,
      cysteine, or methionine
<220> FEATURE:
<221> NAME/KEY: VARIANT
<222> LOCATION: 7, 9, 11
<223> OTHER INFORMATION: Xaa = D or L Lys, His, homolysine,
      diaminobutyric acid, Arg, ornithine, homoarginine, Ala, Val, Leu,
      Ile, Phe, Tyr, Trp, Cys, Met, Gly, Ser, Thr, aspartate,
      glutamate, Asn, or Gln

<400> SEQUENCE: 76
```

```
Xaa Xaa Xaa Xaa Xaa Xaa Xaa Xaa Xaa Xaa Xaa Xaa Xaa
1               5                   10
```

<210> SEQ ID NO 77
<211> LENGTH: 14
<212> TYPE: PRT
<213> ORGANISM: Artificial Sequence
<220> FEATURE:
<223> OTHER INFORMATION: Synthetic Sequence
<220> FEATURE:
<221> NAME/KEY: VARIANT
<222> LOCATION: 14
<223> OTHER INFORMATION: Xaa = any amino acid
<220> FEATURE:
<221> NAME/KEY: VARIANT
<222> LOCATION: 1, 2, 5, 9, 12, 13
<223> OTHER INFORMATION: Xaa = D or L lysine, histidine, homolysine, diaminobutyric acid, arginine, ornithine, or homoarginine
<220> FEATURE:
<221> NAME/KEY: VARIANT
<222> LOCATION: 3, 7, 10, 11
<223> OTHER INFORMATION: Xaa = D or L alanine, valine, leucine, isolecucine, phenylalanine, tyrosine, tryptophan, cysteine, or methionine
<220> FEATURE:
<221> NAME/KEY: VARIANT
<222> LOCATION: 4, 6, 8
<223> OTHER INFORMATION: Xaa = D or L Lys, His, homolysine, diaminobutyric acid, Arg, ornithine, homoarginine, Ala, Val, Leu, Ile, Phe, Tyr, Trp, Cys, Met, Gly, Ser, Thr, aspartate, glutamate, Asn, or Gln

<400> SEQUENCE: 77

```
Xaa Xaa Xaa Xaa Xaa Xaa Xaa Xaa Xaa Xaa Xaa Xaa Xaa
1               5                   10
```

<210> SEQ ID NO 78
<211> LENGTH: 10
<212> TYPE: PRT
<213> ORGANISM: Artificial Sequence
<220> FEATURE:
<223> OTHER INFORMATION: Synthetic Sequence
<220> FEATURE:
<221> NAME/KEY: VARIANT
<222> LOCATION: 1
<223> OTHER INFORMATION: Xaa = an amino acid exhibiting relatively high rotation freedom of a peptide unit (e.g., G or A)
<220> FEATURE:
<221> NAME/KEY: VARIANT
<222> LOCATION: 4
<223> OTHER INFORMATION: Xaa = basic amino acid
<220> FEATURE:
<221> NAME/KEY: VARIANT
<222> LOCATION: 2-10
<223> OTHER INFORMATION: Xaa = any amino acid except that at least three are R or K

<400> SEQUENCE: 78

```
Xaa Xaa Xaa Xaa Xaa Xaa Xaa Xaa Xaa Xaa
1               5                   10
```

<210> SEQ ID NO 79
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 79

```
Tyr Gly Arg Arg Ala Arg Arg Arg Arg Arg
1               5                   10
```

```
<210> SEQ ID NO 80
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 80

Tyr Gly Arg Arg Ala Arg Arg Arg Ala Arg Arg
1               5                   10

<210> SEQ ID NO 81
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 81

Tyr Gly Arg Arg Arg Arg Arg Arg Arg Arg Arg
1               5                   10

<210> SEQ ID NO 82
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 82

His Ala Ile Tyr Pro Arg His
1               5

<210> SEQ ID NO 83
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 83

Thr His Arg Pro Pro Met Trp Ser Pro Val Trp Pro
1               5                   10

<210> SEQ ID NO 84
<211> LENGTH: 8
<212> TYPE: PRT
<213> ORGANISM: Artificial Sequence
<220> FEATURE:
<223> OTHER INFORMATION: Synthetic Sequence
<220> FEATURE:
<221> NAME/KEY: VARIANT
<222> LOCATION: 3
<223> OTHER INFORMATION: Xaa = D-threonine

<400> SEQUENCE: 84

Gly Phe Xaa Thr Gly Phe Leu Ser
1               5

<210> SEQ ID NO 85
<211> LENGTH: 7
<212> TYPE: PRT
<213> ORGANISM: Artificial Sequence
<220> FEATURE:
<223> OTHER INFORMATION: Synthetic Sequence
<220> FEATURE:
<221> NAME/KEY: VARIANT
<222> LOCATION: 2
```

```
<223> OTHER INFORMATION: Xaa = D or L phenylalanine

<400> SEQUENCE: 85

Gly Xaa Thr Gly Phe Leu Ser
1               5

<210> SEQ ID NO 86
<211> LENGTH: 29
<212> TYPE: PRT
<213> ORGANISM: Artificial Sequence
<220> FEATURE:
<223> OTHER INFORMATION: Synthetic Sequence

<400> SEQUENCE: 86

Tyr Thr Ile Trp Met Pro Glu Asn Pro Arg Pro Gly Thr Pro Cys Asp
1               5                   10                  15

Ile Phe Thr Asn Ser Arg Gly Lys Arg Ala Ser Asn Gly
            20                  25

<210> SEQ ID NO 87
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 87

Gly Gly Gly Val Phe Trp Gln
1               5

<210> SEQ ID NO 88
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 88

His Gly Arg Val Arg Pro His
1               5

<210> SEQ ID NO 89
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 89

Val Val Leu Val Thr Ser Ser
1               5

<210> SEQ ID NO 90
<211> LENGTH: 8
<212> TYPE: PRT
<213> ORGANISM: Artificial Sequence
<220> FEATURE:
<223> OTHER INFORMATION: Synthetic Sequence

<400> SEQUENCE: 90

Cys Leu His Arg Gly Asn Ser Cys
1               5

<210> SEQ ID NO 91
<211> LENGTH: 12
<212> TYPE: PRT
```

```
<213> ORGANISM: Artificial Sequence
<220> FEATURE:
<223> OTHER INFORMATION: Synthetic Sequence

<400> SEQUENCE: 91

Cys Arg Ser Trp Asn Lys Ala Asp Asn Arg Ser Cys
1               5                   10

<210> SEQ ID NO 92
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 92

Cys Arg Ser Trp Asn Lys Ala Asp Asn Arg Ser Cys
1               5                   10

<210> SEQ ID NO 93
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 93

Leu Ser Ile Pro Pro Lys Ala
1               5

<210> SEQ ID NO 94
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 94

Phe Gln Thr Pro Pro Gln Leu
1               5

<210> SEQ ID NO 95
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 95

Leu Thr Pro Ala Thr Ala Ile
1               5

<210> SEQ ID NO 96
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 96

Gly Gly Gly Ala Arg Lys Lys Ala Ala Lys Ala Arg Lys Lys Ala
1               5                   10                  15

Ala Lys Ala Ala Arg Lys Lys Ala Ala Lys Ala Arg Lys Lys Ala
            20                  25                  30

Ala Lys Ala
        35
```

<210> SEQ ID NO 97
<211> LENGTH: 22
<212> TYPE: PRT
<213> ORGANISM: Artificial Sequence
<220> FEATURE:
<223> OTHER INFORMATION: Synthetic Sequence

<400> SEQUENCE: 97

Arg Ser Gln Ser Arg Ser Arg Tyr Tyr Arg Gln Arg Gln Arg Ser Arg
1               5                   10                  15

Arg Arg Arg Arg Arg Ser
            20

<210> SEQ ID NO 98
<211> LENGTH: 16
<212> TYPE: PRT
<213> ORGANISM: Artificial Sequence
<220> FEATURE:
<223> OTHER INFORMATION: Synthetic Sequence

<400> SEQUENCE: 98

Gly Leu Phe Gly Ala Ile Ala Gly Phe Ile Glu Asn Gly Trp Glu Gly
1               5                   10                  15

<210> SEQ ID NO 99
<211> LENGTH: 19
<212> TYPE: PRT
<213> ORGANISM: Artificial Sequence
<220> FEATURE:
<223> OTHER INFORMATION: Synthetic Sequence
<220> FEATURE:
<221> NAME/KEY: VARIANT
<222> LOCATION: 12
<223> OTHER INFORMATION: Xaa = Asn or Gly
<220> FEATURE:
<221> NAME/KEY: VARIANT
<222> LOCATION: 18
<223> OTHER INFORMATION: Xaa = Ile or Val

<400> SEQUENCE: 99

Gly Leu Phe Gly Ala Ile Ala Gly Phe Ile Gly Xaa Gly Trp Gly Gly
1               5                   10                  15

Met Xaa Asp

<210> SEQ ID NO 100
<211> LENGTH: 20
<212> TYPE: PRT
<213> ORGANISM: Artificial Sequence
<220> FEATURE:
<223> OTHER INFORMATION: Synthetic Sequence

<400> SEQUENCE: 100

Gly Asp Ile Met Gly Glu Trp Gly Asn Glu Ile Phe Gly Ala Ile Ala
1               5                   10                  15

Gly Phe Leu Gly
            20

<210> SEQ ID NO 101
<211> LENGTH: 30
<212> TYPE: PRT
<213> ORGANISM: Artificial Sequence
<220> FEATURE:
<223> OTHER INFORMATION: Synthetic Sequence

<400> SEQUENCE: 101

-continued

Arg Arg Arg Gln Arg Arg Lys Lys Arg Gly Asp Ile Met Gly Glu
1               5                   10                  15

Trp Gly Asn Glu Ile Phe Gly Ala Ile Ala Gly Phe Leu Gly
            20                  25                  30

<210> SEQ ID NO 102
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 102

Cys His Lys Lys Lys Lys Lys Lys His Cys
1               5                   10

<210> SEQ ID NO 103
<211> LENGTH: 17
<212> TYPE: PRT
<213> ORGANISM: Artificial Sequence
<220> FEATURE:
<223> OTHER INFORMATION: Synthetic Sequence

<400> SEQUENCE: 103

Cys His His His His His His Lys Lys Lys His His His His His
1               5                   10                  15

Cys

<210> SEQ ID NO 104
<211> LENGTH: 8
<212> TYPE: PRT
<213> ORGANISM: Artificial Sequence
<220> FEATURE:
<223> OTHER INFORMATION: Synthetic Sequence

<400> SEQUENCE: 104

His His His His His Trp Tyr Gly
1               5

<210> SEQ ID NO 105
<211> LENGTH: 16
<212> TYPE: PRT
<213> ORGANISM: Artificial Sequence
<220> FEATURE:
<223> OTHER INFORMATION: Synthetic Sequence

<400> SEQUENCE: 105

Phe Phe Gly Ala Val Ile Gly Thr Ile Ala Leu Gly Val Ala Thr Ala
1               5                   10                  15

<210> SEQ ID NO 106
<211> LENGTH: 16
<212> TYPE: PRT
<213> ORGANISM: Artificial Sequence
<220> FEATURE:
<223> OTHER INFORMATION: Synthetic Sequence

<400> SEQUENCE: 106

Phe Leu Gly Phe Leu Leu Gly Val Gly Ser Ala Ile Ala Ser Gly Val
1               5                   10                  15

<210> SEQ ID NO 107
<211> LENGTH: 16
<212> TYPE: PRT
<213> ORGANISM: Artificial Sequence
<220> FEATURE:

```
<223> OTHER INFORMATION: Synthetic Sequence

<400> SEQUENCE: 107

Gly Val Phe Val Leu Gly Phe Leu Gly Phe Leu Ala Thr Ala Gly Ser
1               5                   10                  15

<210> SEQ ID NO 108
<211> LENGTH: 16
<212> TYPE: PRT
<213> ORGANISM: Artificial Sequence
<220> FEATURE:
<223> OTHER INFORMATION: Synthetic Sequence

<400> SEQUENCE: 108

Gly Ala Ala Ile Gly Leu Ala Trp Ile Pro Tyr Phe Gly Pro Ala Ala
1               5                   10                  15

<210> SEQ ID NO 109
<211> LENGTH: 26
<212> TYPE: PRT
<213> ORGANISM: Artificial Sequence
<220> FEATURE:
<223> OTHER INFORMATION: Synthetic Sequence

<400> SEQUENCE: 109

Gly Ile Gly Ala Val Leu Lys Val Leu Thr Thr Gly Leu Pro Ala Leu
1               5                   10                  15

Ile Ser Trp Ile Lys Arg Lys Arg Gln Gln
            20                  25

<210> SEQ ID NO 110
<211> LENGTH: 4
<212> TYPE: PRT
<213> ORGANISM: Artificial Sequence
<220> FEATURE:
<223> OTHER INFORMATION: Synthetic Sequence

<400> SEQUENCE: 110

Glu Ala Leu Ala
1

<210> SEQ ID NO 111
<211> LENGTH: 4
<212> TYPE: PRT
<213> ORGANISM: Artificial Sequence
<220> FEATURE:
<223> OTHER INFORMATION: Synthetic Sequence

<400> SEQUENCE: 111

Gly Ala Leu Ala
1

<210> SEQ ID NO 112
<211> LENGTH: 30
<212> TYPE: PRT
<213> ORGANISM: Artificial Sequence
<220> FEATURE:
<223> OTHER INFORMATION: Synthetic Sequence

<400> SEQUENCE: 112

Trp Glu Ala Ala Leu Ala Glu Ala Leu Ala Glu Ala Leu Ala Glu His
1               5                   10                  15

Leu Ala Glu Ala Leu Ala Glu Ala Leu Glu Ala Leu Ala Ala
            20                  25                  30
```

```
<210> SEQ ID NO 113
<211> LENGTH: 4
<212> TYPE: PRT
<213> ORGANISM: Artificial Sequence
<220> FEATURE:
<223> OTHER INFORMATION: Synthetic Sequence

<400> SEQUENCE: 113

Lys Ala Leu Ala
1

<210> SEQ ID NO 114
<211> LENGTH: 30
<212> TYPE: PRT
<213> ORGANISM: Artificial Sequence
<220> FEATURE:
<223> OTHER INFORMATION: Synthetic Sequence

<400> SEQUENCE: 114

Trp Glu Ala Lys Leu Ala Lys Ala Leu Ala Lys Ala Leu Ala Lys His
1               5                  10                  15

Leu Ala Lys Ala Leu Ala Lys Ala Leu Lys Ala Cys Glu Ala
            20                  25                  30

<210> SEQ ID NO 115
<211> LENGTH: 4
<212> TYPE: PRT
<213> ORGANISM: Artificial Sequence
<220> FEATURE:
<223> OTHER INFORMATION: Synthetic Sequence

<400> SEQUENCE: 115

Glu Gly Leu Ala
1

<210> SEQ ID NO 116
<211> LENGTH: 20
<212> TYPE: PRT
<213> ORGANISM: Artificial Sequence
<220> FEATURE:
<223> OTHER INFORMATION: Synthetic Sequence

<400> SEQUENCE: 116

Gly Leu Phe Glu Ala Leu Leu Glu Leu Leu Glu Ser Leu Trp Glu Leu
1               5                  10                  15

Leu Leu Glu Ala
            20

<210> SEQ ID NO 117
<211> LENGTH: 20
<212> TYPE: PRT
<213> ORGANISM: Artificial Sequence
<220> FEATURE:
<223> OTHER INFORMATION: Synthetic Sequence

<400> SEQUENCE: 117

Gly Leu Phe Lys Ala Leu Leu Lys Leu Leu Lys Ser Leu Trp Lys Leu
1               5                  10                  15

Leu Leu Lys Ala
            20

<210> SEQ ID NO 118
<211> LENGTH: 20
<212> TYPE: PRT
<213> ORGANISM: Artificial Sequence
<220> FEATURE:
```

<223> OTHER INFORMATION: Synthetic Sequence

<400> SEQUENCE: 118

Gly Leu Phe Arg Ala Leu Leu Arg Leu Leu Arg Ser Leu Trp Arg Leu
1               5                   10                  15

Leu Leu Arg Ala
            20

<210> SEQ ID NO 119
<211> LENGTH: 20
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 1, 3, 5, 7, 9, 11, 13, 15, 17, 19
<223> OTHER INFORMATION: 2'-O-methyl nucleoside
<220> FEATURE:
<221> NAME/KEY: misc_feature
<222> LOCATION: 2, 4, 6, 8, 10, 12, 14, 16, 18, 20
<223> OTHER INFORMATION: 2'-fluoro nucleoside
<220> FEATURE:
<221> NAME/KEY: misc_feature
<222> LOCATION: 1-9, 10-11, 12-20
<223> OTHER INFORMATION: phosphorothioate linkage

<400> SEQUENCE: 119
cagaccuaug gaaacuacuu                                           20

<210> SEQ ID NO 120
<211> LENGTH: 20
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 1, 3, 5, 7, 9, 11, 13, 15, 17, 19
<223> OTHER INFORMATION: 2'-O-methyl nucleoside
<220> FEATURE:
<221> NAME/KEY: misc_feature
<222> LOCATION: 2, 4, 6, 8, 10, 12, 14, 16, 18, 20
<223> OTHER INFORMATION: 2'-fluoro nucleoside
<220> FEATURE:
<221> NAME/KEY: misc_feature
<222> LOCATION: 1-9, 12-20
<223> OTHER INFORMATION: phosphorothioate linkage

<400> SEQUENCE: 120
aaguaguuuc cauaggucug                                           20

<210> SEQ ID NO 121
<211> LENGTH: 20
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 1, 3, 5, 7, 9, 11, 13, 15, 17, 19
<223> OTHER INFORMATION: 2'-O-methyl nucleoside
<220> FEATURE:
<221> NAME/KEY: misc_feature
<222> LOCATION: 2, 4, 6, 8, 10, 12, 14, 16, 18, 20
<223> OTHER INFORMATION: 2'-fluoro nucleoside
<220> FEATURE:
<221> NAME/KEY: misc_feature
<222> LOCATION: 1-9, 10-11, 12-20
<223> OTHER INFORMATION: phosphorothioate linkage

<400> SEQUENCE: 121
ccgucccaag caauggacga						20

<210> SEQ ID NO 122
<211> LENGTH: 20
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 1, 3, 5, 7, 9, 11, 13, 15, 17, 19
<223> OTHER INFORMATION: 2'-O-methyl nucleoside
<220> FEATURE:
<221> NAME/KEY: misc_feature
<222> LOCATION: 2, 4, 6, 8, 10, 12, 14, 16, 18, 20
<223> OTHER INFORMATION: 2'-fluoro nucleoside
<220> FEATURE:
<221> NAME/KEY: misc_feature
<222> LOCATION: 1-7, 8-9, 21-13, 14-20
<223> OTHER INFORMATION: phosphorothioate linkage

<400> SEQUENCE: 122
ucguccauug cuugggacgg						20

<210> SEQ ID NO 123
<211> LENGTH: 15
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 1, 3, 5, 7, 9, 11, 13, 15
<223> OTHER INFORMATION: 2'-O-methyl nucleoside
<220> FEATURE:
<221> NAME/KEY: misc_feature
<222> LOCATION: 2, 4, 6, 8, 10, 12, 14
<223> OTHER INFORMATION: 2'-fluoro nucleoside
<220> FEATURE:
<221> NAME/KEY: misc_feature
<222> LOCATION: 1-15
<223> OTHER INFORMATION: phosphorothioate linkage

<400> SEQUENCE: 123
gucccaagca augga						15

<210> SEQ ID NO 124
<211> LENGTH: 20
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 3, 5, 7, 9, 11, 13, 15, 17
<223> OTHER INFORMATION: 2'-O-methyl nucleoside
<220> FEATURE:
<221> NAME/KEY: misc_feature
<222> LOCATION: 1, 2, 4, 6, 8, 10, 12, 14, 16, 18, 19, 20
<223> OTHER INFORMATION: 2'-fluoro nucleoside
<220> FEATURE:
<221> NAME/KEY: misc_feature
<222> LOCATION: 1-7, 8-9, 12-13, 14-20
<223> OTHER INFORMATION: phosphorothioate linkage

<400> SEQUENCE: 124
ucguccauug cuugggacgg						20

<210> SEQ ID NO 125
<211> LENGTH: 18
<212> TYPE: DNA

```
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 1, 3, 5, 7, 9, 11, 13, 15, 17
<223> OTHER INFORMATION: 2'-O-methyl nucleoside
<220> FEATURE:
<221> NAME/KEY: misc_feature
<222> LOCATION: 2, 4, 6, 8, 10, 12, 14, 16, 18
<223> OTHER INFORMATION: 2'-fluoro nucleoside
<220> FEATURE:
<221> NAME/KEY: misc_feature
<222> LOCATION: 1-10, 11-18
<223> OTHER INFORMATION: phosphorothioate linkage

<400> SEQUENCE: 125
ccgaguggaa ggaaauuu                                                18

<210> SEQ ID NO 126
<211> LENGTH: 18
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 1, 3, 5, 7, 9, 11, 13, 15, 17
<223> OTHER INFORMATION: 2'-O-methyl nucleoside
<220> FEATURE:
<221> NAME/KEY: misc_feature
<222> LOCATION: 2, 4, 6, 8, 10, 12, 14, 16, 18
<223> OTHER INFORMATION: 2'-fluoro nucleoside
<220> FEATURE:
<221> NAME/KEY: misc_feature
<222> LOCATION: 1-9, 12-18
<223> OTHER INFORMATION: phosphorothioate linkage

<400> SEQUENCE: 126
aaauuuccuu ccacucgg                                                18

<210> SEQ ID NO 127
<211> LENGTH: 18
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 1, 3, 5, 7, 9, 11, 13, 15, 17
<223> OTHER INFORMATION: 2'-O-methyl nucleoside
<220> FEATURE:
<221> NAME/KEY: misc_feature
<222> LOCATION: 2, 4, 6, 8, 10, 12, 14, 16, 18
<223> OTHER INFORMATION: 2'-fluoro nucleoside
<220> FEATURE:
<221> NAME/KEY: misc_feature
<222> LOCATION: 1-10, 11-18
<223> OTHER INFORMATION: phosphorothioate linkage

<400> SEQUENCE: 127
ggagaauauu ucacccuu                                                18

<210> SEQ ID NO 128
<211> LENGTH: 18
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 1, 3, 5, 7, 9, 11, 13, 15, 17
<223> OTHER INFORMATION: 2'-O-methyl nucleoside
```

```
<220> FEATURE:
<221> NAME/KEY: misc_feature
<222> LOCATION: 2, 4, 6, 8, 10, 12, 14, 16, 18
<223> OTHER INFORMATION: 2'-fluoro nucleoside
<220> FEATURE:
<221> NAME/KEY: misc_feature
<222> LOCATION: 1-9, 12-18
<223> OTHER INFORMATION: phosphorothioate linkage

<400> SEQUENCE: 128
aagggugaaa uauucucc                                                 18

<210> SEQ ID NO 129
<211> LENGTH: 21
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 1, 3, 5, 7, 9, 11, 13, 15, 17, 19, 21
<223> OTHER INFORMATION: 2'-O-methyl nucleoside
<220> FEATURE:
<221> NAME/KEY: misc_feature
<222> LOCATION: 2, 4, 6, 8, 10, 12, 14, 16, 18, 20
<223> OTHER INFORMATION: 2'-fluoro nucleoside
<220> FEATURE:
<221> NAME/KEY: misc_feature
<222> LOCATION: 1-21
<223> OTHER INFORMATION: phosphorothioate linkage

<400> SEQUENCE: 129
ggagggagaa uauuucaccc u                                             21

<210> SEQ ID NO 130
<211> LENGTH: 22
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 3, 5, 7, 9, 11, 13, 15, 17, 19, 21
<223> OTHER INFORMATION: 2'-O-methyl nucleoside
<220> FEATURE:
<221> NAME/KEY: misc_feature
<222> LOCATION: 1, 2, 4, 6, 8, 10, 12, 14, 16, 18, 20, 22
<223> OTHER INFORMATION: 2'-fluoro nucleoside
<220> FEATURE:
<221> NAME/KEY: misc_feature
<222> LOCATION: 1-7, 8-9, 12-13, 14-22
<223> OTHER INFORMATION: phosphorothioate linkage

<400> SEQUENCE: 130
gagggugaaa uauucucccu cc                                            22

<210> SEQ ID NO 131
<211> LENGTH: 20
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 1, 3, 5, 7, 9, 11, 13, 15, 17, 19
<223> OTHER INFORMATION: 2'-O-methyl nucleoside
<220> FEATURE:
<221> NAME/KEY: misc_feature
<222> LOCATION: 2, 4, 6, 8, 10, 12, 14, 16, 18, 20
<223> OTHER INFORMATION: 2'-fluoro nucleoside
<220> FEATURE:
<221> NAME/KEY: misc_feature
<222> LOCATION: 1-10, 11-20
```

<223> OTHER INFORMATION: phosphorothioate linkage

<400> SEQUENCE: 131
ggacggaaca gcuugaggu                                              20

<210> SEQ ID NO 132
<211> LENGTH: 20
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 1, 3, 5, 7, 9, 11, 13, 15, 17, 19
<223> OTHER INFORMATION: 2'-O-methyl nucleoside
<220> FEATURE:
<221> NAME/KEY: misc_feature
<222> LOCATION: 2, 4, 6, 8, 10, 12, 14, 16, 18, 20
<223> OTHER INFORMATION: 2'-fluoro nucleoside
<220> FEATURE:
<221> NAME/KEY: misc_feature
<222> LOCATION: 1-9, 12-20
<223> OTHER INFORMATION: phosphorothioate linkage

<400> SEQUENCE: 132
accucaaagc uguuccgucc                                             20

<210> SEQ ID NO 133
<211> LENGTH: 16
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 4, 7, 9, 11, 15
<223> OTHER INFORMATION: 2'-O-methyl nucleoside
<220> FEATURE:
<221> NAME/KEY: misc_feature
<222> LOCATION: 1, 2, 3, 5, 6, 8, 10, 12, 13, 14, 16
<223> OTHER INFORMATION: 2'-fluoro nucleoside
<220> FEATURE:
<221> NAME/KEY: misc_feature
<222> LOCATION: 1-16
<223> OTHER INFORMATION: phosphorothioate linkage

<400> SEQUENCE: 133
guucaagaca gaaggg                                                 16

<210> SEQ ID NO 134
<211> LENGTH: 21
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 2, 6, 7, 9, 11, 13, 14, 16, 19
<223> OTHER INFORMATION: 2'-O-methyl nucleoside
<220> FEATURE:
<221> NAME/KEY: misc_feature
<222> LOCATION: 1, 3, 4, 5, 8, 10, 12, 15, 17, 18, 20, 21
<223> OTHER INFORMATION: 2'-fluoro nucleoside
<220> FEATURE:
<221> NAME/KEY: misc_feature
<222> LOCATION: 1-9, 12-21
<223> OTHER INFORMATION: phosphorothioate linkage

<400> SEQUENCE: 134
ggcccuucug ucuugaacau g                                           21

-continued

```
<210> SEQ ID NO 135
<211> LENGTH: 20
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 1, 3, 5, 7, 9, 11, 13, 15, 17, 19
<223> OTHER INFORMATION: 2'-O-methyl nucleoside
<220> FEATURE:
<221> NAME/KEY: misc_feature
<222> LOCATION: 2, 4, 6, 8, 10, 12, 14, 16, 18, 20
<223> OTHER INFORMATION: 2'-fluoro nucleoside
<220> FEATURE:
<221> NAME/KEY: misc_feature
<222> LOCATION: 1-20
<223> OTHER INFORMATION: phosphorothioate linkage

<400> SEQUENCE: 135
ggaagacugu uacuacagtt                                              20

<210> SEQ ID NO 136
<211> LENGTH: 20
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 1, 3, 5, 7, 9, 11, 13, 15, 17, 19
<223> OTHER INFORMATION: 2'-O-methyl nucleoside
<220> FEATURE:
<221> NAME/KEY: misc_feature
<222> LOCATION: 2, 4, 6, 8, 10, 12, 14, 16, 18, 20
<223> OTHER INFORMATION: 2'-fluoro nucleoside
<220> FEATURE:
<221> NAME/KEY: misc_feature
<222> LOCATION: 1-9, 12-20
<223> OTHER INFORMATION: phosphorothioate linkage

<400> SEQUENCE: 136
aacuguagua acagucuucc                                              20

<210> SEQ ID NO 137
<211> LENGTH: 21
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 1, 3, 5, 7, 9, 11, 13, 15, 17, 19
<223> OTHER INFORMATION: 2'-O-methyl nucleoside
<220> FEATURE:
<221> NAME/KEY: misc_feature
<222> LOCATION: 2, 4, 6, 8, 10, 12, 14, 16, 18
<223> OTHER INFORMATION: 2'-fluoro nucleoside
<220> FEATURE:
<221> NAME/KEY: misc_feature
<222> LOCATION: 1-9, 10-11, 12-21
<223> OTHER INFORMATION: phosphorothioate linkage

<400> SEQUENCE: 137
ggaagacugu uacuacagtc t                                            21

<210> SEQ ID NO 138
<211> LENGTH: 21
<212> TYPE: DNA
<213> ORGANISM: Artificial Sequence
<220> FEATURE:
<223> OTHER INFORMATION: Synthetic Sequence
<220> FEATURE:
```

```
<221> NAME/KEY: misc_feature
<222> LOCATION: 4, 6, 8, 10, 12, 14, 16, 18, 20
<223> OTHER INFORMATION: 2'-O-methyl nucleoside
<220> FEATURE:
<221> NAME/KEY: misc_feature
<222> LOCATION: 3, 5, 7, 9, 11, 13, 15, 17, 19, 21
<223> OTHER INFORMATION: 2'-fluoro nucleoside
<220> FEATURE:
<221> NAME/KEY: misc_feature
<222> LOCATION: 1-8, 9-10, 13-14, 15-21
<223> OTHER INFORMATION: phosphorothioate linkage

<400> SEQUENCE: 138
agacuguagu aacagucuuc c                                              21

<210> SEQ ID NO 139
<211> LENGTH: 20
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 1, 3, 5, 7, 9, 11, 13, 15, 17, 19, 20
<223> OTHER INFORMATION: 2'-O-methyl nucleoside
<220> FEATURE:
<221> NAME/KEY: misc_feature
<222> LOCATION: 2, 4, 6, 8, 10, 12, 14, 16, 18
<223> OTHER INFORMATION: 2'-fluoro nucleoside
<220> FEATURE:
<221> NAME/KEY: misc_feature
<222> LOCATION: 1-10, 11-20
<223> OTHER INFORMATION: phosphorothioate linkage

<400> SEQUENCE: 139
gugaugaagg acauggcuua                                                20

<210> SEQ ID NO 140
<211> LENGTH: 20
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 1, 3, 5, 7, 9, 11, 13, 15, 17, 19
<223> OTHER INFORMATION: 2'-O-methyl nucleoside
<220> FEATURE:
<221> NAME/KEY: misc_feature
<222> LOCATION: 2, 4, 6, 8, 10, 12, 14, 16, 18, 20
<223> OTHER INFORMATION: 2'-fluoro nucleoside
<220> FEATURE:
<221> NAME/KEY: misc_feature
<222> LOCATION: 1-9, 12-20
<223> OTHER INFORMATION: phosphorothioate linkage

<400> SEQUENCE: 140
uaagccaugu ccuucaucac                                                20

<210> SEQ ID NO 141
<211> LENGTH: 20
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 1, 3, 5, 7, 9, 11, 13, 15, 17, 19, 20
<223> OTHER INFORMATION: 2'-O-methyl nucleoside
<220> FEATURE:
<221> NAME/KEY: misc_feature
<222> LOCATION: 2, 4, 6, 8, 10, 12, 14, 16, 18
<223> OTHER INFORMATION: 2'-fluoro nucleoside
```

-continued

```
<220> FEATURE:
<221> NAME/KEY: misc_feature
<222> LOCATION: 1-10, 11-20
<223> OTHER INFORMATION: phosphorothioate linkage

<400> SEQUENCE: 141
gccaugaagg acauggcuua                                                     20

<210> SEQ ID NO 142
<211> LENGTH: 20
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 1, 3, 5, 7, 9, 11, 13, 15, 17, 19
<223> OTHER INFORMATION: 2'-O-methyl nucleoside
<220> FEATURE:
<221> NAME/KEY: misc_feature
<222> LOCATION: 2, 4, 6, 8, 10, 12, 14, 16, 18, 20
<223> OTHER INFORMATION: 2'-fluoro nucleoside
<220> FEATURE:
<221> NAME/KEY: misc_feature
<222> LOCATION: 1-7, 8-9, 12-13, 14-20
<223> OTHER INFORMATION: phosphorothioate linkage

<400> SEQUENCE: 142
uaagccaugu ccuucauggc                                                     20

<210> SEQ ID NO 143
<211> LENGTH: 20
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 4, 6, 8, 10, 12, 14, 16, 18, 20
<223> OTHER INFORMATION: 2'-O-methyl nucleoside
<220> FEATURE:
<221> NAME/KEY: misc_feature
<222> LOCATION: 1, 2, 3, 5, 7, 9, 10, 11, 13, 15, 17, 19
<223> OTHER INFORMATION: 2'-fluoro nucleoside
<220> FEATURE:
<221> NAME/KEY: misc_feature
<222> LOCATION: 1-10, 11-20
<223> OTHER INFORMATION: phosphorothioate linkage

<400> SEQUENCE: 143
gaagcguaug acacauugat                                                     20

<210> SEQ ID NO 144
<211> LENGTH: 20
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 1, 2, 4, 6, 8, 10, 12, 14, 16, 18
<223> OTHER INFORMATION: 2'-O-methyl nucleoside
<220> FEATURE:
<221> NAME/KEY: misc_feature
<222> LOCATION: 3, 5, 7, 9, 11, 13, 15, 17, 19, 20
<223> OTHER INFORMATION: 2'-fluoro nucleoside
<220> FEATURE:
<221> NAME/KEY: misc_feature
<222> LOCATION: 1-9, 12-20
<223> OTHER INFORMATION: phosphorothioate linkage

<400> SEQUENCE: 144
```
aucaaugugu cauacgcuuc                                               20

<210> SEQ ID NO 145
<211> LENGTH: 19
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 2, 4, 6, 8, 10, 12, 14, 16, 18
<223> OTHER INFORMATION: 2'-O-methyl nucleoside
<220> FEATURE:
<221> NAME/KEY: misc_feature
<222> LOCATION: 1, 3, 5, 7, 9, 11, 13, 15, 17, 19
<223> OTHER INFORMATION: 2'-fluoro nucleoside
<220> FEATURE:
<221> NAME/KEY: misc_feature
<222> LOCATION: 1-10, 11-19
<223> OTHER INFORMATION: phosphorothioate linkage

<400> SEQUENCE: 145
ggacauuacu agugacuca                                                19

<210> SEQ ID NO 146
<211> LENGTH: 19
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 1, 3, 5, 7, 9, 11, 13, 15, 17, 19
<223> OTHER INFORMATION: 2'-O-methyl nucleoside
<220> FEATURE:
<221> NAME/KEY: misc_feature
<222> LOCATION: 2, 4, 6, 8, 10, 12, 14, 16, 18
<223> OTHER INFORMATION: 2'-fluoro nucleoside
<220> FEATURE:
<221> NAME/KEY: misc_feature
<222> LOCATION: 1-9, 12-19
<223> OTHER INFORMATION: phosphorothioate linkage

<400> SEQUENCE: 146
ugagucacua guaaugucc                                                19

<210> SEQ ID NO 147
<211> LENGTH: 21
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 3, 5, 7, 9, 11, 13, 15, 17, 19, 21
<223> OTHER INFORMATION: 2'-O-methyl nucleoside
<220> FEATURE:
<221> NAME/KEY: misc_feature
<222> LOCATION: 1, 2, 4, 6, 8, 10, 12, 14, 16, 18, 20
<223> OTHER INFORMATION: 2'-fluoro nucleoside
<220> FEATURE:
<221> NAME/KEY: misc_feature
<222> LOCATION: 1-10, 11-12, 13-21
<223> OTHER INFORMATION: phosphorothioate linkage

<400> SEQUENCE: 147
gucaucacac ugaauaccaa u                                             21

<210> SEQ ID NO 148
<211> LENGTH: 21
<212> TYPE: DNA
<213> ORGANISM: Artificial Sequence

```
<220> FEATURE:
<223> OTHER INFORMATION: Synthetic Sequence
<220> FEATURE:
<221> NAME/KEY: misc_feature
<222> LOCATION: 2, 4, 6, 8, 10, 12, 14, 16, 18, 20
<223> OTHER INFORMATION: 2'-O-methyl nucleoside
<220> FEATURE:
<221> NAME/KEY: misc_feature
<222> LOCATION: 1, 3, 5, 7, 9, 11, 13, 15, 17, 19, 21
<223> OTHER INFORMATION: 2'-fluoro nucleoside
<220> FEATURE:
<221> NAME/KEY: misc_feature
<222> LOCATION: 1-10, 13-21
<223> OTHER INFORMATION: phosphorothioate linkage

<400> SEQUENCE: 148
auugguauuc agugugauga c                                              21

<210> SEQ ID NO 149
<211> LENGTH: 19
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 2, 5, 7, 9, 11, 13, 16, 18, 19
<223> OTHER INFORMATION: 2'-O-methyl nucleoside
<220> FEATURE:
<221> NAME/KEY: misc_feature
<222> LOCATION: 1, 3, 4, 14, 15, 17
<223> OTHER INFORMATION: 2'-fluoro nucleoside
<220> FEATURE:
<221> NAME/KEY: misc_feature
<222> LOCATION: 1-9, 10-11, 21-19
<223> OTHER INFORMATION: phosphorothioate linkage

<400> SEQUENCE: 149
gguguauggc uucaacccu                                                 19

<210> SEQ ID NO 150
<211> LENGTH: 19
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 2, 3, 6, 8, 10, 12, 14, 16
<223> OTHER INFORMATION: 2'-O-methyl nucleoside
<220> FEATURE:
<221> NAME/KEY: misc_feature
<222> LOCATION: 1, 4, 5, 7, 9, 11, 13, 15, 17, 18, 19
<223> OTHER INFORMATION: 2'-fluoro nucleoside
<220> FEATURE:
<221> NAME/KEY: misc_feature
<222> LOCATION: 1-9, 12-19
<223> OTHER INFORMATION: phosphorothioate linkage

<400> SEQUENCE: 150
aggguugaag ccauacacc                                                 19

<210> SEQ ID NO 151
<211> LENGTH: 21
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 2, 4, 7, 9, 11, 13, 15, 18, 20, 21
<223> OTHER INFORMATION: 2'-O-methyl nucleoside
<220> FEATURE:
```

```
<221> NAME/KEY: misc_feature
<222> LOCATION: 1, 3, 5, 6, 16, 17, 19
<223> OTHER INFORMATION: 2'-fluoro nucleoside
<220> FEATURE:
<221> NAME/KEY: misc_feature
<222> LOCATION: 1-9, 10-11, 12-13, 14-21
<223> OTHER INFORMATION: phosphorothioate linkage

<400> SEQUENCE: 151 agguguaug gcuucaaccc u                                           21

<210> SEQ ID NO 152
<211> LENGTH: 21
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 2, 3, 6, 8, 10, 12, 14, 16
<223> OTHER INFORMATION: 2'-O-methyl nucleoside
<220> FEATURE:
<221> NAME/KEY: misc_feature
<222> LOCATION: 1, 4, 5, 7, 9, 11, 13, 15, 17, 18, 19, 20, 21
<223> OTHER INFORMATION: 2'-fluoro nucleoside
<220> FEATURE:
<221> NAME/KEY: misc_feature
<222> LOCATION: 1-7, 8-9, 12-13, 14-21
<223> OTHER INFORMATION: phosphorothioate linkage

<400> SEQUENCE: 152 agguugaag ccauacaccc u                                           21

<210> SEQ ID NO 153
<211> LENGTH: 23
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 2, 4, 6, 8, 10, 12, 14, 16, 18, 20, 22
<223> OTHER INFORMATION: 2'-O-methyl nucleoside
<220> FEATURE:
<221> NAME/KEY: misc_feature
<222> LOCATION: 1, 3, 5, 7, 9, 11, 15, 17, 19, 21, 23
<223> OTHER INFORMATION: 2'-fluoro nucleoside
<220> FEATURE:
<221> NAME/KEY: misc_feature
<222> LOCATION: 1-8, 9-10, 11-13, 14-23
<223> OTHER INFORMATION: phosphorothioate linkage

<400> SEQUENCE: 153
ggaguuugug acaaauaugg gca                                        23

<210> SEQ ID NO 154
<211> LENGTH: 23
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 1, 3, 5, 7, 9, 11, 13, 15, 17, 19, 21
<223> OTHER INFORMATION: 2'-O-methyl nucleoside
<220> FEATURE:
<221> NAME/KEY: misc_feature
<222> LOCATION: 2, 4, 6, 8, 10, 12, 14, 16, 18, 20, 22, 23
<223> OTHER INFORMATION: 2'-fluoro nucleoside
<220> FEATURE:
<221> NAME/KEY: misc_feature
<222> LOCATION: 1-9, 12-23
<223> OTHER INFORMATION: phosphorothioate linkage
```

<400> SEQUENCE: 154
ugcccauauu ugucacaaac ucc                                                    23

<210> SEQ ID NO 155
<211> LENGTH: 20
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 3, 6, 8, 10, 12, 14, 16, 18, 19, 20
<223> OTHER INFORMATION: 2'-O-methyl nucleoside
<220> FEATURE:
<221> NAME/KEY: misc_feature
<222> LOCATION: 1, 2, 4, 5, 7, 9, 11, 13, 15, 17
<223> OTHER INFORMATION: 2'-fluoro nucleoside
<220> FEATURE:
<221> NAME/KEY: misc_feature
<222> LOCATION: 1-10, 11-12, 13-20
<223> OTHER INFORMATION: phosphorothioate linkage

<400> SEQUENCE: 155
gauugauuga ccuguccauu                                                        20

<210> SEQ ID NO 156
<211> LENGTH: 20
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 1, 2, 4, 6, 8, 12, 14, 16
<223> OTHER INFORMATION: 2'-O-methyl nucleoside
<220> FEATURE:
<221> NAME/KEY: misc_feature
<222> LOCATION: 3, 5, 7, 9, 11, 13, 15, 17, 18, 19, 20
<223> OTHER INFORMATION: 2'-fluoro nucleoside
<220> FEATURE:
<221> NAME/KEY: misc_feature
<222> LOCATION: 1-9, 12-20
<223> OTHER INFORMATION: phosphorothioate linkage

<400> SEQUENCE: 156
aauggacagg ucaaucaauc                                                        20

<210> SEQ ID NO 157
<211> LENGTH: 21
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 1, 3, 5, 7, 9, 11, 13, 15, 17, 19, 21
<223> OTHER INFORMATION: 2'-O-methyl nucleoside
<220> FEATURE:
<221> NAME/KEY: misc_feature
<222> LOCATION: 2, 4, 6, 8, 10, 12, 14, 16, 18, 20
<223> OTHER INFORMATION: 2'-fluoro nucleoside
<220> FEATURE:
<221> NAME/KEY: misc_feature
<222> LOCATION: 1-10, 11-21
<223> OTHER INFORMATION: phosphorothioate linkage

<400> SEQUENCE: 157
gucaucacac ugaauaccaa u                                                      21

<210> SEQ ID NO 158

```
<211> LENGTH: 21
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 2, 4, 6, 8, 10, 12, 14, 16, 18, 20
<223> OTHER INFORMATION: 2'-O-methyl nucleoside
<220> FEATURE:
<221> NAME/KEY: misc_feature
<222> LOCATION: 1, 3, 5, 7, 9, 11, 13, 15, 19, 21
<223> OTHER INFORMATION: 2'-fluoro nucleoside
<220> FEATURE:
<221> NAME/KEY: misc_feature
<222> LOCATION: 1-9, 12-21
<223> OTHER INFORMATION: phosphorothioate linkage

<400> SEQUENCE: 158
auugguauuc agugugauga c                                              21

<210> SEQ ID NO 159
<211> LENGTH: 21
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 1, 3, 5, 7, 9, 11, 13, 15, 17, 19, 21
<223> OTHER INFORMATION: 2'-O-methyl nucleoside
<220> FEATURE:
<221> NAME/KEY: misc_feature
<222> LOCATION: 2, 4, 6, 8, 10, 12, 14, 16, 18, 20
<223> OTHER INFORMATION: 2'-fluoro nucleoside
<220> FEATURE:
<221> NAME/KEY: misc_feature
<222> LOCATION: 1-9, 11-21
<223> OTHER INFORMATION: phosphorothioate linkage

<400> SEQUENCE: 159
guauucacac ugaauaccaa u                                              21

<210> SEQ ID NO 160
<211> LENGTH: 21
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 2, 4, 6, 8, 10, 12, 14, 16, 18, 20
<223> OTHER INFORMATION: 2'-O-methyl nucleoside
<220> FEATURE:
<221> NAME/KEY: misc_feature
<222> LOCATION: 1, 3, 5, 7, 9, 11, 13, 15, 17, 19, 21
<223> OTHER INFORMATION: 2'-fluoro nucleoside
<220> FEATURE:
<221> NAME/KEY: misc_feature
<222> LOCATION: 1-7, 8-9, 12-13, 14-21
<223> OTHER INFORMATION: phosphorothioate linkage

<400> SEQUENCE: 160
auugguauuc agugugaaua c                                              21

<210> SEQ ID NO 161
<211> LENGTH: 22
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
```

```
<222> LOCATION: 1, 3, 5, 7, 9, 11, 13, 15, 17, 19, 21
<223> OTHER INFORMATION: 2'-O-methyl nucleoside
<220> FEATURE:
<221> NAME/KEY: misc_feature
<222> LOCATION: 2, 4, 6, 8, 10, 12, 14, 16, 18, 20, 22
<223> OTHER INFORMATION: 2'-fluoro nucleoside
<220> FEATURE:
<221> NAME/KEY: misc_feature
<222> LOCATION: 1-10, 11-22
<223> OTHER INFORMATION: phosphorothioate linkage

<400> SEQUENCE: 161
ggugcgaagc agacugaggc ta                                            22

<210> SEQ ID NO 162
<211> LENGTH: 22
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 1, 3, 5, 7, 9, 11, 13, 15, 17, 19, 21
<223> OTHER INFORMATION: 2'-O-methyl nucleoside
<220> FEATURE:
<221> NAME/KEY: misc_feature
<222> LOCATION: 2, 4, 6, 8, 10, 12, 14, 16, 18, 20, 22
<223> OTHER INFORMATION: 2'-fluoro nucleoside
<220> FEATURE:
<221> NAME/KEY: misc_feature
<222> LOCATION: 1-9, 12-22
<223> OTHER INFORMATION: phosphorothioate linkage

<400> SEQUENCE: 162
tagccucagu cugcuucgca cc                                            22

<210> SEQ ID NO 163
<211> LENGTH: 15
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 1, 3, 5, 7, 9, 11, 13, 15
<223> OTHER INFORMATION: 2'-O-methyl nucleoside
<220> FEATURE:
<221> NAME/KEY: misc_feature
<222> LOCATION: 2, 4, 6, 8, 10, 12, 14
<223> OTHER INFORMATION: 2'-fluoro nucleoside
<220> FEATURE:
<221> NAME/KEY: misc_feature
<222> LOCATION: 1-15
<223> OTHER INFORMATION: phosphorothioate linkage

<400> SEQUENCE: 163
ugcgaagcag acuga                                                    15

<210> SEQ ID NO 164
<211> LENGTH: 21
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 1, 3, 5, 7, 9, 11, 13, 15, 17, 19, 21
<223> OTHER INFORMATION: 2'-O-methyl nucleoside
<220> FEATURE:
<221> NAME/KEY: misc_feature
<222> LOCATION: 2, 4, 6, 8, 10, 12, 14, 16, 18, 20
<223> OTHER INFORMATION: 2'-fluoro nucleoside
<220> FEATURE:
```

```
<221> NAME/KEY: misc_feature
<222> LOCATION: 1-6, 7--9, 12-13, 14-21
<223> OTHER INFORMATION: phosphorothioate linkage

<400> SEQUENCE: 164
gccucagucu gcuucgcagg c                                              21

<210> SEQ ID NO 165
<211> LENGTH: 19
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 2, 4, 6, 8, 10, 12, 14, 16, 18
<223> OTHER INFORMATION: 2'-O-methyl nucleoside
<220> FEATURE:
<221> NAME/KEY: misc_feature
<222> LOCATION: 1, 3, 5, 7, 9, 11, 13, 15, 17, 19
<223> OTHER INFORMATION: 2'-fluoro nucleoside
<220> FEATURE:
<221> NAME/KEY: misc_feature
<222> LOCATION: 1-19
<223> OTHER INFORMATION: phosphorothioate linkage

<400> SEQUENCE: 165
cggcauucgg cuauguguu                                                 19

<210> SEQ ID NO 166
<211> LENGTH: 19
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 1, 2, 3, 5, 7, 9, 11, 13, 15, 17
<223> OTHER INFORMATION: 2'-O-methyl nucleoside
<220> FEATURE:
<221> NAME/KEY: misc_feature
<222> LOCATION: 4, 6, 8, 10, 12, 14, 16, 18, 19
<223> OTHER INFORMATION: 2'-fluoro nucleoside
<220> FEATURE:
<221> NAME/KEY: misc_feature
<222> LOCATION: 1-9, 21-19
<223> OTHER INFORMATION: phosphorothioate linkage

<400> SEQUENCE: 166
aacacauagc cgaaugccg                                                 19

<210> SEQ ID NO 167
<211> LENGTH: 15
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 1, 3, 5, 7, 9, 11, 13, 15
<223> OTHER INFORMATION: 2'-O-methyl nucleoside
<220> FEATURE:
<221> NAME/KEY: misc_feature
<222> LOCATION: 2, 4, 6, 8, 10, 12, 14
<223> OTHER INFORMATION: 2'-fluoro nucleoside
<220> FEATURE:
<221> NAME/KEY: misc_feature
<222> LOCATION: 1-15
<223> OTHER INFORMATION: phosphorothioate linkage

<400> SEQUENCE: 167
cacagggcuc acccu                                                     15
```

<210> SEQ ID NO 168
<211> LENGTH: 20
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 4, 6, 8, 10, 12, 14
<223> OTHER INFORMATION: 2'-O-methyl nucleoside
<220> FEATURE:
<221> NAME/KEY: misc_feature
<222> LOCATION: 1, 2, 3, 5, 7, 13, 15, 16, 17, 18, 19, 20
<223> OTHER INFORMATION: 2'-fluoro nucleoside
<220> FEATURE:
<221> NAME/KEY: misc_feature
<222> LOCATION: 1-7, 8-9, 12-13, 14-20
<223> OTHER INFORMATION: phosphorothioate linkage

<400> SEQUENCE: 168
ucagggugag cccugugugu                                              20

<210> SEQ ID NO 169
<211> LENGTH: 19
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 1, 3, 5, 7, 9, 11, 13, 15, 17, 19
<223> OTHER INFORMATION: 2'-O-methyl nucleoside
<220> FEATURE:
<221> NAME/KEY: misc_feature
<222> LOCATION: 2, 4, 6, 8, 10, 12, 14, 16, 18
<223> OTHER INFORMATION: 2'-fluoro nucleoside
<220> FEATURE:
<221> NAME/KEY: misc_feature
<222> LOCATION: 1-10, 11-19
<223> OTHER INFORMATION: phosphorothioate linkage

<400> SEQUENCE: 169
gccuggaguu uauucggaa                                               19

<210> SEQ ID NO 170
<211> LENGTH: 19
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 2, 4, 6, 8, 10, 12, 14, 16, 18
<223> OTHER INFORMATION: 2'-O-methyl nucleoside
<220> FEATURE:
<221> NAME/KEY: misc_feature
<222> LOCATION: 1, 3, 5, 7, 9, 11, 13, 15, 17, 19
<223> OTHER INFORMATION: 2'-fluoro nucleoside
<220> FEATURE:
<221> NAME/KEY: misc_feature
<222> LOCATION: 1-9, 12-19
<223> OTHER INFORMATION: phosphorothioate linkage

<400> SEQUENCE: 170
uuccgaauaa acuccaggc                                               19

<210> SEQ ID NO 171
<211> LENGTH: 18
<212> TYPE: DNA
<213> ORGANISM: Artificial Sequence
<220> FEATURE:

-continued

```
<223> OTHER INFORMATION: Synthetic Sequence
<220> FEATURE:
<221> NAME/KEY: misc_feature
<222> LOCATION: 1, 3, 5, 7, 9, 11, 13, 15, 17
<223> OTHER INFORMATION: 2'-O-methyl nucleoside
<220> FEATURE:
<221> NAME/KEY: misc_feature
<222> LOCATION: 2, 4, 6, 8, 10, 12, 14, 16, 18
<223> OTHER INFORMATION: 2'-fluoro nucleoside
<220> FEATURE:
<221> NAME/KEY: misc_feature
<222> LOCATION: 1-10, 11-18
<223> OTHER INFORMATION: phosphorothioate linkage

<400> SEQUENCE: 171
cuagaccugu uuugcuuu                                                    18

<210> SEQ ID NO 172
<211> LENGTH: 18
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 1, 3, 5, 7, 9, 11, 13, 15, 17
<223> OTHER INFORMATION: 2'-O-methyl nucleoside
<220> FEATURE:
<221> NAME/KEY: misc_feature
<222> LOCATION: 2, 4, 6, 8, 10, 12, 14, 16, 18
<223> OTHER INFORMATION: 2'-fluoro nucleoside
<220> FEATURE:
<221> NAME/KEY: misc_feature
<222> LOCATION: 1-9, 12-18
<223> OTHER INFORMATION: phosphorothioate linkage

<400> SEQUENCE: 172
aaagcaaaac aggucuag                                                    18

<210> SEQ ID NO 173
<211> LENGTH: 19
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 3, 5, 7, 9, 11, 13, 15, 18, 19
<223> OTHER INFORMATION: 2'-O-methyl nucleoside
<220> FEATURE:
<221> NAME/KEY: misc_feature
<222> LOCATION: 1, 2, 4, 6, 8, 10, 12, 14, 16, 17
<223> OTHER INFORMATION: 2'-fluoro nucleoside
<220> FEATURE:
<221> NAME/KEY: misc_feature
<222> LOCATION: 1-9, 10-19
<223> OTHER INFORMATION: phosphorothioate linkage

<400> SEQUENCE: 173
gagguguauc uccuagaca                                                   19

<210> SEQ ID NO 174
<211> LENGTH: 19
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 2, 4, 6, 8, 10, 12, 14, 16, 18
<223> OTHER INFORMATION: 2'-O-methyl nucleoside
<220> FEATURE:
<221> NAME/KEY: misc_feature
```

```
<222> LOCATION: 1, 3, 5, 6, 16, 17, 19
<223> OTHER INFORMATION: 2'-fluoro nucleoside
<220> FEATURE:
<221> NAME/KEY: misc_feature
<222> LOCATION: 1-9, 12-19
<223> OTHER INFORMATION: phosphorothioate linkage

<400> SEQUENCE: 174
ugucuaggag auacaccuc                                                    19

<210> SEQ ID NO 175
<211> LENGTH: 19
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 3, 5, 7, 9, 11, 13, 15, 18, 19
<223> OTHER INFORMATION: 2'-O-methyl nucleoside
<220> FEATURE:
<221> NAME/KEY: misc_feature
<222> LOCATION: 1, 2, 4, 6, 8, 10, 12, 14, 16, 17
<223> OTHER INFORMATION: 2'-fluoro nucleoside
<220> FEATURE:
<221> NAME/KEY: misc_feature
<222> LOCATION: 1-9, 10-19
<223> OTHER INFORMATION: phosphorothioate linkage

<400> SEQUENCE: 175
gagguguauc uccucgaca                                                    19

<210> SEQ ID NO 176
<211> LENGTH: 19
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 2, 4, 6, 8, 10, 12, 14, 16, 18
<223> OTHER INFORMATION: 2'-O-methyl nucleoside
<220> FEATURE:
<221> NAME/KEY: misc_feature
<222> LOCATION: 1, 3, 5, 7, 9, 11, 13, 15, 17, 19
<223> OTHER INFORMATION: 2'-fluoro nucleoside
<220> FEATURE:
<221> NAME/KEY: misc_feature
<222> LOCATION: 1-9, 12-19
<223> OTHER INFORMATION: phosphorothioate linkage

<400> SEQUENCE: 176
ugucgaggag auacaccuc                                                    19

<210> SEQ ID NO 177
<211> LENGTH: 19
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 3, 5, 7, 9, 11, 13, 15, 18, 19
<223> OTHER INFORMATION: 2'-O-methyl nucleoside
<220> FEATURE:
<221> NAME/KEY: misc_feature
<222> LOCATION: 1, 2, 4, 6, 8, 10, 12, 14, 16, 17
<223> OTHER INFORMATION: 2'-fluoro nucleoside
<220> FEATURE:
<221> NAME/KEY: misc_feature
<222> LOCATION: 1-8, 9-10, 11-19
<223> OTHER INFORMATION: phosphorothioate linkage
```

<400> SEQUENCE: 177
gagguguauc uccucgaca                                                19

<210> SEQ ID NO 178
<211> LENGTH: 19
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 2, 4, 6, 8, 10, 12, 14, 16, 18
<223> OTHER INFORMATION: 2'-O-methyl nucleoside
<220> FEATURE:
<221> NAME/KEY: misc_feature
<222> LOCATION: 1, 3, 5, 7, 9, 11, 13, 15, 17, 19
<223> OTHER INFORMATION: 2'-fluoro nucleoside
<220> FEATURE:
<221> NAME/KEY: misc_feature
<222> LOCATION: 1-7, 8-9, 12-13, 14-19
<223> OTHER INFORMATION: phosphorothioate linkage

<400> SEQUENCE: 178
ugucgaggag auacaccuc                                                19

<210> SEQ ID NO 179
<211> LENGTH: 20
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 3, 5, 7, 9, 11, 13, 15, 17, 19, 20
<223> OTHER INFORMATION: 2'-O-methyl nucleoside
<220> FEATURE:
<221> NAME/KEY: misc_feature
<222> LOCATION: 1, 2, 4, 6, 8, 10, 12, 14, 16, 18
<223> OTHER INFORMATION: 2'-fluoro nucleoside
<220> FEATURE:
<221> NAME/KEY: misc_feature
<222> LOCATION: 1-10, 11-20
<223> OTHER INFORMATION: phosphorothioate linkage

<400> SEQUENCE: 179
ggguggucag cggccgggau                                               20

<210> SEQ ID NO 180
<211> LENGTH: 20
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 1, 2, 3, 5, 7, 9, 11, 13, 15, 19
<223> OTHER INFORMATION: 2'-O-methyl nucleoside
<220> FEATURE:
<221> NAME/KEY: misc_feature
<222> LOCATION: 4, 6, 8, 10, 12, 14, 16, 17, 18, 20
<223> OTHER INFORMATION: 2'-fluoro nucleoside
<220> FEATURE:
<221> NAME/KEY: misc_feature
<222> LOCATION: 1-9, 21-20
<223> OTHER INFORMATION: phosphorothioate linkage

<400> SEQUENCE: 180
aucccggccg cugaccaccc                                               20

<210> SEQ ID NO 181
<211> LENGTH: 20

```
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 3, 5, 7, 9, 13, 15, 19
<223> OTHER INFORMATION: 2'-O-methyl nucleoside
<220> FEATURE:
<221> NAME/KEY: misc_feature
<222> LOCATION: 1, 2, 4, 6, 8, 10, 11, 12, 14, 16, 18, 20
<223> OTHER INFORMATION: 2'-fluoro nucleoside
<220> FEATURE:
<221> NAME/KEY: misc_feature
<222> LOCATION: 1-20
<223> OTHER INFORMATION: phosphorothioate linkage

<400> SEQUENCE: 181
ggguggucag cggccgggau                                              20

<210> SEQ ID NO 182
<211> LENGTH: 20
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 1, 3, 5, 7, 9, 11, 13, 15, 19
<223> OTHER INFORMATION: 2'-O-methyl nucleoside
<220> FEATURE:
<221> NAME/KEY: misc_feature
<222> LOCATION: 2, 4, 6, 8, 10, 12, 14, 16, 17, 18, 20
<223> OTHER INFORMATION: 2'-fluoro nucleoside
<220> FEATURE:
<221> NAME/KEY: misc_feature
<222> LOCATION: 1-9, 12-20
<223> OTHER INFORMATION: phosphorothioate linkage

<400> SEQUENCE: 182
aucccggccg cugaccaccc                                              20

<210> SEQ ID NO 183
<211> LENGTH: 15
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 4, 6, 8, 10, 12
<223> OTHER INFORMATION: 2'-O-methyl nucleoside
<220> FEATURE:
<221> NAME/KEY: misc_feature
<222> LOCATION: 1, 2, 3, 5, 7, 9, 11, 13, 14, 15
<223> OTHER INFORMATION: 2'-fluoro nucleoside
<220> FEATURE:
<221> NAME/KEY: misc_feature
<222> LOCATION: 1-15
<223> OTHER INFORMATION: phosphorothioate linkage

<400> SEQUENCE: 183
uggucagcgg ccggg                                                   15

<210> SEQ ID NO 184
<211> LENGTH: 20
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 5, 7, 9, 11, 13, 15
```

```
<223> OTHER INFORMATION: 2'-O-methyl nucleoside
<220> FEATURE:
<221> NAME/KEY: misc_feature
<222> LOCATION: 1, 2, 3, 4, 6, 8, 10, 12, 14, 16, 17, 18, 19, 20
<223> OTHER INFORMATION: 2'-fluoro nucleoside
<220> FEATURE:
<221> NAME/KEY: misc_feature
<222> LOCATION: 1-9, 12-20
<223> OTHER INFORMATION: phosphorothioate linkage

<400> SEQUENCE: 184
aucccggccg cugaccaccc                                                     20

<210> SEQ ID NO 185
<211> LENGTH: 15
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 3, 5, 7, 9, 11
<223> OTHER INFORMATION: 2'-O-methyl nucleoside
<220> FEATURE:
<221> NAME/KEY: misc_feature
<222> LOCATION: 1, 2, 4, 6, 8, 10, 12, 13, 14, 15
<223> OTHER INFORMATION: 2'-fluoro nucleoside
<220> FEATURE:
<221> NAME/KEY: misc_feature
<222> LOCATION: 1-15
<223> OTHER INFORMATION: phosphorothioate linkage

<400> SEQUENCE: 185
guggucagcg gccgg                                                          15

<210> SEQ ID NO 186
<211> LENGTH: 19
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 6, 8, 10, 12, 14
<223> OTHER INFORMATION: 2'-O-methyl nucleoside
<220> FEATURE:
<221> NAME/KEY: misc_feature
<222> LOCATION: 1, 2, 3, 4, 5, 7, 9, 11, 13, 15, 16, 17, 18, 19
<223> OTHER INFORMATION: 2'-fluoro nucleoside
<220> FEATURE:
<221> NAME/KEY: misc_feature
<222> LOCATION: 1-10, 13-19
<223> OTHER INFORMATION: phosphorothioate linkage

<400> SEQUENCE: 186
acccggccgc ugaccaccc                                                      19

<210> SEQ ID NO 187
<211> LENGTH: 20
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 2, 5, 7, 9, 11, 13, 15, 17, 19
<223> OTHER INFORMATION: 2'-O-methyl nucleoside
<220> FEATURE:
<221> NAME/KEY: misc_feature
<222> LOCATION: 1, 3, 4, 6, 8, 10, 12, 14, 16, 18, 20
<223> OTHER INFORMATION: 2'-fluoro nucleoside
<220> FEATURE:
<221> NAME/KEY: misc_feature
```

```
<222> LOCATION: 1-8, 9-10, 11-12, 13-20
<223> OTHER INFORMATION: phosphorothioate linkage

<400> SEQUENCE: 187
gcugcccacg uggcuggcau                                                     20

<210> SEQ ID NO 188
<211> LENGTH: 20
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 1, 3, 5, 7, 9, 11, 13, 15, 17
<223> OTHER INFORMATION: 2'-O-methyl nucleoside
<220> FEATURE:
<221> NAME/KEY: misc_feature
<222> LOCATION: 2, 4, 6, 8, 10, 12, 14, 16, 18, 19, 20
<223> OTHER INFORMATION: 2'-fluoro nucleoside
<220> FEATURE:
<221> NAME/KEY: misc_feature
<222> LOCATION: 1-7, 8-9, 12-13, 14-20
<223> OTHER INFORMATION: phosphorothioate linkage

<400> SEQUENCE: 188
augccagcca cgugggcagc                                                     20

<210> SEQ ID NO 189
<211> LENGTH: 20
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 2, 5, 7, 9, 11, 13, 15, 17, 19
<223> OTHER INFORMATION: 2'-O-methyl nucleoside
<220> FEATURE:
<221> NAME/KEY: misc_feature
<222> LOCATION: 1, 3, 4, 6, 8, 10, 14, 16, 18, 20
<223> OTHER INFORMATION: 2'-fluoro nucleoside
<220> FEATURE:
<221> NAME/KEY: misc_feature
<222> LOCATION: 1-8, 9-10, 11-12, 13-20
<223> OTHER INFORMATION: phosphorothioate linkage

<400> SEQUENCE: 189
gcugcccacg uggcuggcau                                                     20

<210> SEQ ID NO 190
<211> LENGTH: 20
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 1, 2, 4, 6, 8, 10, 12, 14, 16, 18, 19, 20
<223> OTHER INFORMATION: 2'-O-methyl nucleoside
<220> FEATURE:
<221> NAME/KEY: misc_feature
<222> LOCATION: 1-7, 8-9, 12-13, 14-20
<223> OTHER INFORMATION: phosphorothioate linkage

<400> SEQUENCE: 190
augccagcca cgugggcagc                                                     20

<210> SEQ ID NO 191
<211> LENGTH: 20
<212> TYPE: DNA
```

```
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 2, 5, 7, 9, 13, 15, 17, 19
<223> OTHER INFORMATION: 2'-O-methyl nucleoside
<220> FEATURE:
<221> NAME/KEY: misc_feature
<222> LOCATION: 1, 3, 4, 6, 8, 10, 11, 12, 14, 16, 18, 20
<223> OTHER INFORMATION: 2'-fluoro nucleoside
<220> FEATURE:
<221> NAME/KEY: misc_feature
<222> LOCATION: 1-20
<223> OTHER INFORMATION: phosphorothioate linkage

<400> SEQUENCE: 191
gcugcccacg uggcuggcau                                              20

<210> SEQ ID NO 192
<211> LENGTH: 20
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 3, 5, 7, 9, 11, 13, 15, 17
<223> OTHER INFORMATION: 2'-O-methyl nucleoside
<220> FEATURE:
<221> NAME/KEY: misc_feature
<222> LOCATION: 1, 2, 4, 6, 8, 10, 12, 14, 16, 18, 19, 20
<223> OTHER INFORMATION: 2'-fluoro nucleoside
<220> FEATURE:
<221> NAME/KEY: misc_feature
<222> LOCATION: 1-7, 8-9, 12-13, 14-20
<223> OTHER INFORMATION: phosphorothioate linkage

<400> SEQUENCE: 192
augccagcca cgugggcagc                                              20

<210> SEQ ID NO 193
<211> LENGTH: 15
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 2, 4, 6, 8, 10, 12, 14
<223> OTHER INFORMATION: 2'-O-methyl nucleoside
<220> FEATURE:
<221> NAME/KEY: misc_feature
<222> LOCATION: 1, 3, 5, 7, 9, 11, 13, 15
<223> OTHER INFORMATION: 2'-fluoro nucleoside
<220> FEATURE:
<221> NAME/KEY: misc_feature
<222> LOCATION: 1-5, 6-7, 8-9, 10-15
<223> OTHER INFORMATION: phosphorothioate linkage

<400> SEQUENCE: 193
gcccacgugg cuggc                                                   15

<210> SEQ ID NO 194
<211> LENGTH: 20
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 1, 3, 5, 7, 9, 11, 13, 15, 17
<223> OTHER INFORMATION: 2'-O-methyl nucleoside
```

<220> FEATURE:
<221> NAME/KEY: misc_feature
<222> LOCATION: 2, 4, 6, 8, 10, 12, 14, 16, 18, 19, 20
<223> OTHER INFORMATION: 2'-fluoro nucleoside
<220> FEATURE:
<221> NAME/KEY: misc_feature
<222> LOCATION: 1-7, 8-9, 12-13, 14-20
<223> OTHER INFORMATION: phosphorothioate linkage

<400> SEQUENCE: 194
augccagcca cgugggcagc                                               20

<210> SEQ ID NO 195
<211> LENGTH: 15
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 2, 4, 5, 7, 9, 11, 12, 14
<223> OTHER INFORMATION: 2'-O-methyl nucleoside
<220> FEATURE:
<221> NAME/KEY: misc_feature
<222> LOCATION: 1, 3, 6, 8, 10, 13, 15
<223> OTHER INFORMATION: 2'-fluoro nucleoside
<220> FEATURE:
<221> NAME/KEY: misc_feature
<222> LOCATION: 1-15
<223> OTHER INFORMATION: phosphorothioate linkage

<400> SEQUENCE: 195
gcugcccacg uggcu                                                    15

<210> SEQ ID NO 196
<211> LENGTH: 20
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 1, 3, 5, 8, 10, 12, 15, 17, 19
<223> OTHER INFORMATION: 2'-O-methyl nucleoside
<220> FEATURE:
<221> NAME/KEY: misc_feature
<222> LOCATION: 2, 4, 6, 14, 16, 18, 20
<223> OTHER INFORMATION: 2'-fluoro nucleoside
<220> FEATURE:
<221> NAME/KEY: misc_feature
<222> LOCATION: 1-7, 8-9, 12-13, 14-20
<223> OTHER INFORMATION: phosphorothioate linkage

<400> SEQUENCE: 196
ccagccacgu gggcagcagc                                               20

<210> SEQ ID NO 197
<211> LENGTH: 14
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 6, 8, 10
<223> OTHER INFORMATION: 2'-O-methyl nucleoside
<220> FEATURE:
<221> NAME/KEY: misc_feature
<222> LOCATION: 1, 2, 3, 4, 5, 7, 9, 11, 12, 13, 14, 15
<223> OTHER INFORMATION: 2'-fluoro nucleoside
<220> FEATURE:
<221> NAME/KEY: misc_feature
<222> LOCATION: 1-14

<223> OTHER INFORMATION: phosphorothioate linkage

<400> SEQUENCE: 197
ggugaggugu cuac                                                        14

<210> SEQ ID NO 198
<211> LENGTH: 21
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 6, 8, 10, 12, 14, 16
<223> OTHER INFORMATION: 2'-O-methyl nucleoside
<220> FEATURE:
<221> NAME/KEY: misc_feature
<222> LOCATION: 1, 2, 3, 4, 5, 7, 9, 11, 13, 15, 18, 19, 20, 21
<223> OTHER INFORMATION: 2'-fluoro nucleoside
<220> FEATURE:
<221> NAME/KEY: misc_feature
<222> LOCATION: 1-7, 8-9, 12-13, 14-21
<223> OTHER INFORMATION: phosphorothioate linkage

<400> SEQUENCE: 198
ggcguagaca cccucaccgc c                                                21

<210> SEQ ID NO 199
<211> LENGTH: 20
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 2, 4, 6, 8, 10, 12, 14, 16, 18, 19, 20
<223> OTHER INFORMATION: 2'-O-methyl nucleoside
<220> FEATURE:
<221> NAME/KEY: misc_feature
<222> LOCATION: 1, 3, 5, 7, 9, 11, 13, 15, 17
<223> OTHER INFORMATION: 2'-fluoro nucleoside
<220> FEATURE:
<221> NAME/KEY: misc_feature
<222> LOCATION: 1-9, 10-11, 12-20
<223> OTHER INFORMATION: phosphorothioate linkage

<400> SEQUENCE: 199
cguuagcaga aacaaaagga                                                  20

<210> SEQ ID NO 200
<211> LENGTH: 20
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 2, 4, 6, 8, 10, 12, 14, 16, 18
<223> OTHER INFORMATION: 2'-O-methyl nucleoside
<220> FEATURE:
<221> NAME/KEY: misc_feature
<222> LOCATION: 1, 3, 5, 7, 9, 11, 13, 15, 17, 19, 20
<223> OTHER INFORMATION: 2'-fluoro nucleoside
<220> FEATURE:
<221> NAME/KEY: misc_feature
<222> LOCATION: 1-9, 12-20
<223> OTHER INFORMATION: phosphorothioate linkage

<400> SEQUENCE: 200
uccuuuuguu ucugcuaacg                                                  20

```
<210> SEQ ID NO 201
<211> LENGTH: 15
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 2, 4, 6, 8, 10, 12, 14
<223> OTHER INFORMATION: 2'-O-methyl nucleoside
<220> FEATURE:
<221> NAME/KEY: misc_feature
<222> LOCATION: 1, 3, 5, 7, 9, 11, 13, 15
<223> OTHER INFORMATION: 2'-fluoro nucleoside
<220> FEATURE:
<221> NAME/KEY: misc_feature
<222> LOCATION: 1-6, 7-8, 9-15
<223> OTHER INFORMATION: phosphorothioate linkage

<400> SEQUENCE: 201
guaaggacca gagac                                              15

<210> SEQ ID NO 202
<211> LENGTH: 19
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 1, 3, 5, 7, 9, 11, 13, 15, 17, 19
<223> OTHER INFORMATION: 2'-O-methyl nucleoside
<220> FEATURE:
<221> NAME/KEY: misc_feature
<222> LOCATION: 2, 4, 6, 8, 10, 12, 14, 16, 18
<223> OTHER INFORMATION: 2'-fluoro nucleoside
<220> FEATURE:
<221> NAME/KEY: misc_feature
<222> LOCATION: 1-9, 12-19
<223> OTHER INFORMATION: phosphorothioate linkage

<400> SEQUENCE: 202
uugucucugg uccuuacuu                                          19

<210> SEQ ID NO 203
<211> LENGTH: 19
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 2, 4, 6, 8, 10, 12, 14, 16, 18
<223> OTHER INFORMATION: 2'-O-methyl nucleoside
<220> FEATURE:
<221> NAME/KEY: misc_feature
<222> LOCATION: 1, 3, 5, 7, 9, 11, 13, 15, 17, 19
<223> OTHER INFORMATION: 2'-fluoro nucleoside
<220> FEATURE:
<221> NAME/KEY: misc_feature
<222> LOCATION: 1-7, 8-9, 10-11, 12-19
<223> OTHER INFORMATION: phosphorothioate linkage

<400> SEQUENCE: 203
ggguaaauac auucuucau                                          19

<210> SEQ ID NO 204
<211> LENGTH: 19
<212> TYPE: DNA
<213> ORGANISM: Artificial Sequence
<220> FEATURE:
<223> OTHER INFORMATION: Synthetic Sequence
<220> FEATURE:
```

```
<221> NAME/KEY: misc_feature
<222> LOCATION: 1, 3, 5, 7, 9, 11, 13, 15, 17, 19
<223> OTHER INFORMATION: 2'-O-methyl nucleoside
<220> FEATURE:
<221> NAME/KEY: misc_feature
<222> LOCATION: 2, 4, 6, 8, 10, 12, 14, 16, 18
<223> OTHER INFORMATION: 2'-fluoro nucleoside
<220> FEATURE:
<221> NAME/KEY: misc_feature
<222> LOCATION: 1-5, 6-7, 8-9, 12-13, 14-19
<223> OTHER INFORMATION: phosphorothioate linkage

<400> SEQUENCE: 204
augaagaaug uauuuaccc                                                19

<210> SEQ ID NO 205
<211> LENGTH: 15
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 2, 4, 6, 8, 10, 12, 14
<223> OTHER INFORMATION: 2'-O-methyl nucleoside
<220> FEATURE:
<221> NAME/KEY: misc_feature
<222> LOCATION: 1, 3, 5, 7, 9, 11, 13, 15
<223> OTHER INFORMATION: 2'-fluoro nucleoside
<220> FEATURE:
<221> NAME/KEY: misc_feature
<222> LOCATION: 1-5, 6-7, 8-9, 10-15
<223> OTHER INFORMATION: phosphorothioate linkage

<400> SEQUENCE: 205
gaaaauacau ucuuc                                                    15

<210> SEQ ID NO 206
<211> LENGTH: 19
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 1, 3, 5, 7, 9, 11, 13, 15, 17, 19
<223> OTHER INFORMATION: 2'-O-methyl nucleoside
<220> FEATURE:
<221> NAME/KEY: misc_feature
<222> LOCATION: 2, 4, 6, 8, 10, 12, 14, 16, 18
<223> OTHER INFORMATION: 2'-fluoro nucleoside
<220> FEATURE:
<221> NAME/KEY: misc_feature
<222> LOCATION: 1-5, 6-7, 8-9, 12-13, 14-19
<223> OTHER INFORMATION: phosphorothioate linkage

<400> SEQUENCE: 206
gggaagaaug uauuuuccc                                                19

<210> SEQ ID NO 207
<211> LENGTH: 19
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 2, 4, 6, 8, 10, 12, 14, 16, 18, 19
<223> OTHER INFORMATION: 2'-O-methyl nucleoside
<220> FEATURE:
<221> NAME/KEY: misc_feature
<222> LOCATION: 1, 3, 5, 7, 9, 11, 13, 15, 17
<223> OTHER INFORMATION: 2'-fluoro nucleoside
```

-continued

```
<220> FEATURE:
<221> NAME/KEY: misc_feature
<222> LOCATION: 1-6, 14-19
<223> OTHER INFORMATION: phosphorothioate linkage

<400> SEQUENCE: 207
ggguaaauac auucuucau                                                 19

<210> SEQ ID NO 208
<211> LENGTH: 19
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 3, 5, 7, 9, 11, 13, 15, 17, 19
<223> OTHER INFORMATION: 2'-O-methyl nucleoside
<220> FEATURE:
<221> NAME/KEY: misc_feature
<222> LOCATION: 1, 2, 4, 6, 8, 10, 12, 14, 16, 18
<223> OTHER INFORMATION: 2'-fluoro nucleoside
<220> FEATURE:
<221> NAME/KEY: misc_feature
<222> LOCATION: 1-6, 14-19
<223> OTHER INFORMATION: phosphorothioate linkage

<400> SEQUENCE: 208
augaagaaug uauuuaccc                                                 19

<210> SEQ ID NO 209
<211> LENGTH: 19
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 2, 4, 6, 8, 10, 12, 14, 16, 18, 19
<223> OTHER INFORMATION: 2'-O-methyl nucleoside
<220> FEATURE:
<221> NAME/KEY: misc_feature
<222> LOCATION: 1, 3, 5, 7, 9, 11, 13, 15, 17
<223> OTHER INFORMATION: 2'-fluoro nucleoside
<220> FEATURE:
<221> NAME/KEY: misc_feature
<222> LOCATION: 1-8, 12-19
<223> OTHER INFORMATION: phosphorothioate linkage

<400> SEQUENCE: 209
ggguaaauac auucuucau                                                 19

<210> SEQ ID NO 210
<211> LENGTH: 19
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 3, 5, 7, 9, 11, 13, 15, 17, 19
<223> OTHER INFORMATION: 2'-O-methyl nucleoside
<220> FEATURE:
<221> NAME/KEY: misc_feature
<222> LOCATION: 1, 2, 4, 6, 8, 10, 12, 14, 16, 18
<223> OTHER INFORMATION: 2'-fluoro nucleoside
<220> FEATURE:
<221> NAME/KEY: misc_feature
<222> LOCATION: 1-8, 12-19
<223> OTHER INFORMATION: phosphorothioate linkage

<400> SEQUENCE: 210
```
augaagaaug uauuuaccc                                        19

<210> SEQ ID NO 211
<211> LENGTH: 19
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 2, 4, 6, 8, 10, 12, 14, 16, 18, 19
<223> OTHER INFORMATION: 2'-O-methyl nucleoside
<220> FEATURE:
<221> NAME/KEY: misc_feature
<222> LOCATION: 1, 3, 5, 7, 9, 11, 13, 15, 17
<223> OTHER INFORMATION: 2'-fluoro nucleoside
<220> FEATURE:
<221> NAME/KEY: misc_feature
<222> LOCATION: 1-3, 7-8, 12-13, 16-19
<223> OTHER INFORMATION: phosphorothioate linkage

<400> SEQUENCE: 211
ggguaaauac auucuucau                                        19

<210> SEQ ID NO 212
<211> LENGTH: 19
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 3, 5, 7, 9, 11, 13, 15, 17, 19
<223> OTHER INFORMATION: 2'-O-methyl nucleoside
<220> FEATURE:
<221> NAME/KEY: misc_feature
<222> LOCATION: 1, 2, 4, 6, 8, 10, 12, 14, 16, 18
<223> OTHER INFORMATION: 2'-fluoro nucleoside
<220> FEATURE:
<221> NAME/KEY: misc_feature
<222> LOCATION: 1-4, 7-8, 12-13, 16-19
<223> OTHER INFORMATION: phosphorothioate linkage

<400> SEQUENCE: 212
augaagaaug uauuuaccc                                        19

<210> SEQ ID NO 213
<211> LENGTH: 19
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 2, 4, 6, 8, 10, 12, 14, 16, 18, 19
<223> OTHER INFORMATION: 2'-O-methyl nucleoside
<220> FEATURE:
<221> NAME/KEY: misc_feature
<222> LOCATION: 1, 3, 5, 7, 9, 11, 13, 15, 17
<223> OTHER INFORMATION: 2'-fluoro nucleoside
<220> FEATURE:
<221> NAME/KEY: misc_feature
<222> LOCATION: 1-7, 8-9, 10-11, 12-19
<223> OTHER INFORMATION: phosphorothioate linkage

<400> SEQUENCE: 213
ggguaaauac auucuucau                                        19

<210> SEQ ID NO 214
<211> LENGTH: 19
<212> TYPE: DNA
<213> ORGANISM: Artificial Sequence

```
<220> FEATURE:
<223> OTHER INFORMATION: Synthetic Sequence
<220> FEATURE:
<221> NAME/KEY: misc_feature
<222> LOCATION: 3, 5, 7, 9, 11, 13, 15, 17, 19
<223> OTHER INFORMATION: 2'-O-methyl nucleoside
<220> FEATURE:
<221> NAME/KEY: misc_feature
<222> LOCATION: 1, 2, 4, 6, 8, 10, 12, 14, 16, 18
<223> OTHER INFORMATION: 2'-fluoro nucleoside
<220> FEATURE:
<221> NAME/KEY: misc_feature
<222> LOCATION: 1-5, 6-7, 8-9, 12-13, 14-19
<223> OTHER INFORMATION: phosphorothioate linkage

<400> SEQUENCE: 214
augaagaaug uauuuaccc                                                19

<210> SEQ ID NO 215
<211> LENGTH: 19
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 2, 4, 6, 8, 10, 12, 14, 16, 18
<223> OTHER INFORMATION: 2'-O-methyl nucleoside
<220> FEATURE:
<221> NAME/KEY: misc_feature
<222> LOCATION: 1, 3, 5, 7, 9, 11, 13, 15, 17, 19
<223> OTHER INFORMATION: 2'-fluoro nucleoside
<220> FEATURE:
<221> NAME/KEY: misc_feature
<222> LOCATION: 1-8, 12-19
<223> OTHER INFORMATION: phosphorothioate linkage

<400> SEQUENCE: 215
ggguaaauac guucuucau                                                19

<210> SEQ ID NO 216
<211> LENGTH: 19
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 1, 3, 5, 7, 9, 11, 13, 15, 17, 19
<223> OTHER INFORMATION: 2'-O-methyl nucleoside
<220> FEATURE:
<221> NAME/KEY: misc_feature
<222> LOCATION: 2, 4, 6, 8, 10, 12, 14, 16, 18
<223> OTHER INFORMATION: 2'-fluoro nucleoside
<220> FEATURE:
<221> NAME/KEY: misc_feature
<222> LOCATION: 1-8, 12-19
<223> OTHER INFORMATION: phosphorothioate linkage

<400> SEQUENCE: 216
augaagaacg uauuuaccc                                                19

<210> SEQ ID NO 217
<211> LENGTH: 19
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 2, 4, 6, 8, 10, 12, 14, 16, 18
<223> OTHER INFORMATION: 2'-O-methyl nucleoside
<220> FEATURE:
```

```
<221> NAME/KEY: misc_feature
<222> LOCATION: 1, 3, 5, 7, 9, 11, 13, 15, 17, 19
<223> OTHER INFORMATION: 2'-fluoro nucleoside
<220> FEATURE:
<221> NAME/KEY: misc_feature
<222> LOCATION: 1-7, 8-9, 10-19
<223> OTHER INFORMATION: phosphorothioate linkage

<400> SEQUENCE: 217
ggguaaauac guucuucau                                             19

<210> SEQ ID NO 218
<211> LENGTH: 19
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 1, 3, 5, 7, 9, 11, 13, 15, 17, 19
<223> OTHER INFORMATION: 2'-O-methyl nucleoside
<220> FEATURE:
<221> NAME/KEY: misc_feature
<222> LOCATION: 2, 4, 6, 8, 10, 12, 14, 16, 18
<223> OTHER INFORMATION: 2'-fluoro nucleoside
<220> FEATURE:
<221> NAME/KEY: misc_feature
<222> LOCATION: 1-5, 6-7, 8-9, 12-13, 14-19
<223> OTHER INFORMATION: phosphorothioate linkage

<400> SEQUENCE: 218
augaagaacg uauuuaccc                                             19

<210> SEQ ID NO 219
<211> LENGTH: 19
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 2, 4, 6, 8, 10, 12, 14, 16, 18, 19
<223> OTHER INFORMATION: 2'-O-methyl nucleoside
<220> FEATURE:
<221> NAME/KEY: misc_feature
<222> LOCATION: 1, 3, 5, 7, 9, 11, 13, 15, 17
<223> OTHER INFORMATION: 2'-fluoro nucleoside
<220> FEATURE:
<221> NAME/KEY: misc_feature
<222> LOCATION: 1-6, 14-19
<223> OTHER INFORMATION: phosphorothioate linkage

<400> SEQUENCE: 219
ggguaaauac guucuucau                                             19

<210> SEQ ID NO 220
<211> LENGTH: 19
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 3, 5, 7, 9, 11, 13, 15, 17, 19
<223> OTHER INFORMATION: 2'-O-methyl nucleoside
<220> FEATURE:
<221> NAME/KEY: misc_feature
<222> LOCATION: 1, 2, 4, 6, 8, 10, 12, 14, 16, 18
<223> OTHER INFORMATION: 2'-fluoro nucleoside
<220> FEATURE:
<221> NAME/KEY: misc_feature
<222> LOCATION: 1-6, 14-19
<223> OTHER INFORMATION: phosphorothioate linkage
```

<400> SEQUENCE: 220
augaagaacg uauuuaccc                                            19

<210> SEQ ID NO 221
<211> LENGTH: 19
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 2, 4, 6, 8, 10, 12, 14, 16, 18, 19
<223> OTHER INFORMATION: 2'-O-methyl nucleoside
<220> FEATURE:
<221> NAME/KEY: misc_feature
<222> LOCATION: 1, 3, 5, 7, 9, 11, 13, 15, 17
<223> OTHER INFORMATION: 2'-fluoro nucleoside
<220> FEATURE:
<221> NAME/KEY: misc_feature
<222> LOCATION: 1-4, 7-8, 12-13, 16-19
<223> OTHER INFORMATION: phosphorothioate linkage

<400> SEQUENCE: 221
ggguaaauac guucuucau                                            19

<210> SEQ ID NO 222
<211> LENGTH: 19
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 3, 5, 7, 9, 11, 13, 15, 17, 19
<223> OTHER INFORMATION: 2'-O-methyl nucleoside
<220> FEATURE:
<221> NAME/KEY: misc_feature
<222> LOCATION: 1, 2, 4, 6, 8, 10, 12, 14, 16, 18
<223> OTHER INFORMATION: 2'-fluoro nucleoside
<220> FEATURE:
<221> NAME/KEY: misc_feature
<222> LOCATION: 1-4, 7-8, 12-13, 16-19
<223> OTHER INFORMATION: phosphorothioate linkage

<400> SEQUENCE: 222
augaagaacg uauuuaccc                                            19

<210> SEQ ID NO 223
<211> LENGTH: 19
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 2, 3, 4, 9, 10, 11, 13, 14, 15
<223> OTHER INFORMATION: 2'-O-methyl nucleoside

<400> SEQUENCE: 223
gccuggaguu uauucggaa                                            19

<210> SEQ ID NO 224
<211> LENGTH: 19
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 8, 15

```
<223> OTHER INFORMATION: 2'-O-methyl nucleoside

<400> SEQUENCE: 224
uuccgaauaa acuccaggc                                              19

<210> SEQ ID NO 225
<211> LENGTH: 19
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 2, 3, 4, 9, 10, 11, 13, 14, 15, 16, 17, 18, 19
<223> OTHER INFORMATION: 2'-O-methyl nucleoside
<220> FEATURE:
<221> NAME/KEY: misc_feature
<222> LOCATION: 1, 5, 12
<223> OTHER INFORMATION: 2'-fluoro nucleoside
<220> FEATURE:
<221> NAME/KEY: misc_feature
<222> LOCATION: 1-6, 14-19
<223> OTHER INFORMATION: phosphorothioate linkage

<400> SEQUENCE: 225
gccuggaguu uauucggaa                                              19

<210> SEQ ID NO 226
<211> LENGTH: 19
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 8, 15, 19
<223> OTHER INFORMATION: 2'-O-methyl nucleoside
<220> FEATURE:
<221> NAME/KEY: misc_feature
<222> LOCATION: 1, 2, 3, 4, 16, 17, 18
<223> OTHER INFORMATION: 2'-fluoro nucleoside
<220> FEATURE:
<221> NAME/KEY: misc_feature
<222> LOCATION: 1-6, 14-19
<223> OTHER INFORMATION: phosphorothioate linkage

<400> SEQUENCE: 226
uuccgaauaa acuccaggc                                              19

<210> SEQ ID NO 227
<211> LENGTH: 19
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 2, 3, 4, 9, 10, 11, 13, 14, 15, 16, 17, 18, 19
<223> OTHER INFORMATION: 2'-O-methyl nucleoside
<220> FEATURE:
<221> NAME/KEY: misc_feature
<222> LOCATION: 1, 5, 12
<223> OTHER INFORMATION: 2'-fluoro nucleoside
<220> FEATURE:
<221> NAME/KEY: misc_feature
<222> LOCATION: 1-8, 12-19
<223> OTHER INFORMATION: phosphorothioate linkage

<400> SEQUENCE: 227
gccuggaguu uauucggaa                                              19
```

```
<210> SEQ ID NO 228
<211> LENGTH: 19
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 8, 15, 19
<223> OTHER INFORMATION: 2'-O-methyl nucleoside
<220> FEATURE:
<221> NAME/KEY: misc_feature
<222> LOCATION: 1, 2, 3, 4, 16, 17, 18
<223> OTHER INFORMATION: 2'-fluoro nucleoside
<220> FEATURE:
<221> NAME/KEY: misc_feature
<222> LOCATION: 1-8, 12-19
<223> OTHER INFORMATION: phosphorothioate linkage

<400> SEQUENCE: 228
uuccgaauaa acuccaggc                                              19

<210> SEQ ID NO 229
<211> LENGTH: 19
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 2, 3, 4, 5, 7, 9, 11, 13, 15, 16, 17, 18, 19
<223> OTHER INFORMATION: 2'-O-methyl nucleoside
<220> FEATURE:
<221> NAME/KEY: misc_feature
<222> LOCATION: 1, 6, 8, 10, 12, 14
<223> OTHER INFORMATION: 2'-fluoro nucleoside
<220> FEATURE:
<221> NAME/KEY: misc_feature
<222> LOCATION: 1-6, 14-19
<223> OTHER INFORMATION: phosphorothioate linkage

<400> SEQUENCE: 229
gccuggaguu uauucggaa                                              19

<210> SEQ ID NO 230
<211> LENGTH: 19
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 6, 8, 10, 12, 14, 19
<223> OTHER INFORMATION: 2'-O-methyl nucleoside
<220> FEATURE:
<221> NAME/KEY: misc_feature
<222> LOCATION: 1, 2, 3, 4, 5, 15, 16, 17, 18
<223> OTHER INFORMATION: 2'-fluoro nucleoside
<220> FEATURE:
<221> NAME/KEY: misc_feature
<222> LOCATION: 1-6, 14-19
<223> OTHER INFORMATION: phosphorothioate linkage

<400> SEQUENCE: 230
uuccgaauaa acuccaggc                                              19

<210> SEQ ID NO 231
<211> LENGTH: 19
<212> TYPE: DNA
<213> ORGANISM: Artificial Sequence
<220> FEATURE:
<223> OTHER INFORMATION: Synthetic Sequence
<220> FEATURE:
```

```
<221> NAME/KEY: misc_feature
<222> LOCATION: 2, 3, 4, 5, 7, 9, 11, 13, 15, 16, 17, 18, 19
<223> OTHER INFORMATION: 2'-O-methyl nucleoside
<220> FEATURE:
<221> NAME/KEY: misc_feature
<222> LOCATION: 1, 6, 8, 10, 12, 14
<223> OTHER INFORMATION: 2'-fluoro nucleoside
<220> FEATURE:
<221> NAME/KEY: misc_feature
<222> LOCATION: 1-6, 8-9, 12-13, 14-19
<223> OTHER INFORMATION: phosphorothioate linkage

<400> SEQUENCE: 231
gccuggaguu uauucggaa                                                  19

<210> SEQ ID NO 232
<211> LENGTH: 19
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 6, 8, 10, 12, 14, 19
<223> OTHER INFORMATION: 2'-O-methyl nucleoside
<220> FEATURE:
<221> NAME/KEY: misc_feature
<222> LOCATION: 1, 2, 3, 4, 5, 15, 16, 17, 18
<223> OTHER INFORMATION: 2'-fluoro nucleoside
<220> FEATURE:
<221> NAME/KEY: misc_feature
<222> LOCATION: 1-6, 7-8, 11-12, 14-19
<223> OTHER INFORMATION: phosphorothioate linkage

<400> SEQUENCE: 232
uuccgaauaa acuccaggc                                                  19

<210> SEQ ID NO 233
<211> LENGTH: 19
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 2, 3, 4, 5, 7, 9, 11, 13, 15, 16, 17, 18, 19
<223> OTHER INFORMATION: 2'-O-methyl nucleoside
<220> FEATURE:
<221> NAME/KEY: misc_feature
<222> LOCATION: 1, 6, 8, 10, 12, 14
<223> OTHER INFORMATION: 2'-fluoro nucleoside
<220> FEATURE:
<221> NAME/KEY: misc_feature
<222> LOCATION: 1-6, 8-9, 12-13, 14-19
<223> OTHER INFORMATION: phosphorothioate linkage

<400> SEQUENCE: 233
gccuggaguu uauucggaa                                                  19

<210> SEQ ID NO 234
<211> LENGTH: 19
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 6, 8, 10, 12, 14, 19
<223> OTHER INFORMATION: 2'-O-methyl nucleoside
<220> FEATURE:
<221> NAME/KEY: misc_feature
<222> LOCATION: 1, 2, 3, 4, 5, 7, 9, 11, 13, 15, 16, 17, 18
<223> OTHER INFORMATION: 2'-fluoro nucleoside
```

```
<220> FEATURE:
<221> NAME/KEY: misc_feature
<222> LOCATION: 1-6, 7-8, 11-12, 14-19
<223> OTHER INFORMATION: phosphorothioate linkage

<400> SEQUENCE: 234
uuccgaauaa acuccaggc                                                    19

<210> SEQ ID NO 235
<211> LENGTH: 19
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 3, 5, 7, 9, 11, 13, 15, 17, 19
<223> OTHER INFORMATION: 2'-O-methyl nucleoside
<220> FEATURE:
<221> NAME/KEY: misc_feature
<222> LOCATION: 1, 2, 4, 6, 8, 10, 12, 14, 16, 18
<223> OTHER INFORMATION: 2'-fluoro nucleoside
<220> FEATURE:
<221> NAME/KEY: misc_feature
<222> LOCATION: 1-6, 8-9, 12-13, 14-19
<223> OTHER INFORMATION: phosphorothioate linkage

<400> SEQUENCE: 235
gccuggaguu uauucggaa                                                    19

<210> SEQ ID NO 236
<211> LENGTH: 19
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 2, 4, 6, 8, 10, 12, 14, 16, 18, 19
<223> OTHER INFORMATION: 2'-O-methyl nucleoside
<220> FEATURE:
<221> NAME/KEY: misc_feature
<222> LOCATION: 1, 3, 5, 7, 9, 11, 13, 15, 17
<223> OTHER INFORMATION: 2'-fluoro nucleoside
<220> FEATURE:
<221> NAME/KEY: misc_feature
<222> LOCATION: 1-5, 7-8, 11-12, 14-19
<223> OTHER INFORMATION: phosphorothioate linkage

<400> SEQUENCE: 236
uuccgaauaa acuccaggc                                                    19

<210> SEQ ID NO 237
<211> LENGTH: 19
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 3, 5, 7, 9, 11, 13, 15, 17, 19
<223> OTHER INFORMATION: 2'-O-methyl nucleoside
<220> FEATURE:
<221> NAME/KEY: misc_feature
<222> LOCATION: 1, 2, 4, 6, 8, 10, 12, 14, 16, 18
<223> OTHER INFORMATION: 2'-fluoro nucleoside
<220> FEATURE:
<221> NAME/KEY: misc_feature
<222> LOCATION: 1-7, 8-10, 11-13, 14-19
<223> OTHER INFORMATION: phosphorothioate linkage

<400> SEQUENCE: 237
```
gccuggaguu uauucggaa					19

<210> SEQ ID NO 238
<211> LENGTH: 19
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 2, 4, 6, 8, 10, 12, 14, 16, 18, 19
<223> OTHER INFORMATION: 2'-O-methyl nucleoside
<220> FEATURE:
<221> NAME/KEY: misc_feature
<222> LOCATION: 1, 3, 5, 7, 9, 11, 13, 15, 17
<223> OTHER INFORMATION: 2'-fluoro nucleoside
<220> FEATURE:
<221> NAME/KEY: misc_feature
<222> LOCATION: 1-9, 12-19
<223> OTHER INFORMATION: phosphorothioate linkage

<400> SEQUENCE: 238
uuccgaauaa acuccaggc					19

<210> SEQ ID NO 239
<211> LENGTH: 19
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 3, 5, 7, 9, 11, 13, 15, 17, 19
<223> OTHER INFORMATION: 2'-O-methyl nucleoside
<220> FEATURE:
<221> NAME/KEY: misc_feature
<222> LOCATION: 1, 2, 4, 6, 8, 10, 12, 14, 16, 18
<223> OTHER INFORMATION: 2'-fluoro nucleoside
<220> FEATURE:
<221> NAME/KEY: misc_feature
<222> LOCATION: 1-6, 7-8, 11-12, 13-19
<223> OTHER INFORMATION: phosphorothioate linkage

<400> SEQUENCE: 239
gaagcccaga ggagcuaua					19

<210> SEQ ID NO 240
<211> LENGTH: 19
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 2, 4, 6, 16, 19
<223> OTHER INFORMATION: 2'-O-methyl nucleoside
<220> FEATURE:
<221> NAME/KEY: misc_feature
<222> LOCATION: 1, 3, 5, 7, 13, 15, 17, 18
<223> OTHER INFORMATION: 2'-fluoro nucleoside
<220> FEATURE:
<221> NAME/KEY: misc_feature
<222> LOCATION: 1-6, 7-8, 12-13, 14-19
<223> OTHER INFORMATION: phosphorothioate linkage

<400> SEQUENCE: 240
uauagcuccu cugggcuuc					19

<210> SEQ ID NO 241
<211> LENGTH: 19
<212> TYPE: DNA
<213> ORGANISM: Artificial Sequence

```
<220> FEATURE:
<223> OTHER INFORMATION: Synthetic Sequence
<220> FEATURE:
<221> NAME/KEY: misc_feature
<222> LOCATION: 3, 5, 7, 9, 11, 13, 15, 17, 19
<223> OTHER INFORMATION: 2'-O-methyl nucleoside
<220> FEATURE:
<221> NAME/KEY: misc_feature
<222> LOCATION: 1, 2, 4, 6, 8, 10, 12, 14, 16, 18
<223> OTHER INFORMATION: 2'-fluoro nucleoside
<220> FEATURE:
<221> NAME/KEY: misc_feature
<222> LOCATION: 1-6, 7-8, 11-12, 13-19
<223> OTHER INFORMATION: phosphorothioate linkage

<400> SEQUENCE: 241
gaagcccaga ggagcuaua                                              19

<210> SEQ ID NO 242
<211> LENGTH: 19
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 2, 4, 6, 16, 19
<223> OTHER INFORMATION: 2'-O-methyl nucleoside
<220> FEATURE:
<221> NAME/KEY: misc_feature
<222> LOCATION: 1, 3, 5, 7, 9, 11, 13, 15, 17, 18
<223> OTHER INFORMATION: 2'-fluoro nucleoside
<220> FEATURE:
<221> NAME/KEY: misc_feature
<222> LOCATION: 1-6, 14-19
<223> OTHER INFORMATION: phosphorothioate linkage

<400> SEQUENCE: 242
uauagcuccu cugggcuuc                                              19

<210> SEQ ID NO 243
<211> LENGTH: 19
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 3, 5, 7, 9, 11, 13, 15, 17, 19
<223> OTHER INFORMATION: 2'-O-methyl nucleoside
<220> FEATURE:
<221> NAME/KEY: misc_feature
<222> LOCATION: 1, 2, 4, 6, 8, 10, 12, 14, 16, 18
<223> OTHER INFORMATION: 2'-fluoro nucleoside
<220> FEATURE:
<221> NAME/KEY: misc_feature
<222> LOCATION: 1-6, 7-8, 11-12, 13-19
<223> OTHER INFORMATION: phosphorothioate linkage

<400> SEQUENCE: 243
gaagcccaga ggagcuaua                                              19

<210> SEQ ID NO 244
<211> LENGTH: 19
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 2, 4, 6, 14, 16, 19
<223> OTHER INFORMATION: 2'-O-methyl nucleoside
<220> FEATURE:
```

```
<221> NAME/KEY: misc_feature
<222> LOCATION: 1, 3, 5, 8, 10, 12, 15, 17, 18
<223> OTHER INFORMATION: 2'-fluoro nucleoside
<220> FEATURE:
<221> NAME/KEY: misc_feature
<222> LOCATION: 1-6, 14-19
<223> OTHER INFORMATION: phosphorothioate linkage

<400> SEQUENCE: 244
uauagcuccu cugggcuuc                                              19

<210> SEQ ID NO 245
<211> LENGTH: 19
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 3, 5, 7, 9, 11, 13, 15, 17, 19
<223> OTHER INFORMATION: 2'-O-methyl nucleoside
<220> FEATURE:
<221> NAME/KEY: misc_feature
<222> LOCATION: 1, 2, 4, 6, 8, 10, 12, 14, 16, 18
<223> OTHER INFORMATION: 2'-fluoro nucleoside
<220> FEATURE:
<221> NAME/KEY: misc_feature
<222> LOCATION: 1-6, 7-8, 11-12, 13-19
<223> OTHER INFORMATION: phosphorothioate linkage

<400> SEQUENCE: 245
gaagcccaga ggagcuaua                                              19

<210> SEQ ID NO 246
<211> LENGTH: 19
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 2, 4, 6, 8, 10, 12, 14, 16, 19
<223> OTHER INFORMATION: 2'-O-methyl nucleoside
<220> FEATURE:
<221> NAME/KEY: misc_feature
<222> LOCATION: 1, 3, 5, 7, 9, 11, 13, 15, 17, 18
<223> OTHER INFORMATION: 2'-fluoro nucleoside
<220> FEATURE:
<221> NAME/KEY: misc_feature
<222> LOCATION: 1-6, 14-19
<223> OTHER INFORMATION: phosphorothioate linkage

<400> SEQUENCE: 246
uauagcuccu cugggcuuc                                              19

<210> SEQ ID NO 247
<211> LENGTH: 19
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 3, 5, 7, 9, 11, 13, 15, 17, 19
<223> OTHER INFORMATION: 2'-O-methyl nucleoside
<220> FEATURE:
<221> NAME/KEY: misc_feature
<222> LOCATION: 1, 2, 4, 6, 8, 10, 12, 14, 16, 18
<223> OTHER INFORMATION: 2'-fluoro nucleoside
<220> FEATURE:
<221> NAME/KEY: misc_feature
<222> LOCATION: 1-8, 11-19
<223> OTHER INFORMATION: phosphorothioate linkage
```

```
<400> SEQUENCE: 247
gaagcccaga ggagcuaua                                                    19

<210> SEQ ID NO 248
<211> LENGTH: 19
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 2, 4, 6, 8, 10, 12, 14, 16, 19
<223> OTHER INFORMATION: 2'-O-methyl nucleoside
<220> FEATURE:
<221> NAME/KEY: misc_feature
<222> LOCATION: 1, 3, 5, 7, 9, 11, 13, 15, 17, 18
<223> OTHER INFORMATION: 2'-fluoro nucleoside
<220> FEATURE:
<221> NAME/KEY: misc_feature
<222> LOCATION: 1-6, 7-8, 12-13, 14-19
<223> OTHER INFORMATION: phosphorothioate linkage

<400> SEQUENCE: 248
uauagcuccu cugggcuuc                                                    19

<210> SEQ ID NO 249
<211> LENGTH: 19
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 19
<223> OTHER INFORMATION: 2'-O-methyl nucleoside
<220> FEATURE:
<221> NAME/KEY: misc_feature
<222> LOCATION: 1, 3, 5, 7, 9, 11, 13, 15, 17
<223> OTHER INFORMATION: 2'-fluoro nucleoside
<220> FEATURE:
<221> NAME/KEY: misc_feature
<222> LOCATION: 1-8, 11-19
<223> OTHER INFORMATION: phosphorothioate linkage

<400> SEQUENCE: 249
gaagcccaga ggagcuaua                                                    19

<210> SEQ ID NO 250
<211> LENGTH: 19
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 19
<223> OTHER INFORMATION: 2'-O-methyl nucleoside
<220> FEATURE:
<221> NAME/KEY: misc_feature
<222> LOCATION: 1, 3, 5, 7, 9, 11, 13, 15, 17
<223> OTHER INFORMATION: 2'-fluoro nucleoside
<220> FEATURE:
<221> NAME/KEY: misc_feature
<222> LOCATION: 1-6, 7-8, 12-13, 14-19
<223> OTHER INFORMATION: phosphorothioate linkage

<400> SEQUENCE: 250
uauagcuccu cugggcuuc                                                    19

<210> SEQ ID NO 251
```

```
<211> LENGTH: 19
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 5, 7, 9, 11, 13, 15, 16, 17, 18, 19
<223> OTHER INFORMATION: 2'-O-methyl nucleoside
<220> FEATURE:
<221> NAME/KEY: misc_feature
<222> LOCATION: 1, 2, 3, 4, 6, 8, 10, 12, 14
<223> OTHER INFORMATION: 2'-fluoro nucleoside
<220> FEATURE:
<221> NAME/KEY: misc_feature
<222> LOCATION: 1-8, 11-19
<223> OTHER INFORMATION: phosphorothioate linkage

<400> SEQUENCE: 251
gaagcccaga ggagcuaua                                                  19

<210> SEQ ID NO 252
<211> LENGTH: 19
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 1, 2, 3, 4, 6, 8, 10, 12, 14, 19
<223> OTHER INFORMATION: 2'-O-methyl nucleoside
<220> FEATURE:
<221> NAME/KEY: misc_feature
<222> LOCATION: 5, 7, 9, 11, 13, 15, 16, 17, 18
<223> OTHER INFORMATION: 2'-fluoro nucleoside
<220> FEATURE:
<221> NAME/KEY: misc_feature
<222> LOCATION: 1-6, 7-8, 12-13, 14-19
<223> OTHER INFORMATION: phosphorothioate linkage

<400> SEQUENCE: 252
uauagcuccu cugggcuuc                                                  19

<210> SEQ ID NO 253
<211> LENGTH: 19
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 1, 2, 7, 8, 9, 15, 16
<223> OTHER INFORMATION: 2'-fluoro nucleoside
<220> FEATURE:
<221> NAME/KEY: misc_feature
<222> LOCATION: 1-6, 7-8, 9-10, 11-12, 13-19
<223> OTHER INFORMATION: phosphorothioate linkage

<400> SEQUENCE: 253
ucaaaguccg agagucagg                                                  19

<210> SEQ ID NO 254
<211> LENGTH: 19
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 4, 5, 11, 12, 13, 18, 19
<223> OTHER INFORMATION: 2'-O-methyl nucleoside
<220> FEATURE:
<221> NAME/KEY: misc_feature
```

<222> LOCATION: 1, 2, 3, 6, 7, 8, 9, 10, 14, 15, 16, 17
<223> OTHER INFORMATION: 2'-fluoro nucleoside
<220> FEATURE:
<221> NAME/KEY: misc_feature
<222> LOCATION: 1-6, 14-19
<223> OTHER INFORMATION: phosphorothioate linkage

<400> SEQUENCE: 254
ccugacucuc ggacuuuga                    19

<210> SEQ ID NO 255
<211> LENGTH: 16
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 2, 4, 6, 8, 10, 12, 14, 15, 16
<223> OTHER INFORMATION: 2'-O-methyl nucleoside
<220> FEATURE:
<221> NAME/KEY: misc_feature
<222> LOCATION: 1, 3, 5, 7, 9, 11, 13
<223> OTHER INFORMATION: 2'-fluoro nucleoside
<220> FEATURE:
<221> NAME/KEY: misc_feature
<222> LOCATION: 1-16
<223> OTHER INFORMATION: phosphorothioate linkage

<400> SEQUENCE: 255
cggcauucgg cuaugu                    16

<210> SEQ ID NO 256
<211> LENGTH: 19
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 1, 2, 7, 8, 9, 15, 16
<223> OTHER INFORMATION: 2'-fluoro nucleoside
<220> FEATURE:
<221> NAME/KEY: misc_feature
<222> LOCATION: 1-6, 7-8, 9-10, 11-12, 13-19
<223> OTHER INFORMATION: phosphorothioate linkage

<400> SEQUENCE: 256
ucaaaguccg agagucagg                    19

<210> SEQ ID NO 257
<211> LENGTH: 19
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 4, 5, 11, 12, 13, 18, 19
<223> OTHER INFORMATION: 2'-O-methyl nucleoside
<220> FEATURE:
<221> NAME/KEY: misc_feature
<222> LOCATION: 1, 2, 3, 6, 7, 8, 9, 10, 14, 15, 16, 17
<223> OTHER INFORMATION: 2'-fluoro nucleoside
<220> FEATURE:
<221> NAME/KEY: misc_feature
<222> LOCATION: 1-8, 12-19
<223> OTHER INFORMATION: phosphorothioate linkage

<400> SEQUENCE: 257
ccugacucuc ggacuuuga                    19

```
<210> SEQ ID NO 258
<211> LENGTH: 19
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 3, 5, 7, 9, 11, 13, 15, 17, 19
<223> OTHER INFORMATION: 2'-O-methyl nucleoside
<220> FEATURE:
<221> NAME/KEY: misc_feature
<222> LOCATION: 1, 2
<223> OTHER INFORMATION: 2'-fluoro nucleoside
<220> FEATURE:
<221> NAME/KEY: misc_feature
<222> LOCATION: 1-8, 10-11, 13-19
<223> OTHER INFORMATION: phosphorothioate linkage

<400> SEQUENCE: 258
ucaaaguccg agagucagg                                              19

<210> SEQ ID NO 259
<211> LENGTH: 19
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 1, 3, 5, 7, 9, 11, 13, 15, 17, 19
<223> OTHER INFORMATION: 2'-O-methyl nucleoside
<220> FEATURE:
<221> NAME/KEY: misc_feature
<222> LOCATION: 18
<223> OTHER INFORMATION: 2'-fluoro nucleoside
<220> FEATURE:
<221> NAME/KEY: misc_feature
<222> LOCATION: 1-6, 7-8, 12-13, 14-19
<223> OTHER INFORMATION: phosphorothioate linkage

<400> SEQUENCE: 259
ccugacucuc ggacuuuga                                              19

<210> SEQ ID NO 260
<211> LENGTH: 19
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 1, 2, 3, 5, 7, 9, 11, 13, 15, 17
<223> OTHER INFORMATION: 2'-O-methyl nucleoside
<220> FEATURE:
<221> NAME/KEY: misc_feature
<222> LOCATION: 4, 6, 8, 10, 12, 14, 16, 18, 19
<223> OTHER INFORMATION: 2'-fluoro nucleoside
<220> FEATURE:
<221> NAME/KEY: misc_feature
<222> LOCATION: 1-8, 10-11, 13-19
<223> OTHER INFORMATION: phosphorothioate linkage

<400> SEQUENCE: 260
ucaaaguccg agagucagg                                              19

<210> SEQ ID NO 261
<211> LENGTH: 19
<212> TYPE: DNA
<213> ORGANISM: Artificial Sequence
<220> FEATURE:
<223> OTHER INFORMATION: Synthetic Sequence
```

```
<220> FEATURE:
<221> NAME/KEY: misc_feature
<222> LOCATION: 1, 3, 5, 7, 9, 11, 13, 15, 17, 19
<223> OTHER INFORMATION: 2'-O-methyl nucleoside
<220> FEATURE:
<221> NAME/KEY: misc_feature
<222> LOCATION: 2, 4, 6, 8, 10, 12, 14, 16, 18
<223> OTHER INFORMATION: 2'-fluoro nucleoside
<220> FEATURE:
<221> NAME/KEY: misc_feature
<222> LOCATION: 1-6, 7-8, 12-13, 14-19
<223> OTHER INFORMATION: phosphorothioate linkage

<400> SEQUENCE: 261
ccugacucuc ggacuuuga                                                 19

<210> SEQ ID NO 262
<211> LENGTH: 20
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 2, 4, 5, 7, 9, 11, 13, 15, 17, 18, 20
<223> OTHER INFORMATION: 2'-O-methyl nucleoside
<220> FEATURE:
<221> NAME/KEY: misc_feature
<222> LOCATION: 1, 3, 6, 8, 10, 12, 14, 16, 19
<223> OTHER INFORMATION: 2'-fluoro nucleoside
<220> FEATURE:
<221> NAME/KEY: misc_feature
<222> LOCATION: 1-6, 8-9, 12-13, 14-20
<223> OTHER INFORMATION: phosphorothioate linkage

<400> SEQUENCE: 262
uggaggagcc gcagucagau                                                20

<210> SEQ ID NO 263
<211> LENGTH: 20
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 1, 2, 3, 5, 7, 13, 15, 18, 20
<223> OTHER INFORMATION: 2'-O-methyl nucleoside
<220> FEATURE:
<221> NAME/KEY: misc_feature
<222> LOCATION: 4, 6, 8, 10, 12, 14, 16, 17, 19
<223> OTHER INFORMATION: 2'-fluoro nucleoside
<220> FEATURE:
<221> NAME/KEY: misc_feature
<222> LOCATION: 1-6, 15-20
<223> OTHER INFORMATION: phosphorothioate linkage

<400> SEQUENCE: 263
aucugacugc ggcuccucca                                                20

<210> SEQ ID NO 264
<211> LENGTH: 20
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 2, 4, 5, 7, 9, 11, 13, 15, 17, 18, 20
<223> OTHER INFORMATION: 2'-O-methyl nucleoside
<220> FEATURE:
<221> NAME/KEY: misc_feature
<222> LOCATION: 1, 3, 6, 8, 10, 12, 14, 16, 19
```

<223> OTHER INFORMATION: 2'-fluoro nucleoside
<220> FEATURE:
<221> NAME/KEY: misc_feature
<222> LOCATION: 1-6, 8-9, 12-13, 15-20
<223> OTHER INFORMATION: phosphorothioate linkage

<400> SEQUENCE: 264
uggaggagcc gcagucagau						20

<210> SEQ ID NO 265
<211> LENGTH: 20
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 1, 2, 3, 5, 7, 13, 15, 18, 20
<223> OTHER INFORMATION: 2'-O-methyl nucleoside
<220> FEATURE:
<221> NAME/KEY: misc_feature
<222> LOCATION: 4, 6, 8, 10, 12, 14, 16, 17, 19
<223> OTHER INFORMATION: 2'-fluoro nucleoside
<220> FEATURE:
<221> NAME/KEY: misc_feature
<222> LOCATION: 1-6, 7-8, 12-13, 15-20
<223> OTHER INFORMATION: phosphorothioate linkage

<400> SEQUENCE: 265
aucugacugc ggcuccucca						20

<210> SEQ ID NO 266
<211> LENGTH: 20
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 2, 4, 5, 7, 9, 11, 13, 15, 17, 18, 20
<223> OTHER INFORMATION: 2'-O-methyl nucleoside
<220> FEATURE:
<221> NAME/KEY: misc_feature
<222> LOCATION: 1, 3, 6, 8, 10, 12, 14, 16, 19
<223> OTHER INFORMATION: 2'-fluoro nucleoside
<220> FEATURE:
<221> NAME/KEY: misc_feature
<222> LOCATION: 1-6, 8-9, 12-13, 15-20
<223> OTHER INFORMATION: phosphorothioate linkage

<400> SEQUENCE: 266
uggaggagcc gcagucagau						20

<210> SEQ ID NO 267
<211> LENGTH: 20
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 1, 2, 3, 5, 7, 13, 15, 18, 20
<223> OTHER INFORMATION: 2'-O-methyl nucleoside
<220> FEATURE:
<221> NAME/KEY: misc_feature
<222> LOCATION: 4, 6, 8, 10, 12, 14, 16, 17, 19
<223> OTHER INFORMATION: 2'-fluoro nucleoside
<220> FEATURE:
<221> NAME/KEY: misc_feature
<222> LOCATION: 1-7, 8-9, 12-13, 14-20
<223> OTHER INFORMATION: phosphorothioate linkage

<400> SEQUENCE: 267
aucugacugc ggcuccucca                                                    20

<210> SEQ ID NO 268
<211> LENGTH: 20
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 2, 4, 5, 7, 9, 11, 13, 15, 18, 20
<223> OTHER INFORMATION: 2'-O-methyl nucleoside
<220> FEATURE:
<221> NAME/KEY: misc_feature
<222> LOCATION: 1, 3, 6, 8, 10, 12, 14, 16, 17, 19
<223> OTHER INFORMATION: 2'-fluoro nucleoside
<220> FEATURE:
<221> NAME/KEY: misc_feature
<222> LOCATION: 1-20
<223> OTHER INFORMATION: phosphorothioate linkage

<400> SEQUENCE: 268
uggaggagcc gcagucagau                                                    20

<210> SEQ ID NO 269
<211> LENGTH: 20
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 2, 4, 7, 13, 15, 18, 20
<223> OTHER INFORMATION: 2'-O-methyl nucleoside
<220> FEATURE:
<221> NAME/KEY: misc_feature
<222> LOCATION: 1, 3, 5, 6, 8, 10, 12, 14, 16, 17, 19
<223> OTHER INFORMATION: 2'-fluoro nucleoside
<220> FEATURE:
<221> NAME/KEY: misc_feature
<222> LOCATION: 1-7, 8-9, 12-13, 14-20
<223> OTHER INFORMATION: phosphorothioate linkage

<400> SEQUENCE: 269
aucugacugc ggcuccucca                                                    20

<210> SEQ ID NO 270
<211> LENGTH: 20
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 2, 4, 5, 7, 10, 13, 15, 18, 20
<223> OTHER INFORMATION: 2'-O-methyl nucleoside
<220> FEATURE:
<221> NAME/KEY: misc_feature
<222> LOCATION: 1, 3, 6, 8, 9, 11, 12, 14, 16, 17, 19
<223> OTHER INFORMATION: 2'-fluoro nucleoside
<220> FEATURE:
<221> NAME/KEY: misc_feature
<222> LOCATION: 1-20
<223> OTHER INFORMATION: phosphorothioate linkage

<400> SEQUENCE: 270
uggaggagcc gcagucagau                                                    20

<210> SEQ ID NO 271
<211> LENGTH: 20
<212> TYPE: DNA

```
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 2, 4, 7, 9, 13, 15, 20
<223> OTHER INFORMATION: 2'-O-methyl nucleoside
<220> FEATURE:
<221> NAME/KEY: misc_feature
<222> LOCATION: 1, 3, 5, 6, 8, 10, 12, 14, 16, 17, 19
<223> OTHER INFORMATION: 2'-fluoro nucleoside
<220> FEATURE:
<221> NAME/KEY: misc_feature
<222> LOCATION: 1-7, 8-9, 12-13, 14-20
<223> OTHER INFORMATION: phosphorothioate linkage

<400> SEQUENCE: 271
aucugacugc ggcuccucca                                              20

<210> SEQ ID NO 272
<211> LENGTH: 16
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 2, 3, 5, 7, 9, 11, 13, 16
<223> OTHER INFORMATION: 2'-O-methyl nucleoside
<220> FEATURE:
<221> NAME/KEY: misc_feature
<222> LOCATION: 1, 4, 6, 8, 10, 12, 14, 15
<223> OTHER INFORMATION: 2'-fluoro nucleoside
<220> FEATURE:
<221> NAME/KEY: misc_feature
<222> LOCATION: 1-8, 9-16
<223> OTHER INFORMATION: phosphorothioate linkage

<400> SEQUENCE: 272
gaggagccgc agucag                                                  16

<210> SEQ ID NO 273
<211> LENGTH: 20
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 1, 2, 3, 4, 6, 8, 10, 12, 14, 19
<223> OTHER INFORMATION: 2'-O-methyl nucleoside
<220> FEATURE:
<221> NAME/KEY: misc_feature
<222> LOCATION: 1, 3, 5, 6, 8, 10, 12, 14, 16, 17, 19
<223> OTHER INFORMATION: 2'-fluoro nucleoside
<220> FEATURE:
<221> NAME/KEY: misc_feature
<222> LOCATION: 1-7, 8-9, 12-13, 14-20
<223> OTHER INFORMATION: phosphorothioate linkage

<400> SEQUENCE: 273
aucugacugc ggcuccucca                                              20

<210> SEQ ID NO 274
<211> LENGTH: 20
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 2, 4, 6, 8, 11, 13, 15, 17, 18, 19, 20
<223> OTHER INFORMATION: 2'-O-methyl nucleoside
```

```
<220> FEATURE:
<221> NAME/KEY: misc_feature
<222> LOCATION: 1, 3, 5, 7, 9, 10, 12, 14, 16
<223> OTHER INFORMATION: 2'-fluoro nucleoside
<220> FEATURE:
<221> NAME/KEY: misc_feature
<222> LOCATION: 1-8, 9-10, 11-12, 13-20
<223> OTHER INFORMATION: phosphorothioate linkage

<400> SEQUENCE: 274
auggaugauu ugaugcuguc                                          20

<210> SEQ ID NO 275
<211> LENGTH: 20
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 1, 3, 5, 7, 12, 14, 16, 18, 20
<223> OTHER INFORMATION: 2'-O-methyl nucleoside
<220> FEATURE:
<221> NAME/KEY: misc_feature
<222> LOCATION: 2, 4, 6, 8, 10, 13, 15, 17, 19
<223> OTHER INFORMATION: 2'-fluoro nucleoside
<220> FEATURE:
<221> NAME/KEY: misc_feature
<222> LOCATION: 1-6, 15-20
<223> OTHER INFORMATION: phosphorothioate linkage

<400> SEQUENCE: 275
gacagcauca aaucauccau                                          20

<210> SEQ ID NO 276
<211> LENGTH: 20
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 2, 4, 6, 8, 11, 13, 15, 17, 18, 19, 20
<223> OTHER INFORMATION: 2'-O-methyl nucleoside
<220> FEATURE:
<221> NAME/KEY: misc_feature
<222> LOCATION: 1, 3, 5, 7, 9, 10, 12, 14, 16
<223> OTHER INFORMATION: 2'-fluoro nucleoside
<220> FEATURE:
<221> NAME/KEY: misc_feature
<222> LOCATION: 1-8, 9-10, 11-12, 13-20
<223> OTHER INFORMATION: phosphorothioate linkage

<400> SEQUENCE: 276
auggaugauu ugaugcuguc                                          20

<210> SEQ ID NO 277
<211> LENGTH: 20
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 1, 3, 5, 7, 12, 14, 16, 18, 20
<223> OTHER INFORMATION: 2'-O-methyl nucleoside
<220> FEATURE:
<221> NAME/KEY: misc_feature
<222> LOCATION: 2, 4, 6, 8, 10, 13, 15, 17, 19
<223> OTHER INFORMATION: 2'-fluoro nucleoside
<220> FEATURE:
<221> NAME/KEY: misc_feature
<222> LOCATION: 1-6, 7-8, 12-13, 15-20
```

-continued

<223> OTHER INFORMATION: phosphorothioate linkage

<400> SEQUENCE: 277
gacagcauca aaucauccau                          20

<210> SEQ ID NO 278
<211> LENGTH: 20
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 2, 4, 7, 9, 11, 13, 15, 17, 18, 19, 20
<223> OTHER INFORMATION: 2'-O-methyl nucleoside
<220> FEATURE:
<221> NAME/KEY: misc_feature
<222> LOCATION: 1, 3, 5, 6, 8, 10, 12, 14, 16
<223> OTHER INFORMATION: 2'-fluoro nucleoside
<220> FEATURE:
<221> NAME/KEY: misc_feature
<222> LOCATION: 1-8, 9-10, 11-12, 13-20
<223> OTHER INFORMATION: phosphorothioate linkage

<400> SEQUENCE: 278
auggaugauu ugaugcuguc                          20

<210> SEQ ID NO 279
<211> LENGTH: 20
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 1, 3, 5, 7, 9, 11, 13, 15, 16, 18, 20
<223> OTHER INFORMATION: 2'-O-methyl nucleoside
<220> FEATURE:
<221> NAME/KEY: misc_feature
<222> LOCATION: 2, 4, 6, 8, 10, 12, 14, 17, 19
<223> OTHER INFORMATION: 2'-fluoro nucleoside
<220> FEATURE:
<221> NAME/KEY: misc_feature
<222> LOCATION: 1-6, 7-8, 12-13, 15-20
<223> OTHER INFORMATION: phosphorothioate linkage

<400> SEQUENCE: 279
gacagcauca aaucauccau                          20

<210> SEQ ID NO 280
<211> LENGTH: 20
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 2, 4, 7, 9, 11, 13, 15, 17, 18, 19, 20
<223> OTHER INFORMATION: 2'-O-methyl nucleoside
<220> FEATURE:
<221> NAME/KEY: misc_feature
<222> LOCATION: 1, 3, 5, 6, 8, 10, 12, 14, 16
<223> OTHER INFORMATION: 2'-fluoro nucleoside
<220> FEATURE:
<221> NAME/KEY: misc_feature
<222> LOCATION: 1-8, 9-10, 11-12, 13-20
<223> OTHER INFORMATION: phosphorothioate linkage

<400> SEQUENCE: 280
auggaugauu ugaugcuguc                          20

```
<210> SEQ ID NO 281
<211> LENGTH: 20
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 1, 3, 5, 7, 9, 11, 13, 15, 16, 18, 20
<223> OTHER INFORMATION: 2'-O-methyl nucleoside
<220> FEATURE:
<221> NAME/KEY: misc_feature
<222> LOCATION: 2, 4, 6, 8, 10, 12, 14, 17, 19
<223> OTHER INFORMATION: 2'-fluoro nucleoside
<220> FEATURE:
<221> NAME/KEY: misc_feature
<222> LOCATION: 1-6, 8-9, 12-13, 15-20
<223> OTHER INFORMATION: phosphorothioate linkage

<400> SEQUENCE: 281
gacagcauca aaucauccau                                            20

<210> SEQ ID NO 282
<211> LENGTH: 22
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 2, 4, 6, 8, 10, 12, 14, 16, 18, 20, 21, 22
<223> OTHER INFORMATION: 2'-O-methyl nucleoside
<220> FEATURE:
<221> NAME/KEY: misc_feature
<222> LOCATION: 1, 3, 5, 7, 9, 11, 13, 15, 17, 19
<223> OTHER INFORMATION: 2'-fluoro nucleoside
<220> FEATURE:
<221> NAME/KEY: misc_feature
<222> LOCATION: 1-8, 9-10, 12-13, 14-22
<223> OTHER INFORMATION: phosphorothioate linkage

<400> SEQUENCE: 282
gcaauggaug auuugaugcu gu                                         22

<210> SEQ ID NO 283
<211> LENGTH: 22
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 2, 4, 6, 8, 10, 12, 14, 16, 18, 20, 22
<223> OTHER INFORMATION: 2'-O-methyl nucleoside
<220> FEATURE:
<221> NAME/KEY: misc_feature
<222> LOCATION: 1, 3, 5, 7, 9, 11, 13, 15, 17, 19, 21
<223> OTHER INFORMATION: 2'-fluoro nucleoside
<220> FEATURE:
<221> NAME/KEY: misc_feature
<222> LOCATION: 1-6, 7-8, 13-14, 15-16, 17-22
<223> OTHER INFORMATION: phosphorothioate linkage

<400> SEQUENCE: 283
acagcaucaa aucauccauu gc                                         22

<210> SEQ ID NO 284
<211> LENGTH: 20
<212> TYPE: DNA
<213> ORGANISM: Artificial Sequence
<220> FEATURE:
<223> OTHER INFORMATION: Synthetic Sequence
<220> FEATURE:
```

```
<221> NAME/KEY: misc_feature
<222> LOCATION: 4, 7, 8, 10, 12, 14, 16, 18, 20
<223> OTHER INFORMATION: 2'-O-methyl nucleoside
<220> FEATURE:
<221> NAME/KEY: misc_feature
<222> LOCATION: 1, 3, 5, 7, 9, 11, 13, 15, 17, 19
<223> OTHER INFORMATION: 2'-fluoro nucleoside
<220> FEATURE:
<221> NAME/KEY: misc_feature
<222> LOCATION: 1-9, 10-11, 12-13, 14-20
<223> OTHER INFORMATION: phosphorothioate linkage

<400> SEQUENCE: 284
gcaauggaug auuugaugcu                                               20

<210> SEQ ID NO 285
<211> LENGTH: 20
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 2, 4, 6, 8, 10, 12, 14, 16, 18, 20
<223> OTHER INFORMATION: 2'-O-methyl nucleoside
<220> FEATURE:
<221> NAME/KEY: misc_feature
<222> LOCATION: 1, 3, 5, 7, 9, 11, 13, 15, 17, 19
<223> OTHER INFORMATION: 2'-fluoro nucleoside
<220> FEATURE:
<221> NAME/KEY: misc_feature
<222> LOCATION: 1-7, 11-12, 13-14, 15-20
<223> OTHER INFORMATION: phosphorothioate linkage

<400> SEQUENCE: 285
agcaucaaau cauccauugc                                               20

<210> SEQ ID NO 286
<211> LENGTH: 21
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 2, 4, 6, 8, 10, 12, 14, 16, 18, 20, 21
<223> OTHER INFORMATION: 2'-O-methyl nucleoside
<220> FEATURE:
<221> NAME/KEY: misc_feature
<222> LOCATION: 1
<223> OTHER INFORMATION: 2'-fluoro nucleoside
<220> FEATURE:
<221> NAME/KEY: misc_feature
<222> LOCATION: 1-8, 9-10, 13-14, 15-21
<223> OTHER INFORMATION: phosphorothioate linkage

<400> SEQUENCE: 286
gucaucacac ugaauaccaa u                                             21

<210> SEQ ID NO 287
<211> LENGTH: 21
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 1, 3, 5, 7, 9, 11, 13, 15, 17, 19, 20
<223> OTHER INFORMATION: 2'-O-methyl nucleoside
<220> FEATURE:
<221> NAME/KEY: misc_feature
<222> LOCATION: 1-7, 15-21
<223> OTHER INFORMATION: phosphorothioate linkage
```

<400> SEQUENCE: 287
auugguauuc agugugauga c    21

<210> SEQ ID NO 288
<211> LENGTH: 21
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 2, 4, 6, 8, 10, 12, 14, 16, 18, 20, 21
<223> OTHER INFORMATION: 2'-O-methyl nucleoside
<220> FEATURE:
<221> NAME/KEY: misc_feature
<222> LOCATION: 1, 3, 5, 7, 9, 11, 13, 15, 17, 19
<223> OTHER INFORMATION: 2'-fluoro nucleoside
<220> FEATURE:
<221> NAME/KEY: misc_feature
<222> LOCATION: 1-8, 9-10, 13-14, 15-21
<223> OTHER INFORMATION: phosphorothioate linkage

<400> SEQUENCE: 288
gucaucacac ugaauaccaa u    21

<210> SEQ ID NO 289
<211> LENGTH: 21
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 1, 3, 5, 7, 9, 11, 13, 15, 17, 19, 21
<223> OTHER INFORMATION: 2'-O-methyl nucleoside
<220> FEATURE:
<221> NAME/KEY: misc_feature
<222> LOCATION: 2, 4, 6, 8, 10, 12, 14, 16, 18, 20
<223> OTHER INFORMATION: 2'-fluoro nucleoside
<220> FEATURE:
<221> NAME/KEY: misc_feature
<222> LOCATION: 1-7, 15-21
<223> OTHER INFORMATION: phosphorothioate linkage

<400> SEQUENCE: 289
auugguauuc agugugauga c    21

<210> SEQ ID NO 290
<211> LENGTH: 21
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 21
<223> OTHER INFORMATION: 2'-O-methyl nucleoside
<220> FEATURE:
<221> NAME/KEY: misc_feature
<222> LOCATION: 1, 2, 4, 6, 8, 10, 12, 14, 16, 18, 20
<223> OTHER INFORMATION: 2'-fluoro nucleoside
<220> FEATURE:
<221> NAME/KEY: misc_feature
<222> LOCATION: 1-8, 9-10, 13-14, 15-21
<223> OTHER INFORMATION: phosphorothioate linkage

<400> SEQUENCE: 290
gucaucacac ugaauaccaa u    21

<210> SEQ ID NO 291

```
<211> LENGTH: 21
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 1, 21
<223> OTHER INFORMATION: 2'-O-methyl nucleoside
<220> FEATURE:
<221> NAME/KEY: misc_feature
<222> LOCATION: 3, 5, 7, 9, 11, 13, 15, 17, 19
<223> OTHER INFORMATION: 2'-fluoro nucleoside
<220> FEATURE:
<221> NAME/KEY: misc_feature
<222> LOCATION: 1-7, 15-21
<223> OTHER INFORMATION: phosphorothioate linkage

<400> SEQUENCE: 291
auugguauuc agugugauga c                                              21

<210> SEQ ID NO 292
<211> LENGTH: 21
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 2, 4, 6, 8, 10, 12, 14, 16, 18, 20, 21
<223> OTHER INFORMATION: 2'-O-methyl nucleoside
<220> FEATURE:
<221> NAME/KEY: misc_feature
<222> LOCATION: 1, 3, 5, 7, 9, 11, 13, 15, 17, 19
<223> OTHER INFORMATION: 2'-fluoro nucleoside
<220> FEATURE:
<221> NAME/KEY: misc_feature
<222> LOCATION: 1-8, 9-10, 13-14, 15-21
<223> OTHER INFORMATION: phosphorothioate linkage

<400> SEQUENCE: 292
gucaucacac ugaauaccaa u                                              21

<210> SEQ ID NO 293
<211> LENGTH: 21
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 1, 3, 5, 7, 9, 11, 13, 15, 17, 19, 21
<223> OTHER INFORMATION: 2'-O-methyl nucleoside
<220> FEATURE:
<221> NAME/KEY: misc_feature
<222> LOCATION: 2, 4, 6, 8, 10, 12, 14, 16, 18, 20
<223> OTHER INFORMATION: 2'-fluoro nucleoside
<220> FEATURE:
<221> NAME/KEY: misc_feature
<222> LOCATION: 1-7, 8-9, 13-14, 15-21
<223> OTHER INFORMATION: phosphorothioate linkage

<400> SEQUENCE: 293
auugguauuc agugugauga c                                              21

<210> SEQ ID NO 294
<211> LENGTH: 21
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
```

<222> LOCATION: 2, 4, 6, 8, 10, 12, 14, 16, 18, 20, 21
<223> OTHER INFORMATION: 2'-O-methyl nucleoside
<220> FEATURE:
<221> NAME/KEY: misc_feature
<222> LOCATION: 1, 3, 5, 7, 9, 11, 13, 15, 17, 19
<223> OTHER INFORMATION: 2'-fluoro nucleoside
<220> FEATURE:
<221> NAME/KEY: misc_feature
<222> LOCATION: 1-8, 9-10, 13-14, 15-21
<223> OTHER INFORMATION: phosphorothioate linkage

<400> SEQUENCE: 294
gucaucacac ugaauaccaa u                                              21

<210> SEQ ID NO 295
<211> LENGTH: 21
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 1, 3, 5, 7, 9, 11, 13, 15, 17, 19, 21
<223> OTHER INFORMATION: 2'-O-methyl nucleoside
<220> FEATURE:
<221> NAME/KEY: misc_feature
<222> LOCATION: 2, 4, 6, 8, 10, 12, 14, 16, 18, 20
<223> OTHER INFORMATION: 2'-fluoro nucleoside
<220> FEATURE:
<221> NAME/KEY: misc_feature
<222> LOCATION: 1-5, 6-7, 8-9, 12-13, 14-15, 16-21
<223> OTHER INFORMATION: phosphorothioate linkage

<400> SEQUENCE: 295
auugguauuc agugugauga c                                              21

<210> SEQ ID NO 296
<211> LENGTH: 20
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 2, 4, 6, 8, 10, 12, 14, 16, 18, 20
<223> OTHER INFORMATION: 2'-O-methyl nucleoside
<220> FEATURE:
<221> NAME/KEY: misc_feature
<222> LOCATION: 1
<223> OTHER INFORMATION: 2'-fluoro nucleoside
<220> FEATURE:
<221> NAME/KEY: misc_feature
<222> LOCATION: 1-8, 10-11, 13-20
<223> OTHER INFORMATION: phosphorothioate linkage

<400> SEQUENCE: 296
gguguauggc uucaacccug                                                20

<210> SEQ ID NO 297
<211> LENGTH: 20
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 1, 2, 4, 6, 8, 10, 12, 14, 16, 18, 20
<223> OTHER INFORMATION: 2'-O-methyl nucleoside
<220> FEATURE:
<221> NAME/KEY: misc_feature
<222> LOCATION: 1-6, 7-8, 13-14, 15-20
<223> OTHER INFORMATION: phosphorothioate linkage

```
<400> SEQUENCE: 297
caggguugaa gccauacacc                                              20

<210> SEQ ID NO 298
<211> LENGTH: 20
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 20
<223> OTHER INFORMATION: 2'-O-methyl nucleoside
<220> FEATURE:
<221> NAME/KEY: misc_feature
<222> LOCATION: 1, 2, 4, 6, 8, 10, 12, 14, 16, 18
<223> OTHER INFORMATION: 2'-fluoro nucleoside
<220> FEATURE:
<221> NAME/KEY: misc_feature
<222> LOCATION: 1-8, 10-11, 13-20
<223> OTHER INFORMATION: phosphorothioate linkage

<400> SEQUENCE: 298
gguguauggc uucaacccug                                              20

<210> SEQ ID NO 299
<211> LENGTH: 20
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 1, 20
<223> OTHER INFORMATION: 2'-O-methyl nucleoside
<220> FEATURE:
<221> NAME/KEY: misc_feature
<222> LOCATION: 2, 4, 6, 8, 10, 12, 14, 16, 18
<223> OTHER INFORMATION: 2'-fluoro nucleoside
<220> FEATURE:
<221> NAME/KEY: misc_feature
<222> LOCATION: 1-6, 7-8, 13-14, 15-20
<223> OTHER INFORMATION: phosphorothioate linkage

<400> SEQUENCE: 299
caggguugaa gccauacacc                                              20

<210> SEQ ID NO 300
<211> LENGTH: 20
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 3, 5, 7, 9, 11, 13, 15, 17, 19, 20
<223> OTHER INFORMATION: 2'-O-methyl nucleoside
<220> FEATURE:
<221> NAME/KEY: misc_feature
<222> LOCATION: 1, 2, 4, 6, 8, 10, 12, 14, 16, 18
<223> OTHER INFORMATION: 2'-fluoro nucleoside
<220> FEATURE:
<221> NAME/KEY: misc_feature
<222> LOCATION: 1-8, 10-11, 13-20
<223> OTHER INFORMATION: phosphorothioate linkage

<400> SEQUENCE: 300
gguguauggc uucaacccug                                              20

<210> SEQ ID NO 301
<211> LENGTH: 20
```

```
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 1, 3, 5, 7, 9, 11, 13, 15, 1, 19, 20
<223> OTHER INFORMATION: 2'-O-methyl nucleoside
<220> FEATURE:
<221> NAME/KEY: misc_feature
<222> LOCATION: 2, 4, 6, 8, 10, 12, 14, 16, 18
<223> OTHER INFORMATION: 2'-fluoro nucleoside
<220> FEATURE:
<221> NAME/KEY: misc_feature
<222> LOCATION: 1-6, 7-8, 13-14, 15-20
<223> OTHER INFORMATION: phosphorothioate linkage

<400> SEQUENCE: 301
caggguugaa gccauacacc                                              20

<210> SEQ ID NO 302
<211> LENGTH: 20
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 1, 3, 5, 7, 9, 11, 13, 15, 17, 19, 20
<223> OTHER INFORMATION: 2'-O-methyl nucleoside
<220> FEATURE:
<221> NAME/KEY: misc_feature
<222> LOCATION: 2, 4, 6, 8, 10, 12, 14, 16, 18
<223> OTHER INFORMATION: 2'-fluoro nucleoside
<220> FEATURE:
<221> NAME/KEY: misc_feature
<222> LOCATION: 1-8, 10-11, 13-20
<223> OTHER INFORMATION: phosphorothioate linkage

<400> SEQUENCE: 302
gguguauggc uucaacccug                                              20

<210> SEQ ID NO 303
<211> LENGTH: 20
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 1, 3, 5, 7, 9, 11, 13, 15, 17, 19, 20
<223> OTHER INFORMATION: 2'-O-methyl nucleoside
<220> FEATURE:
<221> NAME/KEY: misc_feature
<222> LOCATION: 2, 4, 6, 8, 10, 12, 14, 16, 18
<223> OTHER INFORMATION: 2'-fluoro nucleoside
<220> FEATURE:
<221> NAME/KEY: misc_feature
<222> LOCATION: 1-7, 8-9, 12-13, 14-20
<223> OTHER INFORMATION: phosphorothioate linkage

<400> SEQUENCE: 303
caggguugaa gccauacacc                                              20

<210> SEQ ID NO 304
<211> LENGTH: 20
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 3, 5, 7, 15, 19
```

-continued

```
<223> OTHER INFORMATION: 2'-O-methyl nucleoside
<220> FEATURE:
<221> NAME/KEY: misc_feature
<222> LOCATION: 1, 2, 4, 6, 8, 9, 10, 11, 12, 13, 14, 16, 17, 18, 20
<223> OTHER INFORMATION: 2'-fluoro nucleoside
<220> FEATURE:
<221> NAME/KEY: misc_feature
<222> LOCATION: 1-20
<223> OTHER INFORMATION: phosphorothioate linkage

<400> SEQUENCE: 304
gguguauggc uucaacccug                                                      20

<210> SEQ ID NO 305
<211> LENGTH: 20
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 1, 3, 5, 7, 9, 11, 13, 15, 17, 19, 20
<223> OTHER INFORMATION: 2'-O-methyl nucleoside
<220> FEATURE:
<221> NAME/KEY: misc_feature
<222> LOCATION: 2, 4, 6, 8, 10, 12, 14, 16, 18
<223> OTHER INFORMATION: 2'-fluoro nucleoside
<220> FEATURE:
<221> NAME/KEY: misc_feature
<222> LOCATION: 1-6, 7-8, 13-14, 15-20
<223> OTHER INFORMATION: phosphorothioate linkage

<400> SEQUENCE: 305
caggguugaa gccauacacc                                                      20

<210> SEQ ID NO 306
<211> LENGTH: 14
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 2, 4, 6, 8, 10, 12, 14
<223> OTHER INFORMATION: 2'-O-methyl nucleoside
<220> FEATURE:
<221> NAME/KEY: misc_feature
<222> LOCATION: 1, 3, 5, 7, 9, 11, 13
<223> OTHER INFORMATION: 2'-fluoro nucleoside
<220> FEATURE:
<221> NAME/KEY: misc_feature
<222> LOCATION: 1-14
<223> OTHER INFORMATION: phosphorothioate linkage

<400> SEQUENCE: 306
guauggcuuc aacc                                                            14

<210> SEQ ID NO 307
<211> LENGTH: 20
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 1, 3, 5, 7, 9, 11, 13, 15, 17, 19, 20
<223> OTHER INFORMATION: 2'-O-methyl nucleoside
<220> FEATURE:
<221> NAME/KEY: misc_feature
<222> LOCATION: 2, 4, 6, 8, 10, 12, 14, 16, 18
<223> OTHER INFORMATION: 2'-fluoro nucleoside
<220> FEATURE:
<221> NAME/KEY: misc_feature
```

```
<222> LOCATION: 1-6, 7-8, 13-14, 15-20
<223> OTHER INFORMATION: phosphorothioate linkage

<400> SEQUENCE: 307
caggguugaa gccauacacc                                               20

<210> SEQ ID NO 308
<211> LENGTH: 14
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 1, 2, 3, 4, 5, 6, 7, 8, 9, 10, 11, 12, 13, 14
<223> OTHER INFORMATION: 2'-fluoro nucleoside
<220> FEATURE:
<221> NAME/KEY: misc_feature
<222> LOCATION: 1-14
<223> OTHER INFORMATION: phosphorothioate linkage

<400> SEQUENCE: 308
guauggcuuc aacc                                                     14

<210> SEQ ID NO 309
<211> LENGTH: 20
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 1, 3, 5, 7, 9, 11, 13, 15, 17, 19, 20
<223> OTHER INFORMATION: 2'-O-methyl nucleoside
<220> FEATURE:
<221> NAME/KEY: misc_feature
<222> LOCATION: 2, 4, 6, 8, 10, 12, 14, 16, 18
<223> OTHER INFORMATION: 2'-fluoro nucleoside
<220> FEATURE:
<221> NAME/KEY: misc_feature
<222> LOCATION: 1-6, 7-8, 13-14, 15-20
<223> OTHER INFORMATION: phosphorothioate linkage

<400> SEQUENCE: 309
caggguugaa gccauacacc                                               20

<210> SEQ ID NO 310
<211> LENGTH: 19
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 2, 4, 5, 7, 9, 11, 12, 14, 16, 18, 19
<223> OTHER INFORMATION: 2'-O-methyl nucleoside
<220> FEATURE:
<221> NAME/KEY: misc_feature
<222> LOCATION: 1, 3, 6, 8, 10, 13, 15, 17
<223> OTHER INFORMATION: 2'-fluoro nucleoside
<220> FEATURE:
<221> NAME/KEY: misc_feature
<222> LOCATION: 1-8, 9-10, 11-12, 13-19
<223> OTHER INFORMATION: phosphorothioate linkage

<400> SEQUENCE: 310
ggaagaaaaa ggaagcccc                                                19

<210> SEQ ID NO 311
<211> LENGTH: 19
<212> TYPE: DNA
```

```
<213> ORGANISM: Artificial Sequence
<220> FEATURE:
<221> NAME/KEY: modified_base
<222> LOCATION: 2-3
<223> OTHER INFORMATION: n = I
<220> FEATURE:
<223> OTHER INFORMATION: Synthetic Sequence
<220> FEATURE:
<221> NAME/KEY: misc_feature
<222> LOCATION: 1, 2, 3, 5, 7, 9, 10, 12, 14, 17, 19
<223> OTHER INFORMATION: 2'-O-methyl nucleoside
<220> FEATURE:
<221> NAME/KEY: misc_feature
<222> LOCATION: 4, 6, 8, 11, 13, 15, 16, 18
<223> OTHER INFORMATION: 2'-fluoro nucleoside
<220> FEATURE:
<221> NAME/KEY: misc_feature
<222> LOCATION: 1-6, 14-19
<223> OTHER INFORMATION: phosphorothioate linkage

<400> SEQUENCE: 311
gnngcuuccu uuucuucc                                                   19

<210> SEQ ID NO 312
<211> LENGTH: 19
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 2, 4, 5, 7, 9, 11, 12, 14, 16, 18, 19
<223> OTHER INFORMATION: 2'-O-methyl nucleoside
<220> FEATURE:
<221> NAME/KEY: misc_feature
<222> LOCATION: 1, 3, 6, 8, 10, 13, 15, 17
<223> OTHER INFORMATION: 2'-fluoro nucleoside
<220> FEATURE:
<221> NAME/KEY: misc_feature
<222> LOCATION: 1-8, 9-10, 11-12, 13-19
<223> OTHER INFORMATION: phosphorothioate linkage

<400> SEQUENCE: 312
ggaagaaaaa ggaagcccc                                                  19

<210> SEQ ID NO 313
<211> LENGTH: 19
<212> TYPE: DNA
<213> ORGANISM: Artificial Sequence
<220> FEATURE:
<221> NAME/KEY: modified_base
<222> LOCATION: 2-3
<223> OTHER INFORMATION: n = I
<220> FEATURE:
<223> OTHER INFORMATION: Synthetic Sequence
<220> FEATURE:
<221> NAME/KEY: misc_feature
<222> LOCATION: 1, 2, 3, 5, 7, 9, 10, 12, 14, 17, 19
<223> OTHER INFORMATION: 2'-O-methyl nucleoside
<220> FEATURE:
<221> NAME/KEY: misc_feature
<222> LOCATION: 4, 6, 8, 11, 13, 15, 16, 18
<223> OTHER INFORMATION: 2'-fluoro nucleoside
<220> FEATURE:
<221> NAME/KEY: misc_feature
<222> LOCATION: 1-5, 7-8, 12-13, 14-19
<223> OTHER INFORMATION: phosphorothioate linkage

<400> SEQUENCE: 313
gnngcuuccu uuucuucc                                                   19

<210> SEQ ID NO 314
<211> LENGTH: 19
```

```
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 2, 4, 5, 7, 9, 12, 14, 16, 19
<223> OTHER INFORMATION: 2'-O-methyl nucleoside
<220> FEATURE:
<221> NAME/KEY: misc_feature
<222> LOCATION: 1, 3, 6, 8, 10, 11, 13, 15, 17, 18
<223> OTHER INFORMATION: 2'-fluoro nucleoside
<220> FEATURE:
<221> NAME/KEY: misc_feature
<222> LOCATION: 1-19
<223> OTHER INFORMATION: phosphorothioate linkage

<400> SEQUENCE: 314
ggaagaaaaa ggaagcccc                                          19

<210> SEQ ID NO 315
<211> LENGTH: 19
<212> TYPE: DNA
<213> ORGANISM: Artificial Sequence
<220> FEATURE:
<221> NAME/KEY: modified_base
<222> LOCATION: 3
<223> OTHER INFORMATION: n = I
<220> FEATURE:
<223> OTHER INFORMATION: Synthetic Sequence
<220> FEATURE:
<221> NAME/KEY: misc_feature
<222> LOCATION: 2, 3, 5, 7, 9, 12, 14, 17, 19
<223> OTHER INFORMATION: 2'-O-methyl nucleoside
<220> FEATURE:
<221> NAME/KEY: misc_feature
<222> LOCATION: 1, 4, 6, 8, 11, 13, 15, 16, 18
<223> OTHER INFORMATION: 2'-fluoro nucleoside
<220> FEATURE:
<221> NAME/KEY: misc_feature
<222> LOCATION: 1-5, 7-8, 12-13, 14-19
<223> OTHER INFORMATION: phosphorothioate linkage

<400> SEQUENCE: 315
ggngcuuccu uuucuucc                                           19

<210> SEQ ID NO 316
<211> LENGTH: 21
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 2, 4, 5, 7, 9, 11, 12, 14, 16, 18, 21
<223> OTHER INFORMATION: 2'-O-methyl nucleoside
<220> FEATURE:
<221> NAME/KEY: misc_feature
<222> LOCATION: 1, 3, 6, 8, 10, 13, 15, 17, 19, 20
<223> OTHER INFORMATION: 2'-fluoro nucleoside
<220> FEATURE:
<221> NAME/KEY: misc_feature
<222> LOCATION: 1-12, 13-21
<223> OTHER INFORMATION: phosphorothioate linkage

<400> SEQUENCE: 316
ggaagaaaaa ggaagccccu u                                       21

<210> SEQ ID NO 317
<211> LENGTH: 21
<212> TYPE: DNA
<213> ORGANISM: Artificial Sequence
<220> FEATURE:
```

```
<221> NAME/KEY: modified_base
<222> LOCATION: 5
<223> OTHER INFORMATION: n = I
<220> FEATURE:
<223> OTHER INFORMATION: Synthetic Sequence
<220> FEATURE:
<221> NAME/KEY: misc_feature
<222> LOCATION: 2, 5, 6, 8, 12, 14, 16, 19, 21
<223> OTHER INFORMATION: 2'-O-methyl nucleoside
<220> FEATURE:
<221> NAME/KEY: misc_feature
<222> LOCATION: 1, 3, 4, 7, 9, 11, 13, 15, 17, 18, 20
<223> OTHER INFORMATION: 2'-fluoro nucleoside
<220> FEATURE:
<221> NAME/KEY: misc_feature
<222> LOCATION: 1-6, 7-8, 12-13, 15-21
<223> OTHER INFORMATION: phosphorothioate linkage

<400> SEQUENCE: 317
aaggngcuuc cuuuuucuuc c                                            21

<210> SEQ ID NO 318
<211> LENGTH: 21
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 2, 3, 5, 7, 9, 11, 12, 14, 16, 19, 21
<223> OTHER INFORMATION: 2'-O-methyl nucleoside
<220> FEATURE:
<221> NAME/KEY: misc_feature
<222> LOCATION: 1, 4, 6, 8, 10, 13, 15, 17, 18, 20
<223> OTHER INFORMATION: 2'-fluoro nucleoside
<220> FEATURE:
<221> NAME/KEY: misc_feature
<222> LOCATION: 1-9, 10-11, 13-14, 15-21
<223> OTHER INFORMATION: phosphorothioate linkage

<400> SEQUENCE: 318
ggaagaaaaa ggaagccccu u                                            21

<210> SEQ ID NO 319
<211> LENGTH: 21
<212> TYPE: DNA
<213> ORGANISM: Artificial Sequence
<220> FEATURE:
<221> NAME/KEY: modified_base
<222> LOCATION: 5
<223> OTHER INFORMATION: n = I
<220> FEATURE:
<223> OTHER INFORMATION: Synthetic Sequence
<220> FEATURE:
<221> NAME/KEY: misc_feature
<222> LOCATION: 2, 4, 5, 7, 9, 12, 14, 16, 18, 21
<223> OTHER INFORMATION: 2'-O-methyl nucleoside
<220> FEATURE:
<221> NAME/KEY: misc_feature
<222> LOCATION: 1, 3, 6, 8, 11, 13, 15, 17, 19, 20
<223> OTHER INFORMATION: 2'-fluoro nucleoside
<220> FEATURE:
<221> NAME/KEY: misc_feature
<222> LOCATION: 1-6, 7-8, 12-13, 15-21
<223> OTHER INFORMATION: phosphorothioate linkage

<400> SEQUENCE: 319
aaggngcuuc cuuuuucuuc c                                            21

<210> SEQ ID NO 320
<211> LENGTH: 20
<212> TYPE: DNA
<213> ORGANISM: Artificial Sequence
```

```
<220> FEATURE:
<223> OTHER INFORMATION: Synthetic Sequence
<220> FEATURE:
<221> NAME/KEY: misc_feature
<222> LOCATION: 2, 4, 6, 8, 10, 12, 14, 16, 18, 19, 20
<223> OTHER INFORMATION: 2'-O-methyl nucleoside
<220> FEATURE:
<221> NAME/KEY: misc_feature
<222> LOCATION: 1, 3, 5, 7, 9, 11, 13, 15, 17
<223> OTHER INFORMATION: 2'-fluoro nucleoside
<220> FEATURE:
<221> NAME/KEY: misc_feature
<222> LOCATION: 1-8, 9-10, 11-12, 13-20
<223> OTHER INFORMATION: phosphorothioate linkage

<400> SEQUENCE: 320
ggugucuucc agauccugcu                                                       20

<210> SEQ ID NO 321
<211> LENGTH: 20
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 2, 4, 6, 8, 10, 12, 14, 16, 18, 20
<223> OTHER INFORMATION: 2'-O-methyl nucleoside
<220> FEATURE:
<221> NAME/KEY: misc_feature
<222> LOCATION: 1, 3, 5, 7, 9, 11, 13, 15, 17, 19
<223> OTHER INFORMATION: 2'-fluoro nucleoside
<220> FEATURE:
<221> NAME/KEY: misc_feature
<222> LOCATION: 1-6, 15-20
<223> OTHER INFORMATION: phosphorothioate linkage

<400> SEQUENCE: 321
agcaggaucu ggaagacacc                                                       20

<210> SEQ ID NO 322
<211> LENGTH: 20
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 2, 4, 6, 8, 10, 12, 14, 16, 18, 19, 20
<223> OTHER INFORMATION: 2'-O-methyl nucleoside
<220> FEATURE:
<221> NAME/KEY: misc_feature
<222> LOCATION: 1, 3, 5, 7, 9, 11, 13, 15, 17
<223> OTHER INFORMATION: 2'-fluoro nucleoside
<220> FEATURE:
<221> NAME/KEY: misc_feature
<222> LOCATION: 1-8, 10-11, 13-20
<223> OTHER INFORMATION: phosphorothioate linkage

<400> SEQUENCE: 322
ggugucuucc agauccugcu                                                       20

<210> SEQ ID NO 323
<211> LENGTH: 20
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 2, 4, 6, 8, 10, 12, 14, 16, 18, 20
<223> OTHER INFORMATION: 2'-O-methyl nucleoside
<220> FEATURE:
```

```
<221> NAME/KEY: misc_feature
<222> LOCATION: 1, 3, 5, 7, 9, 11, 13, 15, 17, 19
<223> OTHER INFORMATION: 2'-fluoro nucleoside
<220> FEATURE:
<221> NAME/KEY: misc_feature
<222> LOCATION: 1-6, 7-8, 13-14, 15-20
<223> OTHER INFORMATION: phosphorothioate linkage

<400> SEQUENCE: 323
agcaggaucu ggaagacacc                                               20

<210> SEQ ID NO 324
<211> LENGTH: 20
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 2, 4, 6, 8, 10, 12, 14, 16, 18, 19, 20
<223> OTHER INFORMATION: 2'-O-methyl nucleoside
<220> FEATURE:
<221> NAME/KEY: misc_feature
<222> LOCATION: 1, 3, 5, 7, 9, 11, 13, 15, 17
<223> OTHER INFORMATION: 2'-fluoro nucleoside
<220> FEATURE:
<221> NAME/KEY: misc_feature
<222> LOCATION: 1-8, 10-11, 13-20
<223> OTHER INFORMATION: phosphorothioate linkage

<400> SEQUENCE: 324
ggugucuucc agauccugcu                                               20

<210> SEQ ID NO 325
<211> LENGTH: 20
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 2, 4, 6, 8, 10, 12, 14, 16, 18, 20
<223> OTHER INFORMATION: 2'-O-methyl nucleoside
<220> FEATURE:
<221> NAME/KEY: misc_feature
<222> LOCATION: 1, 3, 5, 7, 9, 11, 13, 15, 17, 19
<223> OTHER INFORMATION: 2'-fluoro nucleoside
<220> FEATURE:
<221> NAME/KEY: misc_feature
<222> LOCATION: 1-6, 7-8, 13-14, 15-20
<223> OTHER INFORMATION: phosphorothioate linkage

<400> SEQUENCE: 325
agcaggaucu ggaagacacc                                               20

<210> SEQ ID NO 326
<211> LENGTH: 20
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 2, 4, 6, 10, 16, 18, 20
<223> OTHER INFORMATION: 2'-O-methyl nucleoside
<220> FEATURE:
<221> NAME/KEY: misc_feature
<222> LOCATION: 1, 3, 5, 7, 8, 9, 11, 12, 13, 14, 15, 17, 19
<223> OTHER INFORMATION: 2'-fluoro nucleoside
<220> FEATURE:
<221> NAME/KEY: misc_feature
<222> LOCATION: 1-20
<223> OTHER INFORMATION: phosphorothioate linkage
```

```
<400> SEQUENCE: 326
ggugucuucc agauccugcu                                              20

<210> SEQ ID NO 327
<211> LENGTH: 20
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 2, 4, 6, 8, 10, 12, 14, 16, 18, 20
<223> OTHER INFORMATION: 2'-O-methyl nucleoside
<220> FEATURE:
<221> NAME/KEY: misc_feature
<222> LOCATION: 1, 3, 5, 7, 9, 11, 13, 15, 17, 19
<223> OTHER INFORMATION: 2'-fluoro nucleoside
<220> FEATURE:
<221> NAME/KEY: misc_feature
<222> LOCATION: 1-6, 7-8, 13-14, 15-20
<223> OTHER INFORMATION: phosphorothioate linkage

<400> SEQUENCE: 327
agcaggaucu ggaagacacc                                              20

<210> SEQ ID NO 328
<211> LENGTH: 19
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 4, 6, 8, 10, 12, 14, 16, 18, 19
<223> OTHER INFORMATION: 2'-O-methyl nucleoside
<220> FEATURE:
<221> NAME/KEY: misc_feature
<222> LOCATION: 1, 2, 3, 5, 7, 9, 11, 13, 15, 17
<223> OTHER INFORMATION: 2'-fluoro nucleoside
<220> FEATURE:
<221> NAME/KEY: misc_feature
<222> LOCATION: 1-8, 10-11, 13-19
<223> OTHER INFORMATION: phosphorothioate linkage

<400> SEQUENCE: 328
ggugucuucc agauccugc                                               19

<210> SEQ ID NO 329
<211> LENGTH: 19
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 1, 2, 3, 4, 6, 8, 10, 12, 14, 19
<223> OTHER INFORMATION: 2'-O-methyl nucleoside
<220> FEATURE:
<221> NAME/KEY: misc_feature
<222> LOCATION: 5, 7, 9, 11, 13, 15, 16, 17, 18
<223> OTHER INFORMATION: 2'-fluoro nucleoside
<220> FEATURE:
<221> NAME/KEY: misc_feature
<222> LOCATION: 1-6, 7-8, 12-13, 14-19
<223> OTHER INFORMATION: phosphorothioate linkage

<400> SEQUENCE: 329
gcaggaucug gaagacacc                                               19

<210> SEQ ID NO 330
```

-continued

```
<211> LENGTH: 17
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 4, 6, 8, 10, 12, 14, 15, 16, 17
<223> OTHER INFORMATION: 2'-O-methyl nucleoside
<220> FEATURE:
<221> NAME/KEY: misc_feature
<222> LOCATION: 1, 2, 3, 5, 7, 9, 11, 13
<223> OTHER INFORMATION: 2'-fluoro nucleoside
<220> FEATURE:
<221> NAME/KEY: misc_feature
<222> LOCATION: 1-8, 10-17
<223> OTHER INFORMATION: phosphorothioate linkage

<400> SEQUENCE: 330
ggugucuucc agauccu                                                  17

<210> SEQ ID NO 331
<211> LENGTH: 17
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 1, 2, 4, 6, 8, 10, 12, 17
<223> OTHER INFORMATION: 2'-O-methyl nucleoside
<220> FEATURE:
<221> NAME/KEY: misc_feature
<222> LOCATION: 3, 5, 7, 9, 11, 13, 14, 15, 16
<223> OTHER INFORMATION: 2'-fluoro nucleoside
<220> FEATURE:
<221> NAME/KEY: misc_feature
<222> LOCATION: 1-7, 12-17
<223> OTHER INFORMATION: phosphorothioate linkage

<400> SEQUENCE: 331
aggaucugga agacacc                                                  17

<210> SEQ ID NO 332
<211> LENGTH: 19
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 2, 5, 7, 9, 11, 13, 15, 17, 19
<223> OTHER INFORMATION: 2'-O-methyl nucleoside
<220> FEATURE:
<221> NAME/KEY: misc_feature
<222> LOCATION: 1, 3, 4, 6, 8, 10, 12, 14, 16, 18
<223> OTHER INFORMATION: 2'-fluoro nucleoside
<220> FEATURE:
<221> NAME/KEY: misc_feature
<222> LOCATION: 1-9, 11-19
<223> OTHER INFORMATION: phosphorothioate linkage

<400> SEQUENCE: 332
ggcuggacaa gcugugcau                                                19

<210> SEQ ID NO 333
<211> LENGTH: 19
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
```

<222> LOCATION: 2, 4, 6, 8, 10, 12, 14, 16, 19
<223> OTHER INFORMATION: 2'-O-methyl nucleoside
<220> FEATURE:
<221> NAME/KEY: misc_feature
<222> LOCATION: 1, 3, 5, 7, 9, 11, 13, 15, 17, 18
<223> OTHER INFORMATION: 2'-fluoro nucleoside
<220> FEATURE:
<221> NAME/KEY: misc_feature
<222> LOCATION: 1-6, 14-19
<223> OTHER INFORMATION: phosphorothioate linkage

<400> SEQUENCE: 333
augcacagcu uguccagcc                                            19

<210> SEQ ID NO 334
<211> LENGTH: 19
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 2, 5, 7, 9, 11, 13, 15, 17, 19
<223> OTHER INFORMATION: 2'-O-methyl nucleoside
<220> FEATURE:
<221> NAME/KEY: misc_feature
<222> LOCATION: 1, 3, 4, 6, 8, 10, 12, 14, 16, 18
<223> OTHER INFORMATION: 2'-fluoro nucleoside
<220> FEATURE:
<221> NAME/KEY: misc_feature
<222> LOCATION: 1-8, 10-11, 12-19
<223> OTHER INFORMATION: phosphorothioate linkage

<400> SEQUENCE: 334
ggcuggacaa gcugugcau                                            19

<210> SEQ ID NO 335
<211> LENGTH: 19
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 2, 4, 6, 8, 10, 12, 14, 16, 19
<223> OTHER INFORMATION: 2'-O-methyl nucleoside
<220> FEATURE:
<221> NAME/KEY: misc_feature
<222> LOCATION: 1, 3, 5, 7, 9, 11, 13, 15, 17, 18
<223> OTHER INFORMATION: 2'-fluoro nucleoside
<220> FEATURE:
<221> NAME/KEY: misc_feature
<222> LOCATION: 1-6, 7-8, 12-13, 14-19
<223> OTHER INFORMATION: phosphorothioate linkage

<400> SEQUENCE: 335
augcacagcu uguccagcc                                            19

<210> SEQ ID NO 336
<211> LENGTH: 19
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 2, 5, 7, 9, 11, 13, 15, 17, 19
<223> OTHER INFORMATION: 2'-O-methyl nucleoside
<220> FEATURE:
<221> NAME/KEY: misc_feature
<222> LOCATION: 1, 3, 4, 6, 8, 10, 12, 14, 16, 18
<223> OTHER INFORMATION: 2'-fluoro nucleoside
<220> FEATURE:

```
<221> NAME/KEY: misc_feature
<222> LOCATION: 1-8, 10-11, 12-19
<223> OTHER INFORMATION: phosphorothioate linkage

<400> SEQUENCE: 336
ggcuggacaa gcugugcau                                              19

<210> SEQ ID NO 337
<211> LENGTH: 19
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 2, 4, 6, 8, 10, 12, 14, 16, 19
<223> OTHER INFORMATION: 2'-O-methyl nucleoside
<220> FEATURE:
<221> NAME/KEY: misc_feature
<222> LOCATION: 1, 3, 5, 7, 9, 11, 13, 15, 17, 18
<223> OTHER INFORMATION: 2'-fluoro nucleoside
<220> FEATURE:
<221> NAME/KEY: misc_feature
<222> LOCATION: 1-6, 7-8, 12-13, 14-19
<223> OTHER INFORMATION: phosphorothioate linkage

<400> SEQUENCE: 337
augcacagcu uguccagcc                                              19

<210> SEQ ID NO 338
<211> LENGTH: 15
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 3, 5, 7, 9, 11, 13, 15
<223> OTHER INFORMATION: 2'-O-methyl nucleoside
<220> FEATURE:
<221> NAME/KEY: misc_feature
<222> LOCATION: 1, 2, 4, 6, 8, 10, 12, 14
<223> OTHER INFORMATION: 2'-fluoro nucleoside
<220> FEATURE:
<221> NAME/KEY: misc_feature
<222> LOCATION: 1-7, 8-15
<223> OTHER INFORMATION: phosphorothioate linkage

<400> SEQUENCE: 338
cuggacaagc ugugc                                                  15

<210> SEQ ID NO 339
<211> LENGTH: 19
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 2, 4, 6, 8, 10, 12, 14, 16, 19
<223> OTHER INFORMATION: 2'-O-methyl nucleoside
<220> FEATURE:
<221> NAME/KEY: misc_feature
<222> LOCATION: 1, 3, 5, 7, 9, 11, 13, 15, 17, 18
<223> OTHER INFORMATION: 2'-fluoro nucleoside
<220> FEATURE:
<221> NAME/KEY: misc_feature
<222> LOCATION: 1-6, 7-8, 12-13, 14-19
<223> OTHER INFORMATION: phosphorothioate linkage

<400> SEQUENCE: 339
augcacagcu uguccagcc                                              19
```

<210> SEQ ID NO 340
<211> LENGTH: 19
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 2, 5, 7, 9, 11, 13, 15, 17, 19
<223> OTHER INFORMATION: 2'-O-methyl nucleoside
<220> FEATURE:
<221> NAME/KEY: misc_feature
<222> LOCATION: 1, 3, 4, 6, 8, 10, 12, 14, 16, 18
<223> OTHER INFORMATION: 2'-fluoro nucleoside
<220> FEATURE:
<221> NAME/KEY: misc_feature
<222> LOCATION: 1-19
<223> OTHER INFORMATION: phosphorothioate linkage

<400> SEQUENCE: 340
ggcuggacaa gcugugcau                                                   19

<210> SEQ ID NO 341
<211> LENGTH: 19
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 2, 4, 6, 8, 10, 12, 14, 16, 19
<223> OTHER INFORMATION: 2'-O-methyl nucleoside
<220> FEATURE:
<221> NAME/KEY: misc_feature
<222> LOCATION: 1, 3, 5, 7, 9, 11, 13, 15, 17, 18
<223> OTHER INFORMATION: 2'-fluoro nucleoside
<220> FEATURE:
<221> NAME/KEY: misc_feature
<222> LOCATION: 1-6, 7-8, 12-13, 14-19
<223> OTHER INFORMATION: phosphorothioate linkage

<400> SEQUENCE: 341
augcacagcu uguccagcc                                                   19

<210> SEQ ID NO 342
<211> LENGTH: 19
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 4, 7, 9, 13, 19
<223> OTHER INFORMATION: 2'-O-methyl nucleoside
<220> FEATURE:
<221> NAME/KEY: misc_feature
<222> LOCATION: 1, 2, 3, 5, 6, 8, 10, 11, 12, 14, 15, 16, 17, 18
<223> OTHER INFORMATION: 2'-fluoro nucleoside
<220> FEATURE:
<221> NAME/KEY: misc_feature
<222> LOCATION: 1-19
<223> OTHER INFORMATION: phosphorothioate linkage

<400> SEQUENCE: 342
ggcuggacaa gcugugcau                                                   19

<210> SEQ ID NO 343
<211> LENGTH: 19
<212> TYPE: DNA
<213> ORGANISM: Artificial Sequence
<220> FEATURE:

```
<223> OTHER INFORMATION: Synthetic Sequence
<220> FEATURE:
<221> NAME/KEY: misc_feature
<222> LOCATION: 2, 4, 6, 8, 10, 12, 14, 19
<223> OTHER INFORMATION: 2'-O-methyl nucleoside
<220> FEATURE:
<221> NAME/KEY: misc_feature
<222> LOCATION: 1, 3, 5, 7, 9, 11, 13, 15, 16, 17, 18
<223> OTHER INFORMATION: 2'-fluoro nucleoside
<220> FEATURE:
<221> NAME/KEY: misc_feature
<222> LOCATION: 1-6, 7-8, 12-13, 14-19
<223> OTHER INFORMATION: phosphorothioate linkage

<400> SEQUENCE: 343
augcacagcu uguccagcc                                              19

<210> SEQ ID NO 344
<211> LENGTH: 19
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 2, 4, 6, 8, 10, 12, 14, 16, 19
<223> OTHER INFORMATION: 2'-O-methyl nucleoside
<220> FEATURE:
<221> NAME/KEY: misc_feature
<222> LOCATION: 1, 3, 5, 7, 9, 11, 13, 15, 17, 18
<223> OTHER INFORMATION: 2'-fluoro nucleoside
<220> FEATURE:
<221> NAME/KEY: misc_feature
<222> LOCATION: 1-8, 10-11, 12-19
<223> OTHER INFORMATION: phosphorothioate linkage

<400> SEQUENCE: 344
ggagcuuccu gauucaaaa                                              19

<210> SEQ ID NO 345
<211> LENGTH: 19
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 2, 4, 7, 9, 11, 13, 15, 17, 18, 19, 20
<223> OTHER INFORMATION: 2'-O-methyl nucleoside
<220> FEATURE:
<221> NAME/KEY: misc_feature
<222> LOCATION: 1, 3, 4, 6, 8, 10, 12, 14, 16, 18
<223> OTHER INFORMATION: 2'-fluoro nucleoside
<220> FEATURE:
<221> NAME/KEY: misc_feature
<222> LOCATION: 1-6, 14-19
<223> OTHER INFORMATION: phosphorothioate linkage

<400> SEQUENCE: 345
uuuugaauca ggaagcucc                                              19

<210> SEQ ID NO 346
<211> LENGTH: 19
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 2, 4, 6, 8, 10, 12, 14, 16, 19
<223> OTHER INFORMATION: 2'-O-methyl nucleoside
<220> FEATURE:
<221> NAME/KEY: misc_feature
```

```
<222> LOCATION: 1, 3, 5, 7, 9, 11, 13, 15, 17, 18
<223> OTHER INFORMATION: 2'-fluoro nucleoside
<220> FEATURE:
<221> NAME/KEY: misc_feature
<222> LOCATION: 1-7, 9-10, 11-19
<223> OTHER INFORMATION: phosphorothioate linkage

<400> SEQUENCE: 346
ggagcuuccu gauucaaaa                                                19

<210> SEQ ID NO 347
<211> LENGTH: 19
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 2, 5, 7, 9, 11, 13, 15, 17, 19
<223> OTHER INFORMATION: 2'-O-methyl nucleoside
<220> FEATURE:
<221> NAME/KEY: misc_feature
<222> LOCATION: 1, 3, 4, 6, 8, 10, 12, 14, 16, 18
<223> OTHER INFORMATION: 2'-fluoro nucleoside
<220> FEATURE:
<221> NAME/KEY: misc_feature
<222> LOCATION: 1-6, 7-8, 12-13, 14-19
<223> OTHER INFORMATION: phosphorothioate linkage

<400> SEQUENCE: 347
uuuugaauca ggaagcucc                                                19

<210> SEQ ID NO 348
<211> LENGTH: 19
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 2, 4, 6, 8, 10, 12, 14, 16, 19
<223> OTHER INFORMATION: 2'-O-methyl nucleoside
<220> FEATURE:
<221> NAME/KEY: misc_feature
<222> LOCATION: 1, 3, 5, 7, 9, 11, 13, 15, 17, 18
<223> OTHER INFORMATION: 2'-fluoro nucleoside
<220> FEATURE:
<221> NAME/KEY: misc_feature
<222> LOCATION: 1-7, 9-10, 11-19
<223> OTHER INFORMATION: phosphorothioate linkage

<400> SEQUENCE: 348
ggagcuuccu gauucaaaa                                                19

<210> SEQ ID NO 349
<211> LENGTH: 19
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 2, 5, 7, 9, 11, 13, 15, 17, 19
<223> OTHER INFORMATION: 2'-O-methyl nucleoside
<220> FEATURE:
<221> NAME/KEY: misc_feature
<222> LOCATION: 1, 3, 4, 6, 8, 10, 12, 14, 16, 18
<223> OTHER INFORMATION: 2'-fluoro nucleoside
<220> FEATURE:
<221> NAME/KEY: misc_feature
<222> LOCATION: 1-5, 7-8, 13-14, 15-19
<223> OTHER INFORMATION: phosphorothioate linkage
```

<400> SEQUENCE: 349
uuuugaauca ggaagcucc                                                    19

<210> SEQ ID NO 350
<211> LENGTH: 17
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 2, 4, 6, 8, 10, 12, 14, 16, 17
<223> OTHER INFORMATION: 2'-O-methyl nucleoside
<220> FEATURE:
<221> NAME/KEY: misc_feature
<222> LOCATION: 1, 3, 5, 7, 9, 11, 13, 15
<223> OTHER INFORMATION: 2'-fluoro nucleoside
<220> FEATURE:
<221> NAME/KEY: misc_feature
<222> LOCATION: 1-7, 9-10, 11-17
<223> OTHER INFORMATION: phosphorothioate linkage

<400> SEQUENCE: 350
ggagcuuccu gauucaa                                                      17

<210> SEQ ID NO 351
<211> LENGTH: 17
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 3, 5, 7, 9, 11, 13, 15, 17
<223> OTHER INFORMATION: 2'-O-methyl nucleoside
<220> FEATURE:
<221> NAME/KEY: misc_feature
<222> LOCATION: 1, 2, 4, 6, 8, 10, 12, 14, 16
<223> OTHER INFORMATION: 2'-fluoro nucleoside
<220> FEATURE:
<221> NAME/KEY: misc_feature
<222> LOCATION: 1-6, 7-8, 12-17
<223> OTHER INFORMATION: phosphorothioate linkage

<400> SEQUENCE: 351
uugaaucagg aagcucc                                                      17

<210> SEQ ID NO 352
<211> LENGTH: 19
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 2, 6, 9, 12, 14, 19
<223> OTHER INFORMATION: 2'-O-methyl nucleoside
<220> FEATURE:
<221> NAME/KEY: misc_feature
<222> LOCATION: 1, 3, 4, 5, 7, 8, 10, 11, 13, 15, 16, 17, 18
<223> OTHER INFORMATION: 2'-fluoro nucleoside
<220> FEATURE:
<221> NAME/KEY: misc_feature
<222> LOCATION: 1-19
<223> OTHER INFORMATION: phosphorothioate linkage

<400> SEQUENCE: 352
ggagcuuccu gauucaaaa                                                    19

<210> SEQ ID NO 353
<211> LENGTH: 19

```
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 2, 5, 8, 10, 12, 15, 17, 19
<223> OTHER INFORMATION: 2'-O-methyl nucleoside
<220> FEATURE:
<221> NAME/KEY: misc_feature
<222> LOCATION: 1, 3, 4, 6, 7, 9, 11, 13, 14, 16, 18
<223> OTHER INFORMATION: 2'-fluoro nucleoside
<220> FEATURE:
<221> NAME/KEY: misc_feature
<222> LOCATION: 1-5, 7-8, 13-14, 15-19
<223> OTHER INFORMATION: phosphorothioate linkage

<400> SEQUENCE: 353
uuuugaauca ggaagcucc                                            19

<210> SEQ ID NO 354
<211> LENGTH: 21
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 2, 4, 6, 8, 10, 12, 14, 16, 19, 21
<223> OTHER INFORMATION: 2'-O-methyl nucleoside
<220> FEATURE:
<221> NAME/KEY: misc_feature
<222> LOCATION: 1, 3, 5, 7, 9, 11, 13, 15, 17, 18, 20
<223> OTHER INFORMATION: 2'-fluoro nucleoside
<220> FEATURE:
<221> NAME/KEY: misc_feature
<222> LOCATION: 1-9, 11-12, 13-21
<223> OTHER INFORMATION: phosphorothioate linkage

<400> SEQUENCE: 354
ccgcattgcc tctgaattca a                                         21

<210> SEQ ID NO 355
<211> LENGTH: 21
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 2, 5, 7, 9, 13, 15, 17, 19, 21
<223> OTHER INFORMATION: 2'-O-methyl nucleoside
<220> FEATURE:
<221> NAME/KEY: misc_feature
<222> LOCATION: 1, 3, 4, 6, 8, 12, 14, 16, 18, 20
<223> OTHER INFORMATION: 2'-fluoro nucleoside
<220> FEATURE:
<221> NAME/KEY: misc_feature
<222> LOCATION: 1-7, 15-21
<223> OTHER INFORMATION: phosphorothioate linkage

<400> SEQUENCE: 355
ttgaattcag aggcaatgcg g                                         21

<210> SEQ ID NO 356
<211> LENGTH: 21
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 2, 4, 6, 8, 10, 12, 14, 16, 19, 21
```

```
<223> OTHER INFORMATION: 2'-O-methyl nucleoside
<220> FEATURE:
<221> NAME/KEY: misc_feature
<222> LOCATION: 1, 3, 5, 7, 9, 11, 13, 15, 17, 18, 20
<223> OTHER INFORMATION: 2'-fluoro nucleoside
<220> FEATURE:
<221> NAME/KEY: misc_feature
<222> LOCATION: 1-9, 11-12, 13-21
<223> OTHER INFORMATION: phosphorothioate linkage

<400> SEQUENCE: 356
ccgcattgcc tctgaattca a                                        21

<210> SEQ ID NO 357
<211> LENGTH: 21
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 2, 5, 7, 9, 11, 13, 15, 17, 19, 21
<223> OTHER INFORMATION: 2'-O-methyl nucleoside
<220> FEATURE:
<221> NAME/KEY: misc_feature
<222> LOCATION: 1, 3, 4, 6, 8, 10, 12, 14, 16, 18, 20
<223> OTHER INFORMATION: 2'-fluoro nucleoside
<220> FEATURE:
<221> NAME/KEY: misc_feature
<222> LOCATION: 1-7, 15-21
<223> OTHER INFORMATION: phosphorothioate linkage

<400> SEQUENCE: 357
ttgaattcag aggcaatgcg g                                        21

<210> SEQ ID NO 358
<211> LENGTH: 21
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 2, 4, 6, 8, 10, 12, 14, 16, 19, 21
<223> OTHER INFORMATION: 2'-O-methyl nucleoside
<220> FEATURE:
<221> NAME/KEY: misc_feature
<222> LOCATION: 1, 3, 5, 7, 9, 11, 13, 15, 17, 18, 20
<223> OTHER INFORMATION: 2'-fluoro nucleoside
<220> FEATURE:
<221> NAME/KEY: misc_feature
<222> LOCATION: 1-8, 9-10, 11-12, 13-21
<223> OTHER INFORMATION: phosphorothioate linkage

<400> SEQUENCE: 358
ccgcattgcc tctgaattca a                                        21

<210> SEQ ID NO 359
<211> LENGTH: 21
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 2, 5, 7, 9, 11, 13, 15, 17, 19, 21
<223> OTHER INFORMATION: 2'-O-methyl nucleoside
<220> FEATURE:
<221> NAME/KEY: misc_feature
<222> LOCATION: 1, 3, 4, 6, 8, 10, 12, 14, 16, 18, 20
<223> OTHER INFORMATION: 2'-fluoro nucleoside
<220> FEATURE:
<221> NAME/KEY: misc_feature
```

<222> LOCATION: 1-7, 8-9, 13-14, 15-21
<223> OTHER INFORMATION: phosphorothioate linkage

<400> SEQUENCE: 359
ttgaattcag aggcaatgcg g                                              21

<210> SEQ ID NO 360
<211> LENGTH: 21
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 2, 4, 6, 9, 11, 13, 16, 19, 21
<223> OTHER INFORMATION: 2'-O-methyl nucleoside
<220> FEATURE:
<221> NAME/KEY: misc_feature
<222> LOCATION: 1, 3, 5, 7, 8, 10, 12, 14, 15, 17, 18, 20
<223> OTHER INFORMATION: 2'-fluoro nucleoside
<220> FEATURE:
<221> NAME/KEY: misc_feature
<222> LOCATION: 1-8, 9-10, 11-12, 13-21
<223> OTHER INFORMATION: phosphorothioate linkage

<400> SEQUENCE: 360
ccgcattgcc tctgaattca a                                              21

<210> SEQ ID NO 361
<211> LENGTH: 21
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 2, 5, 6, 8, 10, 12, 14, 17, 19, 21
<223> OTHER INFORMATION: 2'-O-methyl nucleoside
<220> FEATURE:
<221> NAME/KEY: misc_feature
<222> LOCATION: 1, 3, 4, 7, 9, 11, 13, 15, 16, 18, 20
<223> OTHER INFORMATION: 2'-fluoro nucleoside
<220> FEATURE:
<221> NAME/KEY: misc_feature
<222> LOCATION: 1-7, 8-9, 13-14, 15-21
<223> OTHER INFORMATION: phosphorothioate linkage

<400> SEQUENCE: 361
ttgaattcag aggcaatgcg g                                              21

<210> SEQ ID NO 362
<211> LENGTH: 21
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 2, 6, 10, 16, 19, 21
<223> OTHER INFORMATION: 2'-O-methyl nucleoside
<220> FEATURE:
<221> NAME/KEY: misc_feature
<222> LOCATION: 1, 3, 4, 5, 7, 8, 9, 11, 12, 13, 14, 15, 17, 18, 20
<223> OTHER INFORMATION: 2'-fluoro nucleoside
<220> FEATURE:
<221> NAME/KEY: misc_feature
<222> LOCATION: 1-8, 9-10, 11-12, 13-21
<223> OTHER INFORMATION: phosphorothioate linkage

<400> SEQUENCE: 362
ccgcattgcc tctgaattca a                                              21

```
<210> SEQ ID NO 363
<211> LENGTH: 21
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 2, 5, 6, 9, 11, 13, 17, 19, 21
<223> OTHER INFORMATION: 2'-O-methyl nucleoside
<220> FEATURE:
<221> NAME/KEY: misc_feature
<222> LOCATION: 1, 3, 4, 7,8, 10, 12, 14, 15, 16, 18, 20
<223> OTHER INFORMATION: 2'-fluoro nucleoside
<220> FEATURE:
<221> NAME/KEY: misc_feature
<222> LOCATION: 1-7, 8-9, 13-14, 15-21
<223> OTHER INFORMATION: phosphorothioate linkage

<400> SEQUENCE: 363
ttgaattcag aggcaatgcg g                                                 21

<210> SEQ ID NO 364
<211> LENGTH: 16
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 2, 4, 8, 14, 16
<223> OTHER INFORMATION: 2'-O-methyl nucleoside
<220> FEATURE:
<221> NAME/KEY: misc_feature
<222> LOCATION: 1, 3, 5, 6, 7, 9, 10, 11, 12, 13, 15
<223> OTHER INFORMATION: 2'-fluoro nucleoside
<220> FEATURE:
<221> NAME/KEY: misc_feature
<222> LOCATION: 1-16
<223> OTHER INFORMATION: phosphorothioate linkage

<400> SEQUENCE: 364
gcattgcctc tgaatt                                                       16

<210> SEQ ID NO 365
<211> LENGTH: 21
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 2, 5, 7, 9, 11, 13, 15, 17, 19, 21
<223> OTHER INFORMATION: 2'-O-methyl nucleoside
<220> FEATURE:
<221> NAME/KEY: misc_feature
<222> LOCATION: 1, 3, 4, 6, 8, 10, 12, 14, 16, 18, 20
<223> OTHER INFORMATION: 2'-fluoro nucleoside
<220> FEATURE:
<221> NAME/KEY: misc_feature
<222> LOCATION: 1-7, 8-9, 13-14, 15-21
<223> OTHER INFORMATION: phosphorothioate linkage

<400> SEQUENCE: 365
ttgaattcag aggcaatgcg g                                                 21

<210> SEQ ID NO 366
<211> LENGTH: 21
<212> TYPE: DNA
<213> ORGANISM: Artificial Sequence
<220> FEATURE:
<223> OTHER INFORMATION: Synthetic Sequence
```

```
<220> FEATURE:
<221> NAME/KEY: misc_feature
<222> LOCATION: 2, 4, 7, 9, 12, 15, 19, 21
<223> OTHER INFORMATION: 2'-O-methyl nucleoside
<220> FEATURE:
<221> NAME/KEY: misc_feature
<222> LOCATION: 1, 3, 5, 6, 8, 10, 11, 13, 14, 16, 17, 18, 20
<223> OTHER INFORMATION: 2'-fluoro nucleoside
<220> FEATURE:
<221> NAME/KEY: misc_feature
<222> LOCATION: 1-9, 10-11, 13-21
<223> OTHER INFORMATION: phosphorothioate linkage

<400> SEQUENCE: 366
ccucuguugg gagucaucaa a                                              21

<210> SEQ ID NO 367
<211> LENGTH: 21
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 2, 4, 6, 8, 12, 14, 16, 19, 21
<223> OTHER INFORMATION: 2'-O-methyl nucleoside
<220> FEATURE:
<221> NAME/KEY: misc_feature
<222> LOCATION: 1, 3, 5, 7, 9, 11, 13, 15, 17, 18, 20
<223> OTHER INFORMATION: 2'-fluoro nucleoside
<220> FEATURE:
<221> NAME/KEY: misc_feature
<222> LOCATION: 1-7, 15-21
<223> OTHER INFORMATION: phosphorothioate linkage

<400> SEQUENCE: 367
uuugaugacu cccaacagag g                                              21

<210> SEQ ID NO 368
<211> LENGTH: 21
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 2, 4, 7, 9, 12, 15, 19, 21
<223> OTHER INFORMATION: 2'-O-methyl nucleoside
<220> FEATURE:
<221> NAME/KEY: misc_feature
<222> LOCATION: 1, 3, 5, 6, 8, 10, 11, 13, 14, 16, 17, 18, 20
<223> OTHER INFORMATION: 2'-fluoro nucleoside
<220> FEATURE:
<221> NAME/KEY: misc_feature
<222> LOCATION: 1-9, 11-12, 13-21
<223> OTHER INFORMATION: phosphorothioate linkage

<400> SEQUENCE: 368
ccucuguugg gagucaucaa a                                              21

<210> SEQ ID NO 369
<211> LENGTH: 21
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 2, 4, 6, 8, 12, 14, 16, 19, 21
<223> OTHER INFORMATION: 2'-O-methyl nucleoside
<220> FEATURE:
<221> NAME/KEY: misc_feature
<222> LOCATION: 1, 3, 5, 7, 9, 11, 13, 15, 17, 18, 20
```

```
<223> OTHER INFORMATION: 2'-fluoro nucleoside
<220> FEATURE:
<221> NAME/KEY: misc_feature
<222> LOCATION: 1-6, 7-8, 13-14, 15-21
<223> OTHER INFORMATION: phosphorothioate linkage

<400> SEQUENCE: 369
uuugaugacu cccaacagag g                                               21

<210> SEQ ID NO 370
<211> LENGTH: 21
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 2, 4, 7, 9, 12, 15, 19, 21
<223> OTHER INFORMATION: 2'-O-methyl nucleoside
<220> FEATURE:
<221> NAME/KEY: misc_feature
<222> LOCATION: 1, 3, 5, 6, 8, 10, 11, 13, 14, 16, 17, 18, 20
<223> OTHER INFORMATION: 2'-fluoro nucleoside
<220> FEATURE:
<221> NAME/KEY: misc_feature
<222> LOCATION: 1-9, 11-12, 14-21
<223> OTHER INFORMATION: phosphorothioate linkage

<400> SEQUENCE: 370
ccucuguugg gagucaucaa a                                               21

<210> SEQ ID NO 371
<211> LENGTH: 21
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 2, 4, 6, 8, 10, 12, 14, 16, 19, 21
<223> OTHER INFORMATION: 2'-O-methyl nucleoside
<220> FEATURE:
<221> NAME/KEY: misc_feature
<222> LOCATION: 1, 3, 5, 7, 9, 11, 13, 15, 17, 18, 20
<223> OTHER INFORMATION: 2'-fluoro nucleoside
<220> FEATURE:
<221> NAME/KEY: misc_feature
<222> LOCATION: 1-6, 7-8, 13-14, 15-21
<223> OTHER INFORMATION: phosphorothioate linkage

<400> SEQUENCE: 371
uuugaugacu cccaacagag g                                               21

<210> SEQ ID NO 372
<211> LENGTH: 21
<212> TYPE: DNA
<213> ORGANISM: Artificial Sequence
<220> FEATURE:
<221> NAME/KEY: modified_base
<222> LOCATION: 10
<223> OTHER INFORMATION: n = I
<220> FEATURE:
<223> OTHER INFORMATION: Synthetic Sequence
<220> FEATURE:
<221> NAME/KEY: misc_feature
<222> LOCATION: 2, 4, 7, 10, 12, 15, 19, 21
<223> OTHER INFORMATION: 2'-O-methyl nucleoside
<220> FEATURE:
<221> NAME/KEY: misc_feature
<222> LOCATION: 1, 3, 5, 6, 8, 9, 11, 13, 14, 16, 17, 18, 20
<223> OTHER INFORMATION: 2'-fluoro nucleoside
<220> FEATURE:
<221> NAME/KEY: misc_feature
```

<222> LOCATION: 1-9, 11-12, 14-21
<223> OTHER INFORMATION: phosphorothioate linkage

<400> SEQUENCE: 372
ccucuguugn gagucaucaa a                                              21

<210> SEQ ID NO 373
<211> LENGTH: 21
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 2, 4, 6, 8, 10, 12, 14, 16, 19, 21
<223> OTHER INFORMATION: 2'-O-methyl nucleoside
<220> FEATURE:
<221> NAME/KEY: misc_feature
<222> LOCATION: 1, 3, 5, 7, 9, 11, 13, 15, 17, 18, 20
<223> OTHER INFORMATION: 2'-fluoro nucleoside
<220> FEATURE:
<221> NAME/KEY: misc_feature
<222> LOCATION: 1-6, 7-8, 13-14, 15-21
<223> OTHER INFORMATION: phosphorothioate linkage

<400> SEQUENCE: 373
uuugaugacu cccaacagag g                                              21

<210> SEQ ID NO 374
<211> LENGTH: 21
<212> TYPE: DNA
<213> ORGANISM: Artificial Sequence
<220> FEATURE:
<221> NAME/KEY: modified_base
<222> LOCATION: 10
<223> OTHER INFORMATION: n = I
<220> FEATURE:
<223> OTHER INFORMATION: Synthetic Sequence
<220> FEATURE:
<221> NAME/KEY: misc_feature
<222> LOCATION: 2, 4, 8, 10, 12, 14, 17, 19, 21
<223> OTHER INFORMATION: 2'-O-methyl nucleoside
<220> FEATURE:
<221> NAME/KEY: misc_feature
<222> LOCATION: 1, 3, 5, 6, 7, 9, 11, 13, 15, 16, 18, 20
<223> OTHER INFORMATION: 2'-fluoro nucleoside
<220> FEATURE:
<221> NAME/KEY: misc_feature
<222> LOCATION: 1-9, 11-12, 14-21
<223> OTHER INFORMATION: phosphorothioate linkage

<400> SEQUENCE: 374
ccucuguugn gagucaucaa a                                              21

<210> SEQ ID NO 375
<211> LENGTH: 21
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 2, 4, 7, 9, 11, 13, 15, 16, 19, 21
<223> OTHER INFORMATION: 2'-O-methyl nucleoside
<220> FEATURE:
<221> NAME/KEY: misc_feature
<222> LOCATION: 1, 3, 5, 6, 8, 10, 12, 14, 17, 18, 20
<223> OTHER INFORMATION: 2'-fluoro nucleoside
<220> FEATURE:
<221> NAME/KEY: misc_feature
<222> LOCATION: 1-6, 7-8, 13-14, 15-21
<223> OTHER INFORMATION: phosphorothioate linkage

```
<400> SEQUENCE: 375
uuugaugacu cccaacagag g                                              21

<210> SEQ ID NO 376
<211> LENGTH: 21
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 2, 8, 10, 14, 19, 21
<223> OTHER INFORMATION: 2'-O-methyl nucleoside
<220> FEATURE:
<221> NAME/KEY: misc_feature
<222> LOCATION: 1, 3, 4, 5, 6, 7, 9, 11, 12, 13, 15, 16, 17, 18, 20
<223> OTHER INFORMATION: 2'-fluoro nucleoside
<220> FEATURE:
<221> NAME/KEY: misc_feature
<222> LOCATION: 1-21
<223> OTHER INFORMATION: phosphorothioate linkage

<400> SEQUENCE: 376
ccucuguugg gagucaucaa a                                              21

<210> SEQ ID NO 377
<211> LENGTH: 21
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 2, 4, 7, 9, 11, 13, 15, 16, 19, 21
<223> OTHER INFORMATION: 2'-O-methyl nucleoside
<220> FEATURE:
<221> NAME/KEY: misc_feature
<222> LOCATION: 1, 3, 5, 6, 8, 10, 12, 14, 17, 18, 20
<223> OTHER INFORMATION: 2'-fluoro nucleoside
<220> FEATURE:
<221> NAME/KEY: misc_feature
<222> LOCATION: 1-6, 7-8, 13-14, 15-21
<223> OTHER INFORMATION: phosphorothioate linkage

<400> SEQUENCE: 377
uuugaugacu cccaacagag g                                              21

<210> SEQ ID NO 378
<211> LENGTH: 16
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 2, 4, 6, 8, 10, 12, 14
<223> OTHER INFORMATION: 2'-O-methyl nucleoside
<220> FEATURE:
<221> NAME/KEY: misc_feature
<222> LOCATION: 1, 3, 5, 7, 9, 11, 13, 15, 16
<223> OTHER INFORMATION: 2'-fluoro nucleoside
<220> FEATURE:
<221> NAME/KEY: misc_feature
<222> LOCATION: 1-9, 12-16
<223> OTHER INFORMATION: phosphorothioate linkage

<400> SEQUENCE: 378
acauagccga augccg                                                    16
```